US012502427B2

(12) United States Patent
Moniz et al.

(10) Patent No.: US 12,502,427 B2
(45) **Date of Patent: *Dec. 23, 2025**

(54) EXTRACELLULAR VESICLES FOR VACCINE DELIVERY

(71) Applicant: LONZA SALES AG, Basel (CH)

(72) Inventors: Raymond J. Moniz, Brighton, MA (US); Russell E. Mcconnell, Cambridge, MA (US); Nikki Ross, Philadelphia, PA (US); Christine Mccoy, Cambridge, MA (US); Timothy J. Soos, Boston, MA (US); Ke Xu, Belmont, MA (US)

(73) Assignee: LONZA SALES AG, Basel (CH)

( * ) Notice: Subject to any disclaimer, the term of this patent is extended or adjusted under 35 U.S.C. 154(b) by 988 days.

This patent is subject to a terminal disclaimer.

(21) Appl. No.: 17/441,524

(22) PCT Filed: Mar. 20, 2020

(86) PCT No.: PCT/US2020/024023

§ 371 (c)(1),
(2) Date: Sep. 21, 2021

(87) PCT Pub. No.: WO2020/191361

PCT Pub. Date: Sep. 24, 2020

(65) Prior Publication Data

US 2022/0168415 A1 Jun. 2, 2022

Related U.S. Application Data

(60) Provisional application No. 62/984,146, filed on Mar. 2, 2020, provisional application No. 62/946,280, filed on Dec. 10, 2019, provisional application No. 62/901,166, filed on Sep. 16, 2019, provisional application No. 62/891,048, filed on Aug. 23, 2019, provisional application No. 62/840,348, filed on Apr. 29, 2019, provisional application No. 62/835,437, filed on Apr. 17, 2019, provisional application No. 62/822,008, filed on Mar. 21, 2019.

(51) Int. Cl.

| | |
|---|---|
| ***A61K 39/00*** | (2006.01) |
| ***A61K 31/7084*** | (2006.01) |
| ***A61K 39/12*** | (2006.01) |
| ***A61K 39/385*** | (2006.01) |
| ***A61K 47/64*** | (2017.01) |
| ***A61P 37/04*** | (2006.01) |

(52) U.S. Cl.
CPC ............ *A61K 39/385* (2013.01); *A61K 39/00* (2013.01); *A61K 39/0011* (2013.01); *A61P 37/04* (2018.01); *A61K 2039/60* (2013.01)

(58) Field of Classification Search
CPC .......... A61P 37/04; A61P 31/12; A61P 37/02; A61K 2039/55555; A61K 2039/60
See application file for complete search history.

(56) References Cited

U.S. PATENT DOCUMENTS

| | | | |
|---|---|---|---|
| 4,683,195 | A | 7/1987 | Mullis et al. |
| 7,087,229 | B2 | 8/2006 | Zhao et al. |
| 7,375,078 | B2 | 5/2008 | Feng |
| 7,569,657 | B2 | 8/2009 | Zhao et al. |
| 7,754,681 | B2 | 7/2010 | Feng |
| 8,137,695 | B2 | 3/2012 | Rozema et al. |
| 8,354,455 | B2 | 1/2013 | Satyam |
| 8,426,565 | B2 | 4/2013 | Lahoud et al. |
| 8,465,730 | B1 | 6/2013 | O'Lenick |
| 8,617,564 | B2 | 12/2013 | Long et al. |
| 9,695,212 | B2 | 7/2017 | Dubensky et al. |
| 9,790,494 | B2 | 10/2017 | Uhlmann et al. |
| 9,988,431 | B2 | 6/2018 | Lahoud et al. |
| 10,011,630 | B2 | 7/2018 | Vernejoul et al. |
| 10,195,290 | B1 | 2/2019 | Dooley et al. |
| 11,992,527 | B2 | 5/2024 | Moniz et al. |
| 2003/0130189 | A1 | 7/2003 | Senter et al. |
| 2005/0256030 | A1 | 11/2005 | Feng |
| 2006/0269480 | A1 | 11/2006 | Amir et al. |
| 2008/0085869 | A1 | 4/2008 | Yamada et al. |
| 2010/0029585 | A1 | 2/2010 | Howbert et al. |
| 2010/0092496 | A1 | 4/2010 | Boyd et al. |
| 2010/0145036 | A1 | 6/2010 | Sufi et al. |
| 2011/0182942 | A1 | 7/2011 | Zollinger |

(Continued)

FOREIGN PATENT DOCUMENTS

| | | | |
|---|---|---|---|
| JP | 2006518212 | A | 8/2006 |
| WO | 2004073319 | A2 | 8/2004 |

(Continued)

OTHER PUBLICATIONS

International Search Report and Written Opinion for International Application No. PCT/US2020/024023, European Patent Office, Netherlands, mailed on Sep. 23, 2020.
Aasland, R., et al., "Normalization of Nomenclature for Peptide Motifs as Ligands of Modular Protein Domains," FEBS Letters 513(1):141-144 (2002).
Ahrens, S., et al., "F-Actin is an Evolutionarily Conserved Damage-associated Molecular Pattern Recognized by DNGR-1, a Receptor for Dead Cells," Immunity 36(4):635-645 (2012).
Arlehamn, et al., "Dissecting Mechanisms of Immunodominance to the Common Tuberculosis Antigens ESAT-6, CFP10, Rv2031c (hspX), Rv2654c (TB7.7), and Rv1038c (EsxJ)," Journal of Immunology 188(10):5020-5031 (2012).

(Continued)

*Primary Examiner* — Barry A Chestnut
(74) *Attorney, Agent, or Firm* — MEDLER FERRO WOODHOUSE & MILLS PLLC

(57) ABSTRACT

The present disclosure relates to extracellular vesicles (EVs), e.g., exosomes, comprising a payload (e.g., an antigen, adjuvant, and/or immune modulator) and/or a targeting moiety. Also provided herein are methods for producing the EVs (e.g., exosomes) and methods for using the EVs (e.g., exosomes) to treat and/or prevent diseases or disorders, e.g., cancer, graft-versus-host disease (GvHD), autoimmune disease, infectious diseases, or fibrotic diseases.

19 Claims, 46 Drawing Sheets

Specification includes a Sequence Listing.

(56) References Cited

U.S. PATENT DOCUMENTS

| | | | |
|---|---|---|---|
| 2012/0219615 A1 | 8/2012 | Hershberg et al. |
| 2013/0202707 A1 | 8/2013 | Ali et al. |
| 2014/0193849 A1 | 7/2014 | Narayanan et al. |
| 2018/0037639 A1 | 2/2018 | Crowe et al. |
| 2021/0322327 A1 | 10/2021 | Jang et al. |
| 2023/0263885 A1 | 8/2023 | Moniz et al. |

FOREIGN PATENT DOCUMENTS

| | | |
|---|---|---|
| WO | 2008115319 A2 | 9/2008 |
| WO | 2009030996 A1 | 3/2009 |
| WO | 2009088401 A2 | 7/2009 |
| WO | 2011044246 A1 | 4/2011 |
| WO | 2013053008 A2 | 4/2013 |
| WO | 2013185052 A1 | 12/2013 |
| WO | 2014093936 A1 | 6/2014 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |
| WO | 2015017652 A1 | 2/2015 |
| WO | 2015077354 A1 | 5/2015 |
| WO | 2015185565 A1 | 12/2015 |
| WO | 2016096174 A1 | 6/2016 |
| WO | 2016096577 A1 | 6/2016 |
| WO | 2016120305 A1 | 8/2016 |
| WO | 2016145102 A1 | 9/2016 |
| WO | 2016184860 A1 | 11/2016 |
| WO | 2017027645 A1 | 2/2017 |
| WO | 2017027646 A1 | 2/2017 |
| WO | 2017075477 A1 | 5/2017 |
| WO | 2017161349 A1 | 9/2017 |
| WO | 2017175147 A1 | 10/2017 |
| WO | 2017175156 A1 | 10/2017 |
| WO | 2018100558 A2 | 6/2018 |
| WO | 2019040920 A1 | 2/2019 |
| WO | 2019099942 A1 | 5/2019 |
| WO | 2019183578 A1 | 9/2019 |
| WO | 2020191361 A2 | 9/2020 |

OTHER PUBLICATIONS

Besse, B., et al., "Dendritic Cell-derived Exosomes as Maintenance Immunotherapy After First Line Chemotherapy in NSCLC," Oncoimmunology 5(4):e1071008 (2015).

Caculitan, N.G., et al., "Cathepsin B is Dispensable for Cellular Processing of Cathepsin B-Cleavable Antibody-Drug Conjugates," Cancer Research 77(24):7027-7037 (2017).

Collin, M et al., "Human Dendritic Cell Subsets: An Update," Immunology 154(1):3-20 (2018).

Corrales, L., et al., "Direct Activation of STING in the Tumor Microenvironment Leads to Potent and Systemic Tumor Regression and Immunity," Cell Reports 11(7):1018-1030 (2015).

Dobeli, H., et al., "Role of the Carboxy-terminal Sequence on the Biological Activity of Human Interferon (IFN-y)," Journal of Biotechnology 7:199-216 (1988).

Doronina, S.O., et al., "Development of Potent Monoclonal Antibody Auristatin Conjugatesfor Cancer Therapy," Nature Biotechnology 21(7):778-784 (2003).

Fu, J., et al., "STING Agonist Formulated Cancer Vaccines Can Cure Established TumorsResistant to PD-1 Blockade," Science Translational Medicine 7(283):283ra52 (2015).

Gayle, R.B., III., et al., "Identification of Regions in Interleukin-1 Alpha Important forActivity," The Journal of Biological Chemistry 268(29):22105-22111 (1993).

Gupta, S.C., et al., "Inhibiting NF-KB Activation by Small Molecules as a Therapeutic Strategy," Biochimica Et Biophysica Acta 1799(10-12):775-787 (2010).

Hartlage, A.S., et al., "The Epstein-Barr Virus Lytic Protein BZLF1 as a Candidate TargetAntigen for Vaccine Development," Cancer Immunology Research 3(7):787-794 (2015).

Huysamen, C., et al., "CLEC9A Is a Novel Activation C-type Lectin-like Receptor Expressedon BDCA3+ Dendritic Cells and a Subset of Monocytes," The Journal of Biological Chemistry 283(24):16693-16701 (2008).

Kihara, Y., et al., "Lysophospholipid Receptors in Drug Discovery," Experimental Cell Research 333(2):171-177 (2015).

Kuypers, F.A., et al., "Survival of Rabbit and Horse Erythrocytes in Vivo after Changing theFatty Acyl Composition of their Phosphatidylcholine," Biochimica et Biophysica Acta 819(2):170-178 (1985).

Mei, B., et al., "Rational Design of a Fully active, Long-acting PEGylated Factor VIII for Hemophilia A Treatment," Blood 116(2):270-279 (2010).

Miao, L., et al., "Delivery of mRNA Vaccines With Heterocyclic Lipids Increases Anti-tumorEfficacy by STING-Mediated Immune Cell Activation," Nature Biotechnology 37(10):1174- 1185 (2019).

Morishita M. et al., "Exosome-based tumor antigens-adjuvant co-delivery utilizinggenetically engineered tumor cell-derived exosomes with immunostimulatory CpG DNA." Biomaterials 111:55-65 (2016).

Palmer, S.M., et al., "Randomized, Double-Blind, Placebo-Controlled, Phase 2 Trial ofBMS-986020, A Lysophosphatidic Acid Receptor Antagonist for the Treatment of Idiopathic Pulmonary Fibrosis," Chest 154(5):1061-1069 (2018).

Papapetrou, E.P., et al., "Genetic Modification of Hematopoietic Stem Cells With Nonviral Systems: Past Progress and Future Prospects," Gene Therapy 12(Suppl 1):S118-S130 (2005).

Pitt, J.M., et al., "Dendritic Cell-Derived Exosomes for Cancer Therapy," The Journal of Clinical Investigation 126(4):1224-1232 (2016).

Reddy, J.A., et al., "Folate Receptor Specific Anti-tumor Activity of Folate-mitomycinConjugates," Cancer Chemotherapy and Pharmacology 58(2):229-236 (2006).

Rist, M.J., et al., "T Cell Epitope Clustering in the Highly Immunogenic BZLF1 Antigen of Epstein-Barr Virus," Journal of Virology 89(1):703-712 (2015).

Ron, D., et al., "Expression of Biologically Active Recombinant Keratinocyte Growth Factor.Structure/Function Analysis of Amino-terminal Truncation Mutants," The Journal of Biological Chemistry 268(4):2984-2988 (1993).

Rosen, G., et al., "LPA1 antagonists BMS-986020 and BMS-986234 for idiopathic pulmonary fibrosis: Preclinical evaluation of hepatobiliary homeostasis," European Respiratory Journal 50:PA1038 (2017).

Senti G., et al., "Intralymphatic Allergen Administration Renders Specific ImmunotherapyFaster and Safer: a Randomized Controlled Trial," PNAS 105(46):17908-17912 (2008).

Trouet, A., et al., "A Covalent Linkage Between Daunorubicin and Proteins That Is Stable in Serum and Reversible by Lysosomal Hydrolases, as Required for a Lysosomotropic Drug-carrier Conjugate: In Vitro and in Vivo Studies," Proceedings of the National Academy of Sciences of the United States of America 79(2):626-629 (1982).

Umemoto, N., et al., "Preparation and in Vitro Cytotoxicity of a Methotrexate-Anti-MM46 Monoclonal Antibody Conjugate via An Oligopeptide Spacer," International Journal of Cancer 43(4):677-684 (1989).

He, S., et al., "Structure of Nucleosome-Bound Human BAF Complex," Science 367(6480):1-12 (2020).

Yan, Z., et al., "A Novel Peptide Targeting Clec9a on Dendritic Cell for Cancer Immunotherapy," Oncotarget 7(26):40437-40450 (2016).

Yang, J., et al., "Characterization of the pH of Folate Receptor-containing Endosomes andthe Rate of Hydrolysis of Internalized Acid-labile Folate-drug Conjugates," The Journal of Pharmacology and Experimental Therapeutics 321(2):462-468 (2007).

Yuan, Q., et al., "A stimulus-responsive Magnetic Nanoparticle Drug Carrier: Magnetite Encapsulated by Chitosan-grafted-copolymer," Acta Biomaterialia 4(4):1024-1037 (2008).

Zhang, J., et al., "Magnetic Drug-targeting Carrier Encapsulated with Thermosensitive SmartPolymer: Core-shell Nanoparticle Carrier and Drug Release Response," Acta biomaterialia 3(6):838-850 (2007).

(56) References Cited

OTHER PUBLICATIONS

Zhang, J.G., et al., "The Dendritic Cell Receptor Clec9A Binds Damaged Cells via Exposed Actin Filaments," Immunity 36(4):646-657 (2012).
Zhou, L., et al., "Endosomal pH-activatable Poly(ethylene oxide)-graft-doxorubicin Prodrugs: Synthesis, Drug Release, and Biodistribution in Tumor-bearing Mice," Biomacromolecules 12(5):1460-1467 (2011).
Grandi et al., "Synergistic Protective Activity of Tumor-Specific Epitopes Engineered inBacterial Outer Membrane Vesicles," Frontiers in Oncology 7:1-12.
Chen, R., et al., "Exosomes in hepatocellular carcinoma: a new horizon," Cell CommunSignal 17(1): 1, Biomed Central, United Kingdom (Jan. 2019).
Fantappie, L., et al., "Antibody-mediated immunity induced by engineered *Escherichia coli* OMVs carrying heterologous antigens in their lumen," J Extracell Vesicles 3(1), John Wiley & Sons, United States (Aug. 2014).
Gnopo, Y.M.D., et al., "Designer outer membrane vesicles as immunomodulatory systems—Reprogramming bacteria for vaccine delivery," Adv Drug Deliv Rev 114: 13 2-142, Elsevier, Netherlands (May 2017).
He, Y., et al., "Engineering a-fetoprotein-based gene vaccines to prevent and treathepatocellular carcinoma: review and future prospects," Immunotherapy 6(6):725-736, Future Medicine, United Kingdom (Jun. 2014).
Kato, K., et al., "Cyclic GMP-AMP as an Endogenous Second Messenger in Innate Immune Signaling by Cytosolic DNA," Annu Rev Biochem 86:541-566, Annual Reviews, United States (Jun. 2017).
Kitai, Y., et al., "DNA-Containing Exosomes Derived from Cancer Cells Treated with Topotecan Activate a STING-Dependent Pathway and Reinforce Antitumor Immunity," J Immunol 198( 4): 1649-1659, American Association of Immunologists, United States (Feb. 2017).
Koshy, S.T., et al., "Liposomal Delivery Enhances Immune Activation by STING Agonists for Cancer Immunotherapy," AdvBiosyst 1(1-2):1600013, Wiley, United States (Feb. 2017).
Ma, F., et al., "Positive feedback regulation of type I interferon by the interferon-stimulated gene STING," EMBO Rep 16(2):202-212, Nature Portfolio, Germany (Feb. 2015).
Miyabe, H., et al., "A new adjuvant delivery system 'cyclic di-GMP/YSK05 liposome' for cancer immunotherapy," J Control Release 184:20-27, Elsevier, Netherlands (Jun. 2014).
Tan, K., et al., "Outer Membrane Vesicles: Current Status and Future Direction of These NovelVaccine Adjuvants," Front Microbiol 9:783, Frontiers Media S.A., Switzerland (Apr. 2018).

inoculation RX dosing uptake dosing sacrifice

| group | Rx | route | N | 0 | 7 | 14 | 21 | | |
|---|---|---|---|---|---|---|---|---|---|
| 1 | IgG-Px-OVA + CL656 | IN | 10 | | 5 | | 5 | | |
| 2 | IgG-Px-OVA exoVACC | IN | 10 | | 5 | | 5 | | |
| 3 | aCLEC9A-Px-OVA + CL656 | IN | 10 | | 5 | | 5 | | |
| 4 | aCLEC9A-Px-OVA exoVACC | IN | 10 | | 5 | | 5 | | |
| 5 | PyOVA exoVACC | IN | 10 | | 5 | | 5 | | |
| | TOTAL | | 50 | | | | | | |

Aims:
1. Determine whether there is a benefit to targeting CLEC9A+ cells in exoVACC.

Endpoints:
1. FACS analysis of T cell responses in the spleen and lung following intranasal vaccination, 7 days after prime
2. 14 days after boost, serum and T cell analysis

FIG. 6

Key:

- ○ Tumor Inoculation (SC)
- ⊘ Dosing (SC)
- ⊗ Dosing (IT)
- ◍ Sacrifice
- ⊕ Dosing (IP)
- ● Dosing (IN)
- ⊖ Dosing (IV)
- ⦶ Dosing (other)

| Group | Rx | Dose | # Doses | Route | N | 0 | 1 | 2 | 3 | 4 | 5 | 6 | 7 | 8 | 9 | 10 | 11 | 12 | 13 |
|---|---|---|---|---|---|---|---|---|---|---|---|---|---|---|---|---|---|---|---|
| 1 | PBS | | 1 | SQ | 9 | ⊘ | | | | | | | ○ | | | | | | |
| 2 | exoVACC | OVA (0.5 ug) | 1 | IN | 9 | ● | | | | | | | ○ | | | | | | |
| 3 | exoVACC | OVA (0.5 ug) | 1 | SQ | 9 | ⊘ | | | | | | | ○ | | | | | | |
| 4 | OVA +PolyI:C | OVA (0.5 ug) + PolyI:C (5 ug) | 1 | IN | 9 | ● | | | | | | | ○ | | | | | | |
| 5 | OVA + PolyI:C | OVA (0.5 ug) + PolyI:C (50 ug) | 1 | SQ | 9 | ⊘ | | | | | | | ○ | | | | | | |

FIG. 14A

****, *P* <0.001
exoVACC (SC) compared to both Untreated and OVA + poly I:C (SC)
exoVACC (IN) compared to both Untreated and OVA + poly I:C (IN)

| Group | Rx | Dose | # Doses | Route | N | 0 | 7 |
|---|---|---|---|---|---|---|---|
| 1 | Empty (no OVA antigen) Protein Y exosomes | 2e10 | 1 | IN | 5 | ○ | ● |
| 2 | Soluble OVA | 20 ul | 1 | IN | 5 | ○ | ● |
| 3 | Soluble OVS + STING | 20 ul | 1 | IN | 5 | ○ | ● |
| 4 | Protein Y-OVA exosomes | 20 ul (2E10) | 1 | IN | 5 | ○ | ● |
| 5 | Protein Y-OVA + STING exosomes | 20 ul (2E10) | 1 | IN | 5 | ○ | ● |
FIG. 15A
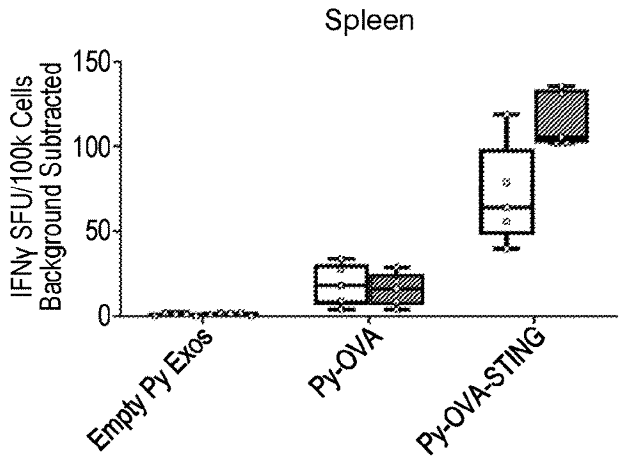
FIG. 15B
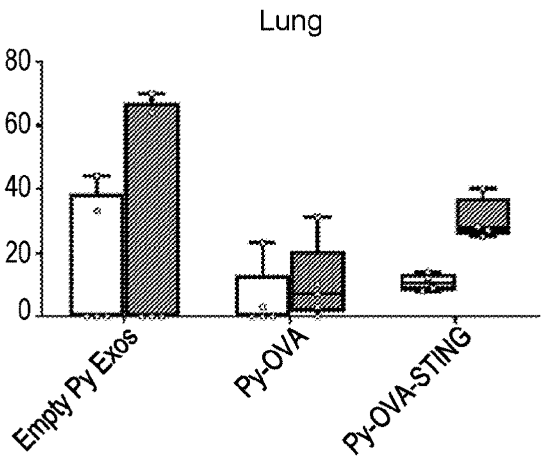
FIG. 15C
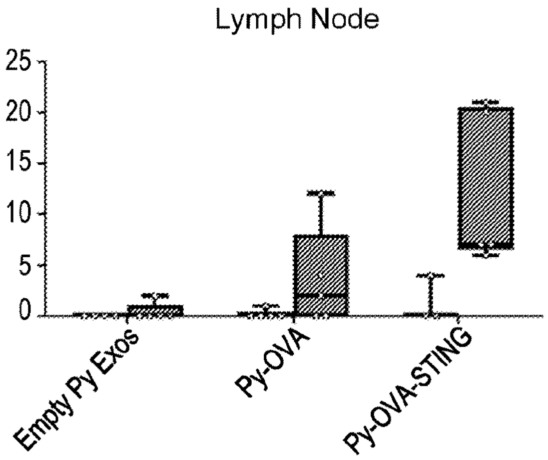
FIG. 15D

| | Composition | Dose | Molec. STING/exo | 0 | 7 | 14 |
|---|---|---|---|---|---|---|
| 1 | PBS | 0.1 mL | NA | ○ | ○ | ● |
| 2 | exo – Lama4+CL656 | Equal STING agonist | 2991 | ○ | ○ | ● |
| 3 | exo – Itgb1+CL656 | | 2158 | ○ | ○ | ● |
| 4 | exo – Lama4+Itgb1+CL656 | | 4372 | ○ | ○ | ● |
| | | | | | | |

FIG. 16A

○ RX dosing ● Sacrifice
| Group | Rx | Dose | 0 | 7 | 14 |
|---|---|---|---|---|---|
| 1 | Protein X exosomes | 1e11 | ○ | ○ | ● |
| 2 | Exo-Lama4 Peptide-CpG | 1e11 | ○ | ○ | ● |
| 3 | Exo-Lama4 & Itgb1 peptides + CpG | 1e11 | ○ | ○ | ● |
| Route: SC n=5 | | | | | |
FIG. 17A
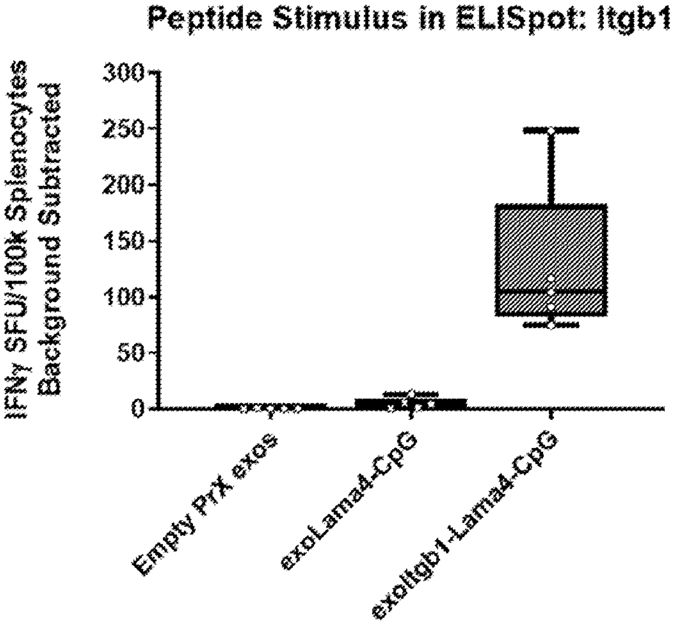
FIG. 17B
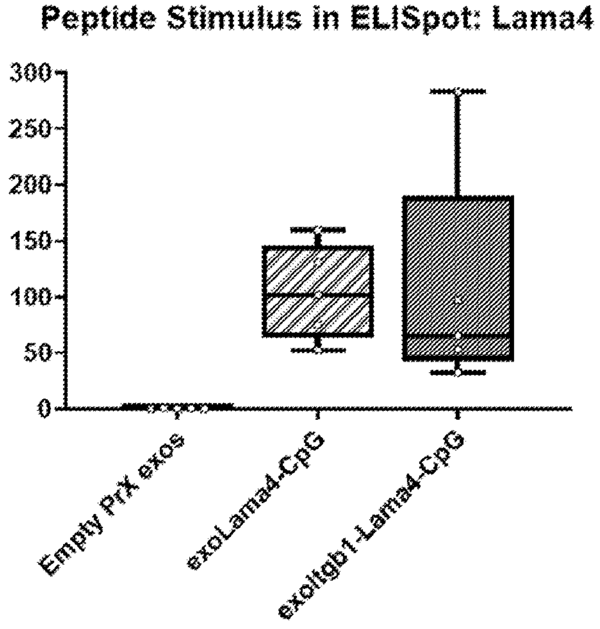
FIG. 17C

| Group | Rx | Route | N | 0 | 7 | 14 |
|---|---|---|---|---|---|---|
| 1 | **IgG**-Px-OVA exoVACC | IN | 10 | | 5 | 5 |
| 2 | **aCLEC9A**-Px-OVA exoVACC | IN | 10 | | 5 | 5 |
| 3 | **PyOVA** exoVACC | IN | 10 | | 5 | 5 |
FIG. 19A
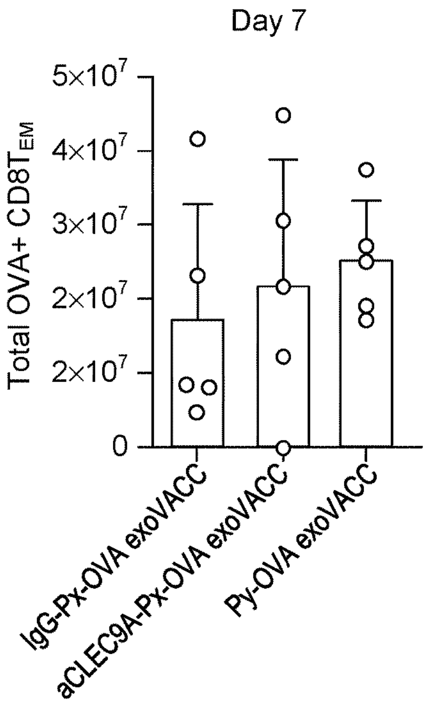
FIG. 19B
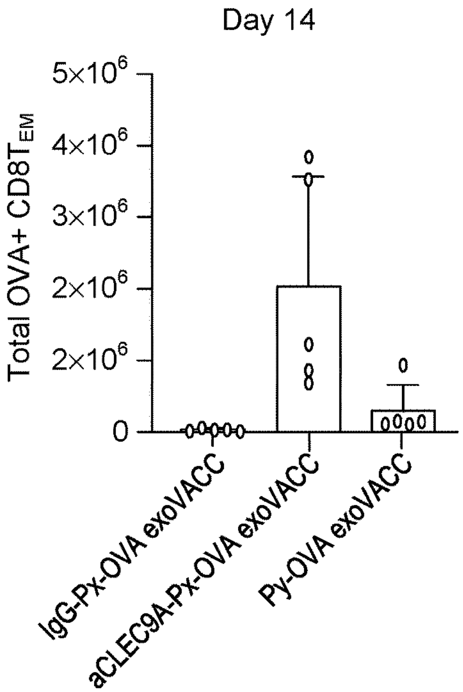
FIG. 19C

| group | Rx | Route | 0 | 14 | 28 |
|---|---|---|---|---|---|
| 1 | OVA | IN | ○ | ○ | 5 |
| 2 | OVA + CL656 | IN | ○ | ○ | 5 |
| 3 | PyOVA | IN | ○ | ○ | 5 |
| 4 | PyOVA + CL656 | IN | ○ | ○ | 4 |
| 5 | PyOVA exoVACC | IN | ○ | ○ | 5 |
| 6 | OVA + Alum | SQ | ○ | ○ | 5 |
FIG. 20A
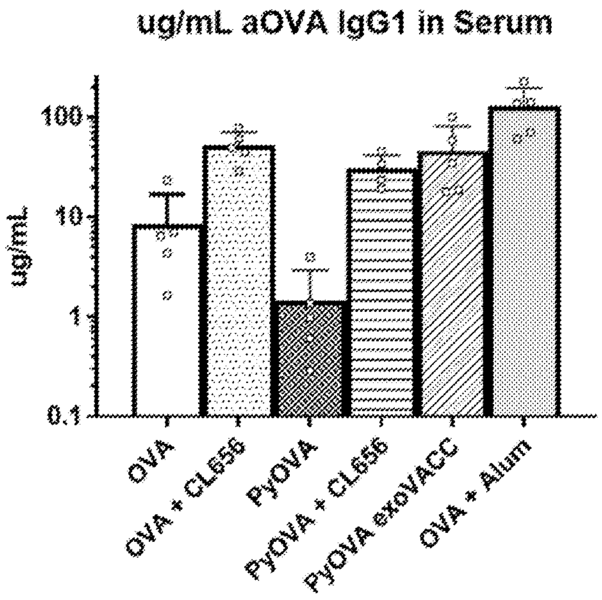
FIG. 20B
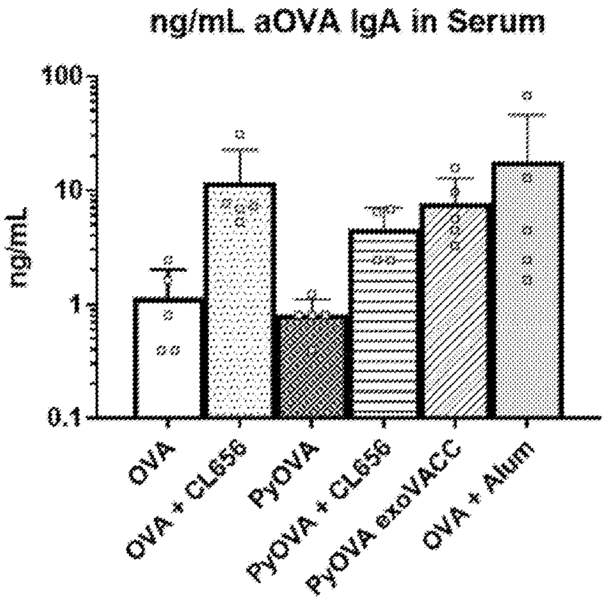
FIG. 20C

AM095

AM152

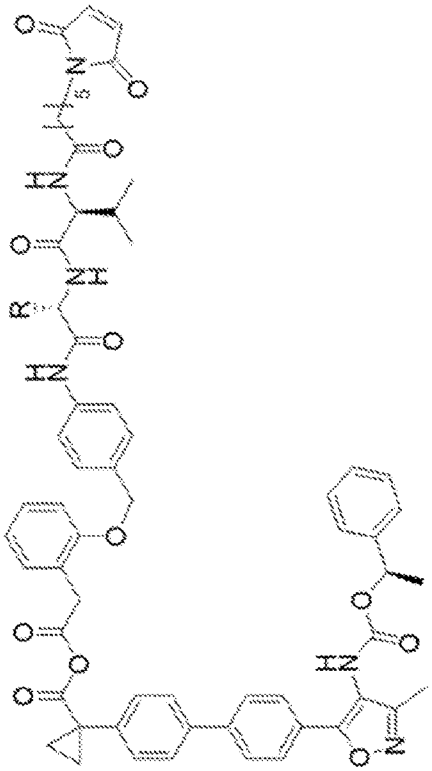
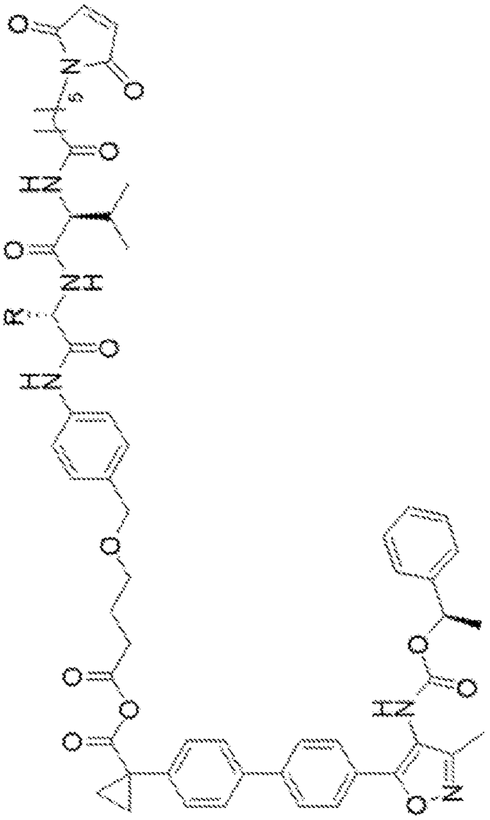
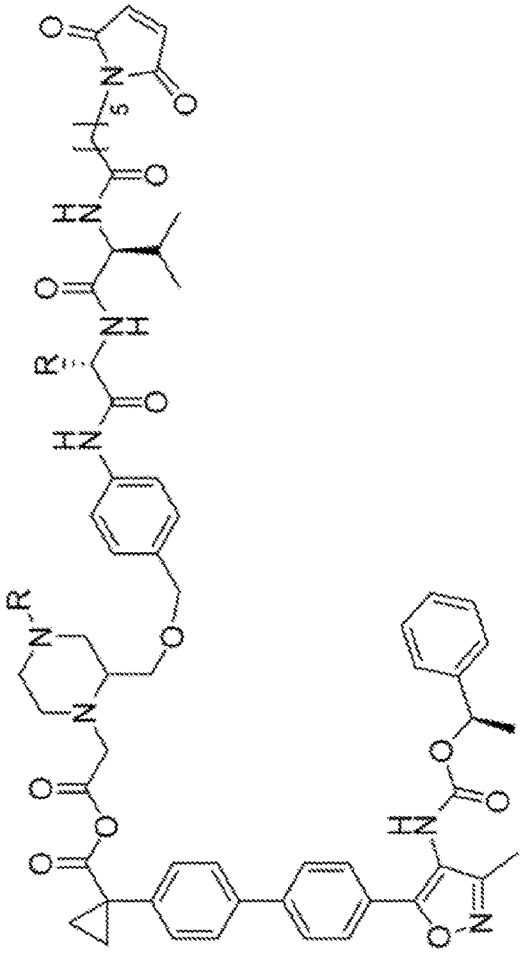
FIG. 26

EXTRACELLULAR VESICLES FOR VACCINE DELIVERY

CROSS-REFERENCE TO RELATED APPLICATIONS

This PCT application claims the priority benefit of U.S. Provisional Application Nos. 62/822,008, filed Mar. 21, 2019; 62/835,437, filed Apr. 17, 2019; 62/840,348, filed Apr. 29, 2019; 62/891,048, filed Aug. 23, 2019; 62/901,166, filed Sep. 16, 2019; 62/946,280, filed Dec. 10, 2019; and 62/984,146, filed Mar. 2, 2020, each of which is herein incorporated by reference in its entirety.

REFERENCE TO SEQUENCE LISTING SUBMITTED ELECTRONICALLY VIA EFS-WEB

The content of the electronically submitted sequence listing (Name: 4000_032PC07_Sequencelisting_ST25.txt, Size: 283,505 bytes; and Date of Creation: Mar. 20, 2020) submitted in this application is incorporated herein by reference in its entirety.

FIELD OF DISCLOSURE

The present disclosure relates to modified extracellular vesicles, e.g., exosomes (e.g., comprises one or more payloads, e.g., an antigen and adjuvant/immune modulator) that is useful as a vaccine that can be used to treat and/or prevent a range of medical disorders, including, but not limited to, cancer, graft-versus-host disease (GvHD), autoimmune disease, infectious diseases, and fibrotic diseases. The present disclosure also relates to methods of producing such EVs, e.g., exosomes, and uses thereof.

BACKGROUND

EVs, e.g., exosomes, are important mediators of intercellular communication. They are also important biomarkers in the diagnosis and prognosis of many diseases, such as cancer. As drug delivery vehicles, EVs, e.g., exosomes, offer many advantages over traditional drug delivery methods (e.g., peptide immunization, DNA vaccines) as a new treatment modality in many therapeutic areas. However, despite its advantages, many EVs, e.g., exosomes, have had limited clinical efficacy. For example, dendritic-cell derived exosomes (DEX) were investigated in a Phase II clinical trial as maintenance immunotherapy after first line chemotherapy in patients with inoperable non-small cell lung cancer (NSCLC). However, the trial was terminated because the primary endpoint (at least 50% of patients with progression-free survival (PFS) at 4 months after chemotherapy cessation) was not reached. Besse, B., et al., *Oncoimmunology* 5(4):e1071008 (2015).

Accordingly, new and more effective engineered-EVs, e.g., exosomes, are necessary to better enable therapeutic use and other applications of EV-based technologies.

SUMMARY OF DISCLOSURE

Provided herein are isolated EVs, e.g., exosomes, comprising (i) at least one antigen and (ii) at least one adjuvant. In some aspects, the EV comprises at least 2, 3, 4, 5, 6, 7, 8, 9, 10 or more different antigens. In some aspects, the EV comprises at least at least 2, 3, 4, 5, 6, 7, 8, 9, 10 or more different adjuvants. In some aspects, the antigen is not presented on MHC class I and/or II molecules In some aspects, an EV, e.g., exosome, is not derived from a naturally-existing antigen-presenting cell. In certain aspects, an EV, e.g., exosome, is not derived from a naturally-existing dendritic cell, a naturally-existing B cell, a naturally-existing mast cell, a naturally-existing macrophage, a naturally-existing neutrophil, naturally-existing Kupffer-Browicz cell, cell derived from any of these cells, or any combination thereof.

In some aspects, an EV, e.g., exosome, induces a cellular immune response, a humoral immune response, or both cellular and humoral immune responses. In certain aspects, the induction of the cellular immune response, the humoral immune response, or both cellular and humor immune responses is increased by at least about 5%, at least about 10%, at least about 20%, at least about 30%, at least about 40%, at least about 50%, at least about 60%, at least about 70%, at least about 80%, at least about 90%, at least about 100% or more, compared to (i) a corresponding EV, e.g., exosome, that does not comprise the adjuvant or the antigen or (ii) the adjuvant or the antigen without the EV (i.e., non-EV delivery vehicle).

In some aspects, an EV, e.g., exosome, described herein induces a CD4+ T cell response, a CD8+ T cell response, or both CD4+ and CD8+ T cell responses. In certain aspects, an EV, e.g., exosome, does not directly interact with T Cell Receptors (TCRs) of T cells.

In some aspects, an EV, e.g., exosome, of the present disclosure further comprises a first scaffold moiety. In certain aspects, the antigen is linked to the first scaffold moiety. In some aspects, the adjuvant is linked to the first scaffold moiety. In some aspects, an EV, e.g., exosome, further comprises a second scaffold moiety. In certain aspects, the antigen is linked to the first scaffold moiety, and the adjuvant is linked to the second scaffold moiety. In some aspects, the first scaffold moiety and the second scaffold moiety are the same. In other aspects, the first scaffold moiety and the second scaffold moiety are different.

In some aspects, a first scaffold moiety is a Scaffold X. In other aspects, a first scaffold moiety is a Scaffold Y. In some aspects, a second scaffold moiety is a Scaffold X. In certain aspects, a second scaffold moiety is a Scaffold Y.

In some aspects, Scaffold X is capable of: (i) anchoring the antigen to the luminal surface of the EV, e.g., exosome; (ii) anchoring the antigen on the exterior surface of the EV, e.g., exosome; (iii) anchoring the adjuvant to the luminal surface of the EV, e.g., exosome; (iv) anchoring the adjuvant on the exterior surface of the EV, e.g., exosome; or (v) combinations thereof. In certain aspects, Scaffold X is selected from the group consisting of prostaglandin F2 receptor negative regulator (the PTGFRN protein); basigin (the BSG protein); immunoglobulin superfamily member 2 (the IGSF2 protein); immunoglobulin superfamily member 3 (the IGSF3 protein); immunoglobulin superfamily member 8 (the IGSF8 protein); integrin beta-1 (the ITGB1 protein); integrin alpha-4 (the ITGA4 protein); 4F2 cell-surface antigen heavy chain (the SLC3A2 protein); a class of ATP transporter proteins (the ATP1A1, ATP1A2, ATP1A3, ATP1A4, ATP1B3, ATP2B1, ATP2B2, ATP2B3, ATP2B4 proteins), and any combination thereof.

In some aspects, Scaffold Y is capable of: (i) anchoring the antigen to the luminal surface of the EV, e.g., exosome; (ii) anchoring the adjuvant to the luminal surface of the EV, e.g., exosome; or (iii) both. In certain aspects, the Scaffold Y is selected from the group consisting of myristoylated alanine rich Protein Kinase C substrate (the MARCKS protein); myristoylated alanine rich Protein Kinase C substrate like 1 (the MARCKSL1 protein); brain acid soluble protein 1 (the BASP1 protein), and any combination thereof.

In some aspects, the antigen is linked to a first scaffold moiety on the luminal surface of the EV, e.g., exosome, (e.g., those described herein), and the adjuvant is linked to a second scaffold moiety on the luminal surface of the EV, e.g., exosome, (e.g., those described herein). In some of such aspects, (a) each of the first scaffold moiety and the second scaffold moiety is Scaffold Y; (b) the first scaffold moiety is Scaffold Y, and the second scaffold moiety is Scaffold X; (c) the first scaffold moiety is Scaffold X, and the second scaffold moiety is Scaffold Y; or (d) each of the first scaffold moiety and the second scaffold moiety is Scaffold X.

In some aspects, the antigen is linked to a first scaffold moiety on the luminal surface of the EV, e.g., exosome, and the adjuvant is in the lumen of the EV. In certain aspects, the antigen is in the lumen of the EV, e.g., exosome, and the adjuvant is linked to a first scaffold moiety on the luminal surface of the EV. In further aspects, the antigen is linked to a first scaffold moiety on the luminal surface of the EV, e.g., exosome, and the adjuvant is linked to a second scaffold moiety on the exterior surface of the exosome. In some of these aspects, (a) the first scaffold moiety is Scaffold Y, and the second scaffold moiety is Scaffold X; or (b) each of the first scaffold moiety and the second scaffold moiety is Scaffold X.

In some aspects, the antigen is linked to a first scaffold moiety on the exterior surface of the EV, e.g., exosome, and the adjuvant is linked to a second scaffold moiety in the luminal surface of the EV. In certain of these aspects, (a) the first scaffold moiety is Scaffold X, and the second scaffold moiety is Scaffold Y; or (b) each of the first scaffold moiety and the second scaffold moiety is Scaffold X.

In some aspects, the antigen is in the lumen or linked to the luminal surface of the EV, e.g., exosome, and the adjuvant is in the lumen or linked to the luminal surface of the EV, e.g., exosome.

In some aspects, the antigen is linked to a first scaffold moiety on the exterior surface of the EV, e.g., exosome, and the adjuvant is linked to a second scaffold moiety on the exterior surface of the EV, e.g., exosome. In some of such aspects, the first scaffold and the second scaffold moiety are Scaffold X.

In some aspects, the antigen is linked to a first scaffold moiety on the exterior surface of the EV, e.g., exosome, and the adjuvant is in the lumen of the EV, e.g., exosome. In certain of these aspects, the first scaffold is Scaffold X.

In some aspects, the antigen is in the lumen of the EV, e.g., exosome, and the adjuvant is linked to a first scaffold moiety on the exterior surface of the EV, e.g., exosome. In some of these aspects, the first scaffold is Scaffold X.

In some aspects, the antigen is linked to a first scaffold moiety on the surface of the EV, e.g., exosome, and the adjuvant is linked to the first scaffold moiety on the luminal surface of the EV, e.g., exosome. In certain aspects, the antigen is linked to a first scaffold moiety on the luminal surface of the EV, e.g., exosome and the adjuvant is linked to the first scaffold moiety on the exterior surface of the EV, e.g., exosome. In some of these aspects, the first scaffold moiety is Scaffold X.

In some aspects, (i) the antigen is linked to the first scaffold moiety by a linker, (ii) the antigen is linked to the second scaffold moiety by a linker, (iii) the adjuvant is linked to the first scaffold moiety by a linker, (iv) the adjuvant is linked to the second moiety by a linker, or (v) combinations thereof. In certain aspects, the linker is a polypeptide. In other aspects, the linker is a non-polypeptide moiety. In some aspects, the linker comprises a maleimide moiety. In some aspects, the linker comprises a cholesterol moiety.

In some aspects, the first scaffold moiety or the second scaffold moiety is PTGFRN protein. In certain aspects, the first scaffold moiety or the second scaffold moiety comprises an amino acid sequence as set forth in SEQ ID NO: 33. In further aspects, the first scaffold moiety or the second scaffold moiety comprises an amino acid sequence at least 50%, at least 60%, at least 70%, at least 80%, at least 85%, at least 90%, at least 95%, at least 96%, at least 97%, at least 98%, at least 99%, or about 100% identical to SEQ ID NO: 1.

In some aspects, the first scaffold moiety or the second scaffold moiety is BASP1 protein. In some aspects, the first scaffold moiety or the second scaffold moiety comprises a peptide of (M)(G)(π)(X)(Φ/π)(π)(+)(+) or (G)(π)(X)(Φ/π)(π)(+)(+), wherein each parenthetical position represents an amino acid, and wherein π is any amino acid selected from the group consisting of Pro, Gly, Ala, and Ser, X is any amino acid, Φ is any amino acid selected from the group consisting of Val, Ile, Leu, Phe, Trp, Tyr, and Met, and (+) is any amino acid selected from the group consisting of Lys, Arg, and His; and wherein position five is not (+) and position six is neither (+) nor (Asp or Glu). In certain aspects, the first scaffold moiety or the second scaffold moiety comprises an amino acid sequence set forth in any one of SEQ ID NO: 50-155. In further aspects, the first scaffold moiety or the second scaffold moiety comprises an amino acid sequence at least 50%, at least 60%, at least 70%, at least 80%, at least 85%, at least 90%, at least 95%, at least 96%, at least 97%, at least 98%, at least 99%, or about 100% identical to SEQ ID NO: 3.

Also provided herein is an EV, e.g., exosome, comprising (i) an antigen and (ii) an adjuvant, wherein: (a) the antigen is linked to a first Scaffold Y on the luminal surface, and the adjuvant is linked to a second Scaffold Y on the luminal surface of the EV, e.g., exosome; (b) the antigen is linked to a Scaffold Y on the luminal surface, and the adjuvant is in the lumen of the EV, e.g., exosome; (c) the antigen is in the lumen of the EV, e.g., exosome, and the adjuvant is linked to a Scaffold Y on the luminal surface of the EV, e.g., exosome; (d) the antigen is linked to a Scaffold Y on the luminal surface of the EV, e.g., exosome, and the adjuvant is linked to a Scaffold X on the exterior surface of the EV, e.g., exosome; (e) the antigen is in the lumen of the EV, e.g., exosome, and the adjuvant is linked to a Scaffold X on the exterior surface of the EV, e.g., exosome; (f) the antigen is linked to a Scaffold Y on the luminal surface of the EV, e.g., exosome, and the adjuvant is linked to a Scaffold X on the luminal surface of the EV, e.g., exosome; (g) the antigen is in the lumen of the EV, e.g., exosome, and the adjuvant is linked to a Scaffold X on the luminal surface of the EV, e.g., exosome; (h) the antigen is linked to a Scaffold X on the luminal surface of the EV, e.g., exosome, and the adjuvant is linked to the Scaffold X on the exterior surface of the EV, e.g., exosome; (i) the antigen is linked to a first Scaffold X on the exterior surface of the EV, e.g., exosome, and the adjuvant is linked to a second Scaffold X on the exterior surface of the EV, e.g., exosome; (j) the antigen is linked to a Scaffold X on the exterior surface of the EV, e.g., exosome, and the adjuvant is linked to a Scaffold Y on the luminal surface of the EV, e.g., exosome; (k) the antigen is linked to a Scaffold X on the exterior surface of the EV, e.g., exosome, and the adjuvant is in the lumen of the EV, e.g., exosome; (l) the antigen is linked to a Scaffold X on the exterior surface of the EV, e.g., exosome, and the adjuvant is linked to the Scaffold X on the luminal surface of the EV, e.g., exosome; (m) the antigen is linked to a first Scaffold X on the luminal surface of the EV, e.g., exosome, and the adjuvant is linked to a second Scaffold X in on the luminal surface of the EV, e.g., exosome; (n) the antigen is linked to a Scaffold X on the luminal surface of the EV, e.g., exosome, and the adjuvant is linked to a Scaffold Y on the luminal surface of the EV, e.g., exosome; (o) the antigen is linked to a Scaffold X on the luminal surface of the EV, e.g., exosome, and the adjuvant is in the lumen of the EV, e.g., exosome; (p) the antigen is linked to a first Scaffold X on the exterior surface of the EV, e.g., exosome, and the adjuvant is linked to a second Scaffold X on the luminal surface of the EV, e.g., exosome; (q) the antigen is linked to a first Scaffold X on the luminal surface of the EV, e.g., exosome, and the adjuvant is linked to a second Scaffold X on the exterior surface of the EV, e.g., exosome; (r) the antigen is in the lumen of the EV, e.g., exosome, and the adjuvant is on the luminal surface of the EV, e.g., exosome; (s) the antigen is linked directly to the luminal surface of the EV, and the adjuvant is linked directly to the luminal surface of the EV; (t) the antigen is linked directly to the luminal surface of the EV, and the adjuvant is in the lumen of the EV; (u) the antigen is linked directly to the luminal surface of the EV, and the adjuvant is linked to a Scaffold Y on the luminal surface of the EV; (v) the antigen is linked directly to the luminal surface of the EV, and the adjuvant is linked to a Scaffold X on the luminal surface of the EV; (w) the antigen is linked directly to the luminal surface of the EV, and the adjuvant is linked directly to the exterior surface of the EV; (x) the antigen is linked directly to the luminal surface of the EV, and the adjuvant is linked to a Scaffold X on the exterior surface of the EV; (y) the antigen is linked to a Scaffold Y on the luminal surface of the EV, and the adjuvant is linked directly to the luminal surface of the EV; (z) the antigen is linked to a Scaffold Y on the luminal surface of the EV, and the adjuvant is linked directly to the exterior surface of the EV; (aa) the antigen is linked to a Scaffold X on the luminal surface of the EV, and the adjuvant is linked directly to the luminal surface of the EV; (bb) the antigen is linked to a Scaffold X on the luminal surface of the EV, and the adjuvant is linked directly to the exterior surface of the EV; (cc) the antigen is in the lumen of the EV, and the adjuvant is linked directly to the luminal surface of the EV; or (dd) the antigen is in the lumen of the EV, and the adjuvant is linked directly to the exterior of the EV.

In some aspects, an EV, e.g., exosome disclosed herein further comprises an immune modulator. In some aspects, the immune modulator is directly linked to the luminal surface or the exterior surface of the EV. In certain aspects, the immune modulator is linked to a Scaffold X on the exterior surface of the EV, e.g., exosome or on the luminal surface of the EV, e.g., exosome. In some aspects, the immune modulator is linked to a Scaffold Y on the luminal surface of the EV, e.g., exosome. In further aspects, the immune modulator is on the luminal surface of the EV, e.g., exosome.

In some aspects, an EV comprises an antigen, adjuvant, and immune modulator, wherein: (i) the antigen is linked directly to the luminal surface by a linker, (ii) the adjuvant is linked directly to the luminal surface by a linker, (iii) the immune modulator is linked directly to the luminal surface by a linker, (iv) the antigen is linked directly to the exterior surface by a linker, (v) the adjuvant is linked directly to the exterior surface by a linker, (vi) the immune modulator is linked directly to the exterior surface by a linker, or (vii) combinations thereof. In some aspects, an EV comprises an antigen, adjuvant, and immune modulator, wherein: (i) the antigen is linked to a Scaffold X by a linker, (ii) the adjuvant is linked to a Scaffold X by a linker, (iii) the immune modulator is linked to a Scaffold X by a linker, (iv) the antigen is linked to a Scaffold Y by a linker, (v) the adjuvant is linked to a Scaffold Y by a linker, (vi) the immune modulator is linked to a Scaffold Y by a linker, or (vii) combinations thereof. In some aspects, the immune modulator is in the lumen of the EV.

In some aspects, the linker is a polypeptide. In certain aspects, the linker is a non-polypeptide moiety. In some aspects, the linker comprises a maleimide moiety. In some aspects, the linker comprises a cholesterol moiety.

In some aspects, an immune modulator comprises an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, an immune modulator comprises an activator for a positive co-stimulatory molecule or an activator for a binding partner of a positive co-stimulatory molecule. In certain aspects, the positive co-stimulatory molecule is a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2). In further aspects, the positive co-stimulatory molecule is a CD28-superfamily co-stimulatory molecule (e.g., ICOS or CD28). In some aspects, the activator for a positive co-stimulatory molecule is ICOSL, CD80, or CD86.

In some aspects, an immune modulator comprises a cytokine or a binding partner of a cytokine. In certain aspects, the cytokine comprises IL-2, IL-4, IL-7, IL-10, IL-12, IL-15, IL-21, IFN-γ, IL-1α, IL-1β, IL-1ra, IL-18, IL-33, IL-36α, IL-36β, IL-36γ, IL-36ra, IL-37, IL-38, IL-3, IL-5, IL-6, IL-11, IL-13, IL-23, granulocyte-macrophage colony stimulating factor (GM-CSF), granulocyte-colony stimulating factor (G-CSF), leukemia inhibitory factor (LIF), stem cell factor (SCF), thrombopoietin (TPO), macrophage-colony stimulating factor (M-CSF), erythropoieticn (EPO), Flt-3, IFN-α, IFN-β, IFN-γ, IL-19, IL-20, IL-22, IL-24, TNF-α, TNF-β, BAFF, APRIL, lymphotoxin beta (TNF-γ), IL-17A, IL-17B, IL-17C, IL-17D, IL-17E, IL-17F, IL-25, TSLP, IL-35, IL-27, TGF-β, or combinations thereof.

In some aspects, an immune modulator comprises a protein that supports intracellular interactions required for germinal center responses. In certain aspects, the protein that supports intracellular interactions required for germinal center responses comprises a signaling lymphocyte activation molecule (SLAM) family member, a SLAM-associated protein (SAP), ICOS-ICOSL, CD40-40L, CD28/B7, PD-1/L1, IL-4/IL4R, IL21/IL21R, TLR4, TLR7, TLR8, TLR9, CD180, CD22, or combinations thereof. In some aspects, the SLAM family member comprises SLAM family member 1, CD48, CD229 (Ly9), Ly108, 2B4, CD84, NTB-A, CRACC, BLAME, CD2F-10, or combinations thereof.

Also provided herein is an isolated EV, e.g., exosome, comprising (i) an antigen and (ii) an immune modulator, wherein: (a) the antigen is linked to a first Scaffold Y on the luminal surface of the EV, and the immune modulator is linked to a second Scaffold Y on the luminal surface of the EV; (b) the antigen is linked to a Scaffold Y on the luminal surface of the EV, and the immune modulator is in the lumen of the EV; (c) the antigen is in the lumen of the EV, and the immune modulator is linked to a Scaffold Y on the luminal surface of the EV; (d) the antigen is linked to a Scaffold Y on the luminal surface of the EV, and the immune modulator is linked to a Scaffold X on the exterior surface the EV; (e) the antigen is in the lumen of the EV, and the immune modulator is linked to a Scaffold X on the exterior surface of the EV; (f) the antigen is linked to a Scaffold Y on the luminal surface of the EV, and the immune modulator is linked to a Scaffold X on the luminal surface of the EV; (g) the antigen is in the lumen of the EV, and the immune modulator is linked to a Scaffold X on the luminal surface of the EV; (h) the antigen is linked to a Scaffold X on the luminal surface of the EV, and the immune modulator is linked to the Scaffold X on the exterior surface of the EV; (i) the antigen is linked to a first Scaffold X on the exterior surface of the EV, and the immune modulator is linked to a second Scaffold X on the exterior surface of the EV; (j) the antigen is linked to a Scaffold X on the exterior surface of the EV, and the immune modulator is linked to a Scaffold Y on the luminal surface of the EV; (k) the antigen is linked to a Scaffold X on the exterior surface of the EV, and the immune modulator is in the lumen of the EV; (l) the antigen is linked to a Scaffold X on the exterior surface of the EV, and the immune modulator is linked to the Scaffold X on the luminal surface of the EV; (m) the antigen is linked to a first Scaffold X on the luminal surface of the EV, and the immune modulator is linked to a second Scaffold X on the luminal surface of the EV; (n) the antigen is linked to a Scaffold X on the luminal surface of the EV, and the immune modulator is linked to a Scaffold Y on the luminal surface of the EV; (o) the antigen is linked to a Scaffold X on the luminal surface of the EV, and the immune modulator is in the lumen of the EV; (p) the antigen is linked to a first Scaffold X on the exterior surface of the EV, and the immune modulator is linked to a second Scaffold X on the luminal surface of the EV; (q) the antigen is linked to a first Scaffold X on the luminal surface of the EV, and the immune modulator is linked to a second Scaffold X on the exterior surface of the EV; (r) the antigen is in the lumen of the EV, and the immune modulator is in the lumen of the EV; (s) the antigen is linked directly to the luminal surface of the EV, and the immune modulator is linked directly to the luminal surface of the EV; (t) the antigen is linked directly to the luminal surface of the EV, and the immune modulator is in the lumen of the EV; (u) the antigen is linked directly to the luminal surface of the EV, and the immune modulator is linked to a Scaffold Y on the luminal surface of the EV; (v) the antigen is linked directly to the luminal surface of the EV, and the immune modulator is linked to a Scaffold X on the luminal surface of the EV; (w) the antigen is linked directly to the luminal surface of the EV, and the immune modulator is linked directly to the exterior of the EV; (x) the antigen is linked directly to the luminal surface of the EV, and the immune modulator is linked to a Scaffold X on the exterior of the EV; (y) the antigen is linked to a Scaffold Y on the luminal surface of the EV, and the immune modulator is linked directly to the luminal surface of the EV; (z) the antigen is linked to a Scaffold Y on the luminal surface of the EV, and the immune modulator is linked directly to the exterior of the EV; (aa) the antigen is linked to a Scaffold X on the luminal surface of the EV, and the immune modulator is linked directly to the luminal surface of the EV; (bb) the antigen is linked to a Scaffold X on the luminal surface of the EV, and the immune modulator is linked directly to the exterior of the EV; (cc) the antigen is in the lumen of the EV, and the immune modulator is linked directly to the luminal surface of the EV; or (dd) the antigen is in the lumen of the EV, and the immune modulator is linked directly to the exterior of the EV.

In some aspects, an EV, e.g., exosome comprising (i) an antigen and (ii) an immune modulatory further comprises an adjuvant (e.g., those described herein). In some of these aspects, the adjuvant is linked to a Scaffold X on the exterior surface of the EV, e.g., exosome or on the luminal surface of the EV, e.g., exosome. In some of these aspects, the adjuvant is linked to a Scaffold Y on the luminal surface of the EV, e.g., exosome. In further aspects, the adjuvant is in the lumen of the EV, e.g., exosome. In some aspects, the adjuvant is directly linked to the luminal surface or the exterior surface of the EV.

In some aspects, an antigen is a tumor antigen. In some aspects, the tumor antigen comprises alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, TNF-related apoptosis-inducing ligand, Brachyury, (e.g., expressed antigen in melanoma (PRAME)), Wilms tumor 1 (WT1), CD19, CD22, or any combination thereof.

In some aspects, an antigen is derived from a bacterium, a virus, fungus, protozoa, or any combination thereof. In certain aspects, the antigen is derived from an oncogenic virus. In some aspects, the antigen is derived from a Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV (e.g., HIV-1, HIV-2), corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and *Burrelia mayonii* (e.g., Lyme disease), herpes simplex virus 2 (HSV2), *Klebsiella* sp., *Pseudomonas aeruginosa, Enterococcus* sp., *Proteus* sp., *Enterobacter* sp., Actinobacter sp., coagulase-negative staphylococci (CoNS), *Mycoplasma* sp., Adenovirus, Adeno-associated virus (AAV), or combinations thereof.

In some aspects, an adjuvant is a Stimulator of Interferon Genes (STING) agonist, a toll-like receptor (TLR) agonist, an inflammatory mediator, RIG-I agonists, alpha-gal-cer (NKT agonist), heat shock proteins (e.g., HSP65 and HSP70), C-type lectin agonists (e.g., beta glucan (Dectin 1), chitin, and curdlan), or any combination thereof.

In some aspects, an adjuvant is a STING agonist. In certain aspects, the STING agonist comprises a cyclic dinucleotide STING agonist or a non-cyclic dinucleotide STING agonist.

In some aspects, an adjuvant is a TLR agonist. In certain aspects, the TLR agonist comprises a TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), or any combination thereof.

In some aspects, an EV disclosed herein is an exosome.

In some aspects, an EV (e.g., exosome) disclosed herein further comprises a targeting moiety. In certain aspects, the targeting moiety specifically binds to a marker for a dendritic cell. In certain aspects, the marker is present only on the dendritic cell. In some aspects, the dendritic cell comprises a plasmacytoid dendritic cell (pDC), a myeloid/conventional dendritic cell 1 (cDC1), a myeloid/conventional dendritic cell 2 (cDC2), inflammatory monocyte derived dendritic cells, Langerhans cells, dermal dendritic cells, lysozyme-expressing dendritic cells (LysoDCs), Kupffer cells, or any combination thereof. In certain aspects, the dendritic cell is cDC1. In further aspects, the marker comprises a C-type lectin domain family 9 member A (Clec9a) protein, a dendritic cell-specific intercellular adhesion molecule-3-grabbing non-integrin (DC-SIGN), CD207, CD40, Clec6, dendritic cell immunoreceptor (DCIR), DEC-205, lectin-like oxidized low-density lipoprotein receptor-1 (LOX-1), MARCO, Clec12a, Clec10a, DC-asialoglycoprotein receptor (DC-ASGPR), DC immunoreceptor 2 (DCIR2), Dectin-1, macrophage mannose receptor (MMR), BDCA-1 (CD303, Clec4c), Dectin-2, Bst-2 (CD317), Langerin, CD206, CD11b, CD11c, CD123, CD304, XCR1, AXL, Siglec 6, CD209, SIRPA, CX3CR1, GPR182, CD14, CD16, CD32, CD34, CD38, CD10, or any combination thereof. In certain aspects, the marker is Clec9a protein.

In some aspects, the targeting moiety specifically binds to a marker for a T cell. In certain aspects, the marker comprises a CD3 molecule.

In some aspects, the targeting moiety is linked directly to the exterior surface of the EV. In some aspects, the targeting moiety is linked to a Scaffold X on the exterior surface of the EV. In some aspects, the targeting moiety is linked directly to the exterior surface of the EV by a linker. In some aspects, the targeting moiety is linked to the Scaffold X by a linker. In certain aspects, the linker is a polypeptide. In some aspects, the linker is a non-polypeptide moiety. In some aspects, the linker comprises a maleimide moiety. In some aspects, the linker comprises a cholesterol moiety.

In some aspects, the Scaffold Y of an EV (e.g., exosome) described herein comprises an N terminus domain (ND) and an effector domain (ED), wherein the ND and/or the ED are associated with the luminal surface of the EV. In some aspects, the ND is associated with the luminal surface of the exosome via myristoylation. In some aspects, the ED is associated with the luminal surface of the exosome by an ionic interaction. In some aspects, the ED comprises (i) a basic amino acid or (ii) two or more basic amino acids in sequence, wherein the basic amino acid is selected from the group consisting of Lys, Arg, His, and any combination thereof. In some aspects, the basic amino acid is (Lys)n, wherein n is an integer between 1 and 10. In some aspects, the ED comprises Lys (K), KK, KKK, KKKK (SEQ ID NO: 205), KKKKK (SEQ ID NO: 206), Arg (R), RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof.

In some aspects, the ND comprises the amino acid sequence as set forth in G:X2:X3:X4:X5:X6, wherein G represents Gly; wherein ":" represents a peptide bond, wherein each of the X2 to the X6 is independently an amino acid, and wherein the X6 comprises a basic amino acid. In some aspects, (i) the X2 is selected from the group consisting of Pro, Gly, Ala, and Ser;
(ii) the X4 is selected from the group consisting of Pro, Gly, Ala, Ser, Val, Ile, Leu, Phe, Trp, Tyr, Gln and Met;
(iii) the X5 is selected from the group consisting of Pro, Gly, Ala, and Ser;
(iv) the X6 is selected from the group consisting of Lys, Arg, and His; or
(v) any combination of (i)-(iv).

In some aspects, the ND comprises the amino acid sequence of G:X2:X3:X4:X5:X6, wherein (i) G represents Gly;
(ii) ":" represents a peptide bond;
(iii) the X2 is an amino acid selected from the group consisting of Pro, Gly, Ala, and Ser;
(iv) the X3 is an amino acid;
(v) the X4 is an amino acid selected from the group consisting of Pro, Gly, Ala, Ser, Val, Ile, Leu, Phe, Trp, Tyr, Gln and Met;
(vi) the X5 is an amino acid selected from the group consisting of Pro, Gly, Ala, and Ser; and
(vii) the X6 is an amino acid selected from the group consisting of Lys, Arg, and His.

In some aspects, the X3 is selected from the group consisting of Asn, Gln, Ser, Thr, Asp, Glu, Lys, His, and Arg.

In some aspects, the ND and the ED are joined by a linker. In some aspects, the linker comprises one or more amino acids. In some aspects, the ND comprises an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), (v) GGKLSK (SEQ ID NO: 215), or (vi) any combination thereof. In some aspects, the ND comprises an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof. In some aspects, the ND comprises the amino acid sequence GGKLSKK (SEQ ID NO: 211).

In some aspects, the Scaffold Y is at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 120, at least about 130, at least about 140, at least about 150, at least about 160, at least about 170, at least about 180, at least about 190, or at least about 200 amino acids in length. In some aspects, the Scaffold Y comprises (i) GGKLSKKKKGYNVN (SEQ ID NO: 246), (ii) GAKLSKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKLSKKKKGYSGG (SEQ ID NO: 250), (vi) GGKLSKKKKGSGGS (SEQ ID NO: 251), (vii) GGKLSKKKKSGGSG (SEQ ID NO: 252), (viii) GGKLSKKKSGGSGG (SEQ ID NO: 253), (ix) GGKLSKKSGGSGGS (SEQ ID NO: 254), (x) GGKLSKSGGSGGSV (SEQ ID NO: 255), or (xi) GAKKSKKRFSFKKS (SEQ ID NO: 256). In certain aspects, the Scaffold Y consists of (i) GGKLSKKKKGYNVN (SEQ ID NO: 246), (ii) GAKLSKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKLSKKKKGYSGG (SEQ ID NO: 250), (vi) GGKLSKKKKGSGGS (SEQ ID NO: 251), (vii) GGKLSKKKKSGGSG (SEQ ID NO: 252), (viii) GGKLSKKKSGGSGG (SEQ ID NO: 253), (ix) GGKLSKKSGGSGGS (SEQ ID NO: 254), (x) GGKLSKSGGSGGSV (SEQ ID NO: 255), or (xi) GAKKSKKRFSFKKS (SEQ ID NO: 256).

In some aspects, the Scaffold Y does not comprise Met at the N terminus. In some aspects, the Scaffold Y comprises a myristoylated amino acid residue at the N terminus of the scaffold protein. In some aspects, the amino acid residue at the N terminus of the Scaffold Y is Gly. In some aspects, the amino acid residue at the N terminus of the Scaffold Y is synthetic. In some aspects, the amino acid residue at the N terminus of the Scaffold Y is a glycine analog.

Provided herein is a pharmaceutical composition comprising an EV, e.g., exosome, described herein and a pharmaceutically acceptable carrier.

Provided herein is a cell that produces an EV, e.g., exosome, of the present disclosure. Present disclosure further provides a cell comprising one or more vectors, wherein the vectors comprises a nucleic acid sequence encoding: (i) an antigen (e.g., those described herein), (ii) adjuvant (e.g., those described herein), (iii) immune modulator, (iv) targeting moiety (e.g., those described herein), or (v) combinations thereof.

Provided herein is a kit comprising an EV, e.g., exosome, described herein and instructions for use. Also provided herein is an EV-drug conjugate comprising any of the EVs (e.g., exosomes) described herein.

Provided herein is a method of making EVs, e.g., exosomes, comprising culturing a cell disclosed herein under a suitable condition and obtaining the EV, e.g., exosome.

Provided herein is a method of inducing an immune response in a subject in need thereof comprising administering an EV, e.g., exosome, of the present disclosure to the subject.

Provided herein is a method of preventing or treating a disease in a subject in need thereof, comprising administering an EV, e.g., exosome, described herein, wherein the disease is associated with the antigen. In certain aspects, the disease is a cancer. In some aspects, the cancer comprises bladder cancer, cervical cancer, renal cell cancer, testicular cancer, colorectal cancer, lung cancer, head and neck cancer, ovarian, lymphoma, liver cancer, glioblastoma, melanoma, myeloma, leukemia, pancreatic cancer, or combinations thereof. In further aspects, the disease is an infection.

In some aspects, an EV, e.g., exosome, is administered parenterally, orally, intravenously, intramuscularly, intratumorally, intranasally, subcutaneously, or intraperitoneally.

In some aspects, methods disclosed herein (e.g., of inducing an immune response or of preventing or treating a disease) comprises administering an additional therapeutic agent.

Provided herein is a method of inhibiting or reducing metastasis of cancer in a subject in need thereof, comprising administering to the subject an EV, e.g., exosome, of the present disclosure.

BRIEF DESCRIPTION OF FIGURES

FIG. 5A shows the CD8 T cell response. FIG. 5B shows the CD4 T cell response. The control animals received one of the following: (i) soluble OVA protein alone ("OVA"); (ii) CL656 in combination with soluble OVA protein ("OVA+CL656"); (iii) EV, e.g., exosome expressing only OVA-Scaffold Y fusion protein ("Py-OVA"); (iv) CL656 in combination with an EV, e.g., exosome, expressing only OVA-Scaffold Y fusion protein ("Py-OVA+CL656"). Data are shown both individually and as mean±S.D. "*" indicates $p<0.05$ by one way ANOVA.

FIG. 6 provides a schematic of the experimental design for assessing the efficacy of Clec9a exosomes in a vaccination model.

FIG. 7A shows superior effector memory, in particular, CD8 T-cell response following administration of a standard vaccine (AddaVax) subcutaneously (SQ), or engineered exosomes subcutaneously (SQ), intranasally (IN) or intravenously (IV). FIG. 7B shows induction of tissue resident memory, in particular, T-cell response in lung (line of defense) following intra-nasal vaccination with a standard vaccine or an engineered exosome.

FIG. 8 is a schematic representation of an engineered EV, e.g., an exosome, comprising an adjuvant (cyclic purine dinucleotides, e.g., CDN) and the EBV BZLF1 antigen attached to the luminal surface of the EV.

FIG. 11A show the uptake of anti-Clec9a expressing exosomes by different dendritic cell populations after administration into mice. The dendritic cell populations shown include the following: (i) conventional DC 1 ("cDC1"), (ii) conventional DC 2 ("cDC2"), and (iii) plasmacytoid DC ("pDC"). Control animals received either PBS alone or an exosome expressing Scaffold X protein alone ("PrX EVs"). **** $p<0.0001$. FIG. 11B provide a comparison of STING activity in mouse dendritic cells after stimulation with one of the following at three different doses (0.4 nM, 1 nM, or 4 nM): (i) soluble STING agonist ("free STING"), (ii) EVs (e.g., exosomes) expressing Scaffold X protein alone (i.e., no anti-Clec9a antibody fragment) and loaded with the STING agonist ("PrX-STING"), (iii) exosome expressing anti-Clec9a antibody fragment linked to Scaffold X protein ("aClec9a-STING"); and (iv) EVs (e.g., exosomes) expressing a non-relevant antibody and loaded with the STING agonist ("Isotype-STING"). STING activity is shown by the amount of IL-12 produced by the DCs.

FIG. 12A provides a bar graph showing the average of the results. *, $p=0.0013$; , $p=0.0074$; ns, not significant compared to OVA+ADDAVAX™ group by one-way ANOVA. FIG. 12B provides a flow cytometry plot of representative samples from the different treatment groups. The percentages provided in the upper right quadrant in each of the flow plots represents the % OVA-specific CD8$^{+}$ $T_{EM}$ cell response observed. The different treatment groups are indicated in the upper left quadrant in each of the flow plots.

FIG. 13C provides a flow cytometry plot of representative samples of the data shown in FIGS. 13A and 13B. The top row corresponds to CD8+ T cells. The bottom row corresponds to CD4+ T cells.

FIGS. 14A, 14B, 14C, 14D, 14E, 14F, 14G, 14H, 14I, 14J, 14K, 14L, 14M, and 14N show the anti-tumor immune response in mice that received one of the following: (i) exosome expressing OVA-Scaffold Y and loaded with the STING agonist CL656 via intranasal administration ("exoVACC (IN)"), (ii) exosome expressing OVA-Scaffold Y and loaded with the STING agonist CL656 via subcutaneous administration ("exoVACC (SQ)"), (iii) soluble OVA+soluble poly I:C via intranasal administration ("OVA+poly I:C (IN)"), and (iv) soluble OVA+soluble poly I:C via subcutaneous administration ("OVA+poly I:C (SC)"). Untreated animals were used as controls. FIG. 14A provides a schematic of the experimental design. FIGS. 14B and 14N provide the survival data from two independent experiments. FIGS. 14C and 14I (untreated), 14D and 14J (OVA+poly I:C (SC)), 14E and 14L (exoVACC (SQ)), 14F and 14K (OVA+poly I:C (IN)), and 14G and 14M (exoVACC (IN)) provide the tumor volume data from two independent experiments. The percentages shown in FIGS. 14E and 14G represent the number of animals (of the total group) that were completely protected. FIG. 14H shows the rate of tumor growth in each of the different treatment groups. In FIG. 14H, *, p=0.028; ns, not significant compared to untreated control by one-way ANOVA.

FIGS. 15A, 15B, 15C, 15D, 15E, and 15F show the ability of the engineered EVs (e.g., exosomes) disclosed herein to migrate to mesenteric lymph nodes after intranasal administration. FIG. 15A provides a schematic of the experimental design. FIGS. 15B, 15C, and 15D show the frequency of OVA-specific CD4+ T cells (left bar in each of the treatment groups) and OVA-specific CD8+ T cells (right bar in each of the treatment groups) in the spleen, lung, and mesenteric lymph nodes, respectively, as measured by IFN-γ ELISPOT. FIGS. 15E and 15F show the frequency of OVA-specific effector memory CD8+ T cells in the lung and spleen, respectively, as measured by flow cytometry.

FIGS. 16A, 16B, and 16C show the ability of surface-engineered EVs (e.g., exosomes) comprising a Scaffold X and loaded with STING agonist to induce an antigen-specific immune response. FIG. 16A provides a schematic of the experimental design. As shown, CD4 peptide (Itgb1) and/or CD8 peptide (Lama4) were linked to the Scaffold X of the EVs (e.g., exosomes). FIGS. 16B and 16C show the frequency of Itgb1-specific CD4+ T cells and Lama4-specific CD8+ T cells, respectively, in the spleen of animals from the different treatment groups, as measured by IFN-γ ELISPOT.

FIGS. 17A, 17B, and 17C show the ability of a surface-engineered EV (e.g., exosome) comprising a Scaffold X and loaded with CpG adjuvant to induce an antigen-specific immune response. FIG. 17A provides a schematic of the experimental design. As shown, either (i) CD8 peptide (Lama4) alone (Group 2) or (ii) both CD8 peptide and CD4 peptide (Itgb1) (Group 3) were linked to Scaffold X using maleimide chemistry. Control EVs expressed only Scaffold X (i.e., no peptide and no CpG adjuvant) (Group 1). FIGS. 17B and 17C show the frequency of Itgb1-specific CD4+ T cells and Lama4-specific CD8+ T cells, respectively, in the spleen of animals from, the different treatment groups, as measured by IFN-γ ELISPOT.

In FIGS. 18A, 18B, 18C, 18D, 18E, and 18F, 293SF cells were transfected with plasmids encoding one of the following full-length proteins: (i) HPV16 E6, (ii) HPV16 E7, (iii) HPV16 E6/E7, (iv) HPV18 E6, (v) HPV18 E7, and (vi) HPV18 E6/E7. In FIGS. 18G, 18H, 18I, 18J, 18K, and 18L, a split protein expression strategy was used. The 293SF cells were transfected with one of the following plasmids: (i) pUC57-Kan-AAVS1HR-CAGGS-PTGFRN-FLAG-coHPV16nE6 ("pCB-2014"), (ii) pUC57-Kan-AAVS1HR-CAGGS-PTGFRN-FLAG-coHPV16cE6 ("pCB-2015"), (iii) pUC57-Kan-AAVS1HR-CAGGS-coHPV16nE6-FLAG-PTGFRN ("pCB-2016"), (iv) pUC57-Kan-AAVS1HR-CAGGS-coHPV16cE6-FLAG-PTGFRN ("pCB-2017"), (v) pUC57-Kan-AAVS1HR-CAGGS-PrY-FLAG-coHPV16nE6 ("pCB-2018"), and (vi) pUC57-Kan-AAVS1HR-CAGGS-PrY-FLAG-coHPV16cE6 ("pCB-2019"). Detailed description of the plasmids can be found in Example 23 (see also Table 11).

FIGS. 19A, 19B, and 19C show the ability of a surface-engineered EV (e.g., exosome) loaded with STING agonist and expressing (i) an anti-Clec9A targeting moiety linked to Scaffold X and (ii) OVA linked to Scaffold Y. FIG. 19A provides a schematic of the experimental design. FIGS. 19B and 19C show the number of OVA-specific CD8+ effector memory T cells observed in the spleen of animals from the different treatment groups shown in FIG. 19A. FIG. 19B shows the results at one-week post a single EV administration. FIG. 19C shows the results at one-week post a second dose of EV administration.

FIGS. 20A, 20B, and 20C show the ability of an EV (e.g., exosome) engineered to express OVA-Scaffold Y and loaded with a STING agonist to induce an antigen-specific humoral immune response after in vivo administration. FIG. 20A provides a schematic of the experimental design. As shown, the animals received one of the following: (i) soluble OVA alone (Group 1), (ii) soluble OVA in combination with free STING agonist (Group 2), (iii) EV (e.g., exosome) expressing OVA-Scaffold Y alone ("PyOVA") (Group 3), (iv) PyOVA in combination with free STING agonist (Group 4), (v) engineered-exosome expressing OVA-Scaffold Y and loaded with the STING agonist CL656 ("Py-OVA exoVACC") (Group 5), and (vi) soluble OVA in combination with alum. FIG. 20B provides a comparison of the amount of OVA-specific IgG1 antibodies in the serum. FIG. 20C provides a comparison of the amount of OVA-specific IgA antibodies in the serum.

FIGS. 26 and 27 show several AM152 derivatives comprising a free maleimide group and different combinations of spacers.

DETAILED DESCRIPTION OF DISCLOSURE

Figure 1A:
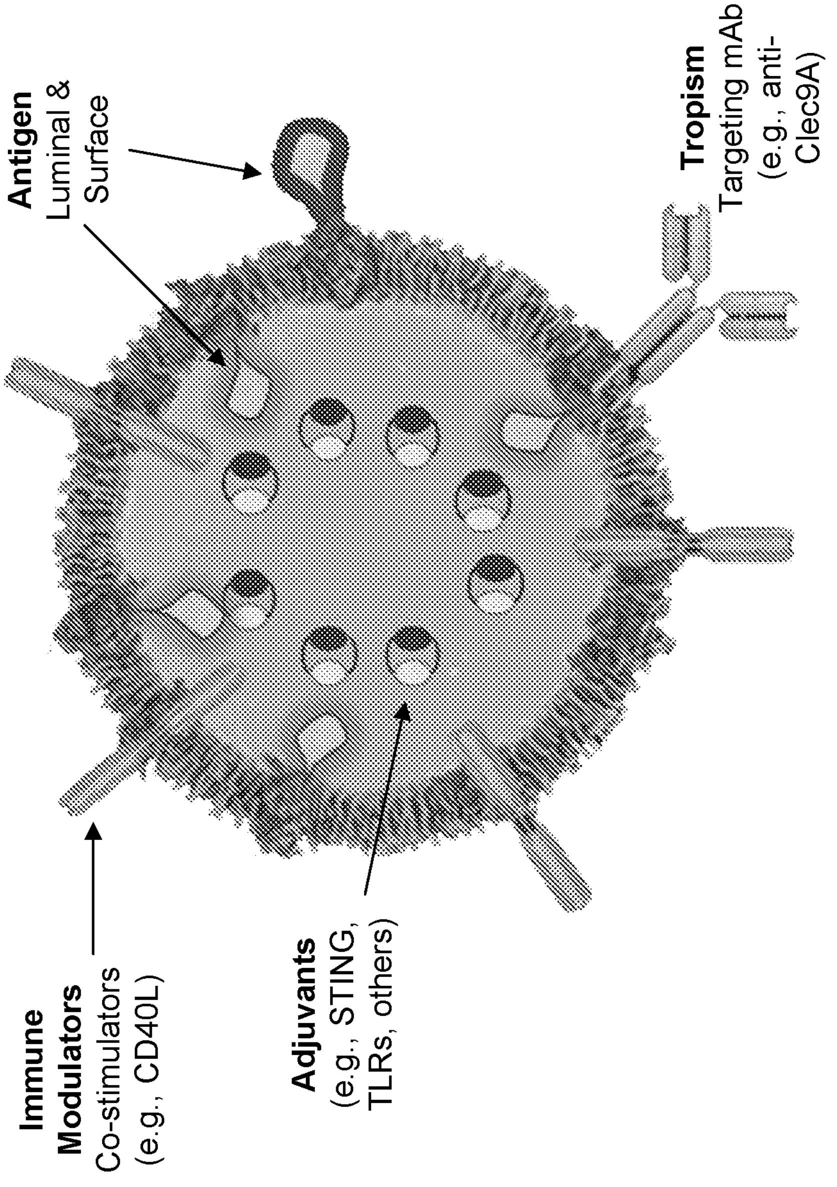
FIG. 1A shows an exemplary EV comprising one or more antigens, one or more adjuvants, one or more molecules for targeting moiety, or any combination thereof.

The present disclosure is directed to an engineered EV, e.g., exosome, that delivers antigens and adjuvants simultaneously to the same antigen presenting cells. The EV platform allows luminal expression of antigens and surface expression of immune co-stimulatory molecules designed to create a modular vaccination system. Various adjuvants can be incorporated into the EVs, e.g., exosomes, to enhance the immune response against a broad array of antigens. The engineered EVs can comprise one or more payloads and can improve at least one property (e.g., such as those disclosed herein) of the EV, and uses thereof. In some aspects, the one or more payloads comprise an antigen, an adjuvant, and/or an immune modulator. In certain aspects, the EV (e.g., exosome) comprises one or more additional moieties (e.g., targeting moiety). In some aspects, the one or more payloads (e.g., antigen, adjuvant, and/or the immune modulator) and/or the one or more additional moieties (e.g., targeting moiety) can be attached (or linked) to one or more scaffold moieties on the surface of EVs, e.g., exosomes, or on the luminal surface of EVs, e.g., exosomes. Therefore, the EVs of the present disclosure allow a platform delivery vehicle for a vaccine (i.e., exoVACC™), wherein the antigen on the EV and/or the In some aspects, the one or more payloads (e.g., antigen, adjuvant, and/or the immune modulator can be combined in a particular way) and/or replaced with a different antigen and/the one or an adjuvant or immune modulator. more additional moieties (e.g., targeting moiety) can be attached (or linked) directly to the exterior surface and/or luminal surface of EVs (e.g., exosomes). Non-limiting examples of the various aspects are shown in the present disclosure.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "extracellular vesicle" or "EV" refers to a cell-derived vesicle comprising a membrane that encloses an internal space. Extracellular vesicles comprise all membrane-bound vesicles (e.g., exosomes, nanovesicles) that have a smaller diameter than the cell from which they are derived. In some aspects, extracellular vesicles range in diameter from 20 nm to 1000 nm, and can comprise various macromolecular payload either within the internal space (i.e., lumen), displayed on the external surface of the extracellular vesicle, and/or spanning the membrane. In some aspects, the payload can comprise nucleic acids, proteins, carbohydrates, lipids, small molecules, and/or combinations thereof. In certain aspects, an extracellular vehicle comprises a scaffold moiety. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, the extracellular vesicles are produced by cells that express one or more transgene products.

As used herein, the term "exosome" refers to an extracellular vesicle with a diameter between 20-300 nm (e.g., between 40-200 nm). Exosomes comprise a membrane that encloses an internal space (i.e., lumen), and, in some aspects, can be generated from a cell (e.g., producer cell) by direct plasma membrane budding or by fusion of the late endosome or multi-vesicular body with the plasma membrane. In certain aspects, an exosome comprises a scaffold moiety. As described infra, exosome can be derived from a producer cell, and isolated from the producer cell based on its size, density, biochemical parameters, or a combination thereof. In some aspects, the EVs, e.g., exosomes, of the present disclosure are produced by cells that express one or more transgene products.

As used herein, the term "nanovesicle" refers to an extracellular vesicle with a diameter between 20-250 mu (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some aspects, production of nanovesicles can result in the destruction of the producer cell. In some aspects, population of nanovesicles described herein are substantially free of vesicles that are derived from cells by way of direct budding from the plasma membrane or fusion of the late endosome with the plasma membrane. In certain aspects, a nanovesicle comprises a scaffold moiety. Nanovesicles, once derived from a producer cell, can be isolated from the producer cell based on its size, density, biochemical parameters, or a combination thereof.

As used herein the term "surface-engineered EVs, e.g., exosomes" (e.g., Scaffold X-engineered EVs, e.g., exosomes) refers to an EV, e.g., exosome, with the membrane or the surface of the EV, e.g., exosome, modified in its composition so that the surface of the engineered EV, e.g., exosome, is different from that of the EV, e.g., exosome, prior to the modification or of the naturally occurring EV, e.g., exosome. The engineering can be on the surface of the EV, e.g., exosome, or in the membrane of the EV, e.g., exosome, so that the surface of the EV, e.g., exosome, is changed. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV, e.g., exosome, comprises an exogenous protein (i.e., a protein that the EV, e.g., exosome, does not naturally express) or a fragment or variant thereof that can be exposed to the surface of the EV, e.g., exosome, or can be an anchoring point (attachment) for a moiety exposed on the surface of the EV, e.g., exosome. In other aspects, a surface-engineered EV, e.g., exosome, comprises a higher expression (e.g., higher number) of a natural exosome protein (e.g., Scaffold X) or a fragment or variant thereof that can be exposed to the surface of the EV, e.g., exosome, or can be an anchoring point (attachment) for a moiety exposed on the surface of the EV, e.g., exosome.

As used herein the term "lumen-engineered exosome" (e.g., Scaffold Y-engineered exosome) refers to an EV, e.g., exosome, with the membrane or the lumen of the EV, e.g., exosome, modified in its composition so that the lumen of the engineered EV, e.g., exosome, is different from that of the EV, e.g., exosome, prior to the modification or of the naturally occurring EV, e.g., exosome. The engineering can be directly in the lumen or in the membrane of the EV, e.g., exosome so that the lumen of the EV, e.g., exosome is changed. For example, the membrane is modified in its composition of a protein, a lipid, a small molecule, a carbohydrate, etc. so that the lumen of the EV, e.g., exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises an exogenous protein (i.e., a protein that the EV, e.g., exosome does not naturally express) or a fragment or variant thereof that can be exposed in the lumen of the EV, e.g., exosome or can be an anchoring point (attachment) for a moiety exposed on the inner layer of the EV, e.g., exosome. In other aspects, a lumen-engineered EV, e.g., exosome, comprises a higher expression of a natural exosome protein (e.g., Scaffold X or Scaffold Y) or a fragment or variant thereof that can be exposed to the lumen of the exosome or can be an anchoring point (attachment) for a moiety exposed in the lumen of the exosome.

The term "modified," when used in the context of EVs, e.g., exosomes described herein, refers to an alteration or engineering of an EV, e.g., exosome and/or its producer cell, such that the modified EV, e.g., exosome is different from a naturally-occurring EV, e.g., exosome. In some aspects, a modified EV, e.g., exosome described herein comprises a membrane that differs in composition of a protein, a lipid, a small molecular, a carbohydrate, etc. compared to the membrane of a naturally-occurring EV, e.g., exosome (e.g., membrane comprises higher density or number of natural exosome proteins and/or membrane comprises proteins that are not naturally found in exosomes (e.g., antigen, adjuvant, and/or immune modulator). In certain aspects, such modifications to the membrane changes the exterior surface of the EV, e.g., exosome (e.g., surface-engineered EVs, e.g., exosomes described herein). In certain aspects, such modifications to the membrane changes the lumen of the EV, e.g., exosome (e.g., lumen-engineered EVs, e.g., exosomes described herein).

As used herein, the term "scaffold moiety" refers to a molecule that can be used to anchor a payload or any other compound of interest (e.g., antigen, adjuvant, and/or immune modulator) to the EV, e.g., exosome either on the luminal surface or on the exterior surface of the EV, e.g., exosome. In certain aspects, a scaffold moiety comprises a synthetic molecule. In some aspects, a scaffold moiety comprises a non-polypeptide moiety. In other aspects, a scaffold moiety comprises a lipid, carbohydrate, or protein that naturally exists in the EV, e.g., exosome. In some aspects, a scaffold moiety comprises a lipid, carbohydrate, or protein that does not naturally exist in the EV, e.g., exosome. In certain aspects, a scaffold moiety is Scaffold X. In some aspects, a scaffold moiety is Scaffold Y. In further aspects, a scaffold moiety comprises both Scaffold X and Scaffold Y. Non-limiting examples of other scaffold moieties that can be used with the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); CD9, CD63, CD81, PDGFR, GPI anchor proteins, lactadherin, LAMP2, and LAMP2B.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome). In some aspects, a Scaffold X can anchor a moiety (e.g., antigen, adjuvant, and/or immune modulator) to the external surface or the luminal surface of the exosome.

As used herein, the term "Scaffold Y" refers to exosome proteins that were newly identified within the lumen of exosomes. See, e.g., International Appl. No. PCT/US2018/061679, which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some aspects, a Scaffold Y protein can be a whole protein or a fragment thereof (e.g., functional fragment, e.g., the smallest fragment that is capable of anchoring a moiety to the luminal surface of the exosome). In some aspects, a Scaffold Y can anchor a moiety (e.g., antigen, adjuvant, and/or immune modulator) to the luminal surface of the EV, e.g., exosome.

As used herein, the term "fragment" of a protein (e.g., therapeutic protein, Scaffold X, or Scaffold Y) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface or on the exterior surface of the EV, e.g., exosome. Similarly, in certain aspects, a functional fragment of a Scaffold Y protein retains the ability to anchor a moiety on the luminal surface of the EV, e.g., exosome. Whether a fragment is a functional fragment can be assessed by any art known methods to determine the protein content of EVs, e.g., exosomes including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein. In some aspects, a functional fragment of a Scaffold Y protein retains at least about 50%, at least about 60%, at least about 70%, at least about 80%, at least about 90% or at least about 100% of the ability, e.g., an ability to anchor another molecule, of the naturally occurring Scaffold Y protein.

As used herein, the term "variant" of a molecule (e.g., functional molecule, antigen, Scaffold X and/or Scaffold Y) refers to a molecule that shares certain structural and functional identities with another molecule upon comparison by a method known in the art. For example, a variant of a protein can include a substitution, insertion, deletion, frameshift or rearrangement in another protein.

In some aspects, a variant of a Scaffold X comprises a variant having at least about 70% identity to the full-length, mature PTGFRN, BSG, IGSF2, IGSF3, IGSF8, ITGB1, ITGA4, SLC3A2, or ATP transporter proteins or a fragment (e.g., functional fragment) of the PTGFRN, BSG, IGSF2, IGSF3, IGSF8, ITGB1, ITGA4, SLC3A2, or ATP transporter proteins. In some aspects, variants or variants of fragments of PTGFRN share at least about 70%, at least about 80%, at least about 85%, at least about 90%, at least about 95%, at least about 96%, at least about 97%, at least about 98%, or at least about 99% sequence identity with PTGFRN according to SEQ ID NO: 1 or with a functional fragment thereof. In some aspects, variants or variants of fragments of BSG share at least about 70%, at least about 80%, at least about 85%, at least about 90%, at least about 95%, at least about 96%, at least about 97%, at least about 98%, or at least about 99% sequence identity with BSG according to SEQ ID NO: 9 or with a functional fragment thereof. In some aspects, variants or variants of fragments of IGSF2 share at least about 70%, at least about 80%, at least about 85%, at least about 90%, at least about 95%, at least about 96%, at least about 97%, at least about 98%, or at least about 99% sequence identity with IGSF2 according to SEQ ID NO: 34 or with a functional fragment thereof. In some aspects, variants or variants of fragments of IGSF3 share at least about 70%, at least about 80%, at least about 85%, at least about 90%, at least about 95%, at least about 96%, at least about 97%, at least about 98%, or at least about 99% sequence identity with IGSF3 according to SEQ ID NO: 20 or with a functional fragment thereof. In some aspects, variants or variants of fragments of IGSF8 share at least about 70%, at least about 80%, at least about 85%, at least about 90%, at least about 95%, at least about 96%, at least about 97%, at least about 98%, or at least about 99% sequence identity with IGSF8 according to SEQ ID NO: 14 or with a functional fragment thereof. In some aspects, variants or variants of fragments of ITGB1 share at least about 70%, at least about 80%, at least about 85%, at least about 90%, at least about 95%, at least about 96%, at least about 97%, at least about 98%, or at least about 99% sequence identity with ITGB1 according to SEQ ID NO: 21 or with a functional fragment thereof. In some aspects, variants or variants of fragments of ITGA4 share at least about 70%, at least about 80%, at least about 85%, at least about 90%, at least about 95%, at least about 96%, at least about 97%, at least about 98%, or at least about 99% sequence identity with ITGA4 according to SEQ ID NO: 22 or with a functional fragment thereof. In some aspects, variants or variants of fragments of SLC3A2 share at least about 70%, at least about 80%, at least about 85%, at least about 90%, at least about 95%, at least about 96%, at least about 97%, at least about 98%, or at least about 99% sequence identity with SLC3A2 according to SEQ ID NO: 23 or with a functional fragment thereof. In some aspects, variants or variants of fragments of ATP1A1 share at least about 70%, at least about 80%, at least about 85%, at least about 90%, at least about 95%, at least about 96%, at least about 97%, at least about 98%, or at least about 99% sequence identity with ATP1A1 according to SEQ ID NO: 24 or with a functional fragment thereof. In some aspects, variants or variants of fragments of ATP1A2 share at least about 70%, at least about 80%, at least about 85%, at least about 90%, at least about 95%, at least about 96%, at least about 97%, at least about 98%, or at least about 99% sequence identity with ATP1A2 according to SEQ ID NO: 25 or with a functional fragment thereof. In some aspects, variants or variants of fragments of ATP1A3 share at least about 70%, at least about 80%, at least about 85%, at least about 90%, at least about 95%, at least about 96%, at least about 97%, at least about 98%, or at least about 99% sequence identity with ATP1A3 according to SEQ ID NO: 26 or with a functional fragment thereof. In some aspects, variants or variants of fragments of ATP1A4 share at least about 70%, at least about 80%, at least about 85%, at least about 90%, at least about 95%, at least about 96%, at least about 97%, at least about 98%, or at least about 99% sequence identity with ATP1A4 according to SEQ ID NO: 27 or with a functional fragment thereof. In some aspects, variants or variants of fragments of ATP1B3 share at least about 70%, at least about 80%, at least about 85%, at least about 90%, at least about 95%, at least about 96%, at least about 97%, at least about 98%, or at least about 99% sequence identity with ATP1B3 according to SEQ ID NO: 28 or with a functional fragment thereof. In some aspects, variants or variants of fragments of ATP2B1 share at least about 70%, at least about 80%, at least about 85%, at least about 90%, at least about 95%, at least about 96%, at least about 97%, at least about 98%, or at least about 99% sequence identity with ATP2B1 according to SEQ ID NO: 29 or with a functional fragment thereof. In some aspects, variants or variants of fragments of ATP2B2 share at least about 70%, at least about 80%, at least about 85%, at least about 90%, at least about 95%, at least about 96%, at least about 97%, at least about 98%, or at least about 99% sequence identity with ATP2B2 according to SEQ ID NO: 30 or with a functional fragment thereof. In some aspects, variants or variants of fragments of ATP2B3 share at least about 70%, at least about 80%, at least about 85%, at least about 90%, at least about 95%, at least about 96%, at least about 97%, at least about 98%, or at least about 99% sequence identity with ATP2B3 according to SEQ ID NO: 31 or with a functional fragment thereof. In some aspects, variants or variants of fragments of ATP2B4 share at least about 70%, at least about 80%, at least about 85%, at least about 90%, at least about 95%, at least about 96%, at least about 97%, at least about 98%, or at least about 99% sequence identity with ATP2B4 according to SEQ ID NO: 32 or with a functional fragment thereof. In some aspects, the variant or variant of a fragment of Scaffold X protein disclosed herein retains the ability to be specifically targeted to EVs, e.g., exosomes. In some aspects, the Scaffold X includes one or more mutations, for example, conservative amino acid substitutions.

In some aspects, a variant of a Scaffold Y comprises a variant having at least about 70% identity to MARCKS, MARCKSL1, BASP1 or a fragment of MARCKS, MARCKSL1, or BASP1. In some aspects, variants or variants of fragments of MARCKS share at least about 70%, at least about 80%, at least about 85%, at least about 90%, at least about 95%, at least about 96%, at least about 97%, at least about 98%, or at least about 99% sequence identity with MARCKS according to SEQ ID NO: 47 or with a functional fragment thereof. In some aspects, variants or variants of fragments of MARCKSL1 share at least about 70%, at least about 80%, at least about 85%, at least about 90%, at least about 95%, at least about 96%, at least about 97%, at least about 98%, or at least about 99% sequence identity with MARCKSL1 according to SEQ ID NO: 48 or with a functional fragment thereof. In some aspects, variants or variants of fragments of BASP1 share at least about 70%, at least about 80%, at least about 85%, at least about 90%, at least about 95%, at least about 96%, at least about 97%, at least about 98%, or at least about 99% sequence identity with BASP1 according to SEQ ID NO: 49 or with a functional fragment thereof. In some aspects, the variant or variant of a fragment of Scaffold Y protein retains the ability to be specifically targeted to the luminal surface of EVs, e.g., exosomes. In some aspects, the Scaffold Y includes one or more mutations, e.g., conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at worldwideweb.tcoffee.org, and alternatively available, e.g., from the EBI. It will also be appreciated that the final alignment used to calculate percent sequence identity can be curated either automatically or manually.

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X and/or Scaffold Y is modified at any convenient location.

As used herein the term "linked to," "fused," or "conjugated to" are used interchangeably and refer to a covalent or non-covalent bond formed between a first moiety and a second moiety, e.g., Scaffold X and an antigen (or adjuvant or immune modulator), respectively, e.g., a scaffold moiety expressed in or on the extracellular vesicle and an antigen, e.g., Scaffold X (e.g., a PTGFRN protein), respectively, in the luminal surface of or on the external surface of the extracellular vesicle. In some aspects, a payload disclosed herein (e.g., antigen, adjuvant, and/or immune modulator) and/or a targeting moiety can be directly linked to the exterior surface and/or the luminal surface of an EV (e.g., exosome). As used herein, the term "directly linked,"

"directly fused," or "directly conjugated to" refer to the process of linking (fusing or conjugating) a moiety (e.g., a payload and/or targeting moiety) to the surface of an EV (e.g., exosome) without the use of a scaffold moiety disclosed herein.

As used herein, the term "fusion protein" refers to two or more proteins that are linked or conjugated to each other. For instance, in some aspects, a fusion protein that can be expressed in an EV (e.g., exosome) disclosed herein comprises (i) a payload (e.g., antigen, adjuvant, and/or immune modulator) and (ii) a scaffold moiety (e.g., Scaffold X and/or Scaffold Y). In some aspects, a fusion protein that can be expressed in an EV (e.g., exosome) useful for the present disclosure comprises (i) a targeting moiety and (ii) a scaffold moiety (e.g., Scaffold X and/or Scaffold Y). As described herein, in some aspects, EVs (e.g., exosomes) of the present disclosure can express multiple fusion proteins, wherein a first fusion protein comprises (i) a payload (e.g., antigen, adjuvant, and/or immune modulator) and (ii) a scaffold moiety (e.g., Scaffold X and/or Scaffold Y), and wherein a second fusion protein comprises (i) a targeting moiety and (ii) a scaffold moiety (e.g., Scaffold X and/or Scaffold Y).

The term "encapsulated", or grammatically different forms of the term (e.g., encapsulation, or encapsulating) refers to a status or process of having a first moiety (e.g., antigen, adjuvant, or immune modulator) inside a second moiety (e.g., an EV, e.g., exosome) without chemically or physically linking the two moieties. In some aspects, the term "encapsulated" can be used interchangeably with the terms "in the lumen of" and "loaded". Non-limiting examples of encapsulating (or loading) a first moiety (e.g., payload, e.g., antigen, adjuvant, or immune modulator) into a second moiety (e.g., EVs, e.g., exosomes) are disclosed elsewhere herein.

As used herein, the term "producer cell" refers to a cell used for generating an EV, e.g., exosome. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In certain aspects, a producer cell is not an antigen-presenting cell. In some aspects, a producer cell is not a dendritic cell, a B cell, a mast cell, a macrophage, a neutrophil, Kupffer-Browicz cell, cell derived from any of these cells, or any combination thereof. In some aspects, a producer cell is not a naturally-existing antigen-presenting cell (i.e., has been modified). In some aspects, a producer cell is not a naturally-existing dendritic cell, a B cell, a mast cell, a macrophage, a neutrophil, Kupffer-Browicz cell, cell derived from any of these cells, or any combination thereof. Additional disclosures relating to such producer cells are provided elsewhere in the present disclosure. In some aspects, the EVs, e.g., exosomes useful in the present disclosure do not carry an antigen on MHC class I or class II molecule (i.e., antigen is not presented on MHC class I or class II molecule) exposed on the surface of the EV, e.g., exosome, but instead can carry an antigen in the lumen of the EV, e.g., exosome, or on the surface of the EV, e.g., exosome, by attachment to Scaffold X and/or Scaffold Y.

As used herein, an "MHC class I molecule" refers to a protein product of a wild-type or variant HLA class I gene encoding an MHC class I molecule. Accordingly, "HLA class I molecule" and "MHC class I molecule" are used interchangeably herein.

MHC class I molecules are one of two primary classes of major histocompatibility complex (MHC) molecules (the other being MHC class II) and are found on the cell surface of all nucleated cells in the bodies of jawed vertebrates. They also occur on platelets, but not on red blood cells. Their function is to display peptide fragments of proteins from within the cell to cytotoxic T cells; this will trigger an immediate response from the immune system against a particular non-self antigen displayed with the help of an MHC class I protein. Because MHC class I molecules present peptides derived from cytosolic proteins, the pathway of MHC class I presentation is often called cytosolic or endogenous pathway.

In humans, the HLAs corresponding to MHC class I are HLA-A, HLA-B, and HLA-C. The MHC Class I molecule comprises two protein chains: the alpha chain and the β2-microglobulin (β2m) chain. Human β2m is encoded by the B2M gene. Class I MHC molecules bind peptides generated mainly from degradation of cytosolic proteins by the proteasome. The MHC I:peptide complex is then inserted via endoplasmic reticulum into the external plasma membrane of the cell. The epitope peptide is bound on extracellular parts of the class I MHC molecule. Thus, the function of the class I MHC is to display intracellular proteins to cytotoxic T cells (CTLs). However, class I MHC can also present peptides generated from exogenous proteins, in a process known as cross-presentation.

A normal cell will display peptides from normal cellular protein turnover on its class I MHC, and CTLs will not be activated in response to them due to central and peripheral tolerance mechanisms. When a cell expresses foreign proteins, such as after viral infection, a fraction of the class I MHC will display these peptides on the cell surface. Consequently, CTLs specific for the MHC:peptide complex will recognize and kill presenting cells. Alternatively, class I MHC itself can serve as an inhibitory ligand for natural killer cells (NKs). Reduction in the normal levels of surface class I MHC, a mechanism employed by some viruses and certain tumors to evade CTL responses, activates NK cell killing.

As used herein, an "MHC class II molecule" refers to a protein product of a wild-type or variant HLA class II gene encoding an MHC class II molecule. Accordingly, "HLA class II molecule" and "MHC class II molecule" are used interchangeably herein.

MHC class II molecules are a class of major histocompatibility complex (MHC) molecules normally found only on professional antigen-presenting cells such as dendritic cells, mononuclear phagocytes, some endothelial cells, thymic epithelial cells, and B cells. These cells are important in initiating immune responses. The antigens presented by class II peptides are derived from extracellular proteins (not cytosolic as in MHC class I).

Like MHC class I molecules, class II molecules are also heterodimers, but in this case consist of two homogenous peptides, an α and β chain, both of which are encoded in the MHC. The subdesignation α1, α2, etc. refers to separate domains within the HLA gene; each domain is usually encoded by a different exon within the gene, and some genes have further domains that encode leader sequences, transmembrane sequences, etc. These molecules have both extracellular regions as well as a transmembrane sequence and a cytoplasmic tail. The α1 and β1 regions of the chains come together to make a membrane-distal peptide-binding domain, while the α2 and β2 regions, the remaining extracellular parts of the chains, form a membrane-proximal immunoglobulin-like domain. The antigen binding groove, where the antigen or peptide binds, is made up of two α-helixes walls and β-sheet. Because the antigen-binding groove of MHC class II molecules is open at both ends while the corresponding groove on class I molecules is closed at each end, the antigens presented by MHC class II molecules are longer, generally between 15 and 24 amino acid residues long. Loading of a MHC class II molecule occurs by phagocytosis; extracellular proteins are endocytosed, digested in lysosomes, and the resulting epitopic peptide fragments are loaded onto MHC class II molecules prior to their migration to the cell surface. In humans, the MHC class II protein complex is encoded by the human leukocyte antigen gene complex (HLA). HLAs corresponding to MHC class II are HLA-DP, HLA-DM, HLA-DOA, HLA-DOB, HLA-DQ, and HLA-DR. Mutations in the HLA gene complex can lead to bare lymphocyte syndrome (BLS), which is a type of MHC class II deficiency.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In other aspects, an isolated EV composition has an amount and/or concentration of desired EVs at or above an acceptable amount and/or concentration. In other aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "immune modulator" refers to an agent (i.e., payload) that acts on a target (e.g., a target cell) that is contacted with the extracellular vesicle, and regulates the immune system. Non-limiting examples of immune modulator that can be introduced into an EV (e.g., exosome) and/or a producer cell include agents such as, modulators of checkpoint inhibitors, ligands of checkpoint inhibitors, cytokines, derivatives thereof, or any combination thereof. The immune modulator can also include an agonist, an antagonist, an antibody, an antigen-binding fragment, a polynucleotide, such as siRNA, antisense oligonucleotide, a phosphorodiamidate morpholino oligomer (PMO), a peptide-conjugated phosphorodiamidate morpholino oligomer (PPMO), miRNA, lncRNA, mRNA DNA, or a small molecule.

As used herein, the term a "bio-distribution modifying agent," which refers to an agent (i.e., payload) that can modify the distribution of extracellular vesicles (e.g., exosomes, nanovesicles) in vivo or in vitro (e.g., in a mixed culture of cells of different varieties). In some aspects, the term "targeting moiety" can be used interchangeably with the term bio-distribution modifying agent. In some aspects, the targeting moiety alters the tropism of the EV (e.g., exosome) ("tropism moiety"). As used herein, the term "tropism moiety" refers to a targeting moiety that when expressed on an EV (e.g., exosome) alters and/or enhances the natural movement of the EV. For example, in some aspects, a tropism moiety can promote the EV to be taken up by a particular cell, tissue, or organ. Non-limiting examples of tropism moieties that can be used with the present disclosure include those that can bind to a marker expressed specifically on a dendritic cell (e.g., Clec9A or DEC205) or T cells (e.g., CD3). Unless indicated otherwise, the term "targeting moiety," as used herein, encompasses tropism moieties. The bio-distribution agent can be a biological molecule, such as a protein, a peptide, a lipid, or a carbohydrate, or a synthetic molecule. For example, the bio-distribution modifying agent can be an affinity ligand (e.g., antibody, VHH domain, phage display peptide, fibronectin domain, camelid, VNAR), a synthetic polymer (e.g., PEG), a natural ligand/molecule (e.g., CD40L, albumin, CD47, CD24, CD55, CD59), a recombinant protein (e.g., XTEN), but not limited thereto.

In certain aspects, the bio-distribution modifying agent, and/or targeting moiety, is displayed on the surface of EVs (e.g., exosomes). The bio-distribution modifying agent can be displayed on the EV surface by being fused to a scaffold protein (e.g., Scaffold X) (e.g., as a genetically encoded fusion molecule). In some aspects, the bio-distribution modifying agent can be displayed on the EV surface by chemical reaction attaching the bio-distribution modifying agent to an EV surface molecule. A non-limiting example is PEGylation. In some aspects, EVs disclosed herein (e.g., exosomes) can further comprise a bio-distribution modifying agent, in addition to an antigen, adjuvant, or immune modulator. Non-limiting examples of bio-distribution modifying agent or targeting moiety that can be used with the present disclosure include a C-type lectin domain family 9 member A (Clec9a) protein, a dendritic cell-specific intercellular adhesion molecule-3-grabbing non-integrin (DC-SIGN), CD207, CD40, Clec6, dendritic cell immunoreceptor (DCIR), DEC-205, lectin-like oxidized low-density lipoprotein receptor-1 (LOX-1), MARCO, Clec12a, DC-asialoglycoprotein receptor (DC-ASGPR), DC immunoreceptor 2 (DCIR2), Dectin-1, macrophage mannose receptor (MMR), BDCA-1 (CD303, Clec4c), Dectin-2, Bst-2 (CD317), CD3, or any combination thereof. In certain aspects, the targeting moiety is Clec9a protein. In some aspects, the targeting moiety is a CD3 molecule.

As used herein, the term "C-type lectin domain family 9 member A" (Clec9a) protein refers to a group V C-type lectin-like receptor (CTLR) that functions as an activation receptor and is expressed on myeloid lineage cells (e.g., DCs). Huysamen et al., *J Biol Chem* 283(24):16693-701 (2008); U.S. Pat. No. 9,988,431 B2, each of which is herein incorporated by reference in its entirety. Synonyms of Clec9a are known and include CD370, DNGR-1, 5B5, HEEE9341, and C-type lectin domain containing 9A. In some aspects, Clec9a protein is expressed on human cDC1 cells. In some aspects, Clec9a protein is expressed on mouse cDC1 and pDC cells. Unless indicated otherwise, Clec9a, as used herein, can refer to Clec9a from one or more species (e.g., humans, non-human primates, dogs, cats, guinea pigs, rabbits, rats, mice, horses, cattle, and bears).

As used herein, the term "CD3" or "cluster of differentiation 3" refers to the protein complex associated with the T cell receptor (TCR). The CD3 molecule is made up of four distinct chains (CD3γ, CD3δ, and two CD3ε chains). These chains associate with the T-cell receptor (TCR) and the ζ-chain to generate an activation signal in T lymphocytes. The TCR, ζ-chain, and CD3 molecules together constitute the TCR complex. CD3 molecules are expressed on all T cells, including both CD4+ T cells and CD8+ T cells. Unless indicated otherwise, CD3, as used herein, can refer to CD3 from one or more species (e.g., humans, non-human primates, dogs, cats, guinea pigs, rabbits, rats, mice, horses, cattle, and bears).

As used herein, the term "payload" refers to an agent that acts on a target (e.g., a target cell) that is contacted with the EV (e.g., exosome). In some aspects, unless indicated otherwise, the term payload can be used interchangeably with the term "biologically active molecules." Non-limiting examples of payload that can be included on the EV, e.g., exosome, are an antigen, an adjuvant, and/or an immune modulator. Payloads that can be introduced into an EV, e.g., exosome, and/or a producer cell include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), a peptide-conjugated phosphorodiamidate morpholino oligomer (PPMO), or combinations thereof), amino acids (e.g., amino acids comprising a detectable moiety or a toxin or that disrupt translation), polypeptides (e.g., enzymes), lipids, carbohydrates, and small molecules (e.g., small molecule drugs and toxins). In certain aspects, a payload comprises an antigen. As used herein, the term "antigen" refers to any agent that when introduced into a subject elicits an immune response (cellular or humoral) to itself.

As used herein, the term "affinity ligand" refers to a molecule that can selectively and preferentially bind to a specific marker, e.g., expressed on a target cell. Non-limiting examples of affinity ligands that can be used with the present disclosure include an antibody, phage display peptide, fibronectin domain, camelid, VNAR, VHH domain, and combinations thereof. As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab1)_2$, Fv, dAb, and Fd fragments, diabodies, and antibody-related polypeptides. Antibody includes bispecific antibodies and multispecific antibodies so long as they exhibit the desired biological activity or function.

The terms "individual," "subject," "host," and "patient," are used interchangeably herein and refer to any mammalian subject for whom diagnosis, treatment, or therapy is desired, particularly humans. The compositions and methods described herein are applicable to both human therapy and veterinary applications. In some aspects, the subject is a mammal, and in other aspects, the subject is a human. As used herein, a "mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substantially free" means that the sample comprising EVs, e.g., exosomes, comprise less than about 10% of macromolecules by mass/volume (m/v) percentage concentration. Some fractions can contain less than about 0.001%, less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in exosomes, including but is not limited to CD9, CD63, CD81, PDGFR, GPI anchor proteins, lactadherin LAMP2, and LAMP2B, a fragment thereof, or a peptide that binds thereto.

"Administering," as used herein, means to give a composition comprising an EV, e.g., exosome, disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. EVs, e.g., exosomes can be administered as part of a pharmaceutical composition comprising at least one excipient.

An "immune response," as used herein, refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4+ cell, a CD8+ T cell, or a Treg cell, or activation or inhibition of any other cell of the immune system, e.g., NK cell. Accordingly an immune response can comprise a humoral immune response (e.g., mediated by B-cells), cellular immune response (e.g., mediated by T cells), or both humoral and cellular immune responses. In some aspects, an immune response is an "inhibitory" immune response. An "inhibitory" immune response is an immune response that blocks or diminishes the effects of a stimulus (e.g., antigen). In certain aspects, the inhibitory immune response comprises the production of inhibitory antibodies against the stimulus. In some aspects, an immune response is a "stimulatory" immune response. A "stimulatory" immune response is an immune response that results in the generation of effectors cells (e.g., cytotoxic T lymphocytes) that can destroy and clear a target antigen (e.g., tumor antigen or viruses).

As used herein, the term "cellular immune response" can be used interchangeably with the term "cell-mediated immune response" and refers to an immune response that does not predominantly involve antibodies. Instead, a cellular immune response involves the activation of different immune cells (e.g., phagocytes and antigen-specific cytotoxic T-lymphocytes) that produce various effector molecules (e.g., cytokines, perforin, granzymes) upon activation (e.g., via antigen stimulation). As used herein, the term "humoral immune response" refers to an immune response predominantly mediated by macromolecules found in extracellular fluids, such as secreted antibodies, complement proteins, and certain antimicrobial peptides. The term "antibody-mediated immune response" refers to an aspect of a humoral immune response that is mediated by antibodies.

As used herein, the term "immune cells" refers to any cells of the immune system that are involved in mediating an immune response. Non-limiting examples of immune cells include a T lymphocyte, B lymphocyte, natural killer (NK) cell, macrophage, eosinophil, mast cell, dendritic cell, neutrophil, or combination thereof. In some aspects, an immune cell expresses CD3. In certain aspects, the CD3-expressing immune cells are T cells (e.g., CD4+ T cells or CD8+ T cells). In some aspects, an immune cell that can be targeted with a targeting moiety disclosed herein (e.g., anti-CD3) comprises a naïve CD4+ T cell. In some aspects, an immune cell comprises a memory CD4+ T cell. In some aspects, an immune cell comprises an effector CD4+ T cell. In some aspects, an immune cell comprises a naïve CD8+ T cell. In some aspects, an immune cell comprises a memory CD8+ T cell. In some aspects, an immune cell comprises an effector CD8+ T cell. In some aspects, an immune cell is a dendritic cell. In certain aspects, a dendritic cell comprises a plasmacytoid dendritic cell (pDC), a conventional dendritic cell 1 (cDC1), a conventional dendritic cell 2 (cDC2), inflammatory monocyte derived dendritic cells, Langerhans cells, dermal dendritic cells, lysozyme-expressing dendritic cells (LysoDCs), Kupffer cells, or any combination thereof. Accordingly, in certain aspects, an immune cell that an EV disclosed herein (e.g., exosomes) can specifically target includes a conventional dendritic cell 1 (cDC1) and/or plasmacytoid dendritic cells (pDC).

As used herein, the term "T cell" or "T-cell" refers to a type of lymphocyte that matures in the thymus. T cells play an important role in cell-mediated immunity and are distinguished from other lymphocytes, such as B cells, by the presence of a T-cell receptor on the cell surface. T-cells include all types of immune cells expressing CD3, including T-helper cells (CD4+ cells), cytotoxic T-cells (CD8+ cells), natural killer T-cells, T-regulatory cells (Treg), and gamma-delta T cells.

A "naïve" T cell refers to a mature T cell that remains immunologically undifferentiated (i.e., not activated). Following positive and negative selection in the thymus, T cells emerge as either CD4+ or CD8+ naïve T cells. In their naïve state, T cells express L-selectin (CD62L+), IL-7 receptor-α (IL-7R-α), and CD132, but they do not express CD25, CD44, CD69, or CD45RO. As used herein, "immature" can also refers to a T cell which exhibits a phenotype characteristic of either a naïve T cell or an immature T cell, such as a TSCM cell or a TCM cell. For example, an immature T cell can express one or more of L-selectin (CD62L+), IL-7Rα, CD132, CCR7, CD45RA, CD45RO, CD27, CD28, CD95, CXCR3, and LFA-1. Naïve or immature T cells can be contrasted with terminal differentiated effector T cells, such as $T_{EM}$ cells and $T_{EFF}$ cells.

As used herein, the term "effector" T cells or "$T_{EFF}$" cells refers to a T cell that can mediate the removal of a pathogen or cell without requiring further differentiation. Thus, effector T cells are distinguished from naïve T cells and memory T cells, and these cells often have to differentiate and proliferate before becoming effector cells.

As used herein, the term "memory" T cells refer to a subset of T cells that have previously encountered and responded to their cognate antigen. In some aspects, the term is synonymous with "antigen-experienced" T cells. In some aspects, memory T cells can be effector memory T cells or central memory T cells. In some aspects, the memory T cells are tissue-resident memory T cells. As used herein, the term "tissue-resident memory T cells" or "TRM cells" refers to a lineage of T cells that occupies tissues (e.g., skin, lung, gastrointestinal tract) without recirculating. TRM cells are transcriptionally, phenotypically and functionally distinct from central memory and effector memory T cells which recirculate between blood, the T cell zones of secondary lymphoid organs, lymph and nonlymphoid tissues. One of the roles of TRM cells is to provide immune protection against infection in extralymphoid tissues.

As used herein, the term "dendritic cells" or "DCs" refers to a class of bone-marrow-derived immune cells that are capable of processing extracellular and intracellular proteins and to present antigens in the context of MHC molecules to prime naïve T cells. In some aspects, dendritic cells can be divided into further subtypes, such as conventional dendritic cell 1 (cDC1), conventional dendritic cell 2 (cDC2), plasmacytoid dendritic cell (pDC), inflammatory monocyte derived dendritic cells, Langerhans cells, dermal dendritic cells, lysozyme-expressing dendritic cells (LysoDCs), Kupffer cells, and combinations thereof. In certain aspects, the different DC subsets can be distinguished based on their phenotypic expression. For example, in some aspects, human cDC1 cells are $CD1c^-$ and $CD141^+$. In some aspects, human cDC2 cells are $CD1c^+$ and $CD141^-$. In some aspects, human pDC cells are $CD123^+$. In some aspects, mouse cDC1 cells are $XCR1^+$, $Clec9a^+$, and $Sirpa^-$. In some aspects, mouse cDC2 cells are $CD8^+$, $CD11b^+$, $Sirpa^+$, $XCR1^-$, and $CD1c,b^+$. In some aspects, mouse pDC cells are $CD137^+$, $XCR1^-$, and $Sirpa^-$. Other phenotypic markers for distinguishing the different DC subsets are known in the art. See, e.g., Collin et al., *Immunology* 154(1): 3-20 (2018). In some aspects, the different DC subsets can be distinguished based on their functional properties. For example, in certain aspects, pDCs produce large amounts of IFN-α, while cDC1s and cDC2s produce inflammatory cytokines, such as IL-12, IL-6, and TNF-α. Other methods of distinguishing the different DC subsets are known in the art. See, e.g., U.S. Pat. Nos. 8,426,565 B2 and 9,988,431, each of which is herein incorporated by reference in its entirety.

The term "immunoconjugate," as used herein, refers to a compound comprising a binding molecule (e.g., an antibody) and one or more moieties, e.g., therapeutic or diagnostic moieties, chemically conjugated to the binding molecule. In general, an immunoconjugate is defined by a generic formula: A-(L-M)n, wherein A is a binding molecule (e.g., an antibody), L is an optional linker, and M is a heterologous moiety which can be for example a therapeutic agent, a detectable label, etc., and n is an integer. In some aspects, multiple heterologous moieties can be chemically conjugated to the different attachment points in the same binding molecule (e.g., an antibody). In other aspects, multiple heterologous moieties can be concatenated and attached to an attachment point in the binding molecule (e.g., an antibody). In some aspects, multiple heterologous moieties (being the same or different) can be conjugated to the binding molecule (e.g., an antibody).

Immunoconjugates can also be defined by the generic formula in reverse order. In some aspects, the immunoconjugate is an "antibody-Drug Conjugate" ("ADC"). In the context of the present disclosure, the term "immunoconjugate" is not limited to chemically or enzymatically conjugates molecules. The term "immunoconjugate" as used in the present disclosure also includes genetic fusions. In some aspects of the present disclosure, the biologically active molecule is an immunoconjugate. The terms "antibody-drug conjugate" and "ADC" are used interchangeably and refer to an antibody linked, e.g., covalently, to a therapeutic agent (sometimes referred to herein as agent, drug, or active pharmaceutical ingredient) or agents. In some aspects of the present disclosure, the biologically active molecule (i.e., a payload) is an antibody-drug conjugate.

"Treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

"Prevent" or "preventing," as used herein, refers to decreasing or reducing the occurrence or severity of a particular outcome. In some aspects, preventing an outcome is achieved through prophylactic treatment.

II. Extracellular Vesicles, e.g., Exosomes

Disclosed herein are EVs, e.g., exosomes, capable of regulating the immune system of a subject. The EVs, e.g., exosomes, useful in the present disclosure have been engineered to produce multiple agents (i.e., payloads) together (e.g., an antigen and an adjuvant in a single EV, e.g., exosome; an antigen and an immune modulator in a single EV, e.g., exosome; and an antigen, an adjuvant, and an immune modulator in a single EV, e.g., exosome; instead of a single agent, e.g., an antigen alone, an adjuvant alone, or an immune modulator alone). In some aspects, an EV, e.g., exosome, comprises (i) an antigen and (ii) an adjuvant. In other aspects, an EV, e.g., exosome, comprises (i) an antigen and (ii) an immune modulator. In some aspects, an EV (e.g., exosome) comprises (i) an antigen, (ii) an adjuvant, and (iii) an immune modulator. In certain aspects, an EV (e.g., exosome) disclosed herein can also comprise additional moieties, such as a targeting moiety. In some aspects, an antigen is not expressed or presented on major histocompatibility complex I and/or II molecules. In other aspects, while an antigen in the EV, e.g., exosome, is not expressed or presented as part of the MHC class I or II complex, the EV, e.g., exosome, can still contain MHC class I/II molecules on the surface of the EV, e.g., exosome. Accordingly, in certain aspects, EVs, e.g., exosomes, disclosed herein do not directly interact with T-cell receptors (TCRs) of T cells to induce an immune response against the antigen. Similarly, in certain aspects, EVs, e.g., exosomes, of the present disclosure do not transfer the antigen directly to the surface of the target cell (e.g., dendritic cell) through cross-dressing. "Cross-dressing" is a mechanism commonly used by EVs, e.g., exosomes, derived from dendritic cells (DEX) to induce T cell activation. See Pitt, J. M., et al., *J Clin Invest* 126(4): 1224-32 (2016). In other aspects, the EVs, e.g., exosomes, of the present disclosure are engulfed by antigen presenting cells and can be expressed on the surface of the antigen presenting cells as MHC class I and/or MHC class II complex.

As will be apparent to those skilled in the art, EVs (e.g., exosomes) disclosed herein do not need to comprise an antigen and can instead comprise multiple other payloads disclosed herein. For example, in some aspects, an EV (e.g., exosome) can comprise multiple different adjuvants. In some aspects, an EV (e.g., exosome) can comprise multiple different immune modulators. In some aspects, an EV (e.g., exosome) can comprise one or more adjuvants in combination with one or more immune modulators. Such antigen-less EVs (e.g., exosomes) can be useful in inducing and/or increasing an innate immune response. Non-limiting examples of therapeutic settings where such antigen-less EVs could be useful include: to treat bacterial and/or viral infections, such as *Pseudomonas aeruginosa* for ventilator-associated pneumonia, influenza and RSV, SARS/MERs, toxoplasma, sepsis, yellow fever, and *Staph aureus* for surgical site infection. In certain aspects, such antigen-less EVs (e.g., exosomes) can be used in combination with one or more additional therapeutic agents. In some aspects, the one or more additional therapeutic agents comprise an antigen, wherein the antigen is not expressed in an EV (e.g., exosome) (e.g., soluble form of the antigen) . . . . Unless indicated otherwise, the relevant disclosures provided herein are equally applicable regardless of whether an EV (e.g., exosome) comprises an antigen or not.

As described supra, EVs, e.g., exosomes, described herein are extracellular vesicles with a diameter between about 20-300 nm. In certain aspects, an EV, e.g., exosome, of the present disclosure has a diameter between about 20-290 nm, between about 20-280 nm, between about 20-270 nm, between about 20-260 nm, between about 20-250 nm, between about 20-240 nm, between about 20-230 nm, between about 20-220 nm, between about 20-210 nm, between about 20-200 nm, between about 20-190 nm, between about 20-180 nm, between about 20-170 nm, between about 20-160 nm, between about 20-150 nm, between about 20-140 nm, between about 20-130 nm, between about 20-120 nm, between about 20-110 nm, between about 20-100 nm, between about 20-90 nm, between about 20-80 nm, between about 20-70 nm, between about 20-60 nm, between about 20-50 nm, between about 20-40 nm, between about 20-30 nm, between about 30-300 nm, between about 30-290 nm, between about 30-280 nm, between about 30-270 nm, between about 30-260 nm, between about 30-250 nm, between about 30-240 nm, between about 30-230 nm, between about 30-220 nm, between about 30-210 nm, between about 30-200 nm, between about 30-190 nm, between about 30-180 nm, between about 30-170 nm, between about 30-160 nm, between about 30-150 nm, between about 30-140 nm, between about 30-130 nm, between about 30-120 nm, between about 30-110 nm, between about 30-100 nm, between about 30-90 nm, between about 30-80 nm, between about 30-70 nm, between about 30-60 nm, between about 30-50 nm, between about 30-40 nm, between about 40-300 nm, between about 40-290 nm, between about 40-280 nm, between about 40-270 nm, between about 40-260 nm, between about 40-250 nm, between about 40-240 nm, between about 40-230 nm, between about 40-220 nm, between about 40-210 nm, between about 40-200 nm, between about 40-190 nm, between about 40-180 nm, between about 40-170 nm, between about 40-160 nm, between about 40-150 nm, between about 40-140 nm, between about 40-130 nm, between about 40-120 nm, between about 40-110 nm, between about 40-100 nm, between about 40-90 nm, between about 40-80 nm, between about 40-70 nm, between about 40-60 nm, between about 40-50 nm, between about 50-300 nm, between about 50-290 nm, between about 50-280 nm, between about 50-270 nm, between about 50-260 nm, between about 50-250 nm, between about 50-240 nm, between about 50-230 nm, between about 50-220 nm, between about 50-210 nm, between about 50-200 nm, between about 50-190 nm, between about 50-180 nm, between about 50-170 nm, between about 50-160 nm, between about 50-150 nm, between about 50-140 nm, between about 50-130 nm, between about 50-120 nm, between about 50-110 nm, between about 50-100 nm, between about 50-90 nm, between about 50-80 nm, between about 50-70 nm, between about 50-60 nm, between about 60-300 nm, between about 60-290 nm, between about 60-280 nm, between about 60-270 nm, between about 60-260 nm, between about 60-250 nm, between about 60-240 nm, between about 60-230 nm, between about 60-220 nm, between about 60-210 nm, between about 60-200 nm, between about 60-190 nm, between about 60-180 nm, between about 60-170 nm, between about 60-160 nm, between about 60-150 nm, between about 60-140 nm, between about 60-130 nm, between about 60-120 nm, between about 60-110 nm, between about 60-100 nm, between about 60-90 nm, between about 60-80 nm, between about 60-70 nm, between about 70-300 nm, between about 70-290 nm, between about 70-280 nm, between about 70-270 nm, between about 70-260 nm, between about 70-250 nm, between about 70-240 nm, between about 70-230 nm, between about 70-220 nm, between about 70-210 nm, between about 70-200 nm, between about 70-190 nm, between about 70-180 nm, between about 70-170 nm, between about 70-160 nm, between about 70-150 nm, between about 70-140 nm, between about 70-130 nm, between about 70-120 nm, between about 70-110 nm, between about 70-100 nm, between about 70-90 nm, between about 70-80 nm, between about 80-300 nm, between about 80-290 nm, between about 80-280 nm, between about 80-270 nm, between about 80-260 nm, between about 80-250 nm, between about 80-240 nm, between about 80-230 nm, between about 80-220 nm, between about 80-210 nm, between about 80-200 nm, between about 80-190 nm, between about 80-180 nm, between about 80-170 nm, between about 80-160 nm, between about 80-150 nm, between about 80-140 nm, between about 80-130 nm, between about 80-120 nm, between about 80-110 nm, between about 80-100 nm, between about 80-90 nm, between about 90-300 nm, between about 90-290 nm, between about 90-280 nm, between about 90-270 nm, between about 90-260 m, between about 90-250 nim, between about 90-240 nm, between about 90-230 nm, between about 90-220 nm, between about 90-210 nm, between about 90-200 nm, between about 90-190 nm, between about 90-180 nm, between about 90-170 nm, between about 90-160 nm, between about 90-150 nm, between about 90-140 nm, between about 90-130 nm, between about 90-120 nm, between about 90-110 nm, between about 90-100 nm, between about 100-300 nm, between about 110-290 nm, between about 120-280 nm, between about 130-270 nm, between about 140-260 nm, between about 150-250 nm, between about 160-240 nm, between about 170-230 nm, between about 180-220 nm, or between about 190-210 nm. The size of the EV, e.g., exosome, described herein can be measured according to methods described, infra.

In some aspects, an EV, e.g., exosome, of the present disclosure comprises a bi-lipid membrane ("EV, e.g., exosome, membrane"), comprising an interior surface and an exterior surface. In certain aspects, the interior surface faces the inner core (i.e., lumen) of the EV, e.g., exosome. In certain aspects, the exterior surface can be in contact with the endosome, the multivesicular bodies, or the membrane/cytoplasm of a producer cell or a target cell In some aspects, the EV, e.g., exosome, membrane comprises lipids and fatty acids. In some aspects, the EV, e.g., exosome, membrane comprises phospholipids, glycolipids, fatty acids, sphingolipids, phosphoglycerides, sterols, cholesterols, and phosphatidylserines.

In some aspects, the EV, e.g., exosome, membrane comprises an inner leaflet and an outer leaflet. The composition of the inner and outer leaflet can be determined by transbilayer distribution assays known in the art, see, e.g., Kuypers et al., *Biohim Biophys Acta* 1985 819:170. In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, the EV, e.g., exosome, membrane comprises one or more polysaccharide, such as glycan.

In some aspects, the EV, e.g., exosome, membrane further comprises one or more scaffold moieties, which are capable of anchoring, e.g., an antigen and/or an adjuvant and/or an immune modulator, to the EV, e.g., exosome, (e.g., either on the luminal surface or on the exterior surface). In certain aspects, scaffold moieties are polypeptides ("exosome proteins"). In other aspects, scaffold moieties are non-polypeptide moieties. In some aspects, exosome proteins include various membrane proteins, such as transmembrane proteins, integral proteins and peripheral proteins, enriched on the exosome membranes. They can include various CD proteins, transporters, integrins, lectins, and cadherins. In certain aspects, a scaffold moiety (e.g., exosome protein) comprises Scaffold X. In other aspects, a scaffold moiety (e.g., exosome protein) comprises Scaffold Y. In further aspects, a scaffold moiety (e.g., exosome protein) comprises both a Scaffold X and a Scaffold Y.

In some aspects, an EV, e.g., exosome, disclosed herein is capable of delivering a payload (e.g., an antigen, an adjuvant, and/or an immune modulator) to a target. The payload is an agent that acts on a target (e.g., a target cell) that is contacted with the EV. Contacting can occur in vitro or in a subject. Non-limiting examples of payloads that can be introduced into an EV include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), or a peptide-conjugated phosphorodiamidate morpholino oligomer (PPMO)), amino acids (e.g., amino acids comprising a detectable moiety or a toxin that disrupt translation), polypeptides (e.g., enzymes), lipids, carbohydrates, and small molecules (e.g., small molecule drugs and toxins).

As demonstrated herein (see, e.g., Example 16), in some aspects, EVs (e.g., exosomes) of the present disclosure are capable of inducing effector and memory T cells. In certain aspects, the memory T cells are tissue-resident memory T cells. Such EVs (e.g., exosomes) could be particularly useful as vaccines for certain infectious diseases. For example, most of the currently available influenza vaccines are inactivated and largely focused on generating neutralizing antibodies against certain influenza surface antigens (e.g., hemagglutinin (HA) and neuraminidase (NA). See Wang et al., *Science* 367(6480): 1-12 (Feb. 21, 2020), which is herein incorporated by reference in its entirety.). However, such antigens undergo constant mutations, requiring the vaccines to be updated annually. Even with the annual updates, there have been years in which influenza vaccines were ineffective because of mismatched HA and/or NA antigenicity between the vaccine viral strains and strains in circulation. Broad immunity can be evoked by natural viral infections or live vector-engineered and attenuated vaccines, as these all induce tissue (lung) resident memory T cells apart from the humoral immunity. However, a delicate balance must be struck between safety and immunogenicity of these "replicating" vaccines and are often suitable for only some individuals. EVs (e.g., exosomes) of the present disclosure do not share such limitations. Accordingly, in some aspects, EVs (e.g., exosomes) disclosed herein (e.g., comprising one or more influenza antigens in combination with a payload disclosed herein, e.g., STING agonist) could be useful as an "universal" vaccine against a particular pathogen (e.g., different influenza subtypes).

In some aspects, EVs (e.g., exosomes) disclosed herein are inherently capable of inducing the activation of a signaling pathway involved in an immune response. In certain aspects, the signaling pathway involved in an immune response comprises toll-like receptors (TLRs), retinoid acid-inducible gene I (RIG-I)-like receptors (RLRs), stimulator of interferon genes (STING) pathway, or combinations thereof. In some aspects, the activation of such signaling pathway can result in the production of a type I interferon. For example, in certain aspects, the bi-lipid membrane of an EV (e.g., exosome) disclosed herein comprises one or more lipids that share one of the following features: (i) unsaturated lipid tail, (ii) dihydroimidazole linker, (iii) cyclic amine head groups, and (iv) combinations thereof. Lipids with such features have been shown to activate the TLR/RLR-independent STING pathway. See Miao et al., *Nature Biotechnology* 37:1174-1185 (October 2019), which is herein incorporated by reference in its entirety.

II.A Antigen

In some aspects, the payload is an antigen, which is capable of inducing an immune response in a subject. In some aspects, an EV (e.g., exosome) disclosed herein comprises a single antigen. In some aspects, an EV (e.g., exosome) disclosed herein comprises multiple antigens. In certain aspects, each of the multiple antigens is different. In some aspects, an EV (e.g., exosome) disclosed herein comprises at least 2, 3, 4, 5, 6, 7, 8, 9, 10 or more different antigens. As disclosed herein, an antigen can be linked to a surface of an EV (e.g., exosome) using a scaffold moiety (e.g., Scaffold X and/or Scaffold Y). In certain aspects, an antigen can be directly linked (i.e., without the use of a scaffold moiety) to a surface of an EV (e.g., exosome). In some aspects, an antigen can be in the lumen of the EV (e.g., exosome).

In some aspects, an EV (e.g., exosome) comprises the one or more antigens in combination with one or more additional payloads described herein (e.g., adjuvant and/or immune modulator). In some aspects, an EV (e.g., exosome) can comprise one or more additional moieties (e.g., targeting moiety). For instance, in certain aspects, an EV (e.g., exosome) disclosed herein can comprise (i) one or more additional antigens, (ii) one or more additional payloads (e.g., adjuvant and/or immune modulator), and (iii) one or more targeting moieties.

In some aspects, the antigen comprises a tumor antigen. Non-limiting examples of tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen (CTA), MART-1 gp100, TNF-related apoptosis-inducing ligand, Brachyury (preferentially expressed antigen in melanoma (PRAME)), Wilms tumor 1 (WT1), CD19, CD22, or combinations thereof.

In some aspects, the antigen is a universal tumor antigen. As used herein, the term "universal tumor antigen" refers to an immunogenic molecule, such as a protein, that is, generally, expressed at a higher level in tumor cells than in non-tumor cells and also is expressed in tumors of different origins. In some aspects, the universal tumor antigen is expressed in more than about 30%, about 40%, about 50%, about 60%, about 70%, about 80%, about 90% or more of cancers (e.g., human cancers). In some aspects, the universal tumor antigen can be expressed in non-tumor cells (e.g., normal cells) but at lower levels than it is expressed in tumor cells. In certain aspects, the expression level of the universal tumor antigen is greater than about 1-fold, about 2-fold, about 3-fold, about 4-fold, about 5-fold, about 6-fold, about 7-fold, about 8-fold, about 9-fold, about 10-fold or more on tumor cells compared to non-tumor cells. In certain aspects, the universal tumor antigen is not expressed in normal cells and only expressed in tumor cells. Non-limiting examples of universal tumor antigens that can be used with the present disclosure include endothelial lining antigens in tumor vasculature, survivin, tumor protein D52 (TPD52), androgen receptor epitopes, ephrin type-A receptor 2 (EphA2), human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

In further aspects, an antigen can comprise a neoantigen. As used herein, the term "neoantigen" refers to antigens encoded by tumor-specific mutated genes.

In some aspects, the antigen is derived from a bacterium, a virus, fungus, protozoa, or any combination thereof. In some aspects, the antigen is derived from an oncogenic virus (also referred to herein as cancer associated viruses (CAVs)). In further aspects, the antigen is derived from a group comprising: a Human Gamma herpes virus 4 (i.e., Epstein Barr virus (EBV)), influenza A virus, influenza B virus, cytomegalovirus, *Staphylococcus aureus, Mycobacterium tuberculosis, Chlamydia trachomatis*, HIV (e.g., HIV-2), corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B virus (HBV), Hepatitis C virus (HCV), human T-lymphotropic virus (HTLV1), human herpes virus 8 (HHV8), Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and *Burrelia mayonii* (e.g., Lyme disease), herpes simplex virus 2 (HSV-2), *Klebsiella* sp., *Pseudomonas aeruginosa, Enterococcus* sp., *Proteus* sp., *Enterobacter* sp., Actinobacter sp., coagulase-negative staphylococci (CoNS), *Mycoplasma* sp., Adenovirus, Adeno-associated virus (AAV), or combinations thereof.

Figure 7A:
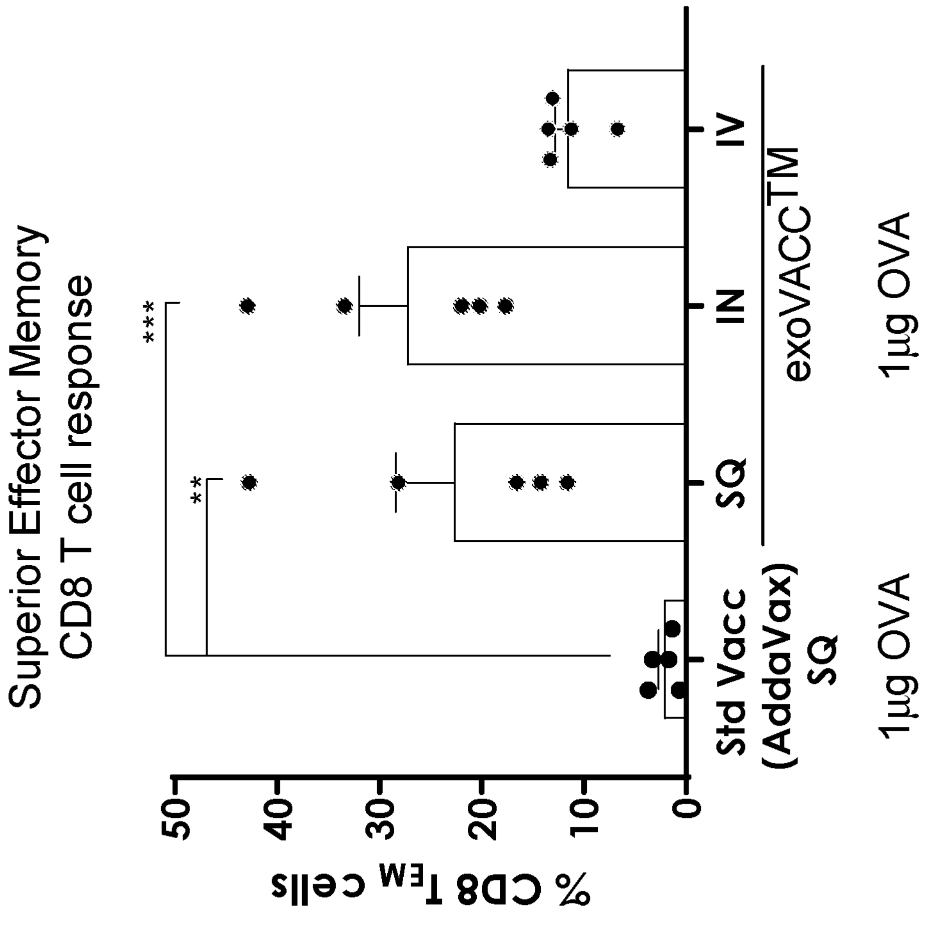
FIGS. 7A and 7B show that an engineered EV, e.g., an exosome, induces superior CD8 T-cell response as compared to standard vaccine formulations.
Figure 7B:
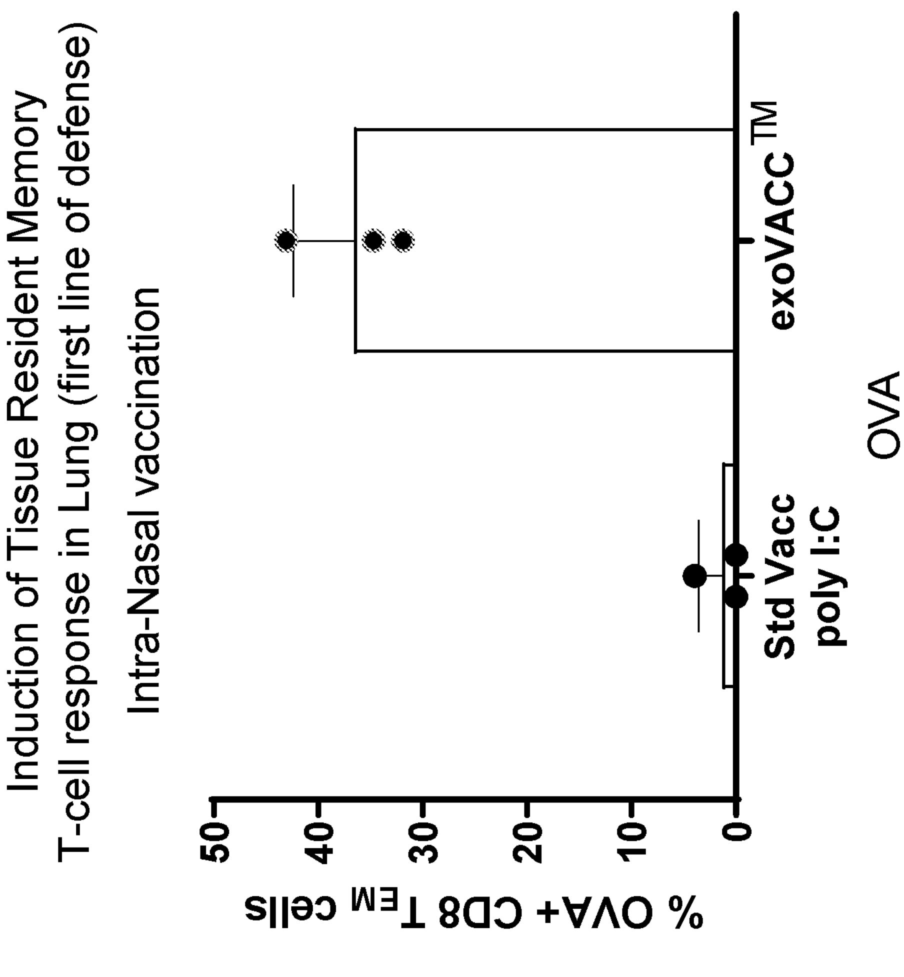

In some aspects, the antigen derived from EBV is BZLF1. BZLF1 (also known as Zta or EB1) is an immediate-early viral gene of EBV, which induces cancers and infects primarily the B-cells of 95% of the human population. This gene (along with others) produces the expression of other EBV genes in other stages of disease progression, and is involved in converting the virus from the latent to the lytic form. ZEBRA (BamHI Z Epstein-Barr virus replication activator, also known as Zta and BZLF1)) is an early lytic protein of EBV encoded by BZLF1. See Hartlage et al. (2015) Cancer Immunol. Res. 3(7): 787-94, and Rist et al. (2015) J. Virology 70:703-12, both of which are incorporated herein by reference in their entireties. EV, e.g., exosomes, disclosed herein comprising an EBV antigen, e.g., BZLF1, can be used, e.g., to treat post-transplant lymphoproliferative disorder (PTLD). Such EV can be administered to EBV negative patients receiving EBV positive transplants. BZLF1 is a dominant T cell antigen associated with durable remission in PTLD patients. The EV, e.g., exosomes, disclosed herein comprising BZLF1 can elicit a potent CD8 T-cell mediated immunity of BZLF1. Accordingly, mucosal immunity and tissue resident memory cells (see FIGS. 7A and 7B) can protect the patient from developing PTLDF. Non-limiting exemplary antigens include, but are not limited to, the antigens disclosed in U.S. Pat. No. 8,617,564 B2, which is herein incorporated by reference in its entirety.

In some aspects, the antigen is derived from *Mycobacterium tuberculosis* to induce cellular and/or humoral immune response. In some aspects, the antigen comprises one or more epitopes of *Mycobacterium tuberculosis* (TB antigen). Various antigens are associated with *Mycobacterium tuberculosis* infection, including ESAT-6, TB10.4, CFP10, Rv2031 (hspX), Rv2654c (TB7.7), and Rv1038c (EsxJ). See, e.g., Lindestam et al., *J. Immunol.* 188(10):5020-31 (2012), which is incorporated herein in its entirety. In some aspects, the antigen useful for the present disclosure comprises one or more epitopes of ESAT6. In some aspects, the antigen useful for the present disclosure comprises one or more epitopes of TB10.4. In some aspects, the antigen useful for the present disclosure comprises one or more epitopes of CFP10. In some aspects, the antigen useful for the present disclosure comprises one or more epitopes of Rv2031 (hspX). In some aspects, the antigen useful for the present disclosure comprises one or more epitopes of Rv2654c (TB7.7). In some aspects, the antigen useful for the present disclosure comprises one or more epitopes of Rv1038c (EsxJ). In some aspects, the antigen useful for the present disclosure comprises an epitope selected from the group consisting of ESAT6, TB10.4 (ESAT-6-like protein EsxH; cfp7), CFP10, Rv2031 (hspX), Rv2654c (TB7.7), Rv1038c (EsxJ), and any combination thereof.

In some aspects, the TB antigen comprises a particular epitope of a TB antigen, e.g., a particular epitope of ESAT6 or TB10.4. In some aspects, the ESAT6 antigen comprises an epitope having at least three amino acids, at least four amino acids, at least five amino acids, at least six amino acids, at least seven amino acids, at least eight amino acids, at least nine amino acids, at least ten amino acids, at least eleven amino acids, at least twelve amino acids, at least thirteen amino acids, at least fourteen amino acids, at least fifteen amino acids of the amino acid sequence as set forth in MTEQQWNFAGIEAAASAIQGNVTSIHSLDE-GKQSLTKLAAAWGGSGSEAYQGVQQKW-DATATELNNALQNL ARTISEAGQAMAS-TEGNVTGMFA (SEQ ID NO: 370). In some aspects, wherein the TB10.4 antigen comprises an epitope having at least three amino acids, at least four amino acids, at least five amino acids, at least six amino acids, at least seven amino acids, at least eight amino acids, at least nine amino acids, at least ten amino acids, at least eleven amino acids, at least twelve amino acids, at least thirteen amino acids, at least fourteen amino acids, at least fifteen amino acids of the amino acid sequence as set forth in MSQIMYNY-PAMLGHAGDMAGYAGTLQSLGAEIAVEQAALQ-SAWQGDTGITYQAWQAQWNQAMEDLVRA YHAM-SSTHEANTMAMMARDTAEAAKWGG (SEQ ID NO: 371).

In some aspects, an antigen comprises a self-antigen. As used herein, the term "self-antigen" refers to an antigen that is expressed by a host cell or tissue. Under normal healthy state, such antigens are recognized by the body as self and do not elicit an immune response. However, under certain diseased conditions, a body's own immune system can recognize self-antigens as foreign and mount an immune response against them, resulting in autoimmunity. In certain aspects, EVs, e.g., exosomes, of the present disclosure can comprise a self-antigen (i.e., the self (germline) protein to which T cell responses have been induced and resulted in autoimmunity). Such EVs, e.g., exosomes, can be used to target the autoreactive T cells and suppress their activity. Non-limiting examples of self-antigens (including the associated disease or disorder) include: (i) beta-cell proteins, insulin, islet antigen 2 (IA-2), glutamic acid decarboxylase (GAD65), and zinc transporter 8 (ZNT8) (type I diabetes), (ii) myelin oligodendrocyte glycoprotein (MOG), myelin basic protein (MBP), proteolipid protein (PLP), and myelin-associated glycoprotein (MAG) (multiple sclerosis), (iii) citrullinated antigens and synovial proteins (rheumatoid arthritis), (iv) aquaporin-4 (AQP4) (neuromyelitis optica), (v) nicotinic acetylcholine receptors (nAChRs) (myasthenia gravis), (vi) desmoglein-1 (DSG1) and desoglein-2 (DSG2) (pemphigus vulgaris), (v) thyrotropin receptor (Graves' disease), (vi) type IV collagen (Goodpasture syndrome), (vii) thyroglobulin, thyroid peroxidase, and thyroid-stimulating hormone receptor (TSHR) (Hashimoto's thyroiditis), or (viii) combinations thereof.

II.B Adjuvants

As described supra, EVs, e.g., exosomes, of the present disclosure can comprise an adjuvant (e.g., in combination with an antigen and/or other payloads disclosed herein). In some aspects, an EV (e.g., exosome) disclosed herein comprises multiple adjuvants. In certain aspects, each of the multiple adjuvants is different. In some aspects, an EV (e.g., exosome) disclosed herein comprises at least 2, 3, 4, 5, 6, 7, 8, 9, 10 or more different adjuvants. As disclosed herein, an adjuvant can be linked to a surface of an EV (e.g., exosome)

using a scaffold moiety (e.g., Scaffold X and/or Scaffold Y). In certain aspects, an adjuvant can be directly linked (i.e., without the use of a scaffold moiety) to a surface of an EV (e.g., exosome). In some aspects, an adjuvant can be in the lumen of the EV (e.g., exosome).

In some aspects, an EV (e.g., exosome) comprises the one or more adjuvants in combination with one or more additional payloads (e.g., antigen, and/or immune modulator). In some aspects, an EV (e.g., exosome) can comprise one or more additional moieties (e.g., targeting moieties). For instance, in certain aspects, an EV (e.g., exosome) disclosed herein can comprise (i) one or more additional adjuvants, (ii) one or more additional payloads (e.g., antigen and/or immune modulator), and (iii) one or more targeting moieties.

As used herein, the term "adjuvant" refers to any substance that enhances the therapeutic effect of the payload (e.g., increasing an immune response to the antigen). Accordingly, EVs, e.g., exosomes, described herein comprising an adjuvant are capable of increasing an immune response, e.g., to an antigen, by at least about 5%, at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more or more, compared to a reference (e.g., corresponding EV without the adjuvant or a non-EV delivery vehicle comprising an antigen alone or in combination with the adjuvant). In some aspects, incorporating an adjuvant disclosed herein to an EV (e.g., exosome) can increase an immune response, e.g., to an antigen, by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV comprising the antigen alone or a non-EV delivery vehicle comprising an antigen alone or in combination with the adjuvant).

Non-limiting examples of adjuvants that can be used with the present disclosure include: Stimulator of Interferon Genes (STING) agonist, a toll-like receptor (TLR) agonist, an inflammatory mediator, RIG-I agonists, alpha-gal-cer (NKT agonist), heat shock proteins (e.g., HSP65 and HSP70), C-type lectin agonists (e.g., beta glucan (Dectin 1), chitin, and curdlan), and combinations thereof.

In some aspects, incorporating an adjuvant (e.g., such as those disclosed herein) to an EV (e.g., exosome) can broaden an immune response induced by the EV. As used herein, to "broaden an immune response" refers to enhancing the diversity of an immune response. In some aspects, the diversity of an immune response can be enhanced through epitope spreading (i.e., inducing and/or increasing an immune response (cellular and/or humoral immune response) against a greater number/variety of epitopes on an antigen). In some aspects, the diversity of an immune response can be enhanced through the production of different and/or multiple antibody isotypes (e.g., IgG, IgA, IgD, IgM, and/or IgE).

In some aspects, an adjuvant (e.g., such as those disclosed herein) can also help regulate the type of immune response induced by the EV (e.g., exosome). For example, in some aspects, incorporating an adjuvant to an EV (e.g., exosome) can help drive an immune response towards a more Th1 phenotype. As used herein, a "Th1" immune response is generally characterized by the production of IFN-γ, which can activate the bactericidal activities of innate cells (e.g., macrophages), help induce B cells to make opsonizing (marking for phagocytosis) and complement-fixing antibodies, and/or lead to cell-mediated immunity (i.e., not mediated by antibodies). In general, Th1 responses are more effective against intracellular pathogens (viruses and bacteria that are inside host cells) and/or cancers.

In some aspects, incorporating an adjuvant to an EV (e.g., exosome) can help drive an immune response towards a more Th2 phenotype. As used herein, a "Th2" immune response can be characterized by the release of certain cytokines, such as IL-5 (induces eosinophils in the clearance of parasites) and IL-4 (facilitates B cell isotype switching). In general, Th2 responses are more effective against extracellular bacteria, parasites including helminths and toxins.

In some aspects, incorporating an adjuvant to an EV (e.g., exosome) can help drive an immune response towards a more Th17 phenotype. As used herein, a "Th17" immune response is mediated by Th17 cells. As used herein, "Th17 cells" refer to a subset of CD4+ T cells characterized by the production of pro-inflammatory cytokines, such as IL-17A, IL-17F, IL-21, IL-22, and granulocyte-macrophage colony-stimulating factor (GM-CSF). Th17 cells are generally thought to play an important role in host defense against infection, by recruiting neutrophils and macrophages to infected tissues.

In some aspects, incorporating an adjuvant to an EV (e.g., exosome) can help drive an immune response towards a more cellular immune response (e.g., T-cell mediated). In some aspects, incorporating an adjuvant to an EV (e.g., exosome) can help drive an immune response towards a more humoral immune response (e.g., antibody-mediated).

In some aspects, an adjuvant induces the activation of a cytosolic pattern recognition receptor. Non-limiting examples of cytosolic pattern recognition receptor includes: stimulator of interferon genes (STING), retinoic acid-inducible gene I (RIG-1), Melanoma Differentiation-Associated protein 5 (MDA5), Nucleotide-binding oligomerization domain, Leucine rich Repeat and Pyrin domain containing (NLRP), inflammasomes, or combinations thereof. In certain aspects, an adjuvant is a STING agonist. Stimulator of Interferon Genes (STING) is a cytosolic sensor of cyclic dinucleotides that is typically produced by bacteria. Upon activation, it leads to the production of type I interferons (e.g., IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin)) and initiates an immune response. In certain aspects, the STING agonist comprises a cyclic dinucleotide STING agonist or a non-cyclic dinucleotide STING agonist. As described herein, in some aspects, the STING agonist is loaded in the lumen of the EV (e.g., exosome). In some aspects, such EVs (e.g., exosomes) are referred to herein as "exoSTING." Non-limiting examples of exoSTING are provided in International Publication No. WO 2019183578A1, which is herein incorporated by reference in its entirety. Further disclosures of useful STING agonists are also provided throughout the present disclosure.

Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, are known to stimulate or enhance an immune or inflammation response in a patient. The CDNs can have 2'2', 2'3', 2'5', 3'3', or 3'5' bonds linking the cyclic dinucleotides, or any combination thereof.

Cyclic purine dinucleotides can be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides can be modified analogues. Any suitable modification known in the art can be used, including, but not limited to, phosphorothioate, biphosphorothioate, fluorinate, and difluorinate modifications.

Non cyclic dinucleotide agonists can also be used, such as 5,6-Dimethylxanthenone-4-acetic acid (DMXAA), or any other non-cyclic dinucleotide agonist known in the art.

Non-limiting examples of STING agonists that can be used with the present disclosure include: DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, and combinations thereof. Non-limiting examples of the STING agonists can be found at U.S. Pat. No. 9,695,212, WO 2014/189805 A1, WO 2014/179335 A1, WO 2018/100558 A1, U.S. Pat. No. 10,011,630 B2, WO 2017/027646 A1, WO 2017/161349 A1, and WO 2016/096174 A1, each of which is incorporated by reference in its entirety.

In some aspects, the STING agonist useful for the present disclosure comprises a compound having the following formula:

Formula 1

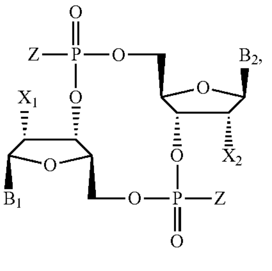

Formula 2

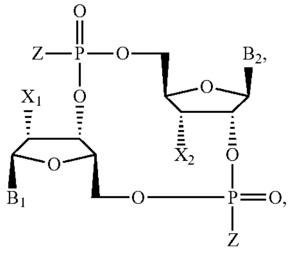

-continued

Formula 3

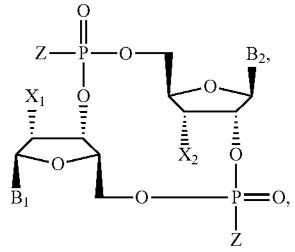

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

Bi and B2 are bases chosen from:

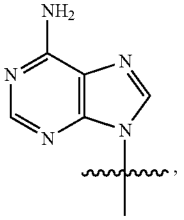

Adenine

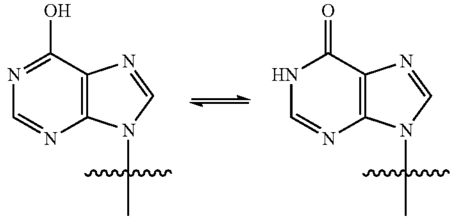

or

Hypoxanthine

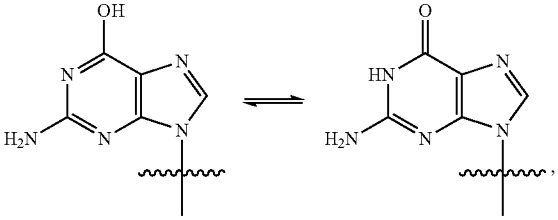

Guanine

With proviso that:

in Formula (I): $X_1$ and X2 are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH.

See WO 2016/096174, the content of which is incorporated herein by reference in its entirety.

In some aspects, the STING agonist useful for the present disclosure comprises:

-continued
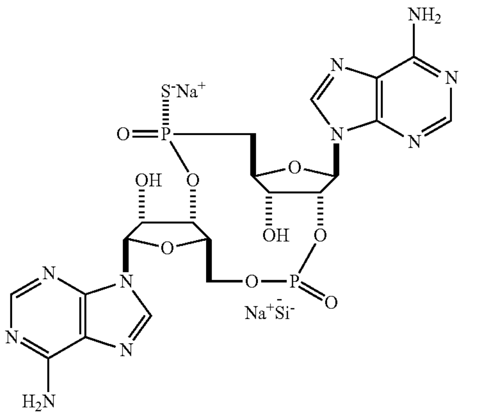
ADU-S100
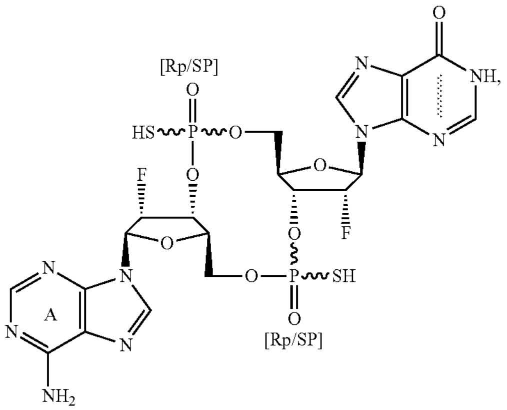
CL-656
c-[2FdAMP(S)-2FdIMP(S)]
CL-592
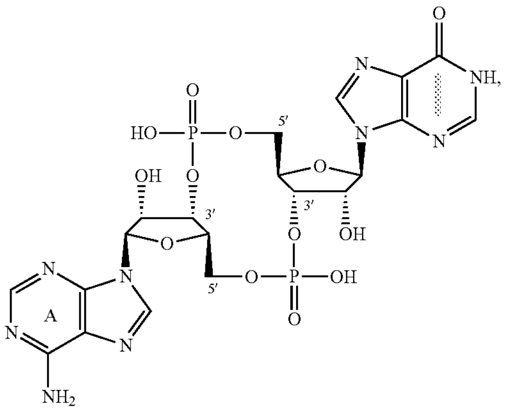
cAIMP
CL-797
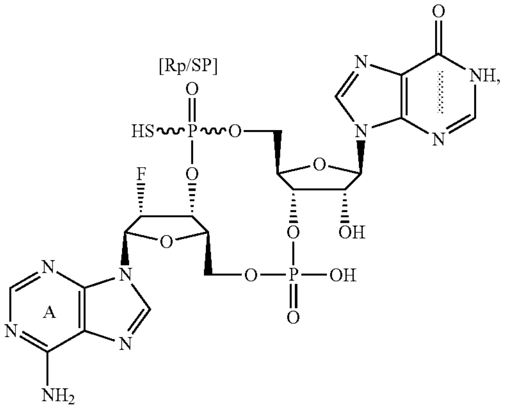
c-[2FdAMP(S)-IMP]
CL614
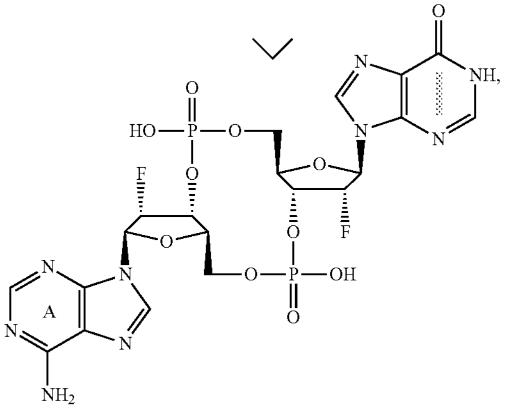
c-[2FdAMP-2FdIMP]
CL-655
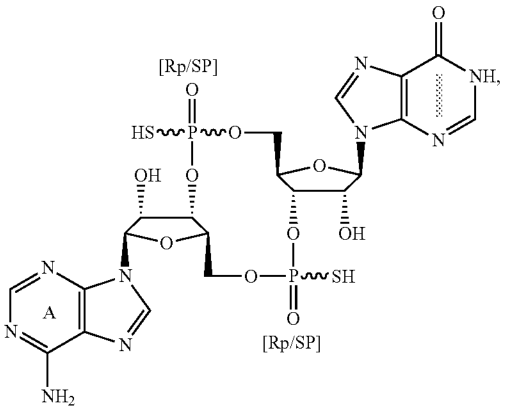
c-[AMP(S)-IMP(S)]

-continued
CL-659
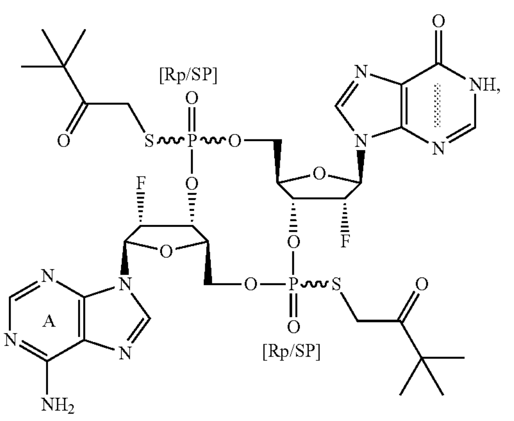
c-[2FdAMP(S)-2FdIMP(S)](POM)$_2$
a pharmaceutically acceptable salt thereof. See WO 2016/096174 A1, which is incorporated herein by reference in its entirety.
In other aspects, the STING agonist useful for the present disclosure comprises a compound having the following formula:
CL606
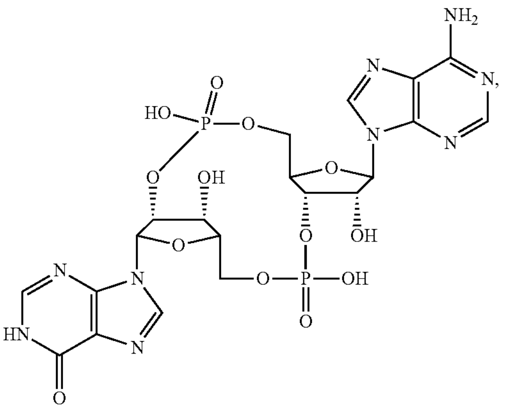
(3′,2′)c-AIMP
CL611
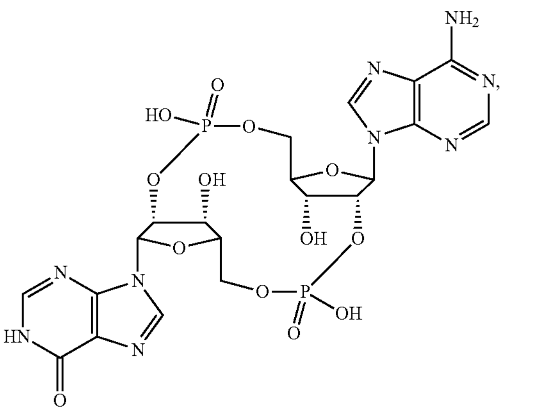
(2′,2′)c-AIMP
-continued
CL602
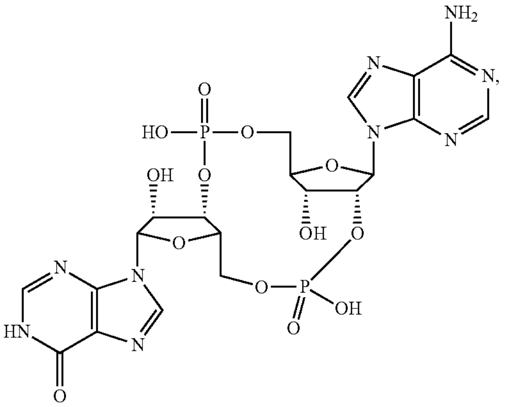
(2′,3′)c-AIMP
CL655
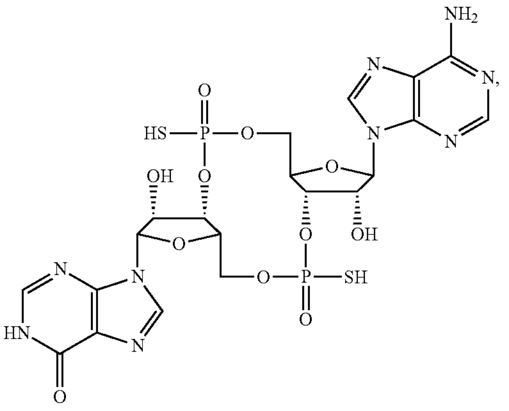
c-AIMP(S)
CL604
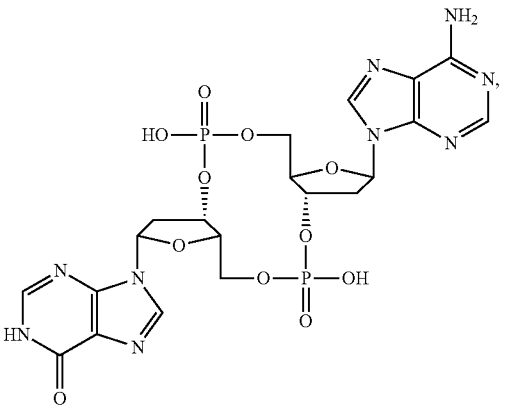
c-(dAMP-dIMP)

-continued
CL609
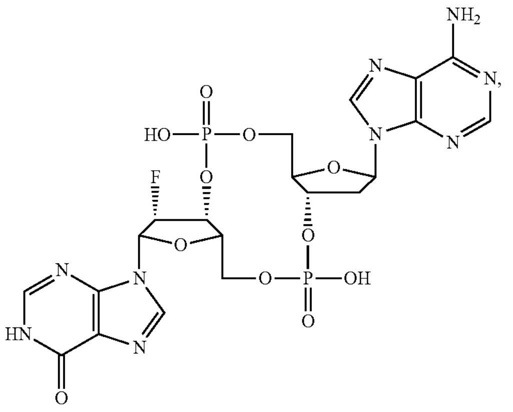
c-(dAMP-2′-FdIMP)
CL614
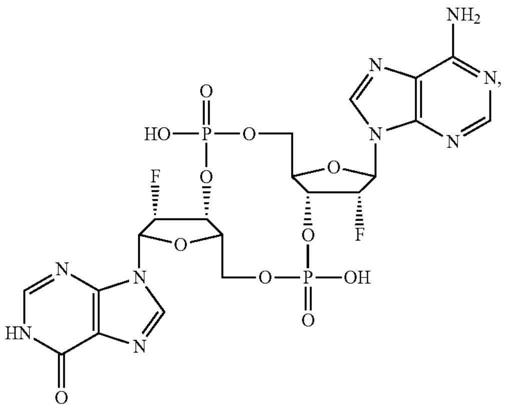
c-(2′-FdAMP-2′FdIMP)
CL656
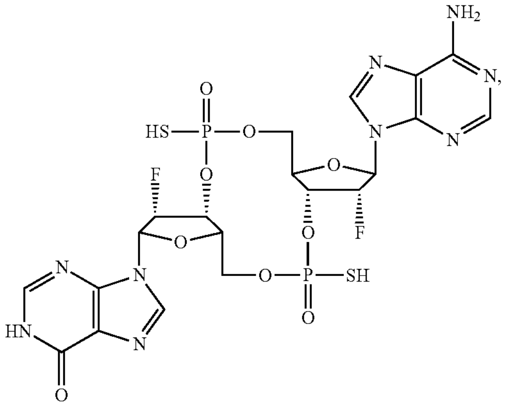
c-(2′-FdAMP(S)-2′FdIMP(S)]
-continued
CL647
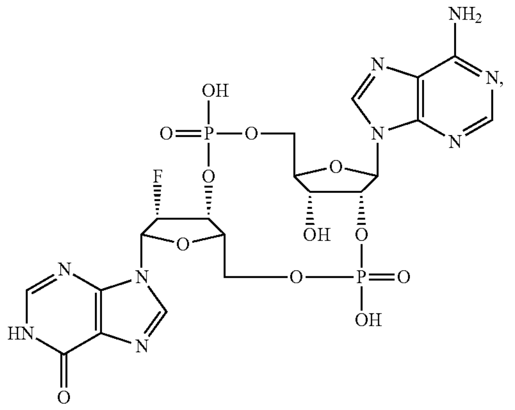
(2′,3′)c-(AMP-2′FdIMP)
CL626
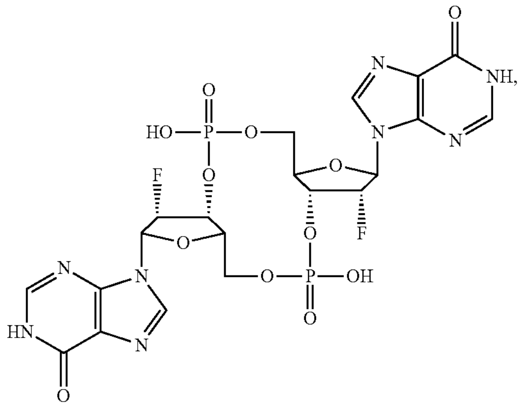
c-dI(2′FdIMP)
CL629
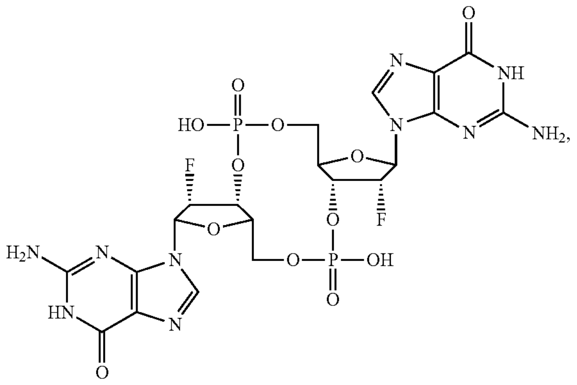
c-dI(2′FdGMP)

-continued

CL603

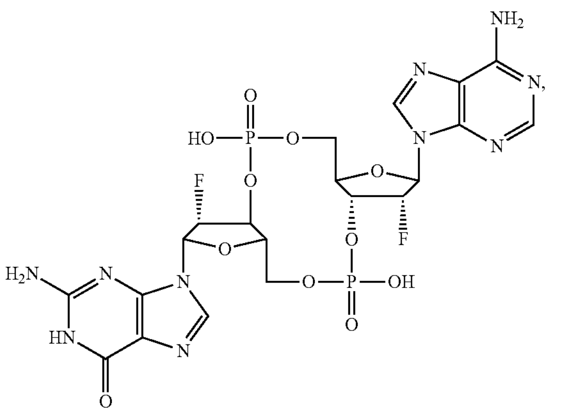

c-(2′FdGMP-2′FdAMP)

CL632

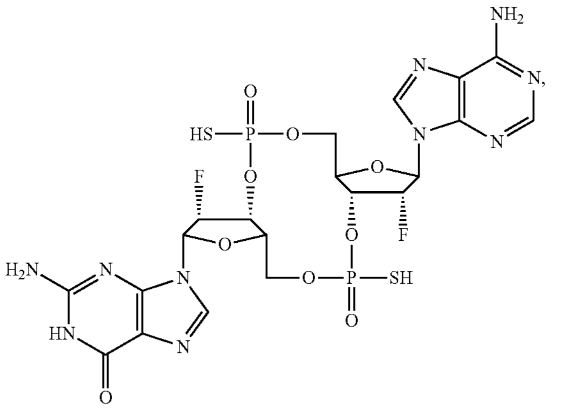

c-(2′FdGMP(S)-2′FdAMP(S)]

CL633

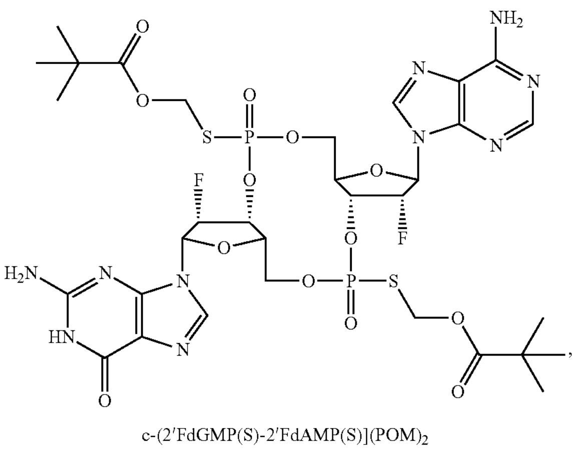

c-(2′FdGMP(S)-2′FdAMP(S)](POM)$_2$

-continued

CL659

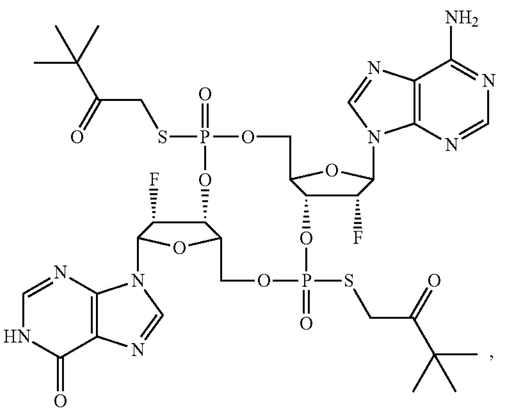

c-[2′FdAMP(S)-2′FdIMP(S)](POM)$_2$ or any pharmaceutically acceptable salts thereof.

In some aspects, the STING agonist useful for the present disclosure comprises a compound having the following formula:

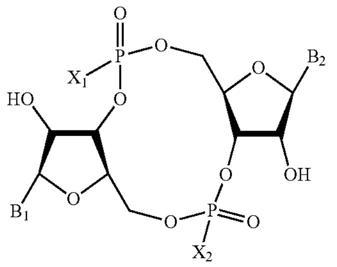

wherein each symbol is defined in WO 2014/093936, the content of which is incorporated herein by reference in its entirety.

In some aspects, the STING agonist useful for the present disclosure comprises a compound having the following formula:

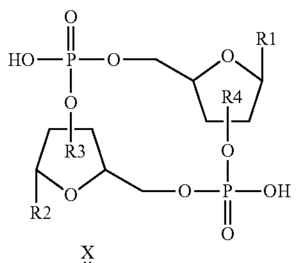

and

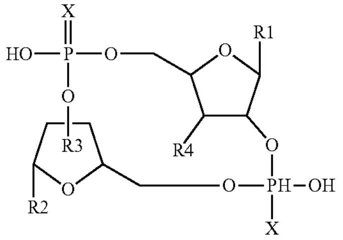

wherein each symbol is defined in WO 2014/189805, the content of which is incorporated herein by reference in its entirety.

In some aspects, the STING agonist useful for the present disclosure comprises a compound having the following formula:

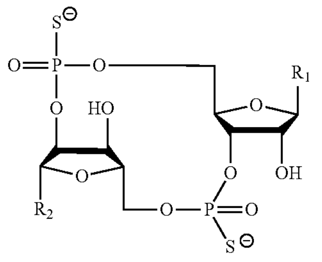

wherein each symbol is defined in WO 2015/077354, the content of which is incorporated herein by reference in its entirety. See also Cell reports 11, 1018-1030 (2015), which is incorporated herein by reference in its entirety.

In some aspects, the STING agonist useful for the present disclosure comprises c-di-AMP, c-di-GMP, c-di-IMP, c-AMP-GMP, c-AMP-IMP, and c-GMP-IMP, described in WO 2013/185052 and Sci. Transl. Med. 283,283ra52 (2015), which are incorporated herein by reference in their entireties.

In some aspects, the STING agonist useful for the present disclosure comprises a compound having the following formula:

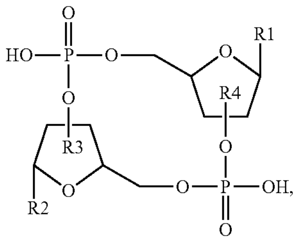

and

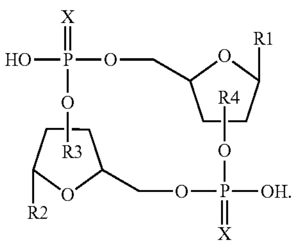

wherein each symbol is defined in WO 2014/189806, the content of which is incorporated herein by reference in its entirety.

In some aspects, the STING agonist useful for the present disclosure comprises a compound having the following formula:

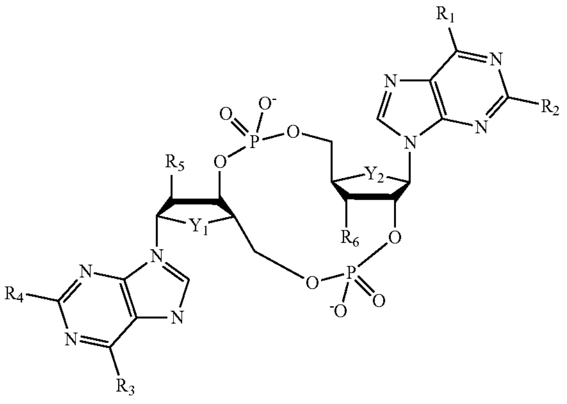

wherein each symbol is defined in WO 2015/185565, the content of which is incorporated herein by reference in its entirety.

In some aspects, the STING agonist useful for the present disclosure comprises a compound having the following formula:

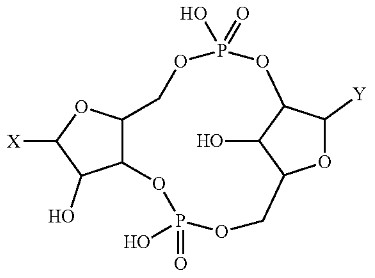

or

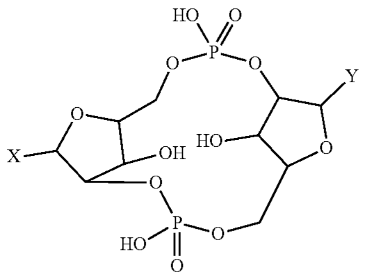

wherein each symbol is defined in WO 2014/179760, the content of which is incorporated herein by reference in its entirety.

In some aspects, the STING agonist useful for the present disclosure comprises a compound having the following formula:

-continued
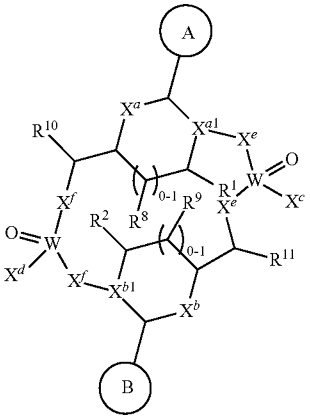
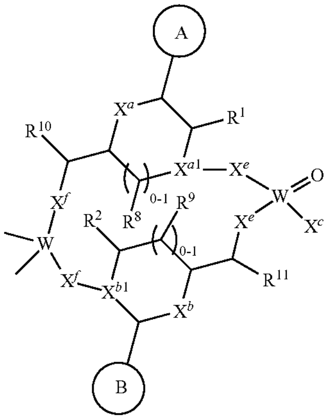
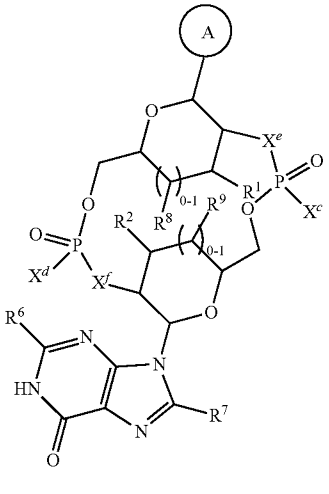
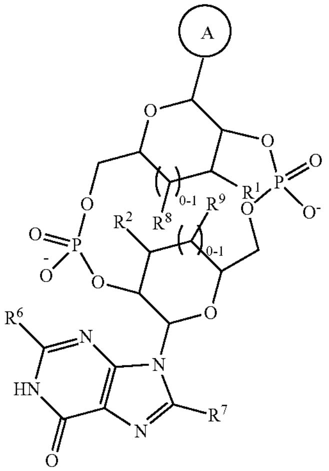
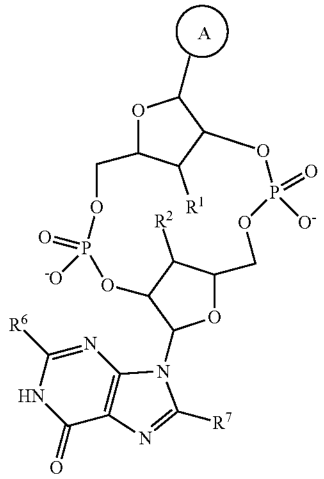
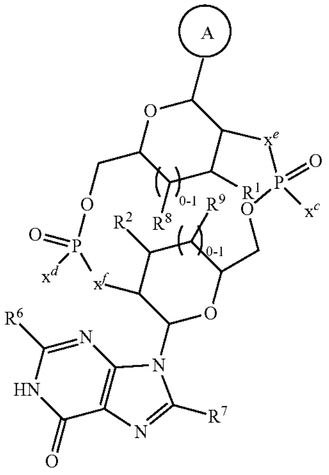

-continued

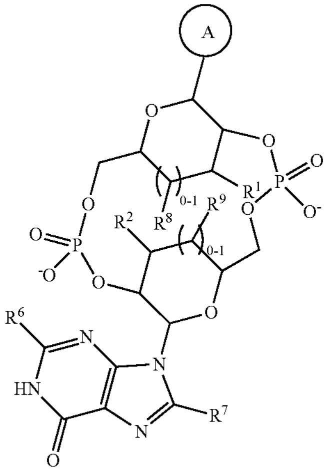

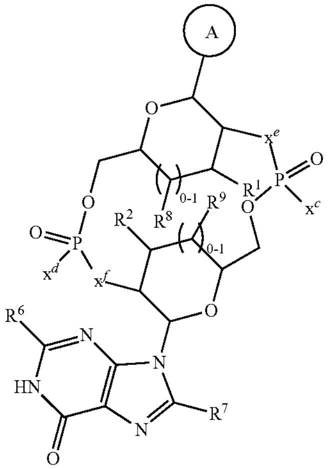

wherein each symbol is defined in WO 2014/179335, the content of which is incorporated herein by reference in its entirety.

In some aspects, the STING agonist useful for the present disclosure comprises a compound having the following formula:

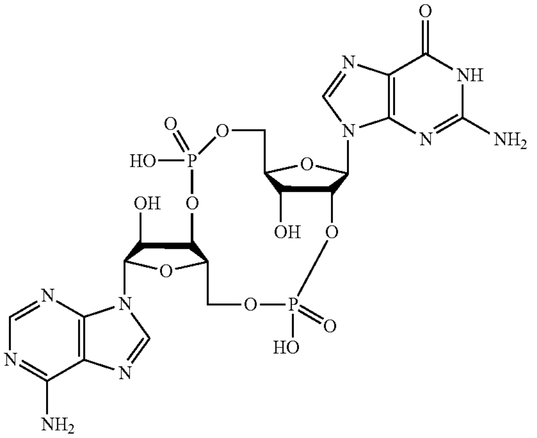

described in WO 2015/017652, the content of which is incorporated herein by reference in its entirety.

In some aspects, the STING agonist useful for the present disclosure comprises a compound having the following formula:

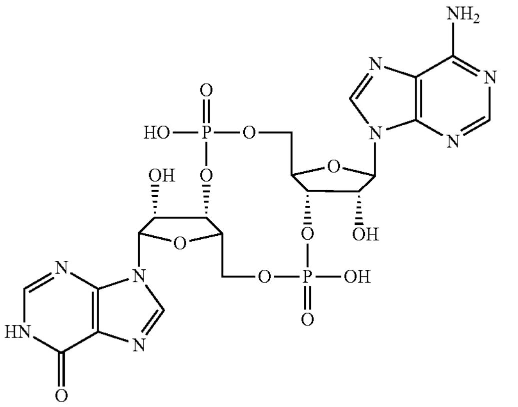 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

described in WO 2016/096577, the content of which is incorporated herein by reference in its entirety.

In some aspects, the STING agonist useful for the present disclosure comprises a compound having the following formula:

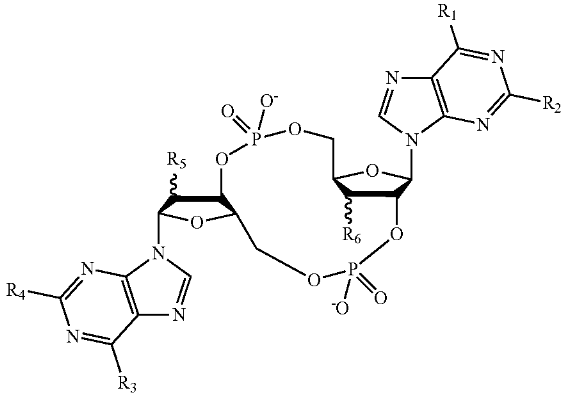

wherein each symbol is defined in WO 2016/120305, the content of which is incorporated herein by reference in its entirety.

In some aspects, the STING agonist useful for the present disclosure comprises a compound having the following formula:

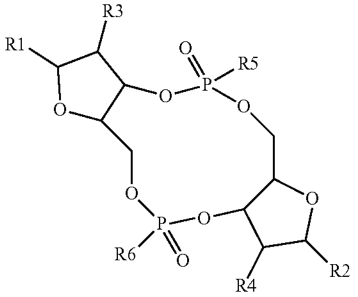

wherein each symbol is defined in WO 2016/145102, the content of which is incorporated herein by reference in its entirety.

In some aspects, the STING agonist useful for the present disclosure comprises a compound having the following formula:

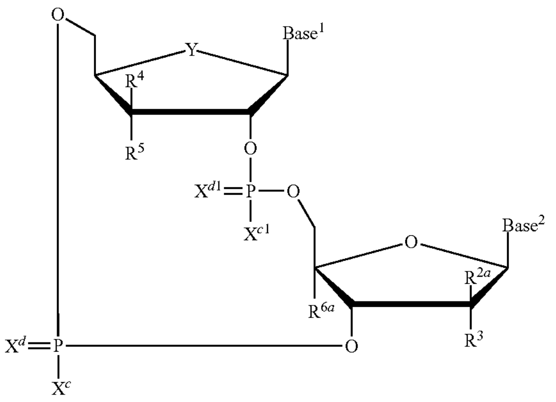

wherein each symbol is defined in WO 2017/027646, the content of which is incorporated herein by reference in its entirety.

In some aspects, the STING agonist useful for the present disclosure comprises a compound having the following formula:

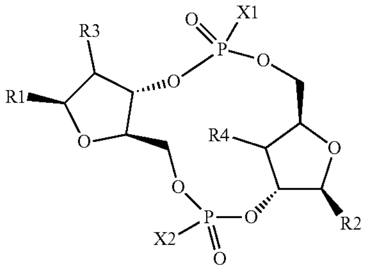

wherein each symbol is defined in WO 2017/075477, the content of which is incorporated herein by reference in its entirety.

In some aspects, the STING agonist useful for the present disclosure comprises a compound having the following formula:

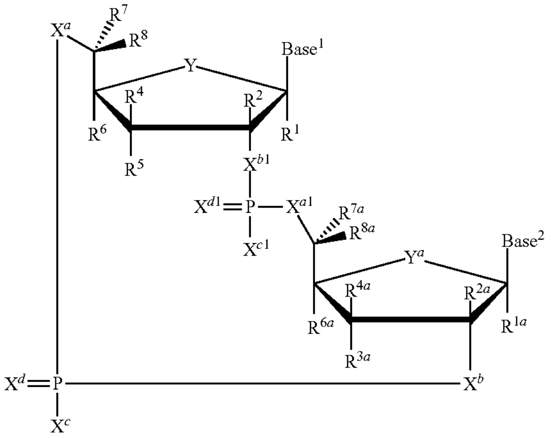

wherein each symbol is defined in WO 2017/027645, the content of which is incorporated herein by reference in its entirety.

In some aspects, the STING agonist useful for the present disclosure comprises a compound having the following formula:

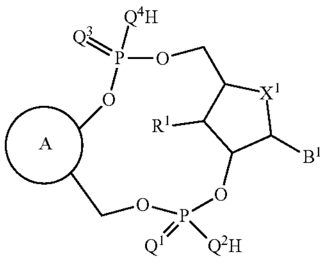

wherein each symbol is defined in WO 2018/100558, the content of which is incorporated herein by reference in its entirety.

In some aspects, the STING agonist useful for the present disclosure comprises a compound having the following formula:

(I-N)

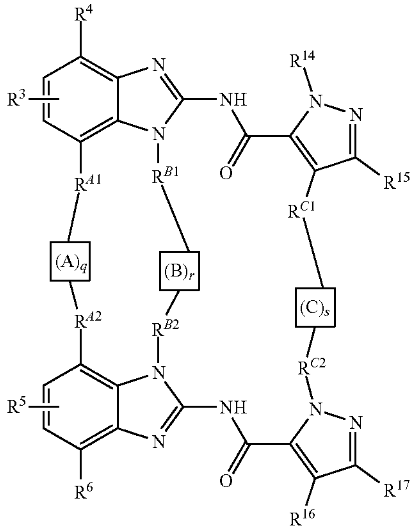

wherein each symbol is defined in WO 2017/175147, the content of which is incorporated herein by reference in its entirety.

In some aspects, the STING agonist useful for the present disclosure comprises a compound having the following formula:

(I)

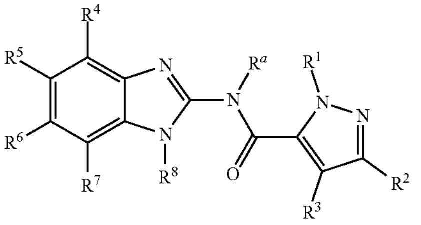

or

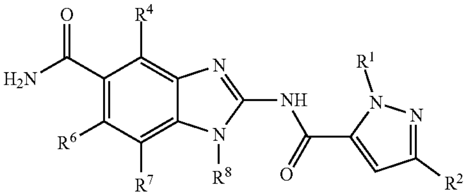

wherein each symbol is defined in WO 2017/175156, the content of which is incorporated herein by reference in its entirety.

In some aspects, the STING agonist useful for the present disclosure is CL606, CL611, CL602, CL655, CL604, CL609, CL614, CL656, CL647, CL626, CL629, CL603, CL632, CL633, CL659, or a pharmaceutically acceptable salt thereof. In some aspects, the STING agonist useful for the present disclosure is CL606 or a pharmaceutically acceptable salt thereof. In some aspects, the STING agonist useful for the present disclosure is CL611 or a pharmaceutically acceptable salt thereof. In some aspects, the STING agonist useful for the present disclosure is CL602 or a pharmaceutically acceptable salt thereof. In some aspects, the STING agonist useful for the present disclosure is CL655 or a pharmaceutically acceptable salt thereof. In some aspects, the STING agonist useful for the present disclosure is CL604 or a pharmaceutically acceptable salt thereof. In some aspects, the STING agonist useful for the present disclosure is CL609 or a pharmaceutically acceptable salt thereof. In some aspects, the STING agonist useful for the present disclosure is CL614 or a pharmaceutically acceptable salt thereof. In some aspects, the STING agonist useful for the present disclosure is CL656 or a pharmaceutically acceptable salt thereof. In some aspects, the STING agonist useful for the present disclosure is CL647 or a pharmaceutically acceptable salt thereof. In some aspects, the STING agonist useful for the present disclosure is CL626 or a pharmaceutically acceptable salt thereof. In some aspects, the STING agonist useful for the present disclosure is CL629 or a pharmaceutically acceptable salt thereof. In some aspects, the STING agonist useful for the present disclosure is CL603 or a pharmaceutically acceptable salt thereof. In some aspects, the STING agonist useful for the present disclosure is CL632 or a pharmaceutically acceptable salt thereof. In some aspects, the STING agonist useful for the present disclosure is CL633 or a pharmaceutically acceptable salt thereof. In some aspects, the STING agonist useful for the present disclosure is CL659 or a pharmaceutically acceptable salt thereof.

In some aspects, the EV, e.g., exosome, comprises a cyclic dinucleotide STING agonist and/or a non-cyclic dinucleotide STING agonist. In some aspects, when several cyclic dinucleotide STING agonist are present on an EV, e.g., exosome, disclosed herein, such STING agonists can be the same or they can be different. In some aspects, when several non-cyclic dinucleotide STING agonist are present, such STING agonists can be the same or they can be different. In some aspects, an EV, e.g., exosome, composition of the present disclosure can comprise two or more populations of EVs, e.g., exosomes, wherein each population of EVs, e.g., exosomes, comprises a different STING agonist or combination thereof.

The STING agonists can also be modified to increase encapsulation (i.e., loading) of the agonist in an extracellular vesicle or EV (e.g., either unbound in the lumen). In some aspects, the STING agonists are linked to a scaffold moiety, e.g., Scaffold Y. In certain aspects, the modification allows better expression of the STING agonist on the exterior surface of the EV, e.g., exosome, (e.g., linked to a scaffold moiety disclosed herein, e.g., Scaffold X). This modification can include the addition of a lipid binding tag by treating the agonist with a chemical or enzyme, or by physically or chemically altering the polarity or charge of the STING agonist. The STING agonist can be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications can be practiced. The modification can increase encapsulation (i.e., loading) of the agonist in the EV (e.g., exosome) by between about 2-fold and about 10,000 fold, between about 10-fold and about 1,000 fold, or between about 100-fold and about 500-fold compared to encapsulation (i.e., loading) of an unmodified agonist. The modification can increase encapsulation (i.e., loading) of the agonist in the EV by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about, 2000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to encapsulation (i.e., loading) of an unmodified agonist.

In some aspects, STING agonists can be modified to allow for better expression of the agonists on the surface of the EV (e.g., exterior and/or luminal surface of the EV, e.g., exosome, (e.g., linked to a scaffold moiety disclosed herein, e.g., Scaffold X and/or Scaffold Y)). Any of the modifications described above can be used. The modification can increase expression of the agonist in the EV, e.g., on the surface and/or luminal surface of the exosome, by about between 2-fold and 10,000-fold, about between 10-fold and 1,000-fold, or about between 100-fold and 500-fold compared to corresponding expression of an unmodified agonist. The modification can increase expression of the agonist on the exterior surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist. The modification can increase expression of the agonist on the luminal surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist.

The concentration of the STING agonist associated with the EV (e.g., exosome) can be about 0.01 μM to about 1000 μM. The concentration of the associated STING agonist can be between about 0.01-0.05 μM, between about 0.05-0.1 μM, between about 0.1-0.5 μM, between about 0.5-1 μM, between about 1-5 μM, between about 5-10 μM, between about 10-15 μM, between about 15-20 μM, between about 20-25 μM, between about 25-30 μM, between about 30-35 μM, between about 35-40 μM, between about 45-50 μM, between about 55-60 μM, between about 65-70 μM, between about 70-75 μM, between about 75-80 μM, between about 80-85 μM, between about 85-90 μM, between about 90-95 μM, between about 95-100 μM, between about 100-150 μM, between about 150-200 μM, between about 200-250 μM, between about 250-300 μM, between about 300-350 μM, between about 250-400 μM, between about 400-450 μM, between about 450-500 μM, between about 500-550 μM, between about 550-600 μM, between about 600-650 μM, between about 650-700 μM, between about 700-750 μM, between about 750-800 μM, between about 800-850 μM, between about 805-900 μM, between about 900-950 μM, or between about 950-1000 μM. The concentration of the associated STING agonist can be equal to or greater than about 0.01 μM, about 0.1 μM, about 0.5 μM, about 1 μM, about 5 μM, about 10 μM, about 15 μM, about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 150 μM, about 200 μM, about 250 μM, about 300 μM, about 350 μM, about 400 μM, about 450 μM, about 500 μM, about 550 μM, about 600 μM, about 650 μM, about 700 μM, about 750 μM, about 800 μM, about 850 μM, about 900 μM, about 950 μM, or about 1,000 μM.

In some aspects, an adjuvant is a TLR agonist. Non-limiting examples of TLR agonists include: TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), and combinations thereof. Non-limiting examples of TLR agonists can be found at WO2008115319A2, US20130202707A1, US20120219615A1, US20100029585A1, WO2009030996A1, WO2009088401A2, and WO2011014246A1, each of which are incorporated by reference in its entirety.

In some aspects, an adjuvant is an inflammatory mediator.

In some aspects, an antigen is expressed on the exterior surface or in the lumen (e.g., on the luminal surface) of the EV, e.g., exosome. In some aspects, an adjuvant is expressed on the exterior surface or in the luminal surface of the EVs, e.g., exosomes, directly connected to the lipid bilayer. In such aspects, the antigen and/or the adjuvant can be linked to a scaffold moiety (e.g., Scaffold X and/or Scaffold Y).

In some aspects, an EVs, e.g., exosomes, described herein comprises a first scaffold moiety. In certain aspects, the antigen is linked to the first scaffold moiety. In other aspects, the adjuvant is linked to the first scaffold moiety. In further aspects, both the antigen and the adjuvant are linked to the first scaffold moiety. In some aspects, an EVs, e.g., exosomes, further comprises a second scaffold moiety. In certain aspects, the antigen is linked to the first scaffold moiety, and the adjuvant is linked to the second scaffold moiety. In some aspects, the first scaffold moiety and the second scaffold moiety are the same (e.g., both Scaffold X or both Scaffold Y). In other aspects, the first scaffold moiety and the second scaffold moiety are different (e.g., first scaffold moiety is Scaffold X and the second scaffold moiety is Scaffold Y; or first scaffold moiety is Scaffold Y and the second scaffold moiety is Scaffold X).

Non-limiting examples of Scaffold X include: prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B). In certain aspects, Scaffold X is a whole protein. In other aspects, Scaffold X is a protein fragment (e.g., functional fragment).

In other aspects, the scaffold moiety useful for the present disclose, a first scaffold moiety, a second scaffold moiety, and/or a third scaffold moiety, includes a conventional exosome protein, including, but not limiting, tetraspanin molecules (e.g., CD63, CD81, CD9 and others), lysosome-associated membrane protein 2 (LAMP2 and LAMP2B), platelet-derived growth factor receptor (PDGFR), GPI anchor proteins, lactadherin and fragments thereof, peptides that have affinity to any of these proteins or fragments thereof, or any combination thereof.

Non-limiting examples of Scaffold Y include: the myristoylated alanine rich Protein Kinase C substrate (MARCKS) protein; myristoylated alanine rich Protein Kinase C substrate like 1 (MARCKSL1) protein; and brain acid soluble protein 1 (BASP1) protein. In some aspects, Scaffold Y is a whole protein. In certain aspects, Scaffold Y is a protein fragment (e.g., functional fragment).

In some aspects, the antigen is linked to a first scaffold moiety on the luminal surface of the EVs, e.g., exosomes, and the adjuvant is in the lumen of the EV, e.g., exosome. As used herein, when a molecule (e.g., antigen or adjuvant) is described as "in the lumen" of the e.g. EV, e.g., exosome, it means that the molecule is not linked to a scaffold moiety described herein. In some aspects, the antigen is in the lumen of the EV, e.g., exosome, and the adjuvant is linked to a first scaffold moiety on the luminal surface of the EV, e.g., exosome. In such aspects, the first scaffold moiety can be Scaffold X or Scaffold Y.

In some aspects, the antigen is linked to a first scaffold moiety on the luminal surface of the EV, e.g., exosome, and the adjuvant is linked to a second scaffold moiety on the exterior surface of the EV, e.g., exosome. In some aspects, the adjuvant is linked to a first scaffold moiety on the luminal surface of the EV, e.g., exosome, and the antigen is linked to a second scaffold moiety on the exterior surface of the EV, e.g., exosome. In these aspects, the first scaffold moiety can be Scaffold Y, and the second scaffold moiety can be Scaffold X. In other aspects, each of the first scaffold moiety and the second scaffold moiety can be Scaffold X.

In some aspects, the antigen is linked to a first scaffold moiety on the exterior surface of the EVs, e.g., exosomes, and the adjuvant is linked to a second scaffold moiety on the luminal surface of the EV, e.g., exosome. In other aspects, the adjuvant is linked to a first scaffold moiety on the exterior surface of the EVs, e.g., exosomes, and the antigen is linked to a second scaffold moiety on the luminal surface of the EV, e.g., exosome. In such aspects, the first scaffold moiety is Scaffold X, and the second scaffold moiety is Scaffold Y; or each of the first scaffold moiety and the second scaffold moiety is Scaffold X.

In some aspects, the antigen is in the lumen of the EVs, e.g., exosomes, and the adjuvant is in the lumen of the EV, e.g., exosome.

In some aspects, the antigen is linked to a first scaffold moiety on the exterior surface of the EVs, e.g., exosomes, and the adjuvant is linked to a second scaffold moiety on the exterior surface of the EV, e.g., exosome. In other aspects, the adjuvant is linked to a first scaffold moiety on the exterior surface of the EVs, e.g., exosomes, and the antigen is linked to a second scaffold moiety on the exterior surface of the EV, e.g., exosome. In some aspects, the first scaffold moiety and the second scaffold moiety are Scaffold X.

In some aspects, the antigen is linked to a first scaffold moiety on the exterior surface of the EVs, e.g., exosomes, and the adjuvant is in the lumen of the EV, e.g., exosome. In some aspects, the antigen is in the lumen of the EVs, e.g., exosomes, and the adjuvant is linked to a first scaffold moiety on the exterior surface of the EV, e.g., exosome. In such aspects, the first scaffold moiety can be Scaffold X.

In some aspects, the antigen is linked to a first scaffold moiety on the exterior surface of the EV, e.g., exosome, and the adjuvant is linked to the first scaffold moiety on the luminal surface of the EV, e.g., exosome. In other aspects, the antigen is linked to a first scaffold moiety on the luminal surface of the EV, e.g., exosome, and the adjuvant is linked to the first scaffold moiety on the exterior surface of the EV, e.g., exosome. In these aspects, the first scaffold moiety can be Scaffold X.

Non-limiting examples of specific aspects, include EVs, e.g., exosomes comprising (i) an antigen and (ii) an adjuvant, wherein:

(a) the antigen is linked to a first Scaffold Y on the luminal surface of the EV, e.g., exosome, and the adjuvant is linked to a second Scaffold Y on the luminal surface of the EV, e.g., exosome;

(b) the antigen is linked to a Scaffold Y on the luminal surface of the EV, e.g., exosome, and the adjuvant is in the lumen of the EV, e.g., exosome, not linked to any scaffold moiety;

(c) the antigen is in the lumen of the EV, e.g., exosome, not linked to any scaffold moiety, and the adjuvant is linked to a Scaffold Y on the luminal surface of the EV, e.g., exosome;

(d) the antigen is linked to a Scaffold Y on the luminal surface of the EV, e.g., exosome, and the adjuvant is linked to a Scaffold X on the exterior surface of the EV, e.g., exosome;

(e) the antigen is in the lumen of the EV, e.g., exosome, not linked to any scaffold moiety, and the adjuvant is linked to a Scaffold X on the exterior surface of the EV, e.g., exosome;

(f) the antigen is linked to a Scaffold Y on the luminal surface of the EV, e.g., exosome, and the adjuvant is linked to a Scaffold X on the luminal surface of the EV, e.g., exosome;

(g) the antigen is in the lumen of the EV, e.g., exosome, not linked to any scaffold moiety, and the adjuvant is linked to a Scaffold X on the luminal surface of the EV, e.g., exosome;

(h) the antigen is linked to a Scaffold X on the luminal surface of the EV, e.g., exosome, and the adjuvant is linked to the Scaffold X on the exterior surface of the EV, e.g., exosome;

(i) the antigen is linked to a first Scaffold X on the exterior surface of the EV, e.g., exosome, and the adjuvant is linked to a second Scaffold X on the exterior surface of the EV, e.g., exosome;

(j) the antigen is linked to a Scaffold X on the exterior surface of the EV, e.g., exosome, and the adjuvant is linked to a Scaffold Y on the luminal surface of the EV, e.g., exosome;

(k) the antigen is linked to a Scaffold X on the exterior surface of the EV, e.g., exosome, and the adjuvant is in the lumen of the EV, e.g., exosome, not linked to any scaffold moiety;

(l) the antigen is linked to a Scaffold X on the exterior surface of the EV, e.g., exosome, and the adjuvant is linked to the Scaffold X on the luminal surface of the EV, e.g., exosome;

(m) the antigen is linked to a first Scaffold X on the luminal surface of the EV, e.g., exosome, and the adjuvant is linked to a second Scaffold X on the luminal surface of the EV, e.g., exosome;

(n) the antigen is linked to a Scaffold X on the luminal surface of the EV, e.g., exosome, and the adjuvant is linked to a Scaffold Y on the luminal surface of the EV, e.g., exosome;

(o) the antigen is linked to a Scaffold X on the luminal surface of the EV, e.g., exosome, and the adjuvant is in the lumen of the EV, e.g., exosome, not linked to any scaffold moiety;

(p) the antigen is linked to a first Scaffold X on the exterior surface of the EV, e.g., exosome, and the adjuvant is linked to a second Scaffold X on the luminal surface of the EV, e.g., exosome;

(q) the antigen is linked to a first Scaffold X on the luminal surface of the EV, e.g., exosome, and the adjuvant is linked to a second Scaffold X on the exterior surface of the EV, e.g., exosome;

(r) the antigen is in the lumen of the EV, e.g., exosome, not linked to any scaffold moiety, and the adjuvant is in the lumen of the EV, e.g., exosome, not linked to any scaffold moiety;

(s) the antigen is linked directly to the luminal surface of the EV, e.g., exosome, and the adjuvant is linked directly to the luminal surface of the EV, e.g., exosome;

(t) the antigen is linked directly to the luminal surface of the EV, e.g., exosome, and the adjuvant is in the lumen of the EV, e.g., exosome;

(u) the antigen is linked directly to the luminal surface of the EV, e.g., exosome, and the adjuvant is linked to a Scaffold Y on the luminal surface of the EV, e.g., exosome;

(v) the antigen is linked directly to the luminal surface of the EV, e.g., exosome, and the adjuvant is linked to a Scaffold X on the luminal surface of the EV, e.g., exosome;

(w) the antigen is linked directly to the luminal surface of the EV, e.g., exosome, and the adjuvant is linked directly to the exterior of the EV, e.g., exosome;

(x) the antigen is linked directly to the luminal surface of the EV, e.g., exosome, and the adjuvant is linked to a Scaffold X on the exterior of the EV, e.g., exosome;

(y) the antigen is linked to a Scaffold Y on the luminal surface of the EV, e.g., exosome, and the adjuvant is linked directly to the luminal surface of the EV, e.g., exosome;

(z) the antigen is linked to a Scaffold Y on the luminal surface of the EV, e.g., exosome, and the adjuvant is linked directly to the exterior of the EV, e.g., exosome;

(aa) the antigen is linked to a Scaffold X on the luminal surface of the EV, e.g., exosome, and the adjuvant is linked directly to the luminal surface of the EV, e.g., exosome;

(bb) the antigen is linked to a Scaffold X on the luminal surface of the EV, e.g., exosome, and the adjuvant is linked directly to the exterior of the EV, e.g., exosome;

(cc) the antigen is in the lumen of the EV, e.g., exosome, and the adjuvant is linked directly to the luminal surface of the EV, e.g., exosome; or (dd) the antigen is in the lumen of the EV, e.g., exosome, and the adjuvant is linked directly to the exterior of the EV, e.g., exosome.

In some aspects, an EV, e.g., exosome of the present disclosure comprises (i) an antigen and (ii) an adjuvant, wherein the antigen is linked to a first Scaffold Y on the luminal surface of the EV, e.g., exosome, and the adjuvant is linked to a second Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold Y on the luminal surface of the EV, e.g., exosome, and the adjuvant is in the lumen of the EV, e.g., exosome, not linked to any scaffold moiety. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold Y on the luminal surface of the EV, e.g., exosome, and the adjuvant is linked to a Scaffold X on the exterior surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold X on the exterior surface of the EV, e.g., exosome. In some aspects, an EV, e.g., exosome of the present disclosure comprises (i) an antigen and (ii) an adjuvant, wherein the antigen is linked to a Scaffold Y on the luminal surface of the, e.g., exosome, and the adjuvant is linked to a Scaffold X on the luminal surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold X on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is linked to the Scaffold X on the exterior surface of the EV, e.g., exosome. In some aspects, an EV, e.g., exosome, of the present disclosure comprises (i) an antigen and (ii) an adjuvant, wherein the antigen is linked to a first Scaffold X on the exterior surface of the EV, e.g., exosome, and the adjuvant is linked to a second Scaffold X on the exterior surface of the EV, e.g., exosome. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is in the lumen of the EV, e.g., exosome, not linked to any scaffold moiety. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is linked to the Scaffold X on the luminal surface of the EV, e.g., exosome. In some aspects, an EV, e.g., exosome of the present disclosure comprises (i) an antigen and (ii) an adjuvant, wherein the antigen is linked to a first Scaffold X on the luminal surface of the EV, e.g., exosome, and the adjuvant is linked to a second Scaffold X on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is in the lumen of the EV, e.g., exosome not linked to any scaffold moiety. In some aspects, an EV, e.g., exosome of the present disclosure comprises (i) an antigen and (ii) an adjuvant, wherein the antigen is linked to a first Scaffold X on the exterior surface of the EV, e.g., exosome, and the adjuvant is linked to a second Scaffold X on the luminal surface of the EV, e.g., exosome. In some aspects, an EV, e.g., exosome of the present disclosure comprises (i) an antigen and (ii) an adjuvant, wherein the antigen is linked to a first Scaffold X on the luminal surface of the EV, e.g., exosome, and the adjuvant is linked to a second Scaffold X on the exterior surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is in the lumen of the EV, e.g., exosome, not linked to any scaffold moiety. In some aspects, an EV, e.g., exosome, comprises (i) an antigen and (ii) an adjuvant, wherein the antigen is linked directly to the luminal surface of the EV, and the adjuvant is linked directly to the luminal surface of the EV. In some aspects, an EV, e.g., exosome, comprises (i) an antigen and (ii) an adjuvant, wherein the antigen is linked directly to the luminal surface of the EV, and the adjuvant is in the lumen of the EV. In some aspects, an EV, e.g., exosome, comprises (i) an antigen and (ii) an adjuvant, wherein the antigen is linked directly to the luminal surface of the EV, and the adjuvant is linked to a Scaffold Y on the luminal surface of the EV. In some aspects, an EV, e.g., exosome, comprises (i) an antigen and (ii) an adjuvant, wherein the antigen is linked directly to the luminal surface of the EV, and the adjuvant is linked to a Scaffold X on the luminal surface of the EV. In some aspects, an EV, e.g., exosome, comprises (i) an antigen and (ii) an adjuvant, wherein the antigen is linked directly to the luminal surface of the EV, and the adjuvant is linked directly to the exterior of the EV. In some aspects, an EV, e.g., exosome, comprises (i) an antigen and (ii) an adjuvant, wherein the antigen is linked directly to the luminal surface of the EV, and the adjuvant is linked to a Scaffold X on the exterior of the EV. In some aspects, an EV, e.g., exosome, comprises (i) an antigen and (ii) an adjuvant, wherein the antigen is linked to a Scaffold Y on the luminal surface of the EV, and the adjuvant is linked directly to the luminal surface of the EV. In some aspects, an EV, e.g., exosome, comprises (i) an antigen and (ii) an adjuvant, wherein the antigen is linked to a Scaffold Y on the luminal surface of the EV, and the adjuvant is linked directly to the exterior of the EV. In some aspects, an EV, e.g., exosome, comprises (i) an antigen and (ii) an adjuvant, wherein the antigen is linked to a Scaffold X on the luminal surface of the EV, and the adjuvant is linked directly to the luminal surface of the EV. In some aspects, an EV, e.g., exosome, comprises (i) an antigen and (ii) an adjuvant, wherein the antigen is linked to a Scaffold X on the luminal surface of the EV, and the adjuvant is linked directly to the exterior of the EV. In some aspects, an EV, e.g., exosome, comprises (i) an antigen and (ii) an adjuvant, wherein the antigen is in the lumen of the EV, and the adjuvant is linked directly to the luminal surface of the EV. In some aspects, an EV, e.g., exosome, comprises (i) an antigen and (ii) an adjuvant, wherein the antigen is in the lumen of the EV, and the adjuvant is linked directly to the exterior of the EV.

In some aspects, an adjuvant and/or antigen can be modified to increase encapsulation (i.e., loading) in an EV, e.g., exosome. This modification can include the addition of a lipid binding tag by treating the agonist (i.e., adjuvant and/or antigen) with a chemical or enzyme, or by physically or chemically altering the polarity or charge of the adjuvant and/or antigen. The adjuvant and/or antigen can be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications can be practiced. The modification can increase encapsulation (i.e., loading) of the adjuvant and/or antigen in the EV, e.g., exosome by between about 2-fold and about 10,000-fold, between about 10-fold and 1,000-fold, or between about 100-fold and about 500-fold compared to encapsulation (i.e., loading) of an unmodified agonist (i.e., adjuvant and/or antigen). The modification can increase encapsulation (i.e., loading) of the adjuvant and/or antigen in the EV, e.g., exosome by at least about 2-fold, about 5-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold, about 700-fold, about 800-fold, about 900-fold, about 1,000-fold, about 2,000-fold, about 3,000-fold, about 4,000-fold, about 5,000-fold, about 6,000-fold, about 7,000-fold, about 8,000-fold, about 9,000-fold, or about 10,000-fold compared to encapsulation (i.e., loading) of an unmodified adjuvant and/or antigen.

In some aspects, an adjuvant and/or antigen can be modified to allow for better expression on the surface of the EV (e.g., exterior and/or luminal surface of the EV, e.g., linked to a scaffold moiety disclosed herein, e.g., Scaffold X and/or Scaffold Y). Any of the modifications described above can be used. The modification can increase expression of the agonist in the EV, e.g., on the surface and/or luminal surface of the exosome, by about between 2-fold and 10,000-fold, about between 10-fold and 1,000-fold, or about between 100-fold and 500-fold compared to corresponding expression of an unmodified agonist. The modification can increase expression of the agonist on the exterior surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist. The modification can increase expression of the agonist on the luminal surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist.

In some aspects, the EV, e.g., exosome, is further modified to display an additional protein (or fragment thereof) that can help direct EV uptake (e.g., targeting moiety), activate, or block cellular pathways to enhance the combinatorial effects associated with the EV (e.g., effect of a payload loaded into an exosome, e.g., STING agonist). In certain aspects, the EV, e.g., exosome, disclosed herein further comprises a targeting moiety that can modify the distribution of the EVs in vivo or in vitro. In some aspects, the targeting moiety can be a biological molecule, such as a protein, a peptide, a lipid, or a synthetic molecule.

In some aspects, a targeting moiety of the present disclosure specifically binds to a marker for a dendritic cell. In certain aspects, the marker is expressed only on dendritic cells. In some aspects, dendritic cells comprise a progenitor (Pre) dendritic cells, inflammatory mono dendritic cells, plasmacytoid dendritic cell (pDC), a myeloid/conventional dendritic cell 1 (cDC1), a myeloid/conventional dendritic cell 2 (cDC2), inflammatory monocyte derived dendritic cells, Langerhans cells, dermal dendritic cells, lysozyme-expressing dendritic cells (LysoDCs), Kupffer cells, non-classical monocytes, or any combination thereof. Markers that are expressed on these dendritic cells are known in the art. See, e.g., Collin et al., *Immunology* 154(1):3-20 (2018). In some aspects, the targeting moiety is a protein, wherein the protein is an antibody or a fragment thereof that can specifically bind to a marker selected from DEC205, CLEC9A, CLEC6, DCIR, DC-SIGN, LOX-1, MARCO, Clec12a, Clec10a, DC-asialoglycoprotein receptor (DC-ASGPR), DC immunoreceptor 2 (DCIR2), Dectin-1, macrophage mannose receptor (MMR), BDCA-2 (CD303, Clec4c), Dectin-2, Bst-2 (CD317), Langerin, CD206, CD11b, CD11c, CD123, CD304, XCR1, AXL, Siglec 6, CD209, SIRPA, CX3CR1, GPR182, CD14, CD16, CD32, CD34, CD38, CD10, or any combination thereof. In some aspects, a marker useful for the present disclosure comprises a C-type lectin like domain. In certain aspects, a marker is Clec9a and the dendritic cell is cDC1.

In some aspects, a targeting moiety disclosed herein can bind to both human and mouse Clec9a, including any variants thereof. In some aspects, a targeting moiety of the present disclosure can bind to Clec9a from other species, including but not limited to chimpanzee, rhesus monkey, dog, cow, horse, or rat. Sequences for such Clec9a protein are known in the art. See, e.g., U.S. Pat. No. 8,426,565 B2, which is herein incorporated by reference in its entirety.

In some aspects, a targeting moiety of the present disclosure specifically binds to a marker for a T cell. In certain aspects, the T cell is a CD4+ T cell. In some aspects, the T cell is a CD8+ T cell.

In some aspects, a targeting moiety disclosed herein binds to human CD3 protein or a fragment thereof. Sequences for human CD3 protein are known in the art.

In some aspects, a targeting moiety disclosed herein can bind to both human and mouse CD3, including any variants thereof. In some aspects, a targeting moiety of the present disclosure can bind to CD3 from other species, including but not limited to chimpanzee, rhesus monkey, dog, cow, horse, or rat. Sequences for such CD3 protein are also known in the art.

In some aspects, a targeting moiety disclosed herein can allow for greater uptake of an EV (e.g., exosome) by a cell expressing a marker specific for the targeting moiety (e.g., CD3: CD4+ T cell and/or CD8+ T cell; Clec9a: dendritic cells). In some aspects, the uptake of an EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV without the targeting moiety or a non-EV delivery vehicle). In some aspects, a reference comprises an EV (e.g., exosome) that does not express a targeting moiety disclosed herein.

In some aspects, the increased uptake of an EV (e.g., exosome) disclosed herein can allow for greater immune response. Accordingly, in certain aspects, an EV (e.g., exosome) expressing a targeting moiety disclosed herein can increase an immune response (e.g., against a tumor antigen loaded onto the exosome) by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about-10,000-fold or more, compared to a reference (e.g., corresponding EV without the targeting moiety or a non-EV delivery vehicle). In some aspects, a reference comprises an EV (e.g., exosome) that does not express a targeting moiety disclosed herein. In certain aspects, an immune response is mediated by T cells (e.g., CD8+ T cells or CD4+ T cells) and/or B cells.

As described supra, a targeting moiety disclosed herein can comprise a peptide, an antibody or an antigen binding fragment thereof, a chemical compound, or any combination thereof.

In some aspects, the targeting moiety is a peptide that can specifically bind to Clec9a. See, e.g., Yan et al., *Oncotarget* 7(26): 40437-40450 (2016). For example, in certain aspects, the peptide comprises a soluble fragment of Clec9a. A non-limiting example of such a peptide is described in U.S. Pat. No. 9,988,431 B2, which is herein incorporated by reference in its entirety. In certain aspects, the peptide comprises a ligand (natural or synthetic) of Clec9a, such as those described in Ahrens et al., *Immunity* 36(4): 635-45 (2012); and Zhang et al., *Immunity* 36(4): 646-57 (2012). A non-limiting example of a peptide comprising a Clec9a ligand is described in International Publ. No. WO 2013/053008 A2, which is herein incorporated by reference in its entirety.

In some aspects, the targeting moiety is a peptide that can specifically bind to CD3. For example, in certain aspects, the peptide comprises a soluble fragment of CD3. In certain aspects, the peptide comprises a ligand (natural or synthetic) of CD3.

In some aspects, the targeting moiety is an antibody or an antigen binding fragment thereof. In certain aspects, a targeting moiety is a single-chain Fv antibody fragment. In certain aspects, a targeting moiety is a single-chain F(ab) antibody fragment. In certain aspects, a targeting moiety is a nanobody. In certain aspects, a targeting moiety is a monobody.

In some aspects, an EV (e.g., exosome) disclosed herein comprises one or more (e.g., 2, 3, 4, 5, or more) targeting moieties. In certain aspects, the one or more targeting moieties are expressed in combination with other exogenous biologically active molecules disclosed herein (e.g., therapeutic molecule, adjuvant, or immune modulator). In some aspects, the one or more targeting moieties can be expressed on the exterior surface of the EV, e.g., exosome. Accordingly, in certain aspects, the one or more targeting moieties are linked to a scaffold moiety (e.g., Scaffold X) on the exterior surface of the EV, e.g., exosome. When the one or more targeting moieties are expressed in combination with other exogenous biologically active molecules (e.g., therapeutic molecule, adjuvant, or immune modulator), the other exogenous biologically active molecules can be expressed on the surface (e.g., exterior surface or luminal surface) or in the lumen of the EV, e.g., exosome.

The producer cell can be modified to comprise an additional exogenous sequence encoding for the additional protein or fragment thereof. Alternatively, the additional protein or fragment thereof can be covalently linked or conjugated to the EV, e.g., exosome, via any appropriate linking chemistry known in the art. Non-limiting examples of appropriate linking chemistry include amine-reactive groups, carboxyl-reactive groups, sulfhydryl-reactive groups, aldehyde-reactive groups, photoreactive groups, ClickIT chemistry, biotin-streptavidin or other avidin conjugation, or any combination thereof.

II.C Immune Modulator

In some aspects, an EV, e.g., exosome, of the present disclosure can comprise an immune modulator (e.g., along with an antigen and/or other payloads disclosed herein). In some aspects, an EV (e.g., exosome) disclosed herein comprises multiple immune modulators. In certain aspects, each of the multiple immune modulators is different. In some aspects, an EV (e.g., exosome) disclosed herein comprises at least 2, 3, 4, 5, 6, 7, 8, 9, 10 or more different immune modulators.

In certain aspects, an EV (e.g., exosome) comprises the one or more immune modulators in combination with one or more additional payloads (e.g., antigen and/or adjuvants). In some aspects, an EV (e.g., exosome) can comprise one or more additional moieties (e.g., targeting moieties). For instance, in certain aspects, an EV (e.g., exosome) disclosed described herein can comprise (i) one or more immune modulators, (ii) one or more additional payloads (e.g., antigen and/or adjuvant), and (iii) one or more targeting moieties.

In some aspects, an immune modulator can be expressed on the surface (e.g., exterior surface or luminal surface) or in the lumen of the EV, e.g., exosome. Accordingly, in certain aspects, the immune modulator is linked to a scaffold moiety (e.g., Scaffold X) on the exterior surface of the EV, e.g., exosome or on the luminal surface of the EV, e.g., exosome. In other aspects, the immune modulator is linked to a scaffold moiety (e.g., Scaffold Y) on the luminal surface of the EV, e.g., exosome. In further aspects, the immune modulator is in the lumen of the exosome (i.e., not linked to either Scaffold X or Scaffold Y). In some aspects, an immune modulator can be directly linked (i.e., without the use of a scaffold moiety) to the exterior surface and/or luminal surface of an EV (e.g., exosome).

Non-limiting examples of such aspects, include EVs, e.g., exosomes, comprising (i) an antigen and (ii) an immune modulator, wherein:

(a) the antigen is linked to a first Scaffold Y on the luminal surface of the EV, e.g., exosome, and the immune modulator is linked to a second Scaffold Y on the luminal surface of the EV, e.g., exosome;

(b) the antigen is linked to a Scaffold Y on the luminal surface of the EV, e.g., exosome, and the immune modulator is in the lumen of the EV, e.g., exosome, not linked to any scaffold moiety;

(c) the antigen is in the lumen of the EV, e.g., exosome, not linked to any scaffold moiety, and the immune modulator is linked to a Scaffold Y on the luminal surface of the EV, e.g., exosome;

(d) the antigen is linked to a Scaffold Y on the luminal surface of the EV, e.g., exosome, and the immune modulator is linked to a Scaffold X on the exterior surface the EV, e.g., exosome;

(e) the antigen is linked to a Scaffold X on the luminal surface of the EV, e.g., exosome, and the immune modulator is linked to a Scaffold Y on the luminal surface of the EV, e.g., exosome;

(f) the antigen is linked to a Scaffold X on the luminal surface of the EV, e.g., exosome, and the immune modulator is linked to a Scaffold Y on the luminal surface of the EV, e.g., exosome; or (g) the antigen is linked to a Scaffold X on the exterior surface of the EV, e.g., exosome, and the immune modulator is linked to a Scaffold Y on the luminal surface of the EV, e.g., exosome.

Non-limiting examples of specific aspects, include EVs, e.g., exosomes, comprising (i) an antigen and (ii) an immune modulator, wherein:

(a) the antigen is linked to a first Scaffold Y on the luminal surface of the EV, e.g., exosome, and the immune modulator is linked to a second Scaffold Y on the luminal surface of the EV, e.g., exosome;

(b) the antigen is linked to a Scaffold Y on the luminal surface of the EV, e.g., exosome, and the immune modulator is in the lumen of the EV, e.g., exosome, not linked to any scaffold moiety;

(c) the antigen is in the lumen of the EV, e.g., exosome, not linked to any scaffold moiety, and the immune modulator is linked to a Scaffold Y on the luminal surface of the EV, e.g., exosome;

(d) the antigen is linked to a Scaffold Y on the luminal surface of the EV, e.g., exosome, and the immune modulator is linked to a Scaffold X on the exterior surface of the EV, e.g., exosome;

(e) the antigen is in the lumen of the EV, e.g., exosome, not linked to any scaffold moiety, and the immune modulator is linked to a Scaffold X on the exterior surface of the EV, e.g., exosome;

(f) the antigen is linked to a Scaffold Y on the luminal surface of the EV, e.g., exosome, and the immune modulator is linked to a Scaffold X on the luminal surface of the EV, e.g., exosome;

(g) the antigen is in the lumen of the EV, e.g., exosome, not linked to any scaffold moiety, and the immune modulator is linked to a Scaffold X on the luminal surface of the EV, e.g., exosome;

(h) the antigen is linked to a Scaffold X on the luminal surface of the EV, e.g., exosome, and the immune modulator is linked to the Scaffold X on the exterior surface of the EV, e.g., exosome;

(i) the antigen is linked to a first Scaffold X on the exterior surface of the EV, e.g., exosome, and the immune modulator is linked to a second Scaffold X on the exterior surface of the EV, e.g., exosome;

(j) the antigen is linked to a Scaffold X on the exterior surface of the EV, e.g., exosome, and the immune modulator is linked to a Scaffold Y on the luminal surface of the EV, e.g., exosome;

(k) the antigen is linked to a Scaffold X on the exterior surface of the EV, e.g., exosome, and the immune modulator is in the lumen of the EV, e.g., exosome, not linked to any scaffold moiety;

(l) the antigen is linked to a Scaffold X on the exterior surface of the EV, e.g., exosome, and the immune modulator is linked to the Scaffold X on the luminal surface of the EV, e.g., exosome;

(m) the antigen is linked to a first Scaffold X on the luminal surface of the EV, e.g., exosome, and the immune modulator is linked to a second Scaffold X on the luminal surface of the EV, e.g., exosome;

(n) the antigen is linked to a Scaffold X on the luminal surface of the EV, e.g., exosome, and the immune modulator is linked to a Scaffold Y on the luminal surface of the EV, e.g., exosome;
(o) the antigen is linked to a Scaffold X on the luminal surface of the EV, e.g., exosome, and the immune modulator is in the lumen of the EV, e.g., exosome, not linked to any scaffold moiety;
(p) the antigen is linked to a first Scaffold X on the exterior surface of the EV, e.g., exosome, and the immune modulator is linked to a second Scaffold X on the luminal surface of the EV, e.g., exosome;
(q) the antigen is linked to a first Scaffold X on the luminal surface of the EV, e.g., exosome, and the immune modulator is linked to a second Scaffold X on the exterior surface of the EV, e.g., exosome;
(r) the antigen is in the lumen of the EV, e.g., exosome, not linked to any scaffold moiety, and the immune modulator is in the lumen of the EV, e.g., exosome, not linked to any scaffold moiety;
(s) the antigen is linked directly to the luminal surface of the EV, e.g., exosome, and the immune modulator is linked directly to the luminal surface of the EV, e.g., exosome;
(t) the antigen is linked directly to the luminal surface of the EV, e.g., exosome, and the immune modulator is in the lumen of the EV, e.g., exosome;
(u) the antigen is linked directly to the luminal surface of the EV, e.g., exosome, and the immune modulator is linked to a Scaffold Y on the luminal surface of the EV, e.g., exosome;
(v) the antigen is linked directly to the luminal surface of the EV, e.g., exosome, and the immune modulator is linked to a Scaffold X on the luminal surface of the EV, e.g., exosome;
(w) the antigen is linked directly to the luminal surface of the EV, e.g., exosome, and the immune modulator is linked directly to the exterior of the EV, e.g., exosome;
(x) the antigen is linked directly to the luminal surface of the EV, e.g., exosome, and the immune modulator is linked to a Scaffold X on the exterior of the EV, e.g., exosome;
(y) the antigen is linked to a Scaffold Y on the luminal surface of the EV, e.g., exosome, and the immune modulator is linked directly to the luminal surface of the EV, e.g., exosome;
(z) the antigen is linked to a Scaffold Y on the luminal surface of the EV, e.g., exosome, and the immune modulator is linked directly to the exterior of the EV, e.g., exosome;
(aa) the antigen is linked to a Scaffold X on the luminal surface of the EV, e.g., exosome, and the immune modulator is linked directly to the luminal surface of the EV, e.g., exosome;
(bb) the antigen is linked to a Scaffold X on the luminal surface of the EV, e.g., exosome, and the immune modulator is linked directly to the exterior of the EV, e.g., exosome;
(cc) the antigen is in the lumen of the EV, e.g., exosome, and the immune modulator is linked directly to the luminal surface of the EV, e.g., exosome; or
(dd) the antigen is in the lumen of the EV, e.g., exosome, and the immune modulator is linked directly to the exterior of the EV, e.g., exosome.

In some aspects, an EV, e.g., exosome, of the present disclosure comprises (i) an antigen and (ii) an immune modulator, wherein the antigen is linked to a first Scaffold Y on the luminal surface of the EV, e.g., exosome, and the immune modulator is linked to a second Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is linked to a Scaffold X on the exterior surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold X on the exterior surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is linked to a Scaffold X on the luminal surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold X on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is linked to the Scaffold X on the exterior surface of the EV, e.g., exosome. In some aspects, an EV, e.g., exosome, of the present disclosure comprises (i) an antigen and (ii) an immune modulator, wherein the antigen is linked to a first Scaffold X on the exterior surface of the EV, e.g., exosome, and the immune modulator is linked to a second Scaffold X on the exterior surface of the EV, e.g., exosome. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is linked to the Scaffold X on the luminal surface of the EV, e.g., exosome. In some aspects, an EV, e.g., exosome, of the present disclosure comprises (i) an antigen and (ii) an immune modulator, wherein the antigen is linked to a first Scaffold X on the luminal surface of the EV, e.g., exosome, and the immune modulator is linked to a second Scaffold X on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is linked to a first Scaffold X on the exterior surface of the EV, e.g., exosome, and the immune modulator is linked to a second Scaffold X on the luminal surface of the EV, e.g., exosome. In some aspects, an EV, e.g., exosome, of the present disclosure comprises (i) an antigen and (ii) an immune modulator, wherein the antigen is linked to a first Scaffold X on the luminal surface of the EV, e.g., exosome, and the immune modulator is linked to a second Scaffold X on the exterior surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is in the lumen of the EV, e.g., exosome, not linked to any scaffold moiety. In some aspects, an EV, e.g., exosome, comprises (i) an antigen and (ii) an immune modulator, wherein the antigen is linked directly to the luminal surface of the EV, and the immune modulator is linked directly to the luminal surface of the EV. In some aspects, an EV, e.g., exosome, comprises (i) an antigen and (ii) an immune modulator, wherein the antigen is linked directly to the luminal surface of the EV, and the immune modulator is in the lumen of the EV. In some aspects, an EV, e.g., exosome, comprises (i) an antigen and (ii) an immune modulator, wherein the antigen is linked directly to the luminal surface of the EV, and the immune modulator is linked to a Scaffold Y on the luminal surface of the EV. In some aspects, an EV, e.g., exosome, comprises (i) an antigen and (ii) an immune modulator, wherein the antigen is linked directly to the luminal surface of the EV, and the immune modulator is linked to a Scaffold X on the luminal surface of the EV. In some aspects, an EV, e.g., exosome, comprises (i) an antigen and (ii) an immune modulator, wherein the antigen is linked directly to the luminal surface of the EV, and the immune modulator is linked directly to the exterior of the EV. In some aspects, an EV, e.g., exosome, comprises (i) an antigen and (ii) an immune modulator, wherein the antigen is linked directly to the luminal surface of the EV, and the immune modulator is linked to a Scaffold X on the exterior of the EV. In some aspects, an EV, e.g., exosome, comprises (i) an antigen and (ii) an immune modulator, wherein the antigen is linked to a Scaffold Y on the luminal surface of the EV, and the immune modulator is linked directly to the luminal surface of the EV. In some aspects, an EV, e.g., exosome, comprises (i) an antigen and (ii) an immune modulator, wherein the antigen is linked to a Scaffold Y on the luminal surface of the EV, and the immune modulator is linked directly to the exterior of the EV. In some aspects, an EV, e.g., exosome, comprises (i) an antigen and (ii) an immune modulator, wherein the antigen is linked to a Scaffold X on the luminal surface of the EV, and the immune modulator is linked directly to the luminal surface of the EV. In some aspects, an EV, e.g., exosome, comprises (i) an antigen and (ii) an immune modulator, wherein the antigen is linked to a Scaffold X on the luminal surface of the EV, and the immune modulator is linked directly to the exterior of the EV. In some aspects, an EV, e.g., exosome, comprises (i) an antigen and (ii) an immune modulator, wherein antigen is in the lumen of the EV, and the immune modulator is linked directly to the luminal surface of the EV. In some aspects, an EV, e.g., exosome, comprises (i) an antigen and (ii) an immune modulator, wherein antigen is in the lumen of the EV, and the immune modulator is linked directly to the exterior of the EV.

Non-limiting examples of specific aspects, include EVs, e.g., exosomes, comprising (i) an antigen, (ii) an adjuvant, and (iii) an immune modulator, wherein:

(a) the antigen is linked to a first Scaffold Y on the luminal surface of the EV, e.g., exosome, the adjuvant is linked to a second Scaffold Y on the luminal surface of the EV, e.g., exosome, and the immune modulator is (a1) in the lumen of the EV, e.g., exosome, not linked to any scaffold moiety, or (a2) linked to a third scaffold moiety, e.g., a Scaffold X on the exterior surface of the exosome or in the lumen of the exosome or a Scaffold Y on the luminal surface of the EV, e.g., exosome;

(b) the antigen is linked to a Scaffold Y on the luminal surface of the EV, e.g., exosome, the adjuvant is in the lumen of the EV, e.g., exosome, not linked to any scaffold moiety, and the immune modulator is (b1) in the lumen of the EV, e.g., exosome, not linked to any scaffold moiety, or (b2) linked to a scaffold moiety, e.g., a Scaffold X on the exterior surface of the exosome or on the luminal surface of the exosome or a Scaffold Y on the luminal surface of the EV, e.g., exosome;

(c) the antigen is in the lumen of the EV, e.g., exosome, not linked to any scaffold moiety, the adjuvant is linked to a Scaffold Y on the luminal surface of the EV, e.g., exosome, and the immune modulator is (c1) in the lumen of the EV, e.g., exosome, not linked to any scaffold moiety, or (c2) linked to a scaffold moiety, e.g., a Scaffold X on the exterior surface of the exosome or on the luminal surface of the exosome or a Scaffold Y on the luminal surface of the EV, e.g., exosome;

(d) the antigen is linked to a Scaffold Y on the luminal surface of the EV, e.g., exosome, the adjuvant is linked to a Scaffold X on the exterior surface of the EV, e.g., exosome, and the immune modulator is (d1) in the lumen of the EV, e.g., exosome, not linked to any scaffold moiety, or (d2) linked to a third scaffold moiety, e.g., a Scaffold X on the exterior surface of the exosome or on the luminal surface of the exosome or a Scaffold Y on the luminal surface of the EV, e.g., exosome;

(e) the antigen is in the lumen of the EV, e.g., exosome, not linked to any scaffold moiety, the adjuvant is linked to a Scaffold X on the exterior surface of the EV, e.g., exosome, and the immune modulator is (e1) in the lumen of the EV, e.g., exosome, not linked to any scaffold moiety, or (e2) linked to a scaffold moiety, e.g., a Scaffold X on the surface of the exosome or on the luminal surface of the exosome or a Scaffold Y on the luminal surface of the EV, e.g., exosome;

(f) the antigen is linked to a Scaffold Y on the luminal surface of the EV, e.g., exosome, the adjuvant is linked to a Scaffold X on the luminal surface of the EV, e.g., exosome, and the immune modulator is (f1) in the lumen of the EV, e.g., exosome, not linked to any scaffold moiety, or (f2) linked to a third scaffold moiety, e.g., a Scaffold X on the exterior surface of the exosome or on the luminal surface of the exosome or a Scaffold Y on the luminal surface of the EV, e.g., exosome;

(g) the antigen is in the lumen of the EV, e.g., exosome, not linked to any scaffold moiety, the adjuvant is linked to a Scaffold X on the luminal surface of the EV, e.g., exosome, and the immune modulator is (g1) in the lumen of the EV, e.g., exosome, not linked to any scaffold moiety, or (g2) linked to a scaffold moiety, e.g., a Scaffold X on the exterior surface of the exosome or on the luminal surface of the exosome or a Scaffold Y on the luminal surface of the EV, e.g., exosome;

(h) the antigen is linked to a Scaffold X on the luminal surface of the EV, e.g., exosome, the adjuvant is linked to the Scaffold X on the exterior surface of the EV, e.g., exosome, and the immune modulator is (h1) in the lumen of the EV, e.g., exosome, not linked to any scaffold moiety, or (h2) linked to a scaffold moiety, e.g., a Scaffold X on the exterior surface of the exosome or on the luminal surface of the exosome or a Scaffold Y on the luminal surface of the EV, e.g., exosome;

(i) the antigen is linked to a first Scaffold X on the exterior surface of the EV, e.g., exosome, the adjuvant is linked to a second Scaffold X on the exterior surface of the EV, e.g., exosome, and the immune modulator is (i1) in the lumen of the EV, e.g., exosome, not linked to any scaffold moiety, or (i2) linked to a third scaffold moiety, e.g., a Scaffold X on the exterior surface of the exosome or on the luminal surface of the exosome or a Scaffold Y on the luminal surface of the EV, e.g., exosome;

(j) the antigen is linked to a Scaffold X on the exterior surface of the EV, e.g., exosome, the adjuvant is linked to a Scaffold Y on the luminal surface of the EV, e.g., exosome, and the immune modulator is (j1) in the lumen of the EV, e.g., exosome, not linked to any scaffold moiety, or (j2) linked to a third scaffold moiety, e.g., a Scaffold X on the exterior surface of the exosome or on the luminal surface of the exosome or a Scaffold Y on the luminal surface of the EV, e.g., exosome;

(k) the antigen is linked to a Scaffold X on the exterior surface of the EV, e.g., exosome, the adjuvant is in the lumen of the EV, e.g., exosome, not linked to any scaffold moiety, and the immune modulator is (k1) in the lumen of the EV, e.g., exosome, not linked to any scaffold moiety, or (k2) linked to a scaffold moiety, e.g., a Scaffold X on the exterior surface of the exosome or on the luminal surface of the exosome or a Scaffold Y on the luminal surface of the EV, e.g., exosome;

(l) the antigen is linked to a Scaffold X on the exterior surface of the EV, e.g., exosome, the adjuvant is linked to the Scaffold X on the luminal surface of the EV, e.g., exosome, and the immune modulator is (l1) in the lumen of the EV, e.g., exosome, not linked to any scaffold moiety, or (l2) linked to a scaffold moiety, e.g., a Scaffold X on the exterior surface of the exosome or on the luminal surface of the exosome or a Scaffold Y on the luminal surface of the EV, e.g., exosome;

(m) the antigen is linked to a first Scaffold X on the luminal surface of the EV, e.g., exosome, the adjuvant is linked to a second Scaffold on the luminal surface of the EV, e.g., exosome, and the immune modulator is (m1) in the lumen of the EV, e.g., exosome, not linked to any scaffold moiety, or (m2) linked to a third scaffold moiety, e.g., a Scaffold X on the exterior surface of the exosome or on the luminal surface of the exosome or a Scaffold Y on the luminal surface of the EV, e.g., exosome;

(n) the antigen is linked to a Scaffold X on the luminal surface of the EV, e.g., exosome, the adjuvant is linked to a Scaffold Y on the luminal surface of the EV, e.g., exosome, and the immune modulator is (n1) in the lumen of the EV, e.g., exosome, not linked to any scaffold moiety, or (n2) linked to a third scaffold moiety, e.g., a Scaffold X on the exterior surface of the exosome or on the luminal surface of the exosome or a Scaffold Y on the luminal surface of the EV, e.g., exosome;

(o) the antigen is linked to a Scaffold X on the luminal surface of the EV, e.g., exosome, the adjuvant is in the lumen of the EV, e.g., exosome, not linked to any scaffold moiety, and the immune modulator is (o1) in the lumen of the EV, e.g., exosome, not linked to any scaffold moiety, or (o2) linked to a scaffold moiety, e.g., a Scaffold X on the exterior surface of the exosome or on the luminal surface of the exosome or a Scaffold Y on the luminal surface of the EV, e.g., exosome;

(p) the antigen is linked to a first Scaffold X on the exterior surface of the EV, e.g., exosome, the adjuvant is linked to a second Scaffold X on the luminal surface of the EV, e.g., exosome, and the immune modulator is (p1) in the lumen of the EV, e.g., exosome, not linked to any scaffold moiety, or (p2) linked to a third scaffold moiety, e.g., a Scaffold X on the surface of the exosome or in the lumen of the exosome or a Scaffold Y on the luminal surface of the EV, e.g., exosome;

(q) the antigen is linked to a first Scaffold X on the luminal surface of the EV, e.g., exosome, the adjuvant is linked to a second Scaffold X on the exterior surface of the EV, e.g., exosome, and the immune modulator is (q1) in the lumen of the EV, e.g., exosome, not linked to any scaffold moiety, or (q2) linked to a third scaffold moiety, e.g., a Scaffold X on the exterior surface of the exosome or on the luminal surface of the exosome or a Scaffold Y on the luminal surface of the EV, e.g., exosome; or (r) the antigen is in the lumen of the EV, e.g., exosome, not linked to any scaffold moiety, the adjuvant is in the lumen of the EV, e.g., exosome, not linked to any scaffold moiety, and the immune modulator is (r1) in the lumen of the exosome or (r2) linked to a scaffold moiety, e.g., a Scaffold X on the exterior surface of the exosome or on the luminal surface of the exosome or a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a third Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is in the lumen of the EV, e.g., exosome, not linked to any scaffold moiety, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a Scaffold X on the exterior surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a Scaffold X on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a Scaffold Y on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a Scaffold Y on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is in the lumen of the EV, e.g., exosome, not linked to any scaffold moiety, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is in the lumen of the EV, e.g., exosome, not linked to any scaffold moiety, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is in the lumen of the EV, e.g., exosome, not linked to any scaffold moiety, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to the Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to the Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to the Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to the Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a Scaffold Y on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a Scaffold Y on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is in the lumen of the EV, e.g., exosome, not linked to any scaffold moiety, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is in the lumen of the EV, e.g., exosome, not linked to any scaffold moiety, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is in the lumen of the EV, e.g., exosome, not linked to any scaffold moiety, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold Y on the luminal surface of the EV, e.g., exosome.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold Y in the lumen of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold X in the lumen of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold X in the exterior surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is in the lumen of the EV.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the external surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold Y on the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold X on the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold X on the exterior surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is in the lumen of the EV, and (a3) the immune modulator is linked directly to the luminal surface of the EV.

In some aspects, an EV (e.g., exosome) comprises: (i) an antigen, (ii) an adjuvant, and (iii) an immune modulator, wherein (a1) the antigen is linked directly to the external surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold Y on the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold X on the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold X on the exterior surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is in the lumen of the EV, (a2) the adjuvant is linked directly to the luminal surface of the EV, and (a3) the immune modulator is linked directly to the luminal surface of the EV.

In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold Y on the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold X on the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold X on the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is in the lumen of the EV.

In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold Y on the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold X on the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold X on the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is in the lumen of the EV, and (a3) the immune modulator is linked directly to the exterior surface of the EV.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold Y on the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold X on the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold X on the exterior surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is in the lumen of the EV, (a2) the adjuvant is linked directly to the exterior surface of the EV, and (a3) the immune modulator is linked directly to the exterior surface of the EV.

In some aspects, an immune modulator that can be used with the EVs, e.g., exosomes, described herein has anti-tumor activity. In other aspects, an immune modulator useful for the present disclosure has tolerogenic activity. In some aspects, an immune modulator can regulate innate immune response. In certain aspects, an immune modulator regulates innate immune response by targeting natural killer cells. In some aspects, an immune modulator can regulate adaptive immune response. In some aspects, the immune modulator regulates adaptive immune response by targeting cytotoxic T cells. In further aspects, the immune modulator regulates adaptive immune response by targeting B cells. In certain aspects, an immune modulator disclosed herein can modulate the distribution of an exosome to a cytotoxic T cell or a B cell (i.e., bio-distribution modifying agent).

In some aspects, an immune modulator comprises an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, the immune modulator is an inhibitor of cytotoxic T-lymphocyte-associate protein 4 (CTLA-4). In certain aspects, the CTLA-4 inhibitor is a monoclonal antibody of CTLA-4 ("anti-CTLA-4 antibody"). In certain aspects, the inhibitor is a fragment of a monoclonal antibody of CTLA-4. In certain aspects, the antibody fragment is a scFv, $(scFv)_2$, Fab, Fab', and $F(ab')_2$, F(ab1)2, Fv, dAb, or Fd of a monoclonal antibody of CTLA-4. In certain aspects, the inhibitor is a nanobody, a bispecific antibody, or a multispecific antibody against CTLA-4. In some aspects, the anti-CTLA-4 antibody is ipilimumab. In other aspects, the anti-CTLA-4 antibody is tremelimumab.

In some aspects, the immune modulator is an inhibitor of programmed cell death protein 1 (PD-1). In some aspects, the immune modulator is an inhibitor of programmed death-ligand 1 (PD-L1). In some aspects, the immune modulator is an inhibitor of programmed death-ligand 2 (PD-L2). In certain aspects, the inhibitor of PD-1, PD-L1, or PD-L2 is a monoclonal antibody of PD-1 ("anti-PD-1 antibody"), PD-L1 ("anti-PD-L1 antibody"), or PD-L2 ("anti-PD-L2 antibody"). In some aspects, the inhibitor is a fragment of an anti-PD-1 antibody, anti-PD-L1 antibody, or anti-PD-L2 antibody. In certain aspects, the antibody fragment is a scFv, $(scFv)_2$, Fab, Fab', and $F(ab')_2$, $F(ab1)_2$, Fv, dAb, or Fd of a monoclonal antibody of PD-1, PD-L1, or PD-L2. In certain aspects, the inhibitor is a nanobody, a bispecific antibody, or a multispecific antibody against PD-1, PD-L1, or PD-L2. In some aspects, the anti-PD-1 antibody is nivolumab. In some aspects, the anti-PD-1 antibody is pembrolizumab. In some aspects, the anti-PD-1 antibody is pidilizumab. In some aspects, the anti-PD-L1 antibody is atezolizumab. In other aspects, the anti-PD-L1 antibody is avelumab.

In some aspects, the immune modulator is an inhibitor of lymphocyte-activated gene 3 (LAG3). In certain aspects, the inhibitor of LAG3 is a monoclonal antibody of LAG3 ("anti-LAG3 antibody"). In some aspects, the inhibitor is a fragment of an anti-LAG3 antibody, e.g., scFv, $(scFv)_2$, Fab, Fab', and $F(ab')_2$, $F(ab1)_2$, Fv, dAb, or Fd. In certain aspects, the inhibitor is a nanobody, a bispecific antibody, or a multispecific antibody against LAG3.

In some aspects, the immune modulator is an inhibitor of T-cell immunoglobulin mucin-containing protein 3 (TIM-3). In some aspects, the immune modulator is an inhibitor of B and T lymphocyte attenuator (BTLA). In some aspects, the immune modulator is an inhibitor of T cell immunoreceptor with Ig and ITIM domains (TIGIT). In some aspects, the immune modulator is an inhibitor of V-domain Ig suppressor of T cell activation (VISTA). In some aspects, the immune modulator is an inhibitor of adenosine A2a receptor (A2aR). In some aspects, the immune modulator is an inhibitor of killer cell immunoglobulin like receptor (KIR). In some aspects, the immune modulator is an inhibitor of indoleamine 2,3-dioxygenase (IDO). In some aspects, the immune modulator is an inhibitor of CD20, CD39, or CD73.

In some aspects, the immune modulator comprises an activator for a positive co-stimulatory molecule or an activator for a binding partner of a positive co-stimulatory molecule. In certain aspects, the positive co-stimulatory molecule comprises a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40L, CD40L, FasL, LIGHT, TLA, CD27L, Siva, CD153, 4-1BB ligand, TRAIL, RANKL, TWEAK, APRIL, BAFF, CAMLG, NGF, BDNF, NT-3, NT-4, GITR ligand, and EDA-2).

In some aspects, the immune modulator is an activator of TNF Receptor Superfamily Member 4 (OX40). In certain aspects, the activator of OX40 is an agonistic anti-OX40 antibody. In further aspects, the activator of OX40 is a OX40 ligand (OX40L).

In some aspects, the immune modulator is an activator of CD27. In certain aspects, the activator of CD27 is an agonistic anti-CD27 antibody. In other aspects, the activator of CD27 is a CD27 ligand (CD27L).

In some aspects, the immune modulator is an activator of CD40. In certain aspects, the activator of CD40 is an agonistic anti-CD40 antibody. In some aspects, the activator of CD40 is a CD40 ligand (CD40L). In certain aspects, the CD40L is a monomeric CD40L. In other aspects, the CD40L is a trimeric CD40L.

In some aspects, the immune modulator is an activator of glucocorticoid-induced TNFR-related protein (GITR). In certain aspects, the activator of GITR is an agonistic anti-GITR antibody. In other aspects, the activator of GITR is a natural ligand of GITR.

In some aspects, the immune modulator is an activator of 4-1BB. In specific aspects, the activator of 4-1BB is an agonistic anti-4-1BB antibody. In certain aspects, the activator of 4-1BB is a natural ligand of 4-1BB.

In some aspects, the immune modulator is a Fas receptor (Fas). In such aspects, the Fas receptor is displayed on the surface of the EV, e.g., exosome. In some aspects, the immune modulator is Fas ligand (FasL). In certain aspects, the Fas ligand is displayed on the surface of the EV, e.g., exosome. In some aspects, the immune modulator is an anti-Fas antibody or an anti-FasL antibody.

In some aspects, the immune modulator is an activator of a CD28-superfamily co-stimulatory molecule. In certain aspects, the CD28-superfamily co-stimulatory molecule is ICOS or CD28. In certain aspects, the immunomodulating component is ICOSL, CD80, or CD86.

In some aspects, the immune modulator is an activator of inducible T cell co-stimulator (ICOS). In certain aspects, the activator of ICOS is an agonistic anti-ICOS antibody. In other aspects, the activator of ICOS is a ICOS ligand (ICOSL).

In some aspects, the immune modulator is an activator of CD28. In some aspects, the activator of CD28 is an agonistic anti-CD28 antibody. In other aspects, the activator of CD28 is a natural ligand of CD28. In certain aspects, the ligand of CD28 is CD80.

In some aspects, the immune modulator comprises a cytokine or a binding partner of a cytokine. In some aspects, the cytokine is selected from (i) common gamma chain family of cytokines; (ii) IL-1 family of cytokines; (iii) hematopoietic cytokines; (iv) interferons (e.g., type I, type II, or type III); (v) TNF family of cytokines; (vi) IL-17 family of cytokines; (vii) damage-associated molecular patterns (DAMPs); (viii) tolerogenic cytokines; or (ix) combinations thereof. In certain aspects, the cytokine comprises IL-2, IL-4, IL-7, IL-10, IL-12, IL-15, IL-21, IFN-γ, IL-1α, IL-1β, IL-1ra, IL-18, IL-33, IL-36α, IL-36β, IL-36γ, IL-36ra, IL-37, IL-38, IL-3, IL-5, IL-6, IL-11, IL-13, IL-23, granulocyte-macrophage colony stimulating factor (GM-CSF), granulocyte-colony stimulating factor (G-CSF), leukemia inhibitory factor (LIF), stem cell factor (SCF), thrombopoietin (TPO), macrophage-colony stimulating factor (M-CSF), erythropoieticn (EPO), Flt-3, IFN-α, IFN-β, IFN-γ, IL-19, IL-20, IL-22, IL-24, TNF-α, TNF-β, BAFF, APRIL, lymphotoxin beta (TNF-γ), IL-17A, IL-17B, IL-17C, IL-17D, IL-17E, IL-17F, IL-25, TSLP, IL-35, IL-27, TGF-β, or combinations thereof.

In some aspects, the immune modulator comprises a chemokine. In certain aspects, chemokine comprises a (i) CC chemokine (e.g., CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28); (ii) CXC chemokine (e.g., CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17); (iii) C chemokine (e.g., XCL1, XCL2); (iv) CX3C chemokine (e.g., CX3CL1); (v) or combinations thereof.

In some aspects, the immune modulator comprises an inhibitor of lysophosphatidic acid (LPA). LPA is a highly potent endogenous lipid mediator that protects and rescues cells from programmed cell death. LPA, through its high affinity LPA-1 receptor, is an important mediator of fibrogenesis.

In some aspects, the LPA-1 inhibitor comprises AM095, which is a potent and orally bioavailable antagonist of LPA-1 with $IC_{50}$ values of 0.73 and 0.98 μM for mouse or recombinant human LPA-1, respectively. In vitro, AM095 has been shown to inhibit LPA-1-induced chemotaxis of both mouse LPA-1/CHO cells and human A2058 melanoma cells with $IC_{50}$ values of 0.78 μM and 0.23 μM. In vivo, AM095 can dose-dependently block LPA-induced histamine release with an $ED_{50}$ value of 8.3 mg/kg in mice. Additionally, AM095 has been revealed to remarkably reduce the BALF collagen and protein with an $ED_{50}$ value of 10 mg/kg in lungs. AM095 has also been shown to decrease both macrophage and lymphocyte infiltration induced by bleomycin in mice. See Swaney et al. (2018) Mol. Can. Res. 16:1601-1613, which is herein incorporated by reference in its entirety.

In some aspects, the LPA-1 inhibitor comprises AM152 (also known as BMS-986020). AM152 is a high-affinity LPA-1 antagonist which inhibits bile acid and phospholipid transporters with $IC_{50}$s of 4.8 μM, 6.2 μM, and 7.5 μM for BSEP, MRP4, and MDR3, respectively. AM152 can be used for the treatment of idiopathic pulmonary fibrosis (IPF). See Kihara et al. (2015) Exp. Cell Res. 333:171-7; Rosen et al. (2017) European Respiratory Journal 50:PA1038; and, Palmer et al. (2018) Chest 154:1061-1069, which are herein incorporated by reference in their entireties. The Phase 2 study of AM152 (described in Palmer 2018) was terminated early due to gall bladder toxicity and early signs of liver toxicity liver transporter (2 specific transporters).

Additional disclosures relating to EVs (e.g., exosomes) comprising an LPA-1 inhibitor are provided elsewhere in the present disclosure (see, e.g., Example 24).

In some aspects, the immune modulator that can be combined with an antigen, e.g., HSV-2 antigen, is IL-21. Non-limiting examples of HSV-2 antigens are disclosed elsewhere herein. In some aspects, the EV, e.g., exosome, of the present disclosure comprises both IL-21 and a HSV-2 antigen in the lumen of the EV. In other aspects, the EV comprises IL-21 on the exterior surface of the EV, optionally linked via a first scaffold moiety (e.g., Scaffold X), and a HSV-2 antigen on the exterior surface of the EV, optionally linked via a second scaffold moiety (e.g., Scaffold X), wherein the first scaffold moiety and the second scaffold moiety are the same or different. In other aspects, the EV comprises IL-21 on the exterior surface of the EV, optionally linked via a scaffold moiety (e.g., Scaffold X), and a HSV-2 antigen on the luminal surface of the EV, optionally linked via the scaffold moiety (e.g., Scaffold X). In other aspects, the EV comprises a HSV-2 antigen on the exterior surface of the EV, optionally linked via a scaffold moiety (e.g., Scaffold X), and IL-21 on the luminal surface of the EV, optionally linked via the scaffold moiety (e.g., Scaffold X). In other aspects, the EV comprises IL-21 on the exterior surface of the EV, optionally linked via a first scaffold moiety (e.g., Scaffold X), and a HSV-2 antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a HSV-2 antigen on the exterior surface of the EV, optionally linked via a first scaffold moiety (e.g., Scaffold X), and IL-21 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-21 on the luminal surface of the EV (e.g., Scaffold X or Scaffold Y), optionally linked via a first scaffold moiety, and a HSV-2 antigen on the luminal surface of the EV (e.g., Scaffold X or Scaffold Y), optionally linked via a second scaffold moiety, wherein the first scaffold moiety and the second scaffold moiety are the same or different.

In some aspect, the immune modulator that can be combined with an antigen, e.g., HSV-2 antigen, is CD40L. Non-limiting examples of HSV-2 antigens are disclosed elsewhere herein. In some aspects, the EV, e.g., exosome, of the present disclosure comprises both CD40L and a HSV-2 antigen in the lumen of the EV. In other aspects, the EV comprises CD40L on the exterior surface of the EV, optionally linked via a first scaffold moiety (e.g., Scaffold X), and a HSV-2 antigen on the exterior surface of the EV, optionally linked via a second scaffold moiety (e.g., Scaffold X), wherein the first scaffold moiety and the second scaffold moiety are the same or different. In other aspects, the EV comprises CD40L on the exterior surface of the EV, optionally linked via a scaffold moiety (e.g., Scaffold X), and a HSV-2 antigen on the luminal surface of the EV, optionally linked via the scaffold moiety (e.g., Scaffold X). In other aspects, the EV comprises a HSV-2 antigen on the exterior surface of the EV, optionally linked via a scaffold moiety (e.g., Scaffold X), and CD40L on the luminal surface of the EV, optionally linked via the scaffold moiety (e.g., Scaffold X). In other aspects, the EV comprises CD40L on the exterior surface of the EV, optionally linked via a first scaffold moiety (e.g., Scaffold X), and a HSV-2 antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a HSV-2 antigen on the exterior surface of the EV, optionally linked via a first scaffold moiety (e.g., Scaffold X), and CD40L on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises CD40L on the luminal surface of the EV (e.g., Scaffold X or Scaffold Y), optionally linked via a first scaffold moiety, and a HSV-2 antigen on the luminal surface of the EV (e.g., Scaffold X or Scaffold Y), optionally linked via a second scaffold moiety, wherein the first scaffold moiety and the second scaffold moiety are the same or different.

In some aspect, an EV (e.g., exosome) comprising a HSV-2 antigen (e.g., disclosed herein) and an immune modulator (e.g., IL-21 or CD40L) can further comprise an adjuvant. Non-limiting examples of adjuvants that can be used with the present disclosure are described elsewhere herein.

In some aspect, an EV (e.g., exosome) comprising a HSV-2 antigen and one or more additional payloads (e.g., an immune modulator and/or adjuvant described above) can enhance an immune response to the HSV-2 antigen compared to a reference. In some aspect, the reference comprises an EV (e.g., exosome) comprising only the HSV-2 antigen. In other aspect, the reference comprises a HSV-2 antigen (alone or in combination with one or more additional payloads (e.g., an adjuvant and/or immune modulator)) that is not linked or present in the EVs disclosed herein (e.g., exosomes). In some aspects, an immune response comprises an innate immune response, a humoral immune response, a cell-mediated immune response, or combinations thereof. In certain aspects, the immune response is enhanced by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more compared to the reference. In some aspects, the immune response is enhanced by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV without the targeting moiety or a non-EV delivery vehicle).

In some aspect, an EV (e.g., exosome) comprising a HSV-2 antigen and one or more additional payloads (e.g., an immune modulator and/or adjuvant described above) can reduce viral shedding when administered to a subject in need thereof. In certain aspect, viral shedding is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads). In some aspect, an EV (e.g., exosome) comprising a HSV-2 antigen and one or more additional payloads (e.g., an immune modulator and/or adjuvant) can increase viral clearance when administered to a subject in need thereof. In certain aspect, viral clearance is increased by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more, compared to a reference (e.g., corresponding EV comprising the antigen alone or a non-EV delivery vehicle comprising the antigen alone or in combination with the one or more additional payloads). In some aspects, viral clearance is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV comprising the antigen alone or a non-EV delivery vehicle comprising the antigen alone or in combination with the one or more additional payloads). In further aspect, an EV (e.g., exosome) comprising a HSV-2 antigen and one or more additional payloads (e.g., an immune modulator and/or adjuvant) can reduce HSV-2-mediated lesion formation when administered to a subject in need thereof. In certain aspect, lesion formation is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads).

In some aspect, the reference comprises an EV (e.g., exosome) comprising only the HSV-2 antigen. In other aspect, the reference comprises a HSV-2 antigen (alone or in combination with an adjuvant and/or immune modulator) that is not linked or present in the EVs disclosed herein.

In some aspects, the immune modulator that can be combined with an antigen, e.g., EBV antigen, is IL-21. Non-limiting examples of EBV antigens (e.g., BZLF1) are disclosed elsewhere herein. In some aspects, the EV, e.g., exosome, of the present disclosure comprises both IL-21 and an EBV antigen (e.g., BZLF1) in the lumen of the EV. In other aspects, the EV comprises IL-21 on the exterior surface of the EV, optionally linked via a first scaffold moiety (e.g., Scaffold X), and an EBV antigen (e.g., BZLF1) on the exterior surface of the EV, optionally linked via a second scaffold moiety (e.g., Scaffold X), wherein the first scaffold moiety and the second scaffold moiety are the same or different. In other aspects, the EV comprises IL-21 on the exterior surface of the EV, optionally linked via a scaffold moiety (e.g., Scaffold X), and an EBV antigen (e.g., BZLF1) on the luminal surface of the EV, optionally linked via the scaffold moiety (e.g., Scaffold X). In other aspects, the EV comprises an EBV antigen (e.g., BZLF1) on the exterior surface of the EV, optionally linked via a scaffold moiety (e.g., Scaffold X), and IL-21 on the luminal surface of the EV, optionally linked via the scaffold moiety (e.g., Scaffold X). In other aspects, the EV comprises IL-21 on the exterior surface of the EV, optionally linked via a first scaffold moiety (e.g., Scaffold X), and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different. In other aspects, the EV comprises an EBV antigen (e.g., BZLF1) on the exterior surface of the EV, optionally linked via a first scaffold moiety (e.g., Scaffold X), and IL-21 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-21 on the luminal surface of the EV (e.g., Scaffold X or Scaffold Y), optionally linked via a first scaffold moiety, and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different.

In some aspect, the immune modulator that can be combined with an antigen, e.g., an EBV antigen (e.g., BZLF1), is CD40L. Non-limiting examples of an EBV antigen (e.g., BZLF1) are disclosed elsewhere herein. In some aspects, the EV, e.g., exosome, of the present disclosure comprises both CD40L and an EBV antigen (e.g., BZLF1) in the lumen of the EV. In other aspects, the EV comprises CD40L on the exterior surface of the EV, optionally linked via a first scaffold moiety (e.g., Scaffold X), and an EBV antigen (e.g., BZLF1) on the exterior surface of the EV, optionally linked via a second scaffold moiety (e.g., Scaffold X), wherein the first scaffold moiety and the second scaffold moiety are the same or different. In other aspects, the EV comprises CD40L on the exterior surface of the EV, optionally linked via a scaffold moiety (e.g., Scaffold X), and an EBV antigen (e.g., BZLF1) on the luminal surface of the EV, optionally linked via the scaffold moiety (e.g., Scaffold X). In other aspects, the EV comprises an EBV antigen (e.g., BZLF1) on the exterior surface of the EV, optionally linked via a scaffold moiety (e.g., Scaffold X), and CD40L on the luminal surface of the EV, optionally linked via the scaffold moiety (e.g., Scaffold X). In other aspects, the EV comprises CD40L on the exterior surface of the EV, optionally linked via a first scaffold moiety (e.g., Scaffold X), and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different. In other aspects, the EV comprises an EBV antigen (e.g., BZLF1) on the exterior surface of the EV, optionally linked via a first scaffold moiety (e.g., Scaffold X), and CD40L on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises CD40L on the luminal surface of the EV (e.g., Scaffold X or Scaffold Y), optionally linked via a first scaffold moiety, and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different.

In some aspects, an EV (e.g., exosome) comprising an EBV antigen and an immune modulator (e.g., IL-21 or CD40L) can further comprise one or more additional payloads (e.g., additional antigen, additional immune modulator, and/or adjuvant) and/or one or more targeting moieties disclosed herein. In some aspect, an EV (e.g., exosome) comprising an EBV antigen (e.g., BZLF1) (e.g., disclosed herein) and an immune modulator (e.g., IL-21 or CD40L) can further comprise an adjuvant. Non-limiting examples of adjuvants that can be used with the present disclosure are described elsewhere herein. In some aspects, the EV can further comprise an additional antigen (e.g., a different EBV antigen). In some aspects, the EV can further comprise an additional immune modulator (e.g., different from IL-21 or CD40L) disclosed herein.

In some aspect, an EV (e.g., exosome) comprising an EBV antigen (e.g., BZLF1) and one or more additional payloads (e.g., an immune modulator and/or adjuvant described above) can enhance an immune response to the EBV antigen (e.g., BZLF1) compared to a reference. In some aspects, the reference comprises an EV (e.g., exosome) comprising only the EBV antigen (e.g., BZLF1). In other aspects, the reference comprises an EBV antigen (e.g., BZLF1) (alone or in combination with an adjuvant and/or immune modulator) that is not linked or present in the EVs disclosed herein (e.g., exosomes). In some aspects, an immune response comprises an innate immune response, a humoral immune response, a cell-mediated immune response, or combinations thereof. In certain aspects, the immune response is enhanced by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more compared to the reference. In some aspects, the immune response is enhanced by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to the reference.

In some aspects, an EV (e.g., exosome) comprising an EBV antigen (e.g., BZLF1) and one or more additional payloads (e.g., an immune modulator and/or adjuvant described above) can reduce viral shedding when administered to a subject in need thereof. In certain aspect, viral shedding is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads). In some aspects, an EV (e.g., exosome) comprising an EBV antigen (e.g., BZLF1) and one or more additional payloads (e.g., an immune modulator and/or adjuvant) can increase viral clearance when administered to a subject in need thereof. In certain aspect, viral clearance is increased by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more, compared to a reference (e.g., corresponding EV comprising the antigen alone or a non-EV delivery vehicle comprising the antigen alone or in combination with the one or more additional payloads). In some aspects, an EV (e.g., exosome) comprising an EBV antigen (e.g., BZLF1) and one or more additional payloads (e.g., an immune modulator and/or adjuvant) can reduce EBV-mediated lesion formation when administered to a subject in need thereof. In certain aspect, lesion formation is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads).

In some aspect, the reference comprises an EV (e.g., exosome) comprising only an EBV antigen (e.g., BZLF1). In other aspect, the reference comprises an EBV antigen (e.g., BZLF1) (alone or in combination with an adjuvant and/or immune modulator) that is not linked or present in the EVs disclosed herein.

In some aspect, the immune modulator that can be combined with an antigen, e.g., TB antigen, is IL-12.

Non-limiting examples of TB antigens are disclosed elsewhere herein. In some aspects, the EV, e.g., exosome, of the present disclosure comprises both IL-12 and a TB antigen in the lumen of the EV. In other aspects, the EV comprises IL-12 on the exterior surface of the EV, optionally linked via a first scaffold moiety (e.g., Scaffold X), and a TB antigen on the exterior surface of the EV, optionally linked via a second scaffold moiety (e.g., Scaffold X), wherein the first scaffold moiety and the second scaffold moiety are the same or different. In other aspects, the EV comprises IL-12 on the exterior surface of the EV, optionally linked via a scaffold moiety (e.g., Scaffold X), and a TB antigen on the luminal surface of the EV, optionally linked via the scaffold moiety (e.g., Scaffold X). In other aspects, the EV comprises a TB antigen on the exterior surface of the EV, optionally linked via a scaffold moiety (e.g., Scaffold X), and IL-12 on the luminal surface of the EV, optionally linked via the scaffold moiety (e.g., Scaffold X). In other aspects, the EV comprises IL-12 on the exterior surface of the EV, optionally linked via a first scaffold moiety (e.g., Scaffold X), and a TB antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a TB antigen on the exterior surface of the EV, optionally linked via a first scaffold moiety (e.g., Scaffold X), and IL-12 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-12 on the luminal surface of the EV (e.g., Scaffold X or Scaffold Y), optionally linked via a first scaffold moiety, and a TB antigen on the luminal surface of the EV (e.g., Scaffold X or Scaffold Y), optionally linked via a second scaffold moiety, wherein the first scaffold moiety and the second scaffold moiety are the same or different.

The EVs comprising IL-12 and a TB antigen can induce an immune response to a subject in need thereof. In some aspects, the immune response is a CD4 T cell response, a CD8 T cell response, or both CD4 and CD8 T cell responses. In some aspects, the immune response is CD4 T-cell immune response with effector function that is specific to the TB antigen, e.g., the ESAT6 antigen. In some aspects, the immune response is CD8 T-cell immune response that is specific to the TB antigen, e.g., TB10.4 antigen.

In some aspects, an EV (e.g., exosome) comprising a TB antigen and an immune modulator (e.g., IL-12) can further comprise one or more additional payloads disclosed herein (e.g., additional antigen, additional immune modulator, and/or adjuvant). For instance, in certain aspects, the EV (e.g., exosome) can further comprise an adjuvant (e.g., such as those disclosed herein). In some aspects, the EV can further comprise an additional antigen (e.g., a different EBV antigen). In some aspects, the EV can further comprise an additional immune modulator (e.g., different from IL-21 or CD40L) disclosed herein.

In some aspects, the immune modulator that can be used with the present disclosure comprises a protein that supports intracellular interactions required for germinal center responses. In certain aspects, such a protein comprises a signaling lymphocyte activation molecule (SLAM) family member or a SLAM-associated protein (SAP). In some aspects, a SLAM family members comprises SLAM, CD48, CD229 (Ly9), Ly108, 2B4, CD84, NTB-A, CRACC, BLAME, CD2F-10, or combinations thereof. Non-limiting examples of other immune modulators that can play a role in germinal center response includes: ICOS-ICOSL, CD40-40L, CD28/B7, PD-1/L1, IL-4/IL4R, IL21/IL21R, TLR4, TLR7, TLR8, TLR9, CD180, CD22, and combinations thereof.

In some aspects, the immune modulator comprises a T-cell receptor (TCR) or a derivative thereof. In certain aspects, the immune modulator is a TCR α-chain or a derivative thereof. In other aspects, the immune modulator is a TCR β-chain or a derivative thereof. In further aspects, the immune modulator is a co-receptor of the T-cell or a derivative thereof.

In some aspects, the immune modulator comprises a chimeric antigen receptor (CAR) or a derivative thereof. In certain aspects, the CAR binds to one or more of the antigens disclosed herein (e.g., tumor antigen, e.g., alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand).

In some aspects, the immune modulator comprises an activator of a T-cell receptor or co-receptor. In certain aspects, the immunomodulating component is an activator of CD3. In certain aspects, the activator is a fragment of a monoclonal antibody of CD3. In certain aspects, the antibody fragment is a scFv, $(scFv)_2$, Fab, Fab', and $F(ab')_2$, $F(ab1)_2$, Fv, dAb, or Fd of a monoclonal antibody against CD3. In certain aspects, the activator is a nanobody, a bispecific antibody, or a multispecific antibody against CD3. In certain aspects, the immunomodulating component is an activator of CD28. In certain aspects, the activator is a fragment of a monoclonal antibody of CD28. In certain aspects, the antibody fragment is a scFv, $(scFv)_2$, Fab, Fab', and $F(ab')_2$, $F(ab1)_2$, Fv, dAb, or Fd of a monoclonal antibody of CD28. In certain aspects, the activator is a nanobody, a bispecific antibody, or a multispecific antibody against CD28.

In some aspects, the immune modulator comprises a tolerance inducing agent. In certain aspects, the tolerance inducing agent comprises a NF-κB inhibitor. Non-limiting examples of NF-κB inhibitors that can be used with the present disclosure includes: IKK complex inhibitors (e.g., TPCA-1, NF-κB Activation Inhibitor VI (BOT-64), BMS 345541, Amlexanox, SC-514 (GK 01140), IMD 0354, IKK-16), IκB degradation inhibitor (e.g., BAY 11-7082, MG-115, MG-132, Lactacystin, Epoxomicin, Parthenolide, Carfilzomib, MLN-4924 (Pevonedistat)), NF-κB nuclear translocation inhibitor (e.g., JSH-23, Rolipram), p65 acetylation inhibitor (e.g., Gallic acid, Anacardic acid), NF-κB-DNA binding inhibitor (e.g., GYY 4137, p-XSC, CV 3988, Prostaglandin E2 (PGE2)), NF-κB transactivation inhibitor (e.g., LY 294002, Wortmannin, Mesalamine), or combinations thereof. See also Gupta, S. C., et al., Biochim Biophys Acta 1799:775-787 (2010), which is herein incorporated by reference in its entirety. In some aspects, an immune modulator that can inhibit NF-κB activity and be used with the EVs (e.g., exosomes) disclosed herein comprises an antisense-oligonucleotide that specifically targets NF-κB. In further aspects, an immune modulator capable of inducing tolerance comprises a COX-2 inhibitor, mTOR inhibitor (e.g., rapamycin and derivatives, e.g., antisense oligonucleotides targeting mTor), prostaglandins, nonsteroidal anti-inflammatory agents (NSAIDS), antileukotriene, aryl hydrocarbon receptor (AhR) ligand, vitamin D, retinoic acid, steroids, Fas receptor/ligand, CD22 ligand, IL-10, IL-35, IL-27, metabolic regulator (e.g., glutamate), glycans (e.g., ES62, LewisX, LNFPIII), peroxisome proliferator-activated receptor (PPAR) agonists, immunoglobulin-like transcript (ILT) family of receptors (e.g., ILT3, ILT4, HLA-G, ILT-2), minocycline, TLR4 agonists, or combinations thereof.

In some aspects, the immune modulator is an agonist. In certain aspects, the agonist is an endogenous agonist, such as a hormone, or a neurotransmitter. In other aspects, the agonist is an exogenous agonist, such as a drug. In some aspects, the agonist is a physical agonist, which can create an agonist response without binding to the receptor. In some aspects, the agonist is a superagonist, which can produce a greater maximal response than the endogenous agonist. In certain aspects, the agonist is a full agonist with full efficacy at the receptor. In other aspects, the agonist is a partial agonist having only partial efficacy at the receptor relative to a full agonist. In some aspects, the agonist is an inverse agonist that can inhibit the constitutive activity of the receptor. In some aspects, the agonist is a co-agonist that works with other co-agonists to produce an effect on the receptor. In certain aspects, the agonist is an irreversible agonist that binds permanently to a receptor through formation of covalent bond. In certain aspects, the agonist is selective agonist for a specific type of receptor In some aspects, the immune modulator is an antagonist. In specific aspects, the antagonist is a competitive antagonist, which reversibly binds to the receptor at the same binding site as the endogenous ligand or agonist without activating the receptor. Competitive antagonist can affect the amount of agonist necessary to achieve a maximal response. In other aspects, the antagonist is a non-competitive antagonist, which binds to an active site of the receptor or an allosteric site of the receptor. Non-competitive antagonist can reduce the magnitude of the maximum response that can be attained by any amount of agonist. In further aspects, the antagonist is an uncompetitive antagonist, which requires receptor activation by an agonist before its binding to a separate allosteric binding site.

In some aspects, the immune modulator comprises an antibody or an antigen-binding fragment. The immunomodulating component can be a full length protein or a fragment thereof. The antibody or antigen-binding fragment can be derived from natural sources, or partly or wholly synthetically produced. In some aspects, the antibody is a monoclonal antibody. In some of these aspects, the monoclonal antibody is an IgG antibody. In certain aspects, the monoclonal antibody is an IgG1, IgG2, IgG3, or IgG4. In some other aspects, the antibody is a polyclonal antibody. In certain aspects, the antigen-binding fragment is selected from Fab, Fab', and $F(ab')_2$, $F(ab1)_2$, Fv, dAb, and Fd fragments. In certain aspects, the antigen-binding fragment is an scFv or $(scFv)_2$ fragment. In certain other aspects, the antibody or antigen-binding fragment is a NANOBODY® (single-domain antibody). In some aspects, the antibody or antigen-binding fragment is a bispecific or multispecific antibody.

In various aspects, the antibody or antigen-binding fragment is fully human. In some aspects, the antibody or antigen-binding fragment is humanized. In some aspects, the antibody or antigen-binding fragment is chimeric. In some of these aspects, the chimeric antibody has non-human V region domains and human C region domains. In some aspects, the antibody or antigen-binding fragment is non-human, such as murine or veterinary.

In certain aspects, the immunomodulating component is a polynucleotide. In some of these aspects, the polynucleotide includes, but is not limited to, an mRNA, a miRNA, an siRNA, an antisense oligonucleotide (e.g., antisense RNA or antisense DNA), a phosphorodiamidate morpholino oligomer (PMO), a peptide-conjugated phosphorodiamidate morpholino oligomer (PPMO), an shRNA, a lncRNA, a dsDNA, and combinations thereof. In some aspects, the polynucleotide is an RNA (e.g., an mRNA, a miRNA, an siRNA, an antisense oligonucleotide (e.g., antisense RNA), an shRNA, or an lncRNA). In some of these aspects, when the polynucleotide is an mRNA, it can be translated into a desired polypeptide. In some aspects, the polynucleotide is a microRNA (miRNA) or pre-miRNA molecule. In some of these aspects, the miRNA is delivered to the cytoplasm of the target cell, such that the miRNA molecule can silence a native mRNA in the target cell. In some aspects, the polynucleotide is a small interfering RNA (siRNA) or a short hairpin RNA (shRNA) capable of interfering with the expression of an oncogene or other dysregulating polypeptides. In some of these aspects, the siRNA is delivered to the cytoplasm of the target cell, such that the siRNA molecule can silence a native mRNA in the target cell. In some aspects, the polynucleotide is an antisense oligonucleotide (e.g., antisense RNA) that is complementary to an mRNA. In some aspects, the polynucleotide is a long non-coding RNA (lncRNA) capable of regulating gene expression and modulating diseases. In some aspects, the polynucleotide is a DNA that can be transcribed into an RNA. In some of these aspects, the transcribed RNA can be translated into a desired polypeptide.

In some aspects, the immunomodulating component is a protein, a peptide, a glycolipid, or a glycoprotein.

In various aspects, the EV (e.g., exosome) composition comprises two or more above mentioned immunomodulating components, including mixtures, fusions, combinations and conjugates, of atoms, molecules, etc. In some aspects, the composition comprises one, two, three, four, five, six, seven, eight, nine, ten, eleven, or twelve different immunomodulating components associated with the membrane or enclosed within the enclosed volume of the extracellular vesicle (e.g., exosome). In certain aspects, the composition comprises a nucleic acid combined with a polypeptide. In certain aspects, the composition comprises two or more polypeptides conjugated to each other. In certain aspects, the composition comprises a protein conjugated to a biologically active molecule. In some of these aspects, the biologically active molecule is a prodrug.

II.D Scaffold X-Engineered EVs, e.g., Exosomes.

In some aspects, EVs, e.g., exosomes, of the present disclosure comprise a membrane modified in its composition. For example, their membrane compositions can be modified by changing the protein, lipid, or glycan content of the membrane.

In some aspects, the surface-engineered EVs, e.g., exosomes, are generated by chemical and/or physical methods, such as PEG-induced fusion and/or ultrasonic fusion. In other aspects, the surface-engineered EVs, e.g., exosomes, are generated by genetic engineering. EVs, e.g., exosomes, produced from a genetically-modified producer cell or a progeny of the genetically-modified cell can contain modified membrane compositions. In some aspects, surface-engineered EVs, e.g., exosomes, have scaffold moiety (e.g., exosome protein, e.g., Scaffold X) at a higher or lower density (e.g., higher number) or include a variant or a fragment of the scaffold moiety.

For example, surface (e.g., Scaffold X)-engineered EVs, can be produced from a cell (e.g., HEK293 cells) transformed with an exogenous sequence encoding a scaffold moiety (e.g., exosome proteins, e.g., Scaffold X) or a variant or a fragment thereof. EVs including scaffold moiety expressed from the exogenous sequence can include modified membrane compositions.

Various modifications or fragments of the scaffold moiety can be used for the aspects, of the present invention. For example, scaffold moiety modified to have enhanced affinity to a binding agent can be used for generating surface-engineered EV that can be purified using the binding agent. Scaffold moieties modified to be more effectively targeted to EVs and/or membranes can be used. Scaffold moieties modified to comprise a minimal fragment required for specific and effective targeting to exosome membranes can be also used.

Scaffold moieties can be engineered to be expressed as a fusion molecule, e.g., fusion molecule of Scaffold X to an antigen, an adjuvant, and/or an immune modulator. For example, the fusion molecule can comprise a scaffold moiety disclosed herein (e.g., Scaffold X, e.g., PTGFRN, BSG, IGSF2, IGSF3, IGSF8, ITGB1, ITGA4, SLC3A2, ATP transporter, or a fragment or a variant thereof) linked to an antigen, an adjuvant, and/or an immune modulator. In case of the fusion molecule, the antigen, adjuvant, and/or immune modulator can be a natural peptide, a recombinant peptide, a synthetic peptide, or any combination thereof.

In some aspects, the surface (e.g., Scaffold X)-engineered EVs described herein demonstrate superior characteristics compared to EVs known in the art. For example, surface (e.g., Scaffold X)-engineered contain modified proteins more highly enriched on their surface than naturally occurring EVs or the EVs produced using conventional exosome proteins. Moreover, the surface (e.g., Scaffold X)-engineered EVs of the present invention can have greater, more specific, or more controlled biological activity compared to naturally occurring EVs or the EVs produced using conventional exosome proteins.

In some aspects, the Scaffold X comprises Prostaglandin F2 receptor negative regulator (the PTGFRN polypeptide). The PTGFRN protein can be also referred to as CD9 partner 1 (CD9P-1), Glu-Trp-Ile EWI motif-containing protein F (EWI-F), Prostaglandin F2-alpha receptor regulatory protein, Prostaglandin F2-alpha receptor-associated protein, or CD315. The full length amino acid sequence of the human PTGFRN protein (Uniprot Accession No. Q9P2B2) is shown at TABLE 7 as SEQ ID NO: 1. The PTGFRN polypeptide contains a signal peptide (amino acids 1 to 25 of SEQ ID NO: 1), the extracellular domain (amino acids 26 to 832 of SEQ ID NO: 1), a transmembrane domain (amino acids 833 to 853 of SEQ ID NO: 1), and a cytoplasmic domain (amino acids 854 to 879 of SEQ ID NO: 1). The mature PTGFRN polypeptide consists of SEQ ID NO: 1 without the signal peptide, i.e., amino acids 26 to 879 of SEQ ID NO: 1. In some aspects, a PTGFRN polypeptide fragment useful for the present disclosure comprises a transmembrane domain of the PTGFRN polypeptide. In other aspects, a PTGFRN polypeptide fragment useful for the present disclosure comprises the transmembrane domain of the PTGFRN polypeptide and (i) at least five, at least 10, at least 15, at least 20, at least 25, at least 30, at least 40, at least 50, at least 70, at least 80, at least 90, at least 100, at least 110, at least 120, at least 130, at least 140, at least 150 amino acids at the N terminus of the transmembrane domain, (ii) at least five, at least 10, at least 15, at least 20, or at least 25 amino acids at the C terminus of the transmembrane domain, or both (i) and (ii).

In some aspects, the fragments of PTGFRN polypeptide lack one or more functional or structural domains, such as IgV.

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 26 to 879 of SEQ ID NO: 1. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 33. In other aspects, the Scaffold X comprises the amino acid sequence of SEQ ID NO: 33, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 33 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 33.

In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 2, 3, 4, 5, 6, or 7. In other aspects, the Scaffold X comprises the amino acid sequence of SEQ ID NO: 2, 3, 4, 5, 6, or 7, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 2, 3, 4, 5, 6, or 7 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 2, 3, 4, 5, 6, or 7.

TABLE 7

Exemplary Scaffold X Protein Sequences

| Protein | Sequence |
|---|---|
| The PTGFRN Protein (SEQ ID NO: 1) | MGRLASRPLLLALLSLALCRGRVVRVPTATLVRVVGTELVIPCNVSDYDGPSEQNFDWSF<br>SSLGSSFVELASTWEVGFPAQLYQERLQRGEILLRRTANDAVELHIKNVQPSDQGHYKCS<br>TPSTDATVQGNYEDTVQVKVLADSLHVGPSARPPPSLSLREGEPFELRCTAASASPLHTH<br>LALLWEVHRGPARRSVLALTHEGRFHPGLGYEQRYHSGDVRLDTVGSDAYRLSVSRALSA<br>DQGSYRCIVSEWIAEQGNWQEIQEKAVEVATVVIQPSVLRAAVPKNVSVAEGKELDLTCN<br>ITTDRADDVRPEVTWSFSRMPDSTLPGSRVLARLDRDSLVHSSPHVALSHVDARSYHLLV<br>RDVSKENSGYYYCHVSLWAPGHNRSWHKVAEAVSSPAGVGVTWLEPDYQVYLNASKVPGF<br>ADDPTELACRVVDTKSGEANVRFTVSWYYRMNRRSDNVVTSELLAVMDGDWTLKYGERSK<br>QRAQDGDFIFSKEHTDTFNFRIQRTTEEDRGNYYCVVSAWTKQRNNSWVKSKDVFSKPVN<br>IFWALEDSVLVVKARQPKPFFAAGNTFEMTCKVSSKNIKSPRYSVLIMAEKPVGDLSSPN<br>ETKYIISLDQDSVVKLENWTDASRVDGVVLEKVQEDEFRYRMYQTQVSDAGLYRCMVTAW<br>SPVRGSLWREAATSLSNPIEIDFQTSGPIFNASVHSDTPSVIRGDLIKLFCIITVEGAAL<br>DPDDMAFDVSWFAVHSFGLDKAPVLLSSLDRKGIVTTSRRDWKSDLSLERVSVLEFLLQV<br>HGSEDQDFGNYYCSVTPWVKSPTGSWQKEAEIHSKPVFITVKMDVLNAFKYPLLIGVGLS<br>TVIGLLSCLIGYCSSHWCCKKEVQETRRERRRLMSMEMD |
| The PTGFRN protein Fragment (SEQ ID NO: 33) | GPIFNASVHSDTPSVIRGDLIKLFCIITVEGAALDPDDMAFDVSWFAVHSFGLDKAPVLL<br>SSLDRKGIVTTSRRDWKSDLSLERVSVLEFLLQVHGSEDQDFGNYYCSVTPWVKSPTGSW<br>QKEAEIHSKPVFITVKMDVLNAFKYPLLIGVGLSTVIGLLSCLIGYCSSHWCCKKEVQET<br>RRERRRLMSMEM<br>687-878 of SEQ ID NO: 1 |
| The BSG protein (SEQ ID NO: 9) | MAAALFVLLG FALLGTHGAS GAAGFVQAPL SQQRWVGGSV ELHCEAVGSP<br>VPEIQWWFEG QGPNDTCSQL WDGARLDRVH IHATYHQHAA STISIDTLVE<br>EDTGTYECRA SNDPDRNHLT RAPRVKWVRA QAVVLVLEPG TVFTTVEDLG<br>SKILLTCSLN DSATEVTGHR WLKGGVVLKE DALPGQKTEF KVDSDDQWGE<br>YSCVFLPEPM GTANIQLHGP PRVKAVKSSE HINEGETAML VCKSESVPPV<br>TDWAWYKITD SEDKALMNGS ESRFFVSSSQ GRSELHIENL NMEADPGQYR<br>CNGTSSKGSD QAIITLRVRS HLAALWPFLG IVAEVLVLVT IIFIYEKRRK<br>PEDVLDDDDA GSAPLKSSGQ HQNDKGKNVR QRNSS |
| The IGSF8 protein | MGALRPTLLP PSLPLLLLLM LGMGCWAREV LVPEGPLYRV AGTAVSISCN<br>VTGYEGPAQQ NFEWFLYRPE APDTALGIVS TKDTQFSYAV FKSRVVAGEV |

TABLE 7-continued

Exemplary Scaffold X Protein Sequences

| Protein | Sequence |
|---|---|
| (SEQ ID NO: 14) | QVQRLQGDAV VLKIARLQAQ DAGIYECHTP STDTRYLGSY SGKVELRVLP DVLQVSAAPP GPRGRQAPTS PPRMTVHEGQ ELALGCLART STQKHTHLAV SFGRSVPEAP VGRSTLQEVV GIRSDLAVEA GAPYAERLAA GELRLGKEGT DRYRMVVGGA QAGDAGTYHC TAAEWIQDPD GSWAQIAEKR AVLAHVDVQT LSSQLAVTVG PGERRIGPGE PLELLCNVSG ALPPAGRHAA YSVGWEMAPA GAPGPGRLVA QLDTEGVGSL GPGYEGRHIA MEKVASRTYR LRLEAARPGD AGTYRCLAKA YVRGSGTRLR EAASARSRPL PVHVREEGVV LEAVAWLAGG TVYRGETASL LCNISVRGGP PGLRLAASWW VERPEDGELS SVPAQLVGGV GQDGVAELGV RPGGGPVSVE LVGPRSHRLR LHSLGPEDEG VYHCAPSAWV QHADYSWYQA GSARSGPVTV YPYMHALDTL FVPLLVGTGV ALVTGATVLG TITCCFMKRL RKR |
| The ITGB1 protein (SEQ ID NO: 21) | MNLQPIFWIG LISSVCCVFA QTDENRCLKA NAKSCGECIQ AGPNCGWCTN STFLQEGMPT SARCDDLEAL KKKGCPPDDI ENPRGSKDIK KNKNVTNRSK GTAEKLKPED ITQIQPQQLV LRLRSGEPQT FTLKFKRAED YPIDLYYLMD LSYSMKDDLE NVKSLGTDLM NEMRRITSDF RIGFGSFVEK TVMPYISTTP AKLRNPCTSE QNCTSPFSYK NVLSLTNKGE VFNELVGKQR ISGNLDSPEG GFDAIMQVAV CGSLIGWRNV TRLLVFSTDA GFHFAGDGKL GGIVLPNDGQ CHLENNMYTM SHYYDYPSIA HLVQKLSENN IQTIFAVTEE FQPVYKELKN LIPKSAVGTL SANSSNVIQL IIDAYNSLSS EVILENGKLS EGVTISYKSY CKNGVNGTGE NGRKCSNISI GDEVQFEISI TSNKCPKKDS DSFKIRPLGF TEEVEVILQY ICECECQSEG IPESPKCHEG NGTFECGACR CNEGRVGRHC ECSTDEVNSE DMDAYCRKEN SSEICSNNGE CVCGQCVCRK RDNTNEIYSG ASNGQICNGR GICECGVCKC TDPKFQGQTC EMCQTCLGVC AEHKECVQCR AFNKGEKKDT CTQECSYFNI TKVESRDKLP QPVQPDPVSH CKEKDVDDCW FYFTYSVNGN NEVMVHVVEN PECPTGPDII PIVAGVVAGI VLIGLALLLI WKLLMIIHDR REFAKFEKEK MNAKWDTGEN PIYKSAVTTV VNPKYEGK |
| The ITGA4 protein (SEQ ID NO: 22) | MAWEARREPG PRRAAVRETV MLLLCLGVPT GRPYNVDTES ALLYQGPHNT LFGYSVVLHS HGANRWLLVG APTANWLANA SVINPGAIYR CRIGKNPGQT CEQLQLGSPN GEPCGKTCLE ERDNQWLGVT LSRQPGENGS IVTCGHRWKN IFYIKNENKL PTGGCYGVPP DLRTELSKRI APCYQDYVKK FGENFASCQA GISSFYTKDL IVMGAPGSSY WTGSLFVYNI TTNKYKAFLD KQNQVKFGSY LGYSVGAGHF RSQHTTEVVG GAPQHEQIGK AYIFSIDEKE LNILHEMKGK KLGSYFGASV CAVDLNADGF SDLLVGAPMQ STIREEGRVF VYINSGSGAV MNAMETNLVG SDKYAARFGE SIVNLGDIDN DGFEDVAIGA PQEDDLQGAI YIYNGRADGI SSTFSQRIEG LQISKSLSMF GQSISGQIDA DNNGYVDVAV GAFRSDSAVL LRTRPVVIVD ASLSHPESVN RTKFDCVENG WPSVCIDLTL CFSYKGKEVP GYIVLFYNMS LDVNRKAESP PRFYFSSNGT SDVITGSIQV SSREANCRTH QAFMRKDVRD ILTPIQIEAA YHLGPHVISK RSTEEFPPLQ PILQQKKEKD IMKKTINFAR FCAHENCSAD LQVSAKIGFL KPHENKTYLA VGSMKTLMLN VSLFNAGDDA YETTLHVKLP VGLYFIKILE LEEKQINCEV TDNSGVVQLD CSIGYIYVDH LSRIDISFLL DVSSLSRAEE DLSITVHATC ENEEEMDNLK HSRVTVAIPL KYEVKLTVHG FVNPTSFVYG SNDENEPETC MVEKMNLTFH VINTGNSMAP NVSVEIMVPN SFSPQTDKLF NILDVQTTTG ECHFENYQRV CALEQQKSAM QTLKGIVRFL SKTDKRLLYC IKADPHCLNF LCNFGKMESG KEASVHIQLE GRPSILEMDE TSALKFEIRA TGFPEPNPRV IELNKDENVA HVLLEGLHHQ RPKRYFTIVI ISSSLLLGLI VLLLISYVMW KAGFFKRQYK SILQEENRRD SWSYINSKSN DD |
| The SLC3A2 Protein, where the first Met is processed. (SEQ ID NO: 23) | MELQPPEASI AVVSIPRQLP GSHSEAGVQG LSAGDDSELG SHCVAQTGLE LLASGDPLPS ASQNAEMIET GSDCVTQAGL QLLASSDPPA LASKNAEVTG TMSQDTEVDM KEVELNELEP EKQPMNAASG AAMSLAGAEK NGLVKIKVAE DEAEAAAAAK FTGLSKEELL KVAGSPGWVR TRWALLLLFW LGWLGMLAGA VVIIVRAPRC RELPAQKWWH TGALYRIGDL QAFQGHGAGN LAGLKGRLDY LSSLKVKGLV LGPIHKNQKD DVAQTDLLQI DPNFGSKEDF DSLLQSAKKK SIRVILDLTP NYRGENSWFS TQVDTVATKV KDALEFWLQA GVDGFQVRDI ENLKDASSFL AEWQNITKGF SEDRLLIAGT NSSDLQQILS LLESNKDLLL TSSYLSDSGS TGEHTKSLVT QYLNATGNRW CSWSLSQARL LTSFLPAQLL RLYQLMLFTL PGTPVFSYGD EIGLDAAALP GQPMEAPVML WDESSFPDIP GAVSANMTVK GQSEDPGSLL SLFRRLSDQR SKERSLLHGD FHAFSAGPGL FSYIRHWDQN ERFLVVLNFG DVGLSAGLQA SDLPASASLP AKADLLLSTQ PGREEGSPLE LERLKLEPHE GLLLRFPYAA |

In some aspects, a Scaffold X comprises Basigin (the BSG protein), represented by SEQ ID NO: 9. The BSG protein is also known as 5F7, Collagenase stimulatory factor, Extracellular matrix metalloproteinase inducer (EMMPRIN), Leukocyte activation antigen M6, OK blood group antigen, Tumor cell-derived collagenase stimulatory factor (TCSF), or CD147. The Uniprot number for the human BSG protein is P35613. The signal peptide of the BSG protein is amino acid 1 to 21 of SEQ ID NO: 9. Amino acids 138-323 of SEQ ID NO: 9 is the extracellular domain, amino acids 324 to 344 is the transmembrane domain, and amino acids 345 to 385 of SEQ ID NO: 9 is the cytoplasmic domain.

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 22 to 385 of SEQ ID NO: 9. In some aspects, the fragments of BSG polypeptide lack one or more functional or structural domains, such as IgV, e.g., amino acids 221 to 315 of SEQ ID NO: 9. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 10, 11, or 12. In other aspects, the Scaffold X comprises the amino acid sequence of SEQ ID NO: 10, 11, or 12, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 10, 11, or 12 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 10, 11, or 12.

In some aspects, a Scaffold X comprises Immunoglobulin superfamily member 8 (IgSF8 or the IGSF8 protein), which is also known as CD81 partner 3, Glu-Trp-Ile EWI motif-containing protein 2 (EWI-2), Keratinocytes-associated transmembrane protein 4 (KCT-4), LIR-D1, Prostaglandin regulatory-like protein (PGRL) or CD316. The full length human IGSF8 protein is accession no. Q969P0 in Uniprot and is shown as SEQ ID NO: 14 herein. The human IGSF8 protein has a signal peptide (amino acids 1 to 27 of SEQ ID NO: 14), an extracellular domain (amino acids 28 to 579 of SEQ ID NO: 14), a transmembrane domain (amino acids 580 to 600 of SEQ ID NO: 14), and a cytoplasmic domain (amino acids 601 to 613 of SEQ ID NO: 14).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 14. In some aspects, the IGSF8 protein lack one or more functional or structural domains, such as IgV. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 15, 16, 17, or 18. In other aspects, the Scaffold X comprises the amino acid sequence of SEQ ID NO: 15, 16, 17, or 18, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID 15, 16, 17, or 18 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 15, 16, 17, or 18.

In some aspects, a Scaffold X for the present disclosure comprises Immunoglobulin superfamily member 3 (IgSF3 or the IGSF3 protein), which is also known as Glu-Trp-Ile EWI motif-containing protein 3 (EWI-3), and is shown as the amino acid sequence of SEQ ID NO: 20. The human IGSF3 protein has a signal peptide (amino acids 1 to 19 of SEQ ID NO: 20), an extracellular domain (amino acids 20 to 1124 of SEQ ID NO: 20), a transmembrane domain (amino acids 1125 to 1145 of SEQ ID NO: 20), and a cytoplasmic domain (amino acids 1146 to 1194 of SEQ ID NO: 20).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 20. In some aspects, the IGSF3 protein lack one or more functional or structural domains, such as IgV.

In some aspects, a Scaffold X for the present disclosure comprises Integrin beta-1 (the ITGB1 protein), which is also known as Fibronectin receptor subunit beta, Glycoprotein IIa (GPIIA), VLA-4 subunit beta, or CD29, and is shown as the amino acid sequence of SEQ ID NO: 21. The human ITGB1 protein has a signal peptide (amino acids 1 to 20 of SEQ ID NO: 21), an extracellular domain (amino acids 21 to 728 of SEQ ID NO: 21), a transmembrane domain (amino acids 729 to 751 of SEQ ID NO: 21), and a cytoplasmic domain (amino acids 752 to 798 of SEQ ID NO: 21).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 21 to 798 of SEQ ID NO: 21. In some aspects, the ITGB1 protein lack one or more functional or structural domains, such as IgV.

In other aspects, the Scaffold X comprises the ITGA4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 22 without the signal peptide (amino acids 1 to 33 of SEQ ID NO: 22). In some aspects, the ITGA4 protein lacks one or more functional or structural domains, such as IgV.

In other aspects, the Scaffold X comprises the SLC3A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 23 without the signal peptide. In some aspects, the SLC3A2 protein lacks one or more functional or structural domains, such as IgV.

In other aspects, the Scaffold X comprises the ATP1A1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 24 without the signal peptide. In some aspects, the ATP1A1 protein lacks one or more functional or structural domains, such as IgV.

In other aspects, the Scaffold X comprises the ATP1A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 25 without the signal peptide. In some aspects, the ATP1A2 protein lacks one or more functional or structural domains, such as IgV.

In other aspects, the Scaffold X comprises the ATP1A3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 26 without the signal peptide. In some aspects, the ATP1A3 protein lacks one or more functional or structural domains, such as IgV.

In other aspects, the Scaffold X comprises the ATP1A4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 27 without the signal peptide. In some aspects, the ATP1A4 protein lacks one or more functional or structural domains, such as IgV.

In other aspects, the Scaffold X comprises the ATP1A5 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 28 without the signal peptide. In some aspects, the ATP1A5 protein lacks one or more functional or structural domains, such as IgV.

In other aspects, the Scaffold X comprises the ATP2B1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 29 without the signal peptide. In some aspects, the ATP2B1 protein lacks one or more functional or structural domains, such as IgV.

In other aspects, the Scaffold X comprises the ATP2B2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 30 without the signal peptide. In some aspects, the ATP2B2 protein lacks one or more functional or structural domains, such as IgV.

In other aspects, the Scaffold X comprises the ATP2B3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 31 without the signal peptide. In some aspects, the ATP2B3 protein lacks one or more functional or structural domains, such as IgV.

In other aspects, the Scaffold X comprises the ATP2B4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 32 without the signal peptide. In some aspects, the ATP2B4 protein lacks one or more functional or structural domains, such as IgV.

In other aspects, the Scaffold X comprises the IGSF2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 34 without the signal peptide. In some aspects, the IGSF2 protein lacks one or more functional or structural domains, such as IgV.

Non-limiting examples of other Scaffold X proteins can be found at U.S. Pat. No. 10,195,290B1, issued Feb. 5, 2019, which is incorporated by reference in its entireties.

In some aspects, the sequence encodes a fragment of the scaffold moiety lacking at least 5, 10, 50, 100, 200, 300, 400, 500, 600, 700, or 800 amino acids from the N-terminus of the native protein. In some aspects, the sequence encodes a fragment of the scaffold moiety lacking at least 5, 10, 50, 100, 200, 300, 400, 500, 600, 700, or 800 amino acids from the C-terminus of the native protein. In some aspects, the sequence encodes a fragment of the scaffold moiety lacking at least 5, 10, 50, 100, 200, 300, 400, 500, 600, 700, or 800 amino acids from both the N-terminus and C-terminus of the native protein. In some aspects, the sequence encodes a fragment of the scaffold moiety lacking one or more functional or structural domains of the native protein.

In some aspects, the scaffold moieties, e.g., Scaffold X, e.g., a PTGFRN protein, are linked to one or more heterologous proteins. The one or more heterologous proteins can be linked to the N-terminus of the scaffold moieties. The one or more heterologous proteins can be linked to the C-terminus of the scaffold moieties. In some aspects, the one or more heterologous proteins are linked to both the N-terminus and the C-terminus of the scaffold moieties. In some aspects, the heterologous protein is a mammalian protein. In some aspects, the heterologous protein is a human protein.

In some aspects, Scaffold X can be used to link any moiety to the luminal surface and on the exterior surface of the EV, e.g., exosome, at the same time. For example, the PTGFRN polypeptide can be used to link one or more payloads disclosed herein (e.g., an antigen, an adjuvant, and/or an immune modulator) inside the lumen (e.g., on the luminal surface) in addition to the exterior surface of the EV, e.g., exosome. Therefore, in certain aspects, Scaffold X can be used for dual purposes, e.g., an antigen on the luminal surface and an adjuvant or immune modulator on the exterior surface of the EV, e.g., exosome, an antigen on the exterior surface of the EV, e.g., exosome, and the adjuvant or immune modulator on the luminal surface, an adjuvant on the luminal surface and an immune modulator on the exterior surface of the EV, e.g., exosome, or an immune modulator on the luminal surface and an adjuvant on the exterior surface of the EV, e.g., exosome.

II.E Scaffold Y-Engineered EVs, e.g., Exosomes

In some aspects, EVs, e.g., exosomes, of the present disclosure comprise an internal space (i.e., lumen) that is different from that of the naturally occurring EVs. For example, the EV can be changed such that the composition in the luminal surface of the EV, e.g., exosome has the protein, lipid, or glycan content different from that of the naturally-occurring exosomes.

In some aspects, engineered EVs, e.g., exosomes, can be produced from a cell transformed with an exogenous sequence encoding a scaffold moiety (e.g., exosome proteins, e.g., Scaffold Y) or a modification or a fragment of the scaffold moiety that changes the composition or content of the luminal surface of the EV, e.g., exosome. Various modifications or fragments of the exosome protein that can be expressed on the luminal surface of the EV, e.g., exosome, can be used for the aspects of the present disclosure.

In some aspects, the exosome proteins that can change the luminal surface of the EVs, e.g., exosomes, include, but are not limited to, the myristoylated alanine rich Protein Kinase C substrate (MARCKS) protein, the myristoylated alanine rich Protein Kinase C substrate like 1 (MARCKSL1) protein, the brain acid soluble protein 1 (BASP1) protein, or any combination thereof.

In some aspects, Scaffold Y comprises the MARCKS protein (Uniprot accession no. P29966). The MARCKS protein is also known as protein kinase C substrate, 80 kDa protein, light chain. The full-length human MARCKS protein is 332 amino acids in length and comprises a calmodulin-binding domain at amino acid residues 152-176. In some aspects, Scaffold Y comprises the MARCKSL1 protein (Uniprot accession no. P49006). The MARCKSL1 protein is also known as MARCKS-like protein 1, and macrophage myristoylated alanine-rich C kinase substrate. The full-length human MARCKSL1 protein is 195 amino acids in length. The MARCKSL1 protein has an effector domain involved in lipid-binding and calmodulin-binding at amino acid residues 87-110. In some aspects, the Scaffold Y comprises the BASP1 protein (Uniprot accession number P80723). The BASP1 protein is also known as 22 kDa neuronal tissue-enriched acidic protein or neuronal axonal membrane protein NAP-22. The full-length human BASP1 protein sequence (isomer 1) is 227 amino acids in length. An isomer produced by an alternative splicing is missing amino acids 88 to 141 from SEQ ID NO: 49 (isomer 1). TABLE 8 provides the full-length sequences for the exemplary Scaffold Y disclosed herein (i.e., the MARCKS, MARCKSL1, and BASP1 proteins).

TABLE 8

Exemplary Scaffold Y Protein Sequences

| Protein | Sequence |
|---|---|
| The MARCKS protein (SEQ ID NO: 47) | MGAQESKTAA KGEAAAERPG EAAVASSPSK ANGQENGHVK VNGDASPAAA ESGAKEELQA NGSAPAADKE EPAAAGSGAA SPSAAEKGEP AAAAAPEAGA SPVEKEAPAE GEAAEPGSPT AAEGEAASAA SSTSSPKAED GATPSPSNET AAAAAEAGAA SGEQAAAPGE EAAAGEEGAA GGDPQEAKPQ EAAVAPEKPP ASKETKAAEE PSKVEEKKAE EAGASAAACE APSAAGPGAP PEQEAAPAEE PAAAAASSAC AAPSQEAQPE CSPEAPPAEA AE |
| The MARCKSL1 protein (SEQ ID NO: 48) | MGSQSSKAPR GDVTAEEAAG ASPAKANGQE NGHVKSNGDL SPKGEGESPP VNGTDEAAGA TGDAIEPAPP SQGAEAKGEV PPKETPKKKK KFSFKKPFKL SGLSFKRNRK EGGGDSSASS PTEEEQEQGE IGACSDEGTA QEGKAAATPE SQEPQAKGAE ASAASEEEAG PQATEPSTPS GPESGPTPAS AEQNE |
| The BASP1 protein (SEQ ID NO: 49) | MGGKLSKKKK GYNVNDEKAK EKDKKAEGAA TEEEGTPKES EPQAAAEPAE AKEGKEKPDQ DAEGKAEEKE GEKDAAAAKE EAPKAEPEKT EGAAEAKAEP PKAPEQEQAA PGPAAGGEAP KAAEAAAAPA ESAAPAAGEE PSKEEGEPKK TEAPAAPAAQ ETKSDGAPAS DSKPGSSEAA PSSKETPAAT EAPSSTPKAQ GPAASAEEPK PVEAPAANSD QTVTVKE |

The mature BASP1 protein sequence is missing the first Met from SEQ ID NO: 49 and thus contains amino acids 2 to 227 of SEQ ID NO: 49. Similarly, the mature MARCKS and MARCKSL1 proteins also lack the first Met from SEQ ID NOs: 47 and 48, respectively. Accordingly, the mature MARCKS protein contains amino acids 2 to 332 of SEQ ID NO: 47. The mature MARCKSL1 protein contains amino acids 2 to 227 of SEQ ID NO: 48.

In other aspects, Scaffold Y useful for the present disclosure comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 2 to 227 of SEQ ID NO: 49. In other aspects, the Scaffold Y comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to any one of SEQ ID NOs: 50-155. In other aspects, a Scaffold Y useful for the present disclosure comprises the amino acid sequence of SEQ ID NO: 49, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, a Scaffold Y useful for the present disclosure comprises the amino acid sequence of any one of SEQ ID NOs: 50-155 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NOs: 50-155.

In some aspects, the protein sequence of any of SEQ ID NOs: 47-155 is sufficient to be a Scaffold Y for the present disclosure (e.g., scaffold moiety linked to an antigen and/or an adjuvant and/or an immune modulator).

In certain aspects, a Scaffold Y useful for the present disclosure comprises a peptide with the MGXKLSKKK, where X is alanine or any other amino acid (SEQ ID NO: 163). In some aspects, a Scaffold Y useful for the present disclosure comprises a peptide with the GXKLSKKK (S, where X is alanine or any other amino acid (SEQ ID NO: 372). In some aspects, an EV, e.g., exosome, comprises a peptide with sequence of (M)(G)(π)(ξ)(Φ/π)(S/A/G/N)(+)(+) or (G)(π)(ξ)(Φ/π)(S/A/G/N)(+)(+), wherein each parenthetical position represents an amino acid, and wherein π is any amino acid selected from the group consisting of (Pro, Gly, Ala, Ser), ξ is any amino acid selected from the group consisting of (Asn, Gln, Ser, Thr, Asp, Glu, Lys, His, Arg), Φ is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). In further aspects, an exosome described herein (e.g., engineered exosome) comprises a peptide with sequence of (M)(G)(π)(X)(Φ/π)(π)(+)(+) or (G)(π)(X)(Φ/π)(π)(+)(+), wherein each parenthetical position represents an amino acid, and wherein π is any amino acid selected from the group consisting of (Pro, Gly, Ala, Ser), X is any amino acid, Φ is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). See Aasland et al., FEBS Letters 513 (2002) 141-144 for amino acid nomenclature.

In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to any one of SEQ ID NO: 47-155.

Scaffold Y-engineered EVs, e.g., exosomes described herein can be produced from a cell transformed with a sequence set forth in SEQ ID NOs: 47-155.

In some aspects, the Scaffold Y protein useful for the present disclosure comprises an "N-terminus domain" (ND) and an "effector domain" (ED), wherein the ND and/or the ED are associated with the luminal surface of the EV, e.g., an exosome. In some aspects, the Scaffold Y protein useful for the present disclosure comprises an intracellular domain, a transmembrane domain, and an extracellular domain; wherein the intracellular domain comprises an "N-terminus domain" (ND) and an "effector domain" (ED), wherein the ND and/or the ED are associated with the luminal surface of the EV, e.g., an exosome. As used herein the term "associated with" refers to the interaction between a scaffold protein with the luminal surface of the EV, e.g., and exosome, that does not involve covalent linking to a membrane component. For example, the scaffolds useful for the present disclosure can be associated with the luminal surface of the EV, e.g., via a lipid anchor (e.g., myristic acid), and/or a polybasic domain that interacts electrostatically with the negatively charged head of membrane phospholipids. In other aspects, the Scaffold Y protein comprises an N-terminus domain (ND) and an effector domain (ED), wherein the ND is associated with the luminal surface of the EV and the ED are associated with the luminal surface of the EV by an ionic interaction, wherein the ED comprises at least two, at least three, at least four, at least five, at least six, or at least seven contiguous basic amino acids, e.g., lysines (Lys), in sequence.

In other aspects, the Scaffold Y protein comprises an N-terminus domain (ND) and an effector domain (ED), wherein the ND is associated with the luminal surface of the EV, e.g., exosome, and the ED is associated with the luminal surface of the EV by an ionic interaction, wherein the ED comprises at least two, at least three, at least four, at least five, at least six, or at least seven contiguous basic amino acids, e.g., lysines (Lys), in sequence.

In some aspects, the ND is associated with the luminal surface of the EV, e.g., an exosome, via lipidation, e.g., via myristoylation. In some aspects, the ND has Gly at the N terminus. In some aspects, the N-terminal Gly is myristoylated.

In some aspects, the ED is associated with the luminal surface of the EV, e.g., an exosome, by an ionic interaction. In some aspects, the ED is associated with the luminal surface of the EV, e.g., an exosome, by an electrostatic interaction, in particular, an attractive electrostatic interaction.

In some aspects, the ED comprises (i) a basic amino acid (e.g., lysine), or (ii) two or more basic amino acids (e.g., lysine) next to each other in a polypeptide sequence. In some aspects, the basic amino acid is lysine (Lys; K), arginine (Arg, R), or Histidine (His, H). In some aspects, the basic amino acid is (Lys)n, wherein n is an integer between 1 and 10.

In other aspects, the ED comprises at least a lysine and the ND comprises a lysine at the C terminus if the N terminus of the ED is directly linked to lysine at the C terminus of the ND, i.e., the lysine is in the N terminus of the ED and is fused to the lysine in the C terminus of the ND. In other aspects, the ED comprises at least two lysines, at least three lysines, at least four lysines, at least five lysines, at least six lysines, or at least seven lysines when the N terminus of the ED is linked to the C terminus of the ND by a linker, e.g., one or more amino acids.

In some aspects, the ED comprises K, KK, KKK, KKKK (SEQ ID NO: 205), KKKKK (SEQ ID NO: 206), R, RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof. In some aspects, the ED comprises KK, KKK, KKKK (SEQ ID NO: 205), KKKKK (SEQ ID NO: 206), or any combination thereof. In some aspects, the ND comprises the amino acid sequence as set forth in G:X2:X3:X4:X5:X6, wherein G represents Gly; wherein ":" represents a peptide bond; wherein each of the X2 to the X6 independently represents an amino acid; and wherein the X6 represents a basic amino acid. In some aspects, the X6 amino acid is selected is selected from the group consisting of Lys, Arg, and His. In some aspects, the X5 amino acid is selected from the group consisting of Pro, Gly, Ala, and Ser. In some aspects, the X2 amino acid is selected from the group consisting of Pro, Gly, Ala, and Ser. In some aspects, the X4 is selected from the group consisting of Pro, Gly, Ala, Ser, Val, Ile, Leu, Phe, Trp, Tyr, Gln, and Met.

In some aspects, the Scaffold Y protein comprises an N-terminus domain (ND) and an effector domain (ED), wherein the ND comprises the amino acid sequence as set forth in G:X2:X3:X4:X5:X6, wherein G represents Gly; wherein ":" represents a peptide bond; wherein each of the X2 to the X6 is independently an amino acid; wherein the X6 comprises a basic amino acid, and wherein the ED is linked to X6 by a peptide bond and comprises at least one lysine at the N terminus of the ED.

In some aspects, the ND of the Scaffold Y protein comprises the amino acid sequence of G:X2:X3:X4:X5:X6, wherein G represents Gly; ":" represents a peptide bond; the X2 represents an amino acid selected from the group consisting of Pro, Gly, Ala, and Ser; the X3 represents any amino acid; the X4 represents an amino acid selected from the group consisting of Pro, Gly, Ala, Ser, Val, Ile, Leu, Phe, Trp, Tyr, Gln, and Met; the X5 represents an amino acid selected from the group consisting of Pro, Gly, Ala, and Ser; and the X6 represents an amino acid selected from the group consisting of Lys, Arg, and His.

In some aspects, the X3 amino acid is selected from the group consisting of Asn, Gln, Ser, Thr, Asp, Glu, Lys, His, and Arg.

In some aspects, the ND and ED are joined by a linker. In some aspects, the linker comprises one or more amino acids. In some aspects, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. Generally, linkers provide flexibility or prevent/ameliorate steric hindrances. Linkers are not typically cleaved; however, in certain aspects, such cleavage can be desirable. Accordingly, in some aspects, a linker can comprise one or more protease-cleavable sites, which can be located within the sequence of the linker or flanking the linker at either end of the linker sequence. When the ND and ED are joined by a linker, the ED comprise at least two lysines, at least three lysines, at least four lysines, at least five lysines, at least six lysines, or at least seven lysines.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the linker is a glycine/serine linker. In some aspects, the peptide linker is glycine/serine linker according to the formula [(Gly)n-Ser]m where n is any integer from 1 to 100 and m is any integer from 1 to 100. In other aspects, the glycine/serine linker is according to the formula [(Gly)x-Sery]z wherein x in an integer from 1 to 4, y is 0 or 1, and z is an integers from 1 to 50. In some aspects, the peptide linker comprises the sequence Gn, where n can be an integer from 1 to 100. In some aspects, the peptide linker can comprise the sequence (GlyAla)n, wherein n is an integer between 1 and 100. In other aspects, the peptide linker can comprise the sequence (GlyGlySer)n, wherein n is an integer between 1 and 100.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect, the peptide linker can comprise non-naturally occurring polypeptides which are modified forms of naturally occurring polypeptides (e.g., comprising a mutation such as an addition, substitution or deletion).

In other aspects, the peptide linker can comprise non-naturally occurring amino acids. In yet other aspects, the peptide linker can comprise naturally occurring amino acids occurring in a linear sequence that does not occur in nature. In still other aspects, the peptide linker can comprise a naturally occurring polypeptide sequence.

The present disclosure also provides an isolated extracellular vesicle (EV), e.g., an exosome, comprising a biologically active molecule (e.g., an antigen, an adjuvant, and/or an immune modulator) linked to a Scaffold Y protein, wherein the Scaffold Y protein comprises ND-ED, wherein: ND comprises G:X2:X3:X4:X5:X6; wherein: G represents Gly; ":" represents a peptide bond; X2 represents an amino acid selected from the group consisting of Pro, Gly, Ala, and Ser; X3 represents any amino acid; X4 represents an amino acid selected from the group consisting of Pro, Gly, Ala, Ser, Val, Ile, Leu, Phe, Trp, Tyr, Glu, and Met; X5 represents an amino acid selected from the group consisting of Pro, Gly, Ala, and Ser; X6 represents an amino acid selected from the group consisting of Lys, Arg, and His; "-" represents an optional linker; and ED is an effector domain comprising (i) at least two contiguous lysines (Lys), which is linked to the X6 by a peptide bond or one or more amino acids or (ii) at least one lysine, which is directly linked to the X6 by a peptide bond.

In some aspects, the X2 amino acid is selected from the group consisting of Gly and Ala. In some aspects, the X3 amino acid is Lys. In some aspects, the X4 amino acid is Leu or Glu. In some aspects, the X5 amino acid is selected from the group consisting of Ser and Ala. In some aspects, the X6 amino acid is Lys. In some aspects, the X2 amino acid is Gly, Ala, or Ser; the X3 amino acid is Lys or Glu; the X4 amino acid is Leu, Phe, Ser, or Glu; the X5 amino acid is Ser or Ala; and X6 amino acid is Lys. In some aspects, the "-" linker comprises a peptide bond or one or more amino acids.

In some aspects, the ED in the scaffold protein comprises Lys (K), KK, KKK, KKKK (SEQ ID NO: 205), KKKKK (SEQ ID NO: 206), Arg (R), RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof.

In some aspects, the Scaffold Y protein comprises an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), or (v) any combination thereof.

In some aspects, the ND in the Scaffold Y protein comprises an amino acid sequence selected from the group consisting of (i) GGKLSK (SEQ ID NO: 215), (ii) GAKLSK (SEQ ID NO: 216), (iii) GGKQSK (SEQ ID NO: 217), (iv) GGKLAK (SEQ ID NO: 218), or (v) any combination thereof and the ED in the scaffold protein comprises K, KK, KKK, KKKG (SEQ ID NO: 219), KKKGY (SEQ ID NO: 220), KKKGYN (SEQ ID NO: 221), KKKGYNV (SEQ ID NO: 222), KKKGYNVN (SEQ ID NO: 223), KKKGYS (SEQ ID NO: 224), KKKGYG (SEQ ID NO: 225), KKKGYGG (SEQ ID NO: 226), KKKGS (SEQ ID NO: 227), KKKGSG (SEQ ID NO: 228), KKKGSGS (SEQ ID NO: 229), KKKS (SEQ ID NO: 230), KKKSG (SEQ ID NO: 231), KKKSGG (SEQ ID NO: 232), KKKSGGS (SEQ ID NO: 233), KKKSGGSG (SEQ ID NO: 234), KKSGGSGG (SEQ ID NO: 235), KKKSGGSGGS (SEQ ID NO: 236), KRFSFKKS (SEQ ID NO: 237).

In some aspects, the polypeptide sequence of a Scaffold Y protein useful for the present disclosure consists of an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), or (v) any combination thereof.

In some aspects, the Scaffold Y protein comprises an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof.

In some aspects, the polypeptide sequence of a Scaffold Y protein useful for the present disclosure consists of an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof.

In some aspects, the Scaffold Y protein is at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least 31, at least about 32, at least about 33, at least about 34, at least about 35, at least about 36, at least about 37, at least about 38, at least about 39, at least about 39, at least about 40, at least about 41, at least about 42, at least about 43, at least about 44, at least about 50, at least about 46, at least about 47, at least about 48, at least about 49, at least about 50, at least about 55, at least about 60, at least about 65, at least about 70, at least about 75, at least about 80, at least 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 305, at least about 310, at least about 315, at least about 320, at least about 325, at least about 330, at least about 335, at least about 340, at least about 345, or at least about 350 amino acids in length.

In some aspects, the Scaffold Y protein is between about 5 and about 10, between about 10 and about 20, between about 20 and about 30, between about 30 and about 40, between about 40 and about 50, between about 50 and about 60, between about 60 and about 70, between about 70 and about 80, between about 80 and about 90, between about 90 and about 100, between about 100 and about 110, between about 110 and about 120, between about 120 and about 130, between about 130 and about 140, between about 140 and about 150, between about 150 and about 160, between about 160 and about 170, between about 170 and about 180, between about 180 and about 190, between about 190 and about 200, between about 200 and about 210, between about 210 and about 220, between about 220 and about 230, between about 230 and about 240, between about 240 and about 250, between about 250 and about 260, between about 260 and about 270, between about 270 and about 280, between about 280 and about 290, between about 290 and about 300, between about 300 and about 310, between about 310 and about 320, between about 320 and about 330, between about 330 and about 340, or between about 340 and about 250 amino acids in length.

In some aspects, the Scaffold Y protein comprises (i) GGKLSKKKKGYNVN (SEQ ID NO: 246), (ii) GAKLSKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKLSKKKKGYSGG (SEQ ID NO: 250), (vi) GGKLSKKKKGSGGS (SEQ ID NO: 251), (vii) GGKLSKKKKSGGSG (SEQ ID NO: 252), (viii) GGKLSKKKSGGSGG (SEQ ID NO: 253), (ix) GGKLSKKSGGSGGS (SEQ ID NO: 254), (x) GGKLSKSGGSGGSV (SEQ ID NO: 255), or (xi) GAKKSKKRFSFKKS (SEQ ID NO: 256).

In some aspects, the polypeptide sequence of a Scaffold Y protein useful for the present disclosure consists of (i) GGKLSKKKKGYNVN (SEQ ID NO: 246), (ii) GAKLSKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKLSKKKKGYSGG (SEQ ID NO: 250), (vi) GGKLSKKKKGSGGS (SEQ ID NO: 251), (vii) GGKLSKKKKSGGSG (SEQ ID NO: 252), (viii) GGKLSKKKSGGSGG (SEQ ID NO: 253), (ix) GGKLSKKSGGSGGS (SEQ ID NO: 254), (x) GGKLSKSGGSGGSV (SEQ ID NO: 255), or (xi) GAKKSKKRFSFKKS (SEQ ID NO: 256).

Non-limiting examples of the Scaffold Y protein useful for the present disclosure are listed below. In some aspects, the Scaffold Y protein comprises an amino acid sequence set forth in TABLE 9. In some aspects, the Scaffold Y protein consists of an amino acid sequence set forth in TABLE 9.

TABLE 9

| SEQ ID NO: | Scaffold Protein: GX2X3X4X5X6-ED |
|---|---|
| 257 | GGKLSKKKKGYNVNDEKAKEKDKKAEGAA |
| 258 | GGKLSKKKKGYNVNDEKAKEKDKKAEGA |
| 259 | GGKLSKKKKGYNVNDEKAKEKDKKAEG |
| 260 | GGKLSKKKKGYNVNDEKAKEKDKKAE |
| 261 | GGKLSKKKKGYNVNDEKAKEKDKKA |
| 262 | GGKLSKKKKGYNVNDEKAKEKDKK |
| 263 | GGKLSKKKKGYNVNDEKAKEKDK |
| 264 | GGKLSKKKKGYNVNDEKAKEKD |
| 265 | GGKLSKKKKGYNVNDEKAKEK |
| 266 | GGKLSKKKKGYNVNDEKAKE |
| 267 | GGKLSKKKKGYNVNDEKAK |
| 268 | GGKLSKKKKGYNVNDEKA |
| 269 | GGKLSKKKKGYNVNDEK |
| 270 | GGKLSKKKKGYNVNDE |
| 271 | GGKLSKKKKGYNVND |
| 246 | GGKLSKKKKGYNVN |
| 272 | GGKLSKKKKGYNV |
| 273 | GGKLSKKKKGYN |
| 274 | GGKLSKKKKGY |
| 275 | GGKLSKKKKG |
| 276 | GGKLSKKKK |
| 238 | GGKLSKKK |
| 211 | GGKLSKK |
| 300 | GAKKSKKRFSFKKSFKLSGFSFKKNKKEA |

TABLE 9-continued

| SEQ ID NO: | Scaffold Protein: GX2X3X4X5X6-ED |
|---|---|
| 277 | GAKKSKKRFSFKKSFKLSGFSFKKNKKE |
| 278 | GAKKSKKRFSFKKSFKLSGFSFKKNKK |
| 279 | GAKKSKKRFSFKKSFKLSGFSFKKNK |
| 280 | GAKKSKKRFSFKKSFKLSGFSFKKN |
| 281 | GAKKSKKRFSFKKSFKLSGFSFKK |
| 282 | GAKKSKKRFSFKKSFKLSGFSFK |
| 283 | GAKKSKKRFSFKKSFKLSGFSF |
| 284 | GAKKSKKRFSFKKSFKLSGFS |
| 285 | GAKKSKKRFSFKKSFKLSGF |
| 286 | GAKKSKKRFSFKKSFKLSG |
| 287 | GAKKSKKRFSFKKSFKLS |
| 288 | GAKKSKKRFSFKKSFKL |
| 289 | GAKKSKKRFSFKKSFK |
| 290 | GAKKSKKRFSFKKSF |
| 291 | GAKKSKKRFSFKKS |
| 292 | GAKKSKKRFSFKK |
| 293 | GAKKSKKRFSFK |
| 294 | GAKKSKKRFSF |
| 295 | GAKKSKKRFS |
| 296 | GAKKSKKRF |
| 297 | GAKKSKKR |
| 298 | GAKKSKK |
| 301 | GAKKAKKRFSFKKSFKLSGFSFKKNKKEA |
| 348 | GAKKAKKRFSFKKSFKLSGFSFKKNKKE |
| 349 | GAKKAKKRFSFKKSFKLSGFSFKKNKK |
| 350 | GAKKAKKRFSFKKSFKLSGFSFKKNK |
| 351 | GAKKAKKRFSFKKSFKLSGFSFKKN |
| 352 | GAKKAKKRFSFKKSFKLSGFSFKK |
| 353 | GAKKAKKRFSFKKSFKLSGFSFK |
| 354 | GAKKAKKRFSFKKSFKLSGFSF |
| 355 | GAKKAKKRFSFKKSFKLSGFS |
| 356 | GAKKAKKRFSFKKSFKLSGF |
| 357 | GAKKAKKRFSFKKSFKLSG |
| 358 | GAKKAKKRFSFKKSFKLS |
| 359 | GAKKAKKRFSFKKSFKL |
| 360 | GAKKAKKRFSFKKSFK |
| 361 | GAKKAKKRFSFKKSF |
| 362 | GAKKAKKRFSFKKS |
| 363 | GAKKAKKRFSFKK |

TABLE 9-continued

| SEQ ID NO: | Scaffold Protein: GX2X3X4X5X6-ED |
|---|---|
| 364 | GAKKAKKRFSFK |
| 365 | GAKKAKKRFSF |
| 366 | GAKKAKKRFS |
| 367 | GAKKAKKRF |
| 368 | GAKKAKKR |
| 369 | GAKKAKK |
| 302 | GAQESKKKKKKRFSFKKSFKLSGFSFKK |
| 303 | GAQESKKKKKKRFSFKKSFKLSGFSFK |
| 304 | GAQESKKKKKKRFSFKKSFKLSGFSF |
| 305 | GAQESKKKKKKRFSFKKSFKLSGFS |
| 306 | GAQESKKKKKKRFSFKKSFKLSGF |
| 307 | GAQESKKKKKKRFSFKKSFKLSG |
| 308 | GAQESKKKKKKRFSFKKSFKLS |
| 309 | GAQESKKKKKKRFSFKKSFKL |
| 310 | GAQESKKKKKKRFSFKKSFK |
| 311 | GAQESKKKKKKRFSFKKSF |
| 312 | GAQESKKKKKKRFSFKKS |
| 313 | GAQESKKKKKKRFSFKK |
| 314 | GAQESKKKKKKRFSFK |
| 315 | GAQESKKKKKKRFSF |
| 316 | GAQESKKKKKKRFS |
| 317 | GAQESKKKKKKRF |
| 318 | GAQESKKKKKKR |
| 319 | GAQESKKKKKK |
| 320 | GAQESKKKKK |
| 321 | GAQESKKKK |
| 322 | GAQESKKK |
| 323 | GAQESKK |
| 324 | GSQSSKKKKKKFSFKKPFKLSGLSFKRNRK |
| 325 | GSQSSKKKKKKFSFKKPFKLSGLSFKRNR |
| 326 | GSQSSKKKKKKFSFKKPFKLSGLSFKRN |
| 327 | GSQSSKKKKKKFSFKKPFKLSGLSFKR |
| 328 | GSQSSKKKKKKFSFKKPFKLSGLSFK |
| 329 | GSQSSKKKKKKFSFKKPFKLSGLSF |
| 330 | GSQSSKKKKKKFSFKKPFKLSGLS |
| 331 | GSQSSKKKKKKFSFKKPFKLSGL |
| 332 | GSQSSKKKKKKFSFKKPFKLSG |
| 333 | GSQSSKKKKKKFSFKKPFKLS |
| 334 | GSQSSKKKKKKFSFKKPFKL |

TABLE 9-continued

| SEQ ID NO: | Scaffold Protein: GX2X3X4X5X6-ED |
|---|---|
| 335 | GSQSSKKKKKKFSFKKPFK |
| 336 | GSQSSKKKKKKFSFKKPF |
| 337 | GSQSSKKKKKKFSFKKP |
| 338 | GSQSSKKKKKKFSFKK |
| 339 | GSQSSKKKKKKFSFK |
| 340 | GSQSSKKKKKKFSF |
| 341 | GSQSSKKKKKKFS |
| 342 | GSQSSKKKKKKF |
| 343 | GSQSSKKKKKK |
| 344 | GSQSSKKKKK |
| 345 | GSQSSKKKK |
| 346 | GSQSSKKK |
| 347 | GSQSSKK |

In some aspects, the Scaffold Y protein useful for the present disclosure does not contain an N-terminal Met. In some aspects, the Scaffold Y protein comprises a lipidated amino acid, e.g., a myristoylated amino acid, at the N-terminus of the scaffold protein, which functions as a lipid anchor. In some aspects, the amino acid residue at the N-terminus of the scaffold protein is Gly. The presence of an N-terminal Gly is an absolute requirement for N-myristoylation. In some aspects, the amino acid residue at the N-terminus of the scaffold protein is synthetic. In some aspects, the amino acid residue at the N-terminus of the scaffold protein is a glycine analog, e.g., allylglycine, butylglycine, or propargylglycine.

In other aspects, the lipid anchor can be any lipid anchor known in the art, e.g., palmitic acid or glycosylphosphatidylinositols. Under unusual circumstances, e.g., by using a culture medium where myristic acid is limiting, some other fatty acids including shorter-chain and unsaturated, can be attached to the N-terminal glycine. For example, in BK channels, myristate has been reported to be attached post-translationally to internal serine/threonine or tyrosine residues via a hydroxyester linkage. Membrane anchors known in the art are presented in the following table:

| Modification | Modifying Group |
|---|---|
| S-Palmitoylation | 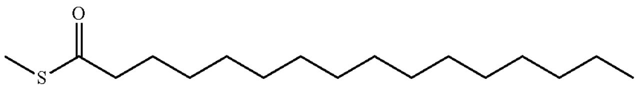 [SMILES: CCCCCCCCCCCCCCCC(=O)SC] |
| N-Palmitoylation | 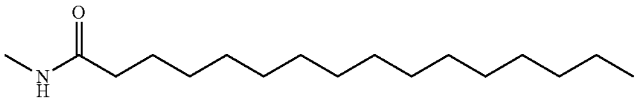 [SMILES: CCCCCCCCCCCCCCCC(=O)NC] |
| N-Myristoylation | 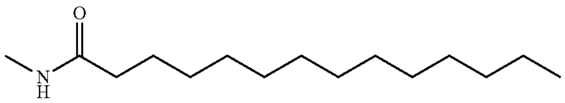 [SMILES: CCCCCCCCCCCCCC(=O)NC] |
| O-Acylation | 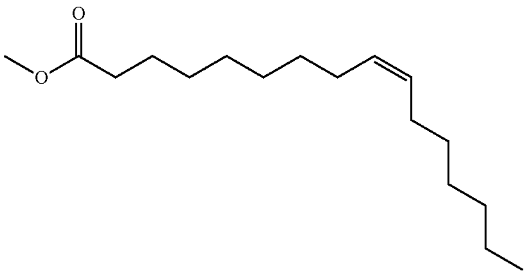 [SMILES: CCCCCC/C=C\CCCCCCCC(=O)OC] |
| Farnesylation | 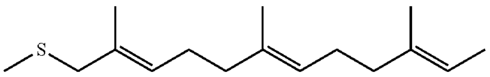 [SMILES: C/C=C(\C)CC/C=C(\C)CC/C=C(\C)CSC] |
| Geranylgeranylation | 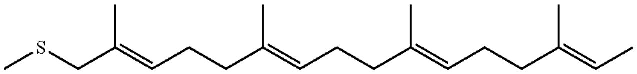 [SMILES: C/C=C(\C)CC/C=C(\C)CC/C=C(\C)CC/C=C(\C)CSC] |

-continued

| Modification | Modifying Group |
| --- | --- |
| Cholesterol | 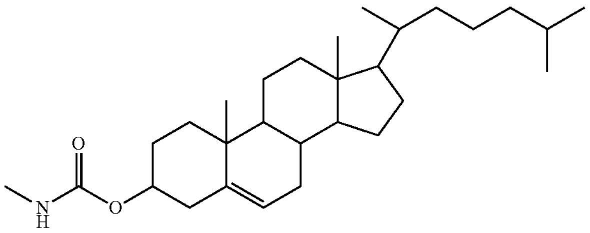 [SMILES: CNC(=O)OC1CCC2(C)C(=CCC3C2CCC2(C)C(C(C)CCCC(C)C)CCC32)C1] |

II.F Conjugated EVs (e.g., Exosomes)

Unlike antibodies, EVs (e.g., exosomes) can accommodate large numbers of molecules attached to their surface, e.g., on the order of thousands to tens of thousands of molecules per EV (e.g., exosome). EV (e.g., exosome)-drug conjugates thus represent a platform to deliver a high concentration of therapeutic compound to discrete cell types, while at the same time limiting overall systemic exposure to the compound, which in turn reduces off-target toxicity.

Figure 31:
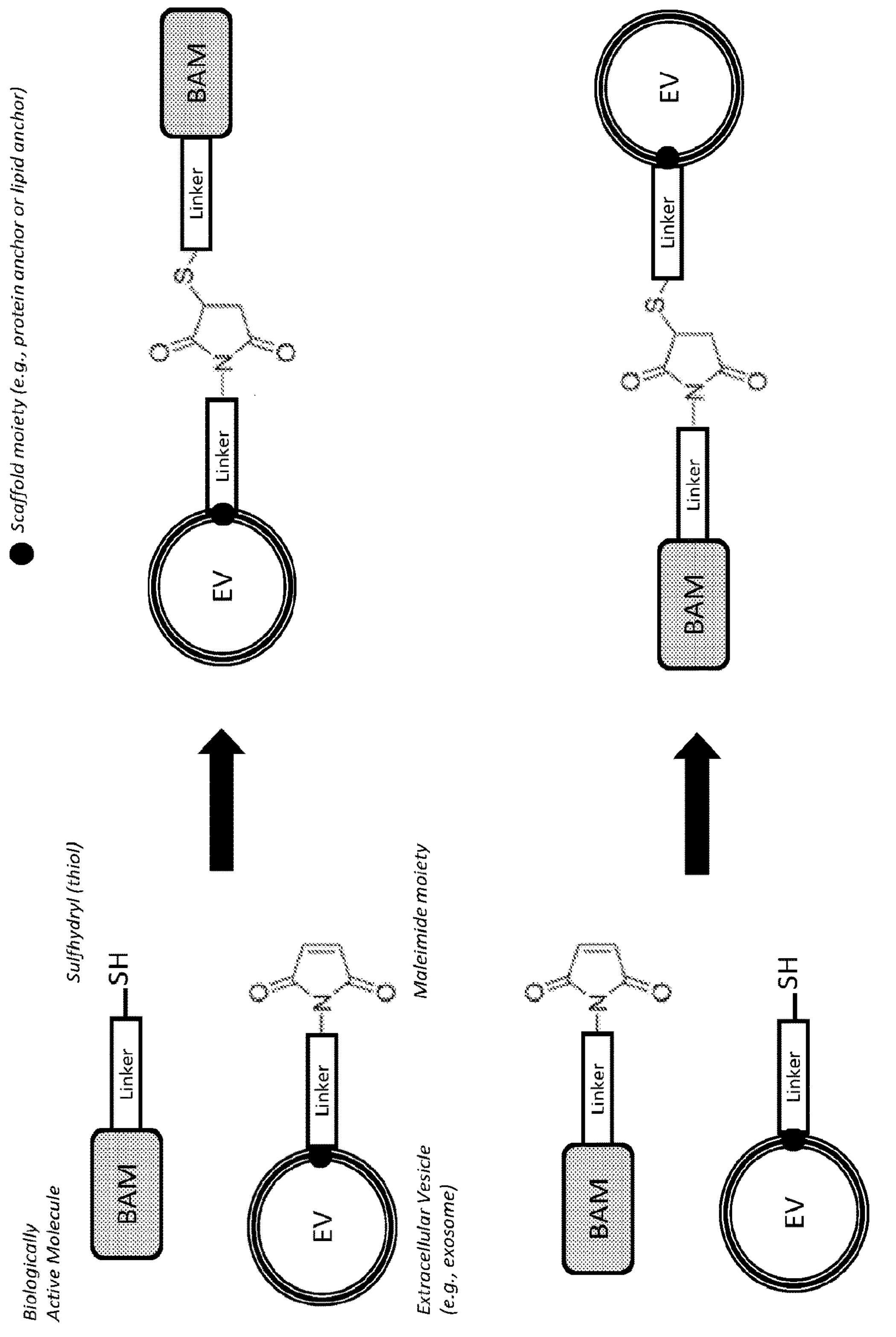
FIG. 31 is a schematic representation showing how maleimide chemistry can be used to chemically link a biologically active molecule (BAM) to an EV (e.g., an exosome), e.g., via a scaffold moiety described herein (e.g., a Scaffold X protein or fragment thereof or a lipid). The linkers depicted in the drawing are optional and when present can comprise a linker (e.g., a cleavable linker) or a combination thereof.

The present disclosure provide EVs, e.g., exosomes, that have been engineered by reacting a first molecular entity comprising a free thiol group with a second molecular entity comprising a maleimide group, wherein the maleimide moiety covalently links the first molecular entity with the second molecular entity via a maleimide moiety as presented in FIG. 31.

Non-limiting examples of biologically active molecules that can attached to an EV (e.g., exosome) via a maleimide moiety include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), morpholino, amino acids (e.g., amino acids comprising a detectable moiety or a toxin that disrupt translation), polypeptides (e.g., enzymes), lipids, carbohydrates, small molecules (e.g., small molecule drugs and toxins), antigens (e.g., vaccine antigens), adjuvants (e.g., vaccine adjuvants), etc.

In some aspects, an EV (e.g., exosome) of the present disclosure can comprise more than one type of biologically active molecule. In some aspects, biologically active molecules can be, e.g., small molecules such as cyclic dinucleotides, toxins such as auristatins (e.g., monoethyl auristatin E, MMAE), antibodies (e.g., naked antibodies or antibody-drug conjugates), STING agonists, tolerizing agents, antisense oligonucleotides, PROTACs, morpholinos, lysophosphatidic acid receptor antagonists (e.g., LPA1 antagonists) or any combinations thereof. In some aspects, an EV (e.g., exosome) of the present disclosure can comprise, e.g., a vaccine antigen and optionally a vaccine adjuvant. In some aspects, an EV (e.g., exosome) of the present disclosure can comprise a therapeutic payload (e.g., a STING or one payload disclosed below) and a targeting moiety and/or a tropism moiety.

Accordingly, in some aspects, the present disclosure provides molecular entities as presented in FIG. 31, wherein an EV (e.g., an exosome) or any molecular component thereof such as a polypeptide (e.g., a Scaffold X protein or fragment thereof), a lipid, a lipoprotein, a glycoprotein, or any variant or derivative of a naturally occurring or non-naturally occurring protein located on an EV (e.g., exosome) can be chemically linked via a maleimide moiety to a biologically active molecule, e.g., a therapeutic payload, a targeting moiety, a tropism moiety, or any combination thereof. As depicted in FIG. 31, in some aspects, an EV (e.g., an exosome) or molecular component thereof comprising a sulfhydryl (thiol) group can react with a maleimide group attached to a biologically active moiety. In other aspects, an EV (e.g., an exosome) or molecular component thereof comprising a maleimide group can react with a sulfhydryl (thiol) group present in a biologically active moiety. In both cases, the final product is a biologically active molecule chemically attached to an EV (e.g., an exosome) via a thioether bond.

II.G Malemide Moiety

As described above, in some aspects, a linker that can be used with the present disclosure can comprise a maleimide moiety (i.e., a "maleimide linker"). Linkers can be introduced into maleimide moieties using techniques known in the art (e.g., chemical conjugation, recombinant techniques, or peptide synthesis). In some aspects, the linkers can be introduced using recombinant techniques. In other aspects, the linkers can be introduced using solid phase peptide synthesis. In certain aspects, a maleimide moiety disclosed herein can contain simultaneously one or more linkers that have been introduced using recombinant techniques and one or more linkers that have been introduced using solid phase peptide synthesis or methods of chemical conjugation known in the art.

Accordingly, in some aspects, an EV (e.g., exosome) disclosed herein can comprise one or more payloads (e.g., antigen, adjuvant, and/or immune modulator), wherein one or more of the payloads are attached to the EV via a maleimide linker. In certain aspects, an EV (e.g., exosome) disclosed herein can further comprise one or more targeting moieties, wherein one or more of the targeting moieties are attached to the EV via a maleimide linker. As described herein, in some aspects, one or more of the payloads and/or one or more of the targeting moieties are linked to an EV (e.g., exosome) via a scaffold moiety (e.g., Scaffold X and/or Scaffold Y). In certain aspects, one or more of the payloads and/or one or more of the targeting moieties are covalently attached to a scaffold moiety via a maleimide moiety. In some aspects, the scaffold moiety comprises Scaffold X and/or Scaffold Y. Non-limiting examples of other scaffold moieties that can be used with the present disclosure include: aminopeptidase N (CD13); Neprilysin (membrane metalloendopeptidase; MME); ectonucleotide pyrophosphatase/phosphodiesterase family member 1 (ENPP1); neuropilin-1 (NRP1); CD9, CD63, CD81, PDGFR, GPI anchor proteins, lactadherin, LAMP2, and LAMP2B, a fragment thereof, and any combination thereof.

As used herein the term "maleimide moiety" or "MM" refers to a bifunctional chemical moiety linking an EV, e.g., exosome, to a linker or a biologically active molecule and comprises the maleimide group:

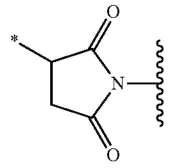 [SMILES: *C1CC(=O)N(*)C1=O]

wherein * indicates the attachment point to any thiol group on the EV, e.g., exosome, (e.g., a free thiol present in a Scaffold X), and the wavy line indicates the attachment site to the rest of the maleimide moiety. In some aspects, * indicates at attachment point to any thiol group on a payload and/or targeting moiety, and the wavy line indicates the attachment site to the rest of the maleimide moiety to the EV, e.g., exosome (e.g., a Scaffold X).

In some aspects, the maleimide moiety attaches to a sulfur atom attached to the EV (e.g., exosome), e.g., a naturally occurring sulfur atom in a thiol group or a sulfur atom introduced via chemical modification or via mutation.

In some aspects, the maleimide moiety has the formula (I):

(I)

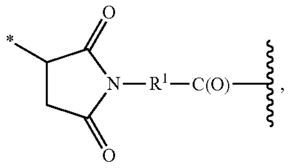

wherein (i) $R^1$ is selected from the group consisting of —$C_{1-10}$ alkylene-, —$C_{3-8}$ carbocyclo-, —O—($C_{1-8}$ alkylene)-, -arylene-, —$C_{1-10}$ alkylene-arylene-, -arylene-$C_{1-10}$ alkylene-, —$C_{1-10}$ alkylene-($C_{3-8}$ carbocyclo)-, —($C_{3-8}$ carbocyclo)-$C_{1-10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, —$(CH_2CH_2O)_r$—, and —$(CH_2CH_2O)_r$—$CH_2$—;

(ii) r is an integer, e.g., from 1 to 10;

(iii) * indicates the attachment point to any available reactive sulfur atom, e.g., a sulfur in a thiol group, present on the EV (e.g., exosome); and, (iv) the wavy line indicates the attachment site of the maleimide moiety to the biologically active molecule (i.e., payload).

In some aspects, $R^1$ is —$C_{1-8}$ alkylene-, —$C_{3-6}$ carbocyclo-, —O—($C_{1-6}$ alkylene)-, -arylene-, —$C_{1-8}$ alkylene-arylene-, -arylene-$C_{1-8}$ alkylene-, —$C_{1-8}$ alkylene-($C_{3-6}$ carbocyclo)-, —($C_{3-6}$ carbocyclo)-$C_{1-8}$ alkylene-, —$C_{3-6}$ heterocyclo-, —$C_{1-8}$ alkylene-($C_{3-6}$ heterocyclo)-, —($C_{3-6}$ heterocyclo)-$C_{1-8}$ alkylene-, —$(CH_2CH_2O)_r$—, and —$(CH_2CH_2O)_r$—$CH_2$—; where r is an integer, e.g., from 1 to 10.

In some aspects, $R^1$ is —$(CH_2)_s$—, cyclopentyl, cyclohexyl, —O—$(CH_2)_s$—, -phenyl-, —$CH_2$-phenyl-, -phenyl-$CH_2$—, —$CH_2$-cyclopentyl-, -cyclopentyl-$CH_2$—, —$CH_2$-cyclohexyl-, -cyclohexyl-$CH_2$—, —$(CH_2CH_2O)_r$—, and —$(CH_2CH_2O)_r$—$CH_2$—; where r is an integer, e.g., from 1 to 6.

In some aspects, $R^1$ is —$(CH_2)_s$—, wherein s is, e.g., 4, 5, or 6.

In some aspects, the maleimide moiety has the formula (II), wherein $R^1$ is —$(CH_2)_5$—:

(II)

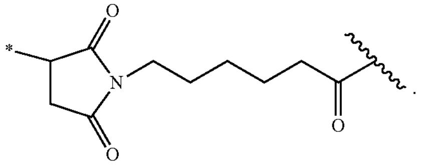

In some aspects, the maleimide moiety has the formula (III), wherein $R^1$ is —$(CH_2CH_2O)_r$—$CH_2$—, and wherein r is 2:

(III)

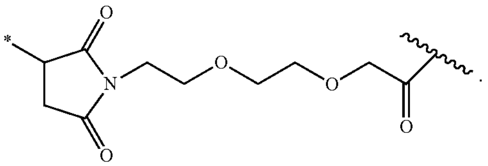

In some aspects, the maleimide moiety is covalently linked to a functional group present on the EV (e.g., exosome), wherein the functional group is a sulfhydryl (thiol) group. In one aspect, the sulfhydryl group is on a protein on the surface of the EV (e.g., exosome), e.g., Scaffold X, or a variant thereof. For example, in some aspects, the sulfhydryl group can be present on a thiol lipid, e.g., cholesterol-SH, DSPE-SH, or derivatives thereof, e.g., cholesterol-PEG-SH or DSPE-PEG-SH.

In some aspects, the maleimide moiety is covalently linked to a functional group present on the EV (e.g., exosome) which has been chemically derivatized to provide a maleimide moiety. For example, in certain aspects, an amine functional group present on the EV (e.g., exosome) (e.g., an amine on the side chain of a lysine or an arginine, or terminal amine group of a protein) can be derivatized with a bifunctional reagent comprising a succinimide moiety and a maleimide moiety.

In some aspects, a carboxyl functional group present on the EV (e.g., exosome) (e.g., a carboxyl on the side chain of a glutamic acid or aspartic acid, or terminal carboxyl group of a protein) can be derivatized with a bifunctional reagent comprising an isocyanate moiety and a maleimide moiety. In yet other aspects, a carbonyl (oxidized carbohydrate) present on the EV (e.g., exosome) can be derivatized with a bifunctional reagent comprising a hydrazine moiety and a maleimide moiety.

In general, the disclosures provided herein can be practiced using any reagent, e.g., a bifunctional or multifunctional reagent, that upon reacting with a molecule present on the surface (external surface or luminal surface) of the EV (e.g., exosome) (e.g., a protein, lipid, sugar) will covalently or non-covalently modify the molecule to yield a modified molecule comprising at least one maleimide moiety. The molecule present on the surface (external surface or luminal surface) of the EV (e.g., exosome) can be naturally occurring, or it can be non-naturally occurring, i.e., it has been modified, e.g., via chemical modification, incubation with a composition comprising the non-naturally occurring molecule, or via mutation (e.g., by introducing one or more cysteine amino acids into a protein via mutation).

Bifunctional reagents comprising a maleimide moiety, reagents in which a number of maleimide-containing units can multimerize, or maleimide-containing reagents that can add a functional moiety (e.g., a PEG) via the maleimide group include, e.g., bifunctional reagents comprising a hydrazine moiety and a maleimide moiety, bifunctional reagents comprising an isocyanate moiety and a maleimide moiety, bifunctional reagents comprising an N-hydroxy succinimidyl ester moiety and a maleimide moiety, bifunctional reagents comprising a succinimide moiety and a maleimide moiety, biotin-maleimide, streptavidin-maleimide, N-4-maleimide butyric acid, N-(4-maleimidebutyloxy) succinimide, N-[5-(3'-maleimide propylamide)-1-carboxypentyl]iminodiacetic acid, maleimide-PEG-succinimidyl esters (e.g., maleimide-$PEG_{12}$-succinimidyl ester, maleimide-$PEG_2$-succinimidyl ester, maleimide-$PEG_{2000}$-succinimidyl ester, maleimide-$PEG_{5000}$-succinimidyl ester, or maleimide-$PEG_n$-succinimidyl ester wherein 1<n<5000), maleimide-PEG-maleimide (e.g., maleimide-$PEG_{12}$-maleimide, maleimide-$PEG_2$-maleimide, maleimide-$PEG_{2000}$-maleimide, maleimide-$PEG_{5000}$-maleimide, or maleimide-$PEG_n$-maleimide wherein 1<n<5000), maleimide-OH, maleimide-$PEG_n$-OH wherein 1<n<5000, Maleimide-poly(ethylene glycol)-b-poly(ε-caprolactone), (S)-(−)-N-(1-phenylethyl) maleimide, N-(4-Chlorophenyl)maleimide, N-(1-Pyrenyl) maleimide, methoxypolyethylene glycol maleimide, poly (ethylene glycol) methyl ether maleimide, N-(4,4,5,5,6,6,7,7,8,8,9,9,10,10,11,11,11-Heptadecafluoroundecyl) maleimide, deferoxamine-maleimide (i.e., a chelator-maleimide), maleimide glycidyl ether, bifunctional maleimido DTPA, bifunctional NOTA-maleimide chelators, homobifunctional maleimide crosslinkers (i.e., those which have a maleimide group at each end), bis-maleimidopolyalkylene glycol, DBCO-maleimide, benzotriazole maleimide, alkyne maleimide, maleimide functionalized lipids, maleimide functionalized PEG lipid, and in general any molecule comprising at least one maleimide moiety at least one additional reactive moiety (e.g., maleimide or another reactive group) and one or more optional linkers (e.g., PEG or another polymer such as polyglycerol).

II.H Linkers

As described supra, extracellular vesicles (EVs) of the present disclosure (e.g., exosomes and nanovesicles) can comprises one or more linkers that link a molecule of interest (e.g., antigen, adjuvant, or immune modulator) to the EVs (e.g., to the exterior surface or on the luminal surface). In some aspects, the molecule of interest (i.e., payload) (e.g., antigen, adjuvant, or immune modulator) is linked to the EVs directly or via a scaffold moiety (e.g., Scaffold X or Scaffold Y). For example, in certain aspects, a payload (e.g., an antigen, adjuvant, and/or immune modulator) is linked to the exterior surface of an exosome via Scaffold X. In further aspects, a payload (e.g., an antigen, adjuvant, and/or immune modulator) is linked to the luminal surface of an exosome via Scaffold X or Scaffold Y. In some aspects, a payload (e.g., an antigen, adjuvant, and/or immune modulator) is linked to the luminal surface of an exosome via Scaffold X. In some aspects, a payload (e.g., an antigen, adjuvant, and/or immune modulator) is linked to the luminal surface of an exosome via Scaffold Y. In some aspects, a payload (e.g., an antigen, adjuvant, and/or immune modulator) is linked to the luminal surface of an exosome via Scaffold X and Scaffold Y. In some aspects, a payload (e.g., an antigen, adjuvant, and/or immune modulator) is conjugated to Scaffold X via a linker (e.g., those described herein). In certain aspects, a payload (e.g., an antigen, adjuvant, and/or immune modulator) is conjugated to Scaffold X using more than one linker (i.e., "linker combination"). In some aspects, a payload (e.g., an antigen, adjuvant, and/or immune modulator) is conjugated to Scaffold Y via a linker (e.g., those described herein). In certain aspects, a payload (e.g., an antigen, adjuvant, and/or immune modulator) is conjugated to Scaffold Y using a linker combination. In some aspects, a linker combination comprises at least 2, at least 3, at least 4, at least 5, or at least 6 or more different linkers disclosed herein. In some aspects, linkers in a linker combination can be linked by an ester linkage (e.g., phosphodiester or phosphorothioate ester).

The linker can be any chemical moiety known in the art.

As used herein, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. When multiple linkers are present, each of the linkers can be the same or different. Generally, linkers provide flexibility or prevent/ameliorate steric hindrances. Linkers are not typically cleaved; however in certain aspects, such cleavage can be desirable. Accordingly, in some aspects, a linker can comprise one or more protease-cleavable sites, which can be located within the sequence of the linker or flanking the linker at either end of the linker sequence.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker can comprise at least about 110, at least about 120, at least about 130, at least about 140, at least about 150, at least about 160, at least about 170, at least about 180, at least about 190, or at least about 200 amino acids.

In other aspects, the peptide linker can comprise at least about 200, at least about 300, at least about 400, at least about 500, at least about 600, at least about 700, at least about 800, at least about 900, or at least about 1,000 amino acids. The peptide linker can comprise between 1 and about 5 amino acids, between 1 and about 10 amino acids, between 1 and about 20 amino acids, between about 10 and about 50 amino acids, between about 50 and about 100 amino acids, between about 100 and about 200 amino acids, between about 200 and about 300 amino acids, between about 300 and about 400 amino acids, between about 400 and about 500 amino acids, between about 500 and about 600 amino acids, between about 600 and about 700 amino acids, between about 700 and about 800 amino acids, between about 800 and about 900 amino acids, or between about 900 and about 1000 amino acids.

As described herein, in some aspects, a linker useful for the present disclosure comprises a glycine/serine linker. In some aspects, the peptide linker is glycine/serine linker according to the formula [(Gly)n-Ser]m (SEQ ID NO: 374), where n is any integer from 1 to 100 and m is any integer from 1 to 100. In some aspects, the glycine/serine linker is according to the formula [(Gly)x-Sery]z (SEQ ID NO: 375), wherein x in an integer from 1 to 4, y is 0 or 1, and z is an integers from 1 to 50. In some aspects, the peptide linker comprises the sequence Gn (SEQ ID NO: 376), where n can be an integer from 1 to 100. In some aspects, the peptide linker can comprise the sequence (GlyAla)n (SEQ ID NO: 377), wherein n is an integer between 1 and 100. In some aspects, the peptide linker can comprise the sequence (GlyGlySer)n (SEQ ID NO: 378), wherein n is an integer between 1 and 100. In certain aspects, the peptide linker comprises the sequence GGGG (SEQ ID NO: 197).

In some aspects, the peptide linker comprises the sequence (GGGS)n (SEQ ID NO: 203). In certain aspects, the peptide linker comprises the sequence (GGS)n (GGGGS)n (SEQ ID NO: 204). In such aspects, n can be an integer from 1 to 100. In some aspects, n can be an integer from one to 20, i.e., 1, 2, 3, 4, 5, 6, 7, 8, 9, 10, 11, 12, 13, 14, 15, 16, 17, 18, 19, or 20. In some aspects, n is an integer from 1 to 100.

Examples of linkers that are useful for the present disclosure include, but are not limited to, GGG, SGGSGGS (SEQ ID NO: 198), GGSGGSGGSGGSGGG (SEQ ID NO: 199), GGSGGSGGGGSGGGGS (SEQ ID NO: 200), GGSGGSGGSGGSGGSGGS (SEQ ID NO: 201), or GGGGSGGGGSGGGGS (SEQ ID NO: 202). In some aspects, the linker is a poly-G sequence (GGGG)n (SEQ ID NO: 373), where n can be an integer from 1-100.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect, the peptide linker can comprise non-naturally occurring polypeptides which are modified forms of naturally occurring polypeptides (e.g., comprising a mutation such as an addition, substitution or deletion).

In some aspects, the peptide linker can comprise non-naturally occurring amino acids. In yet other aspects, the peptide linker can comprise naturally occurring amino acids occurring in a linear sequence that does not occur in nature. In still other aspects, the peptide linker can comprise a naturally occurring polypeptide sequence.

In some aspects, the linker comprises a non-peptide linker. In other aspects, the linker consists of a non-peptide linker. In some aspects, the non-peptide linker can be, e.g., maleimido caproyl (MC), maleimido propanoyl (MP), methoxyl polyethyleneglycol (MPEG), succinimidyl 4-(N-maleimidomethyl)-cyclohexane-1-carboxylate (SMCC), m-maleimidobenzoyl-N-hydroxysuccinimide ester (MBS), succinimidyl 4-(p-maleimidophenyl)butyrate (SMPB), N-succinimidyl(4-iodoacetyl)aminobenzonate (SIAB), succinimidyl 6-[3-(2-pyridyldithio)-propionamide]hexanoate (LC-SPDP), 4-succinimidyloxycarbonyl-alpha-methyl-alpha-(2-pyridyldithio)toluene (SMPT), etc. (see, e.g., U.S. Pat. No. 7,375,078, which is herein incorporated by reference in its entirety).

In some aspects, linkers disclosed herein can be introduced into maleimide moieties using techniques known in the art (e.g., chemical conjugation, recombinant techniques, or peptide synthesis). In some aspects, the linkers can be introduced using recombinant techniques. In other aspects, the linkers can be introduced using solid phase peptide synthesis. In certain aspects, a maleimide moiety disclosed herein can contain simultaneously one or more linkers that have been introduced using recombinant techniques and one or more linkers that have been introduced using solid phase peptide synthesis or methods of chemical conjugation known in the art. In some aspects, a linker can comprise a cholesterol moiety. See, e.g., US 2008/0085869 A1, which is herein incorporated by reference in its entirety.

Linkers can be susceptible to cleavage ("cleavable linker") thereby facilitating release of the biologically active molecule (e.g., antigen, adjuvant, or immune modulator). Therefore, in some aspects, a linker that can be used with the present disclosure comprises a cleavable linker. Such cleavable linkers can be susceptible, for example, to acid-induced cleavage, photo-induced cleavage, peptidase-induced cleavage, esterase-induced cleavage, and disulfide bond cleavage, at conditions under which the biologically active molecule remains active. In some aspects, a cleavable linker comprises a spacer. In certain aspects, a spacer comprises PEG.

In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof.

In some aspects, the linker comprises a non-cleavable linker (i.e., resistant or substantially resistant to cleavage).

In some aspects, a linker combination disclosed herein comprises only cleavable linkers. In some aspects, a linker combination disclosed herein comprises only non-cleavable linkers. In some aspects, a linker combination disclosed herein comprises both cleavable and non-cleavable linkers. Additional disclosure relating to cleavable and non-cleavable linkers that can be used with the present disclosure are provided below.

II.H.1 Non-Cleavable Linkers

Non-cleavable linkers are any chemical moiety capable of linking two or more components of a modified biologically active molecule of the present disclosure (e.g., a biologically active molecule and an anchoring moiety; a biologically active molecule and a cleavable linker; an anchoring moiety and a cleavable linker) in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage.

Furthermore, "non-cleavable" refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which a cyclic dinucleotide and/or the antibody does not lose its activity. In some aspects, the biologically active molecule is attached to the linker via another linker, e.g., a self-immolative linker.

In some aspects, a linker combination disclosed herein comprises a non-cleavable linker comprising, e.g., tetraethylene glycol (TEG), hexaethylene glycol (HEG), polyethylene glycol (PEG), succinimide, or any combination thereof. In some aspects, the non-cleavable linker comprises a spacer unit to link the biologically active molecule to the non-cleavable linker.

In some aspects, one or more non-cleavable linkers comprise smaller units (e.g., HEG, TEG, glycerol, C2 to C12 alkyl, and the like) linked together. In some aspects, the linkage is an ester linkage (e.g., phosphodiester or phosphorothioate ester) or other linkage. Examples of non-cleavable linkers that can be used with the present disclosure are known in the art, see, e.g., U.S. Pat. No. 7,569,657 B2; U.S. Pat. No. 8,465,730 B1; U.S. Pat. No. 7,087,229 B2; and U.S. Publ. No. 2014/0193849 A1, each of which is herein incorporated by reference in its entirety.

II.H.2 Cleavable Linkers

As described herein, the one or more linkers (i.e., linker combination) that can be used to link a molecule of interest (e.g., antigen, adjuvant, or immune modulator) to the EVs (e.g., exosomes) can comprise cleavable linkers. The term "cleavable linker" refers to a linker comprising at least one linkage or chemical bond that can be broken or cleaved. As used herein, the term "cleave" refers to the breaking of one or more chemical bonds in a relatively large molecule in a manner that produces two or more relatively smaller molecules. Cleavage can be mediated, e.g., by a nuclease, peptidase, protease, phosphatase, oxidase, or reductase, for example, or by specific physicochemical conditions, e.g., redox environment, pH, presence of reactive oxygen species, or specific wavelengths of light.

In some aspects, the term "cleavable," as used herein, refers, e.g., to rapidly degradable linkers, such as, e.g., phosphodiester and disulfides, while the term "non-cleavable" refers, e.g., to more stable linkages, such as, e.g., nuclease-resistant phosphorothioates.

In some aspects, the cleavable linker comprises a dinucleotide or trinucleotide linker, a disulfide, an imine, a thioketal, a val-cit dipeptide, or any combination thereof.

In some aspects, the cleavable linker comprises valine-alanine-p-aminobenzylcarbamate, valine-citrulline-p-aminobenzylcarbamate, or both.

In some aspects, the cleavable linker comprises redox cleavable linkers, reactive oxygen species (ROS) cleavable linkers, pH dependent cleavable linkers, enzymatic cleavable linkers, protease cleavable linkers, esterase cleavable linkers, phosphatase cleavable linkers, photoactivated cleavable linkers, self-immolative linkers, or combinations thereof. Additional disclosure relating to one or more of these cleavable linkers are provided further below and also known in the art, see, e.g., US 2018/0037639 A1; Trout et al., 79 Proc. Natl. Acad. Sci. USA, 626-629 (1982); Umemoto et al. 43 Int. J. Cancer, 677-684 (1989); Cancer Res. 77(24):7027-7037 (2017); Doronina et al. Nat. Biotechnol. 21:778-784 (2003); U.S. Pat. No. 7,754,681 B2; US 2006/0269480; US 2010/0092496; US 2010/0145036; US 2003/0130189; US 2005/0256030, each of which is herein incorporated by reference in its entirety.

II.H.2.a Redox Cleavable Linkers

In some aspects, the linker combination comprises a redox cleavable linker. In certain aspects, such a linker can comprise a redox cleavable linking group that is cleaved upon reduction or upon oxidation.

In some aspects, the redox cleavable linker contains a disulfide bond, i.e., it is a disulfide cleavable linker. In some aspects, the redox cleavable linker can be reduced, e.g., by intracellular mercaptans, oxidases, reductases, or combinations thereof.

II.H.2.b Reactive Oxygen Species (ROS) Cleavable Linkers

In some aspects, the linker combination can comprise a cleavable linker which can be cleaved by a reactive oxygen species (ROS), such as superoxide (Of) or hydrogen peroxide (H2O2), generated, e.g., by inflammation processes such as activated neutrophils. In some aspects, the ROS cleavable linker is a thioketal cleavable linker. See, e.g., U.S. Pat. No. 8,354,455B2, which is herein incorporated by reference in its entirety.

II.H.2.c pH Dependent Cleavable Linkers

In some aspects, the linker is an acid labile linker comprising an acid cleavable linking group, which is a linking group that is selectively cleaved under acidic conditions ($pH<7$).

In some aspects, the acid cleavable linking group is cleaved in an acidic environment, e.g., about 6.0, about 5.5, about 5.0 or less. In some aspects, the pH is about 6.5 or less. In some aspects, the linker is cleaved by an agent such as an enzyme that can act as a general acid, e.g., a peptidase (which can be substrate specific) or a phosphatase. Within cells, certain low pH organelles, such as endosomes and lysosomes, can provide a cleaving environment to the acid cleavable linking group. Although the pH of human serum is 7.4, the average pH in cells is slightly lower, ranging from about 7.1 to 7.3. Endosomes also have an acidic pH, ranging from 5.5 to 6.0, and lysosomes are about 5.0 at an even more acidic pH. Accordingly, pH dependent cleavable linkers are sometimes called endosomically labile linkers in the art.

In some aspects, the acid cleavable group can have the general formula —C═NN—, C (O)O, or —OC(O). In another non-limiting example, when the carbon attached to the ester oxygen (alkoxy group) is attached to an aryl group, a substituted alkyl group, or a tertiary alkyl group such as dimethyl pentyl or t-butyl, for example. Examples of acid cleavable linking groups include, but are not limited to, amine, imine, amino ester, benzoic imine, diortho ester, polyphosphoester, polyphosphazene, acetal, vinyl ether, hydrazone, cis-aconitate, hydrazide, thiocarbamoyl, imizine, azidomethyl-methylmaleic anhydride, thiopropionate, a masked endosomolytic agent, a citraconyl group, or any combination thereof. Disulfide linkages are also susceptible to pH.

In some aspects, the linker comprises a low pH-labile hydrazone bond. Such acid-labile bonds have been extensively used in the field of conjugates, e.g., antibody-drug conjugates. See, for example, Zhou et al, Biomacromolecules 2011, 12, 1460-7; Yuan et al, Acta Biomater. 2008, 4, 1024-37; Zhang et al, Acta Biomater. 2007, 6, 838-50; Yang et al, J. Pharmacol. Exp. Ther. 2007, 321, 462-8; Reddy et al, Cancer Chemother. Pharmacol. 2006, 58, 229-36; Doronina et al, Nature Biotechnol. 2003, 21, 778-84, each of which are hereby incorporated by reference in its entirety.

In some aspects, the linker comprises a low pH-labile bond selected from the following: ketals that are labile in acidic environments (e.g., pH less than 7, greater than about 4) to form a diol and a ketone; acetals that are labile in acidic environments (e.g., pH less than 7, greater than about 4) to form a diol and an aldehyde; imines or iminiums that are labile in acidic environments (e.g., pH less than 7, greater than about 4) to form an amine and an aldehyde or a ketone; silicon-oxygen-carbon linkages that are labile under acidic condition; silicon-nitrogen (silazane) linkages; silicon-carbon linkages (e.g., arylsilanes, vinylsilanes, and allylsilanes); maleamates (amide bonds synthesized from maleic anhydride derivatives and amines); ortho esters; hydrazones; activated carboxylic acid derivatives (e.g., esters, amides) designed to undergo acid catalyzed hydrolysis); or vinyl ethers.

Further examples can be found in U.S. Pat. Nos. 9,790,494 B2 and 8,137,695 B2, the contents of which are incorporated herein by reference in their entireties.

II.H.2.d Enzymatic Cleavable Linkers

In some aspects, the linker combination can comprise a linker cleavable by intracellular or extracellular enzymes, e.g., proteases, esterases, nucleases, amidades. The range of enzymes that can cleave a specific linker in a linker combination depends on the specific bonds and chemical structure of the linker. Accordingly, peptidic linkers can be cleaved, e.g., by peptidades, linkers containing ester linkages can be cleaved, e.g., by esterases; linkers containing amide linkages can be cleaved, e.g., by amidades; etc.

II.H.2.e Esterase Cleavable Linkers

Some linkers are cleaved by esterases ("esterase cleavable linkers"). Only certain esters can be cleaved by esterases and amidases present inside or outside of cells. Esters are formed by the condensation of a carboxylic acid and an alcohol. Simple esters are esters produced with simple alcohols, such as aliphatic alcohols, and small cyclic and small aromatic alcohols. Examples of ester-based cleavable linking groups include, but are not limited to, esters of alkylene, alkenylene and alkynylene groups. The ester cleavable linking group has the general formula —C (O)O— or —OC(O)—.

II.H.2.f Phosphatase Cleavable Linkers

In some aspects, a linker combination can includes a phosphate-based cleavable linking group is cleaved by an agent that degrades or hydrolyzes phosphate groups. An example of an agent that cleaves intracellular phosphate groups is an enzyme such as intracellular phosphatase. Examples of phosphate-based linking groups are —O—P(O)(OR k)-O—, —O—P(S)($OR_k$) O—, —O—P(S)($SR_k$)—O—, —S—P(O)($OR_k$)—O—, —O—P(O)($OR_k$)—S—, —S—P(O)($OR_k$)—S—, —O—P(S)($OR_k$)—S—, —SP(S)($OR_k$)—O—, —OP(O)($R_k$)—O—, —OP(S)($R_k$)—O—, —SP(O)($R_k$)—O—, —SP(S)($R_k$)—O—, —SP(O)($R_k$)—S—, or —OP(S)($R_k$)—S—.

In some aspects, $R_k$ is any of the following: $NH_2$, $BH_3$, $CH_3$, $C_{1-6}$ alkyl, $C_{6-10}$ aryl, $C_{1-6}$ alkoxy and $C_{6-10}$ aryl-oxy. In some aspects, $C_{1-6}$ alkyl and $C_{6-10}$ aryl are unsubstituted. Further non-limiting examples include —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S) (OH)—O—, —O—P(O)(H)—O—, —O—P(S)(H)—O—, —S—P(O)(H)—O—, —SP(S)(H)—O—, —SP(O)(H)—S—, —OP(S)(H)—S—, or —O—P(O)(OH)—O—.

II.H.2.g Photoactivated Cleavable Linkers

In some aspects, the combination linker comprises a photoactivated cleavable linker, e.g., a nitrobenzyl linker or a linker comprising a nitrobenzyl reactive group.

Conventional vaccines have demonstrated a few challenges. In some aspects, conventional vaccines are not capable of inducing robust T cell response. Moreover, any response generated by conventional vaccines can be limited to tissue specific responses and/or lack antibody diversity. In some aspects, the EVs, e.g., exosomes, comprising an antigen useful for the present disclosure exhibit advantageous properties compared to an antigen (vaccine) alone. In some aspects, the EVs (e.g., exosomes) of the present disclosure is capable of inducing improved T cell directed immune response compared to the antigen alone. In some aspects, the EVs (e.g., exosomes) of the present disclosure is capable of inducing T cell response in peripheral tissues. In some aspects, the EVs (e.g., exosomes) of the present disclosure exhibit enhanced antibody diversity and/or avidity.

Conventional vaccines, e.g., antigens, also face problems of poor uptake by antigen presenting cells, poor immunogenicity, and/or limited complexity. Compared to the conventional antigens, the EVs (e.g., exosomes) of the present disclosure is capable of presenting multiple antigens on an EV (e.g., exosomes) and/or modulating antigen exposure to specific immune cells (e.g., B cells and/or dendritic cells).

Adjuvants for conventional vaccines also have challenges. For example, the potential toxicity of adjuvants limit its route of administration, dose, and combinations of adjuvants. In addition, RNA and/or DNAs are poor adjuvants. The EVs (e.g., exosomes) of the present disclosure overcome these problems. The EVs (e.g., exosomes) of the present disclosure allow selective co-delivery of antigen(s) and adjuvant(s) (and/or other payloads disclosed herein) to antigen presenting cells; this can reduce the adjuvant dose and enables combinations, thereby improving overall safety of the vaccine.

III. Producer Cell for Production of Engineered EVs, e.g., Exosomes

EVs, e.g., exosomes, of the present disclosure can be produced from a cell grown in vitro or a body fluid of a subject. When exosomes are produced from in vitro cell culture, various producer cells, e.g., HEK293 cells, CHO cells, and MSCs, can be used. In certain aspects, a producer cell is not a naturally-existing dendritic cell, macrophage, B cell, mast cell, neutrophil, Kupffer-Browicz cell, cell derived from any of these cells, or any combination thereof (i.e., non-naturally existing producer cell). As used herein, the term "non-naturally existing producer cell" refers to a producer cell (e.g., dendritic cell, macrophage, B cell, mast cell, neutrophil, Kupffer-Browicz cell, cell derived from any of these cells, or any combination thereof) that has been modified, such that the producer cell differs in structure and/or function compared to the naturally-existing counterpart. As described further below, in some aspects, the non-naturally existing producer cell has been modified to express one or more payloads disclosed herein (e.g., antigen, immune modulator, and/or adjuvant. In certain aspects, the non-naturally existing producer cell has been modified to express one or more targeting moieties disclosed herein. In some aspects, the non-naturally existing producer cell has been modified to express one or more scaffold moieties disclosed herein (e.g., Scaffold X and/or Scaffold Y).

The producer cell can be genetically modified to comprise one or more exogenous sequences (e.g., encoding an antigen, adjuvant, immune modulator, and/or targeting moiety) to produce the EVs (e.g., exosomes) described herein. The genetically-modified producer cell can contain the exogenous sequence by transient or stable transformation. The exogenous sequence can be transformed as a plasmid. The exogenous sequences can be stably integrated into a genomic sequence of the producer cell, at a targeted site or in a random site. In some aspects, a stable cell line is generated for production of lumen-engineered EVs (e.g., exosomes).

The exogenous sequences can be inserted into a genomic sequence of the producer cell, located within, upstream (5'-end) or downstream (3'-end) of an endogenous sequence encoding an EV (e.g., exosome) protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present disclosure.

The exogenous sequences can comprise a sequence encoding a scaffold moiety disclosed herein or a fragment or variant thereof. An extra copy of the sequence encoding a scaffold moiety can be introduced to produce an EV (e.g., exosome) described herein (e.g., having a higher density of a scaffold moiety on the surface or on the luminal surface of the EV, e.g., exosome). An exogenous sequence encoding a modification or a fragment of a scaffold moiety can be introduced to produce a lumen-engineered and/or surface-engineered exosome containing the modification or the fragment of the scaffold moiety.

In some aspects, a producer cell can be modified, e.g., transfected, with one or more vectors encoding a scaffold moiety linked to a payload (e.g., an antigen, an adjuvant, and/or an immune modulator) and/or a targeting moiety.

In some aspects, a producer cell disclosed herein is further modified to comprise an additional exogenous sequence. For example, an additional exogenous sequence can be introduced to modulate endogenous gene expression, or produce an EV (e.g., exosome) including a certain polypeptide as a payload (e.g., antigen, adjuvant, and/or immune modulator) and/or targeting moiety. In some aspects, the producer cell is modified to comprise two exogenous sequences, one encoding a scaffold moiety (e.g., Scaffold X and/or Scaffold Y), or a variant or a fragment thereof, and the other encoding a payload and/or targeting moiety. In certain aspects, the producer cell can be further modified to comprise an additional exogenous sequence conferring additional functionalities to EVs (e.g., exosomes) (e.g., adjuvants or immune modulators). In some aspects, the producer cell is modified to comprise two exogenous sequences, one encoding a scaffold moiety disclosed herein, or a variant or a fragment thereof, and the other encoding a protein conferring the additional functionalities to EVs (e.g., exosomes) (e.g., adjuvants or immune modulators). In some aspects, the producer cell is further modified to comprise one, two, three, four, five, six, seven, eight, nine, or ten or more additional exogenous sequences. In certain aspects, the additional exogenous sequences encode any of the payloads (e.g., antigen, adjuvant, and/or immune modulator) and/or targeting moieties disclosed herein.

In some aspects, EVs, e.g., exosomes, of the present disclosure (e.g., surface-engineered and/or lumen-engineered exosomes) can be produced from a cell transformed with a sequence encoding a full-length, mature scaffold moiety disclosed herein or a scaffold moiety linked to a payload (e.g., an antigen, an adjuvant, and/or an immune modulator) and/or targeting moiety. Any of the scaffold moieties described herein can be expressed from a plasmid, an exogenous sequence inserted into the genome, or other exogenous nucleic acid, such as a synthetic messenger RNA (mRNA).

IV. Pharmaceutical Compositions

Provided herein are pharmaceutical compositions comprising an EV, e.g., exosome, of the present disclosure having the desired degree of purity, and a pharmaceutically acceptable carrier or excipient, in a form suitable for administration to a subject. Pharmaceutically acceptable excipients or carriers can be determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some aspects, a pharmaceutical composition comprises one or more therapeutic agents and an exosome described herein. In certain aspects, the EVs, e.g., exosomes, are co-administered with of one or more additional therapeutic agents, in a pharmaceutically acceptable carrier. In some aspects, the pharmaceutical composition comprising the EV, e.g., exosome is administered prior to administration of the additional therapeutic agents. In other aspects, the pharmaceutical composition comprising the EV, e.g., exosome is administered after the administration of the additional therapeutic agents. In further aspects, the pharmaceutical composition comprising the EV, e.g., exosome is administered concurrently with the additional therapeutic agents.

Acceptable carriers, excipients, or stabilizers are nontoxic to recipients (e.g., animals or humans) at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The EVs, e.g., exosomes, can be administered by parenteral, topical, intravenous, oral, subcutaneous, intra-arterial, intradermal, transdermal, rectal, intracranial, intraperitoneal, intranasal, intratumoral, intramuscular route or as inhalants. In certain aspects, the pharmaceutical composition comprising exosomes is administered intravenously, e.g. by injection. The EVs, e.g., exosomes, can optionally be administered in combination with other therapeutic agents that are at least partly effective in treating the disease, disorder or condition for which the EVs, e.g., exosomes, are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the EVs, e.g., exosomes, in an effective amount and in an appropriate solvent with one or a combination of ingredients enumerated herein, as desired. Generally, dispersions are prepared by incorporating the EVs, e.g., exosomes, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The EVs, e.g., exosomes, can be administered in the form of a depot injection or implant preparation which can be formulated in such a manner to permit a sustained or pulsatile release of the EV, e.g., exosomes.

Systemic administration of compositions comprising exosomes can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain aspects, the pharmaceutical composition comprising exosomes is administered intravenously into a subject that would benefit from the pharmaceutical composition. In certain other aspects, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain aspects, the pharmaceutical composition comprising exosomes is administered as a liquid suspension. In certain aspects, the pharmaceutical composition is administered as a formulation that is capable of forming a depot following administration. In certain preferred aspects, the depot slowly releases the EVs, e.g., exosomes, into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the EVs, e.g., exosomes, described herein and optionally a pharmaceutically active or therapeutic agent. The therapeutic agent can be a biological agent, a small molecule agent, or a nucleic acid agent.

Dosage forms are provided that comprise a pharmaceutical composition comprising the EVs, e.g., exosomes, described herein. In some aspects, the dosage form is formulated as a liquid suspension for intravenous injection. In some aspects, the dosage form is formulated as a liquid suspension for intratumoral injection.

In certain aspects, the preparation of exosomes is subjected to radiation, e.g., X rays, gamma rays, beta particles, alpha particles, neutrons, protons, elemental nuclei, UV rays in order to damage residual replication-competent nucleic acids.

In certain aspects, the preparation of exosomes is subjected to gamma irradiation using an irradiation dose of more than 1, 5, 10, 15, 20, 25, 30, 35, 40, 50, 60, 70, 80, 90, 100, or more than 100 kGy.

In certain aspects, the preparation of exosomes is subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

V. Kits

Also provided herein are kits comprising one or more exosomes described herein. In some aspects, provided herein is a pharmaceutical pack or kit comprising one or more containers filled with one or more of the ingredients of the pharmaceutical compositions described herein, such as one or more exosomes provided herein, optional an instruction for use. In some aspects, the kits contain a pharmaceutical composition described herein and any prophylactic or therapeutic agent, such as those described herein.

VI. Methods of Producing EVs, e.g., Exosomes

EVs (e.g., exosomes) of the present disclosure differ from traditional vaccines in that the EVs can be rapidly engineered to express a moiety of interest (e.g., antigen, adjuvant, immune modulator, and/or targeting moiety). As described herein, the moieties of interest (i) can be directly linked to a surface of the EV (e.g., exterior surface and/or luminal surface), (ii) can be linked to a scaffold moiety (e.g., Scaffold X and/or Scaffold Y) and then expressed on a surface of the EV (e.g., exterior surface and/or luminal surface), (iii) can be expressed in the lumen of the EV, or (iv) combinations thereof. Such ability to rapidly engineer EVs (e.g., exosomes) is particularly useful in developing EV (e.g., exosome)-based vaccines. For instance, a single EV (e.g., exosome) engineered to express certain payloads and/ or targeting moieties can be used in treating a wide range of diseases or disorders by simply "plugging" an antigen of interest into the EVs.

Accordingly, in some aspects, the present disclosure is directed to methods of producing such modular or "plug and play" EV (e.g., exosome) vaccines. In certain aspects, a method of producing an EV (e.g., exosome)-based vaccine comprises mixing an engineered EV (e.g., exosome) with an antigen of interest, such that the antigen of interest is expressed in the engineered EV. In some aspects, the engineered EV (e.g., exosome) comprises one or more of the payloads disclosed herein (e.g., antigen, adjuvant, and/or immune modulator). In certain aspects, the engineered EV (e.g., exosome) further comprises one or more scaffold moieties (e.g., Scaffold X and/or Scaffold Y). In some aspects, the engineered EV (e.g., exosome) additionally comprises one or more targeting moieties. In some aspects, the engineered EV (e.g., exosome) can be produced using any of the methods disclosed herein.

In some aspects, the present disclosure is also directed to methods of producing EVs (e.g., exosomes) described herein. In some aspects, the method comprises: obtaining the EV, e.g., exosome, from a producer cell, wherein the producer cell contains two or more components of the EV, e.g., exosome (e.g., (i) antigen and adjuvant, (ii) antigen and immune modulator, (iii) antigen and targeting moiety, (iv) antigen, adjuvant, and targeting moiety, (v) antigen, immune modulator, and targeting moiety, (vi) antigen, adjuvant, and immune modulator, (vii) antigen, adjuvant, immune modulator, and targeting moiety); and optionally isolating the obtained EV, e.g., exosome. In some aspects, the method comprises: modifying a producer cell by introducing two or more components of an EV (e.g., exosome) disclosed herein (e.g., (i) antigen and adjuvant, (ii) antigen and immune modulator, (iii) antigen and targeting moiety, (iv) antigen, adjuvant, and targeting moiety, (v) antigen, immune modulator, and targeting moiety, (vi) antigen, adjuvant, and immune modulator, (vii) antigen, adjuvant, immune modulator, and targeting moiety); obtaining the EV, e.g., exosome from the modified producer cell; and optionally isolating the obtained EV, e.g., exosome. In further aspects, the method comprises: obtaining an EV (e.g., exosome) from a producer cell; isolating the obtained EV (e.g., exosome); and modifying the isolated EV (e.g., exosome) (e.g., by inserting multiple exogenous biologically active molecules, e.g., antigens, adjuvants, and/or immune modulators, and/or targeting moieties). In certain aspects, the method further comprises formulating the isolated EV (e.g., exosome) into a pharmaceutical composition.

VI.A Methods of Modifying a Producer Cell

As described supra, in some aspects, a method of producing an EV (e.g., exosome) comprises modifying a producer cell with multiple (e.g., two or more) molecule of interest (e.g., exogenous biologically active molecules described herein (e.g., antigen, adjuvant, immune modulator), and/or targeting moiety). In some aspects, a producer cell disclosed herein can be further modified with a scaffold moiety disclosed herein (e.g., Scaffold X or Scaffold Y).

In some aspects, the producer cell can be a mammalian cell line, a plant cell line, an insect cell line, a fungi cell line, or a prokaryotic cell line. In certain aspects, the producer cell is a mammalian cell line. Non-limiting examples of mammalian cell lines include: a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, a mesenchymal stem cell (MSC) cell line, and combinations thereof. In certain aspects, the mammalian cell line comprises HEK-293 cells, BJ human foreskin fibroblast cells, fHDF fibroblast cells, AGE.HN® neuronal precursor cells, CAP® amniocyte cells, adipose mesenchymal stem cells, RPTEC/TERT1 cells, or combinations thereof. In some aspects, the producer cell is a primary cell. In certain aspects, the primary cell can be a primary mammalian cell, a primary plant cell, a primary insect cell, a primary fungi cell, or a primary prokaryotic cell.

In some aspects, the producer cell is not an immune cell, such an antigen presenting cell, a T cell, a B cell, a natural killer cell (NK cell), a macrophage, a T helper cell, or a regulatory T cell (Treg cell). In other aspects, the producer cell is not an antigen presenting cell (e.g., dendritic cells, macrophages, B cells, mast cells, neutrophils, Kupffer-Browicz cell, or a cell derived from any such cells). In some aspects, a producer cell is not a naturally-existing antigen-presenting cell (i.e., has been modified). In some aspects, a producer cell is not a naturally-existing dendritic cell, a B cell, a mast cell, a macrophage, a neutrophil, Kupffer-Browicz cell, cell derived from any of these cells, or any combination thereof.

In some aspects, the one or more moieties (e.g., payload and/or targetin moiety) can be a transgene or mRNA, and introduced into the producer cell by transfection, viral transduction, electroporation, extrusion, sonication, cell fusion, or other methods that are known to the skilled in the art.

In some aspects, the one or more moieties (e.g., payload and/or targetin moiety) is introduced to the producer cell by transfection. In some aspects, the one or more moieties (e.g., payload and/or targetin moiety) can be introduced into suitable producer cells using synthetic macromolecules, such as cationic lipids and polymers (Papapetrou et al., *Gene Therapy* 12: S118-S130 (2005)). In some aspects, the cationic lipids form complexes with the one or more moieties (e.g., payload and/or targetin moiety) through charge interactions. In some of these aspects, the positively charged complexes bind to the negatively charged cell surface and are taken up by the cell by endocytosis. In some other aspects, a cationic polymer can be used to transfect producer cells. In some of these aspects, the cationic polymer is polyethylenimine (PEI). In certain aspects, chemicals such as calcium phosphate, cyclodextrin, or polybrene, can be used to introduce the one or more moieties (e.g., payload and/or targetin moiety) to the producer cells. The one or more moieties (e.g., payload and/or targetin moiety) can also be introduced into a producer cell using a physical method such as particle-mediated transfection, "gene gun", biolistics, or particle bombardment technology (Papapetrou et al., *Gene Therapy* 12: S118-S130 (2005)). A reporter gene such as, for example, beta-galactosidase, chloramphenicol acetyltransferase, luciferase, or green fluorescent protein can be used to assess the transfection efficiency of the producer cell.

In certain aspects, the one or more moieties (e.g., payload and/or targetin moiety) are introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain aspects, the one or more moieties (e.g., payload and/or targetin moiety) are introduced to the producer cell by electroporation. Electroporation creates transient pores in the cell membrane, allowing for the introduction of various molecules into the cell. In some aspects, DNA and RNA as well as polypeptides and non-polypeptide therapeutic agents can be introduced into the producer cell by electroporation.

In certain aspects, the one or more moieties (e.g., payload and/or targetin moiety) introduced to the producer cell by microinjection. In some aspects, a glass micropipette can be used to inject the one or more moieties (e.g., payload and/or targetin moiety) into the producer cell at the microscopic level.

In certain aspects, the one or more moieties (e.g., payload and/or targetin moiety) are introduced to the producer cell by extrusion.

In certain aspects, the one or more moieties (e.g., payload and/or targetin moiety) are introduced to the producer cell by sonication. In some aspects, the producer cell is exposed to high intensity sound waves, causing transient disruption of the cell membrane allowing loading of the one or more moieties (e.g., payload and/or targetin moiety).

In certain aspects, the one or more moieties (e.g., payload and/or targetin moiety) are introduced to the producer cell by cell fusion. In some aspects, the one or more moieties (e.g., payload and/or targetin moiety) are introduced by electrical cell fusion. In other aspects, polyethylene glycol (PEG) is used to fuse the producer cells. In further aspects, sendai virus is used to fuse the producer cells.

In some aspects, the one or more moieties (e.g., payload and/or targetin moiety) are introduced to the producer cell by hypotonic lysis. In such aspects, the producer cell can be exposed to low ionic strength buffer causing them to burst allowing loading of the one or more moieties (e.g., payload and/or targetin moiety). In other aspects, controlled dialysis against a hypotonic solution can be used to swell the producer cell and to create pores in the producer cell membrane. The producer cell is subsequently exposed to conditions that allow resealing of the membrane.

In some aspects, the one or more moieties (e.g., payload and/or targetin moiety) are introduced to the producer cell by detergent treatment. In certain aspects, producer cell is treated with a mild detergent which transiently compromises the producer cell membrane by creating pores allowing loading of the one or more moieties (e.g., payload and/or targetin moiety). After producer cells are loaded, the detergent is washed away thereby resealing the membrane.

In some aspects, the one or more moieties (e.g., payload and/or targetin moiety) introduced to the producer cell by receptor mediated endocytosis. In certain aspects, producer cells have a surface receptor which upon binding of the one or more moieties (e.g., payload and/or targetin moiety) induces internalization of the receptor and the associated moieties.

In some aspects, the one or more moieties (e.g., payload and/or targetin moiety) are introduced to the producer cell by filtration. In certain aspects, the producer cells and the one or more moieties (e.g., payload and/or targetin moiety) can be forced through a filter of pore size smaller than the producer cell causing transient disruption of the producer cell membrane and allowing the one or more moieties (e.g., payload and/or targetin moiety) to enter the producer cell.

In some aspects, the producer cell is subjected to several freeze thaw cycles, resulting in cell membrane disruption allowing loading of the one or more moieties (e.g., payload and/or targetin moiety).

VI.B Methods of Modifying an EV (e.g., Exosome)

In some aspects, a method of producing an EV (e.g., exosome) comprises modifying the isolated EV (e.g., exosome) by directly introducing one or more moieties (e.g., payload and/or targetin moiety) into the EVs (e.g., exosomes). In certain aspects, the one or more moieties comprise an antigen, adjuvant, immune modulator, targeting moiety, or combinations thereof. In some aspects, the one or more moieties comprise a scaffold moiety disclosed herein (e.g., Scaffold X or Scaffold Y).

In certain aspects, the one or more moieties (e.g., payload and/or targetin moiety) are introduced to the EV (e.g., exosome) by transfection. In some aspects, the one or more moieties (e.g., payload and/or targetin moiety) can be introduced into the EV (e.g., exosome) using synthetic macromolecules such as cationic lipids and polymers (Papapetrou et al., Gene Therapy 12: S118-S130 (2005)). In certain aspects, chemicals such as calcium phosphate, cyclodextrin, or polybrene, can be used to introduce the one or more moieties (e.g., payload and/or targetin moiety) to the EV (e.g., exosome).

In certain aspects, the one or more moieties (e.g., payload and/or targetin moiety) are introduced to the EV (e.g., exosome) by electroporation. In some aspects, EVs (e.g., exosomes) are exposed to an electrical field which causes transient holes in the EV (e.g., exosome) membrane, allowing loading of the one or more moieties (e.g., payload and/or targetin moiety).

In certain aspects, the one or more moieties (e.g., payload and/or targetin moiety) are introduced to the EV (e.g., exosome) by microinjection. In some aspects, a glass micropipette can be used to inject the one or more moieties (e.g., payload and/or targetin moiety) directly into the EV (e.g., exosome) at the microscopic level.

In certain aspects, the one or more moieties (e.g., payload and/or targetin moiety) are introduced to the EV (e.g., exosome) by extrusion.

In certain aspects, the one or more moieties (e.g., payload and/or targetin moiety) are introduced to the EV (e.g., exosome) by sonication. In some aspects, EVs (e.g., exosomes) are exposed to high intensity sound waves, causing transient disruption of the EV (e.g., exosome) membrane allowing loading of the one or more moieties (e.g., payload and/or targetin moiety).

In some aspects, one or more moieties (e.g., payload and/or targetin moiety) can be conjugated to the surface of the EV (e.g., exosome) (i.e., conjugated or linked directly to the exterior surface of the EV or to the luminal surface of the EV). Conjugation can be achieved chemically or enzymatically, by methods known in the art.

In some aspects, the EV (e.g., exosome) comprises one or more moieties (e.g., payload and/or targetin moiety) that are chemically conjugated. Chemical conjugation can be accomplished by covalent bonding of the one or more moieties (e.g., payload and/or targetin moiety) to another molecule, with or without use of a linker. The formation of such conjugates is within the skill of artisans and various techniques are known for accomplishing the conjugation, with the choice of the particular technique being guided by the materials to be conjugated. In certain aspects, polypeptides are conjugated to the EV (e.g., exosome). In some aspects, non-polypeptides, such as lipids, carbohydrates, nucleic acids, and small molecules, are conjugated to the EV (e.g., exosome).

In some aspects, the one or more moieties (e.g., payload and/or targetin moiety) are introduced to the EV (e.g., exosome) by hypotonic lysis. In such aspects, the EVs (e.g., exosomes) can be exposed to low ionic strength buffer causing them to burst allowing loading of the one or more moieties (e.g., payload and/or targetin moiety). In other aspects, controlled dialysis against a hypotonic solution can be used to swell the EV (e.g., exosome) and to create pores in the EV (e.g., exosome) membrane. The EV (e.g., exosome) is subsequently exposed to conditions that allow resealing of the membrane.

In some aspects, the one or more moieties (e.g., payload and/or targetin moiety) are introduced to the EV (e.g., exosome) by detergent treatment. In certain aspects, extracellular vesicles are treated with a mild detergent which transiently compromises the EV (e.g., exosome) membrane by creating pores allowing loading of the one or more moieties (e.g., payload and/or targetin moiety). After EVs (e.g., exosomes) are loaded, the detergent is washed away thereby resealing the membrane.

In some aspects, the one or more moieties (e.g., payload and/or targetin moiety) are introduced to the EV (e.g., exosome) by receptor mediated endocytosis. In certain aspects, EVs (e.g., exosomes) have a surface receptor which upon binding of the one or more moieties (e.g., payload and/or targetin moiety) induces internalization of the receptor and the associated moieties.

In some aspects, the one or more moieties (e.g., payload and/or targetin moiety) are introduced to the EV (e.g., exosome) by mechanical firing. In certain aspects, extracellular vesicles can be bombarded with one or more moieties (e.g., payload and/or targetin moiety) attached to a heavy or charged particle such as gold microcarriers. In some of these aspects, the particle can be mechanically or electrically accelerated such that it traverses the EV (e.g., exosome) membrane.

In some aspects, extracellular vesicles (e.g., exosomes) are subjected to several freeze thaw cycles, resulting in EV (e.g., exosome) membrane disruption allowing loading of the one or more moieties (e.g., payload and/or targetin moiety).

VI.C Methods of Isolating an EV, e.g., Exosome

In some aspects, methods of producing EVs (e.g., exosomes) disclosed herein comprises isolating the EV (e.g., exosome) from the producer cells. In certain aspects, the EVs (e.g., exosomes) released by the producer cell into the cell culture medium. It is contemplated that all known manners of isolation of EVs (e.g., exosomes) are deemed suitable for use herein. For example, physical properties of EVs (e.g., exosomes) can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using EV (e.g., exosome) or producer cell-specific surface markers. For example, specific surface markers can be used in immunoprecipitation, FACS sorting, affinity purification, and magnetic separation with bead-bound ligands.

In some aspects, size exclusion chromatography can be utilized to isolate the EVs (e.g., exosomes). Size exclusion chromatography techniques are known in the art. Exemplary, non-limiting techniques are provided herein. In some aspects, a void volume fraction is isolated and comprises the EVs (e.g., exosomes) of interest. Further, in some aspects, the EVs (e.g., exosomes) can be further isolated after chromatographic separation by centrifugation techniques (of one or more chromatography fractions), as is generally known in the art. In some aspects, for example, density gradient centrifugation can be utilized to further isolate the extracellular vesicles. In certain aspects, it can be desirable to further separate the producer cell-derived EVs (e.g., exosomes) from EVs (e.g., exosomes) of other origin. For example, the producer cell-derived EVs (e.g., exosomes) can be separated from non-producer cell-derived EVs (e.g., exosomes) by immunosorbent capture using an antigen antibody specific for the producer cell.

In some aspects, the isolation of EVs (e.g., exosomes) can involve combinations of methods that include, but are not limited to, differential centrifugation, size-based membrane filtration, immunoprecipitation, FACS sorting, and magnetic separation.

VII. Methods of Treatment

Present disclosure also provides methods of preventing and/or treating a disease or disorder in a subject in need thereof, comprising administering an EV (e.g., exosome) disclosed herein to the subject. In some aspects, a disease or disorder that can be treated with the present methods comprises a cancer, graft-versus-host disease (GvHD), autoimmune disease, infectious diseases, or fibrotic diseases. Other non-limiting examples of diseases or disorders that can be treated with the present disclosure include tolerance, allergy, atopy, pain, addiction, and combinations thereof. Not to be bound by any one theory, in some aspects, an EV (e.g., exosome) disclosed herein can treat and/or prevent these diseases or disorders by inducing neutralizing antibodies that can specifically bind to a molecule associated with the disease or disorder (e.g., addiction: nicotine; pain: CGRP or substance P). For example, an EV (e.g., exosome) favoring a humoral response against a pain-mediating neuropeptide such as substance-P, nerve growth factor, bradykinin, or calcitonin-related gene product (CGRP) can be used in lieu of passive antibody therapy against these targets to treat or prevent pain syndromes. The recent regulatory approval of several preventative passive antibody therapies targeting CGRP for migraine treatment provides strong rationale for the proposed humoral active vaccine approach. By chemically conjugating illicit drugs such as nicotine, cocaine, fentanyl, heroin, methamphetamine and others to proteins or other molecules expressed on EV (e.g., exosome) vaccines it is possible to generate antibody responses against these small molecules. Such anti-drug abuse vaccines can limit brain exposure of the abused substance, thereby reducing its ability to create euphoria and CNS toxicity. Thus, illicit drug conjugated EVs combined with potent TH2 orienting adjuvants can provide a vaccine treatment strategy for drug abuse rehabilitation. In some aspects, the treatment is prophylactic. In other aspects, the EVs (e.g., exosomes) for the present disclosure are used to induce an immune response. In other aspects, the EVs (e.g., exosomes) for the present disclosure are used to vaccinate a subject.

In some aspects, the disease or disorder is a cancer. When administered to a subject with a cancer, in certain aspects, EVs of the present disclosure can up-regulate an immune response and enhance the tumor targeting of the subject's immune system. In some aspects, the cancer being treated is characterized by infiltration of leukocytes (T-cells, B-cells, macrophages, dendritic cells, monocytes) into the tumor microenvironment, or so-called "hot tumors" or "inflammatory tumors". In some aspects, the cancer being treated is characterized by low levels or undetectable levels of leukocyte infiltration into the tumor microenvironment, or so-called "cold tumors" or "non-inflammatory tumors". In some aspects, an EV (e.g., exosome) is administered in an amount and for a time sufficient to convert a "cold tumor" into a "hot tumor", i.e., said administering results in the infiltration of leukocytes (such as T-cells) into the tumor microenvironment. In certain aspects, cancer comprises bladder cancer, cervical cancer, renal cell cancer, testicular cancer, colorectal cancer, lung cancer, head and neck cancer, and ovarian, lymphoma, liver cancer, glioblastoma, melanoma, myeloma, leukemia, pancreatic cancers, or combinations thereof. In other term, "distal tumor" or "distant tumor" refers to a tumor that has spread from the original (or primary) tumor to distant organs or distant tissues, e.g., lymph nodes. In some aspects, the EVs of the disclosure treats a tumor after the metastatic spread.

In some aspects, the disease or disorder is a graft-versus-host disease (GvHD). In some aspects, the disease or disorder that can be treated with the present disclosure is an autoimmune disease. Non-limiting examples of autoimmune diseases include: multiple sclerosis, peripheral neuritis, Sjogren's syndrome, rheumatoid arthritis, alopecia, autoimmune pancreatitis, Behcet's disease, Bullous pemphigoid, Celiac disease, Devic's disease (neuromyelitis optica), Glomerulonephritis, IgA nephropathy, assorted vasculitides, scleroderma, diabetes, arteritis, vitiligo, ulcerative colitis, irritable bowel syndrome, psoriasis, uveitis, systemic lupus erythematosus, Graves' disease, myasthenia gravis, pemphigus vulgaris, anti-glomerular basement membrane disease (Goodpasture syndrome), Hashimoto's thyroiditis, autoimmune hepatitis, and combinations thereof.

In some aspects, the disease or disorder is an infectious disease. In certain aspects, the disease or disorder is an oncogenic virus. In some aspects, infectious diseases that can be treated with the present disclosure includes, but not limited to, Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV (e.g., HIV-2)) corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and *Burrelia mayonii* (e.g., Lyme disease), herpes simplex virus 2 (HSV2), *Klebsiella* sp., *Pseudomonas aeruginosa, Enterococcus* sp., *Proteus* sp., *Enterobacter* sp., Actinobacter sp., coagulase-negative staphylococci (CoNS), *Mycoplasma* sp., or combinations thereof.

In some aspects, the disease or disorder includes pain. As used herein, the term "pain" refers to all categories of pain, including, but not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV (e.g., HIV-1, HIV-2) pain, post-herpetic pain, non-cardiac chest pain, irritable bowel syndrome and pain associated with bowel disorders and dyspepsia, pain associated with narcotic drug addiction withdrawal, and combinations thereof.

In some aspects, the disease or disorder includes allergy. As used herein, the term "allergy" refers to an acquired potential to develop immunologically mediated adverse reaction to normally innocuous substances ("allergens"). Non-limiting examples of allergies include eczema, allergic rhinitis or coryza, hay fever, conjunctivitis, bronchial or allergic asthma, urticaria (hives), food allergies, atopic dermatitis, drug allergy, angioedema, allergic conjunctivitis, hypersensitivity, and combinations thereof. In certain aspects, an allergy that can be treated with the present disclosure is caused by food allergens (e.g., peanut, milk, egg, shellfish, and tree nut) (i.e., food allergy). In some aspects, an allergy that can be treated with the present disclosure is caused by environmental allergens (e.g., cat dander, ragweed, grass pollen, house dust mite, bee venom, latex, and poison ivy).

EVs (e.g., exosomes) of the present disclosure can be administered to a subject by any useful method and/or route known in the art. In some aspects, the EVs (e.g., exosomes) are administered intravenously to the circulatory system of the subject. In some aspects, the EVs (e.g., exosomes) are infused in suitable liquid and administered into a vein of the subject.

In some aspects, the EVs (e.g., exosomes) are administered intra-arterially to the circulatory system of the subject. In some aspects, the EVs (e.g., exosomes) are infused in suitable liquid and administered into an artery of the subject.

In some aspects, the EVs (e.g., exosomes) are administered to the subject by intrathecal administration. In some aspects, the EVs (e.g., exosomes) are administered via an injection into the spinal canal, or into the subarachnoid space so that it reaches the cerebrospinal fluid (CSF).

In some aspects, the EVs (e.g., exosomes) are administered intratumorally into one or more tumors of the subject.

In some aspects, the EVs (e.g., exosomes) are administered to the subject by intranasal administration. In some aspects, the EVs (e.g., exosomes) can be insufflated through the nose in a form of either topical administration or systemic administration. In certain aspects, the EVs (e.g., exosomes) are administered as nasal spray. In some aspects, intranasal administration can allow for the effective delivery of an EV (e.g., exosome) disclosed herein to the gastrointestinal tissues (see, e.g., Example 20). Such EVs (e.g., exosomes) delivered to the gastrointestinal tissues could be useful in providing protection against various gut-associated pathogens.

In some aspects, the EVs (e.g., exosomes) are administered to the subject by intraperitoneal administration. In some aspects, the EVs (e.g., exosomes) are infused in suitable liquid and injected into the peritoneum of the subject. In some aspects, the intraperitoneal administration results in distribution of the EVs (e.g., exosomes) to the lymphatics. In some aspects, the intraperitoneal administration results in distribution of the EVs (e.g., exosomes) to the thymus, spleen, and/or bone marrow. In some aspects, the intraperitoneal administration results in distribution of the EVs (e.g., exosomes) to one or more lymph nodes. In some aspects, the intraperitoneal administration results in distribution of the EVs (e.g., exosomes) to one or more of the cervical lymph node, the inguinal lymph node, the mediastinal lymph node, or the sternal lymph node. In some aspects, the intraperitoneal administration results in distribution of the EVs (e.g., exosomes) to the pancreas.

In some aspects, the EVs, e.g., exosomes, are administered to the subject by intra-ocular administration (e.g., periocular administration). In some aspects, the EVs, e.g., exosomes, are injected into the periocular tissues. Periocular drug administration includes the routes of subconjunctival, anterior sub-Tenon's, posterior sub-Tenon's, and retrobulbar administration.

Non-limiting examples of other routes of administration that can be used to administer the EVs (e.g., exosomes) disclosed herein include parenteral, topical, oral, subcutaneous, intradermal, transdermal, rectal, intraperitoneal, intramuscular, sublingual, or combinations thereof.

As disclosed herein, in some aspects, EVs (e.g., exosomes) disclosed herein can be administered to a subject in combination with one or more additional therapeutic agents. In certain aspects, the one or more additional therapeutic agents and the EVs (e.g., exosomes) are administered concurrently. In some aspects, the one or more additional therapeutic agents and the EVs (e.g., exosomes) are administered sequentially. In some aspects, the EVs (e.g., exosomes) are administered to the subject prior to administering the one or more additional therapeutic agents. In certain aspects, the EVs (e.g., exosome) are administered to the subject after administering the one or more additional therapeutic agents. As used herein, the term "therapeutic agents" refers to any agents that can be used in treating a disease or disorder disclosed herein (e.g., chemotherapy or immune checkpoint inhibitors (e.g., anti-PD-1 antibody) for treating a cancer). In some aspects, the one or more additional therapeutic agents that can be used in combination with the EVs (e.g., exosomes) of the present disclosure include a payload (e.g., antigen, adjuvant, and/or immune modulator) which is not expressed in an EV (e.g., exosome). For instance, a treatment method disclosed herein can comprise administering to a subject in need thereof (i) an antigen-less EV (e.g., exosome) and (ii) an antigen that is not expressed in an EV (e.g., soluble antigen).

In some aspects, a subject that can be treated with the present disclosure is a human. In some aspects, a subject is a non-human mammal (e.g., non-human primates, dogs, cats, guinea pigs, rabbits, rats, mice, horses, cattle, chickens, birds, and bears). Accordingly, in some aspects, the EVs (e.g., exosomes) disclosed herein can be used to improve the health of an animal (i.e., non-human mammal).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); Crooke, Antisense drug Technology: Principles, Strategies and Applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1: Generation of Engineered-Exosomes

Figure 1B:
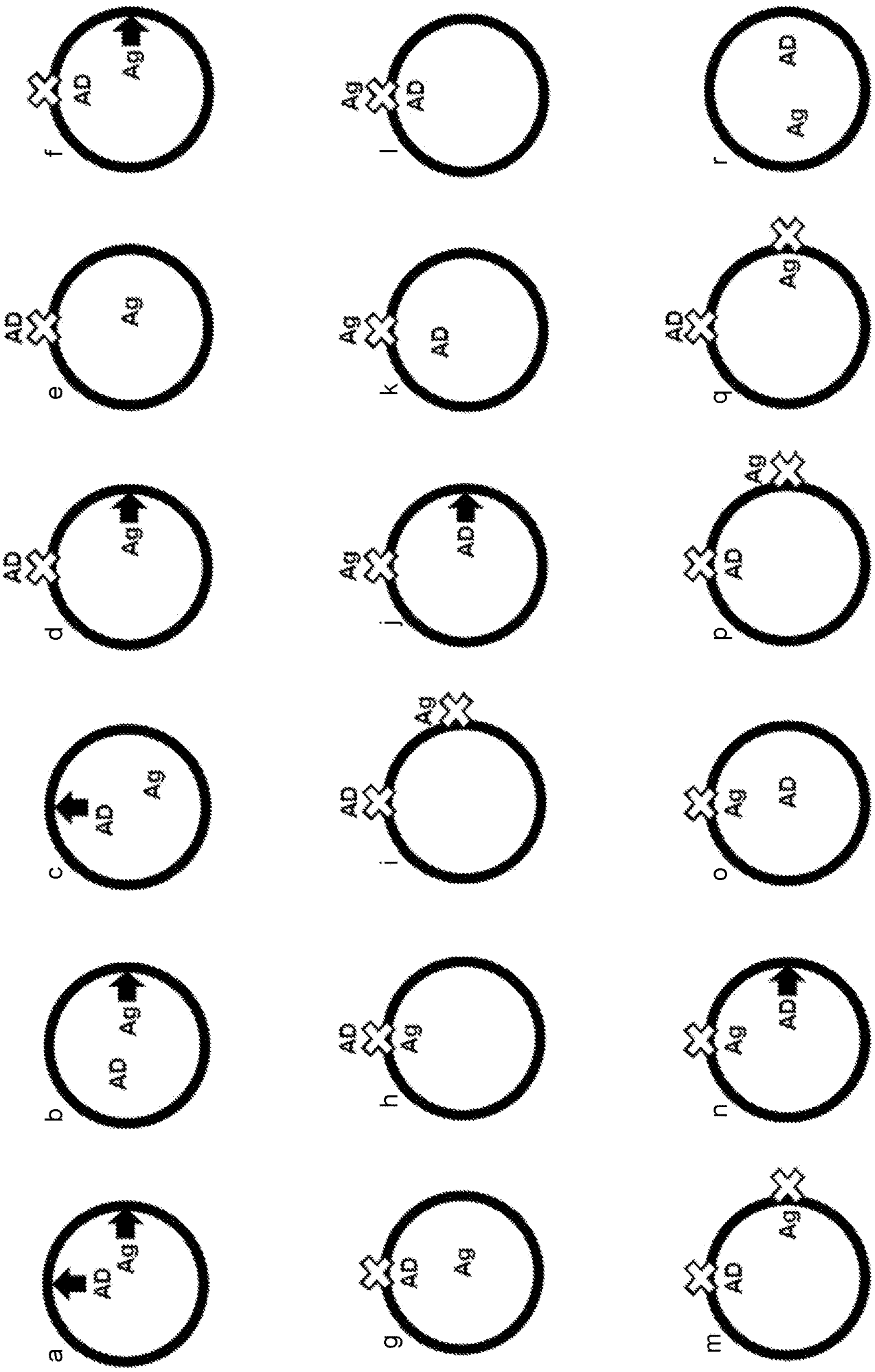
FIG. 1B shows non-limiting examples (a-r) of EVs, e.g., exosomes, comprising an antigen and an adjuvant. “Ag” and “AD” represent antigen and adjuvant, respectively. Arrowheads represent Scaffold Y moiety. “X” represents Scaffold X moiety. As will be apparent from the present disclosure, the EVs (e.g., exosomes) shown in FIG. 1B can comprise multiple antigens, multiple adjuvants, or both multiple antigens and multiple adjuvants. The EVs (e.g., exosomes) can also further comprise one or more additional moieties (e.g., immune modulator and/or targeting moiety). Further description of such EVs (e.g., exosomes) are provided throughout the present disclosure.
Figure 2:
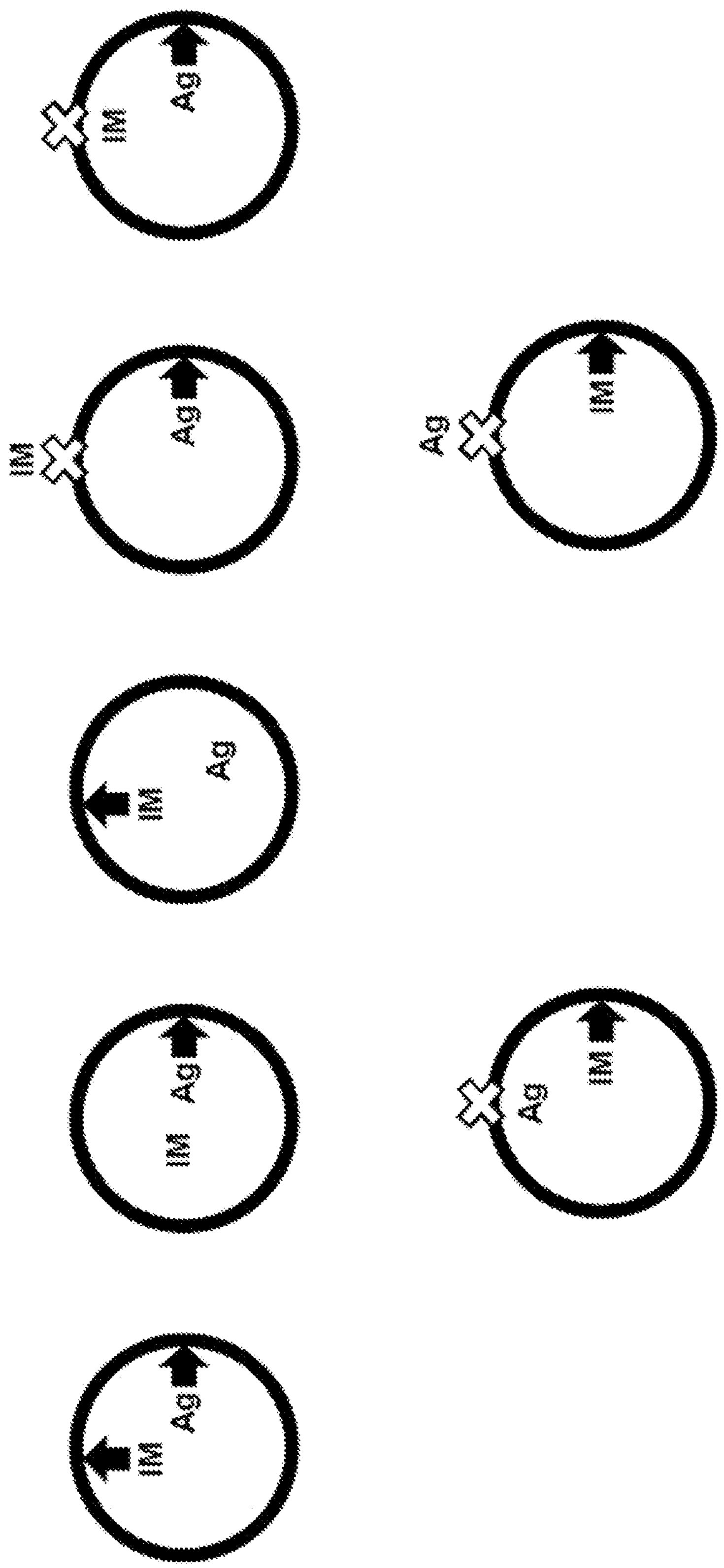
FIG. 2 shows seven selected examples of exosomes comprising an antigen and an immune modulator. “Ag” and “IM” represent antigen and immune modulator, respectively. Arrowheads represent Scaffold Y moiety. “X” represents Scaffold X moiety. As will be apparent from the present disclosure, the EVs (e.g., exosomes) shown in FIG. 2 can comprise multiple antigens, multiple immune modulators, or both multiple antigens and multiple immune modulators. The EVs (e.g., exosomes) can also further comprise one or more additional moieties (e.g., adjuvant and/or targeting moiety). Further description of such EVs (e.g., exosomes) are provided throughout the present disclosure.

To generate exosomes described herein, human embryonic kidney (HEK) cell line (HEK293SF) was used. The cells were then stably transfected with Scaffold X and/or Scaffold Y linked to an agent of interest (e.g., antigen, adjuvant, or immune modulator). See FIGS. 1A, 1B, and 2. For example, CD40L-expressing exosomes were generated by transfecting HEK293SF cells with CD40L-GFP PTGFRN fusion molecules, which were expressed as a monomer (pCB-518 to pCB-526) or as a forced trimer (pCB-607 and pCB-527). An example of a trimeric CD40L-GFP PTGFRN fusion molecule is shown in FIG. 1A. Similarly, to generate chicken ovalbumin (OVA)-expressing exosomes, ovalbumin was stably expressed in HEK293SF cells as a fusion to amino acids 1-10 of BASP1 ("BASP1(1-10)-OVA").

Upon transfection, HEK293SF cells were grown to high density in chemically defined medium for 7 days. Conditioned cell culture media was collected and centrifuged at 300-800×g for 5 minutes at room temperature to remove cells and large debris. Media supernatant was then supplemented with 1000 U/L BENZONASE® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and any residual media was aspirated from the bottom of the tube. The pellet was resuspended in 200-1000 μL PBS (—Ca-Mg).

To further enrich exosome populations, the pellet was processed via density gradient purification (sucrose or OPTIPREP™).

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 μL) and stored at 4° C.

For OPTIPREP™ gradient, a 3-tier sterile gradient is prepared with equal volumes of 10%, 30%, and 45% OPTIPREP™ in a 12 mL Ultra-Clear (344059) tube for a SW 41 Ti rotor. The pellet was added to the OPTIPREP™ gradient and ultracentrifuged at 200,000×g for 16 hours at 4° C. to separate the exosome fraction. The exosome layer was then gently collected from the top ~3 ml of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 μL) and stored at 4° C. until ready to be used.

Example 2: Efficacy of Engineered-Exosomes to Induce Antigen-Specific T Cell Responses To assess the ability of the exosomes disclosed herein to induce immune response, an engineered-exosome expressing OVA-Scaffold Y and loaded with the STING agonist CL656 ("Py-OVA-exoSTING") was administered to mice either intravenously or intranasally. One week after administration, the frequency of CD8+ T cells reactive to OVA was assessed via both flow cytometry and/or IFN-γ ELISPOT assay by enzymatic dissociation of spleens and blood or lungs and spleens following intravenous or intranasal administration, respectively. Control animals received one of the following: (i) intra-peritoneal injected anti-CD40 antibody in combination with soluble OVA protein (not part of an exosome) ("IP aCD40+OVA"); (ii) cAIM(PS)2 Difluor (Rp/Sp) ("CL656"; STING agonist) in combination with soluble OVA protein (not part of an exosome) ("CL656+OVA"); (iii) exosome over-expressing only Scaffold X and loaded with STING agonist in combination with soluble OVA protein (OVA is not part of the exosome) ("Px-exoSTING+OVA"); and (iv) exosome expressing only OVA-Scaffold Y fusion protein ("Py-OVA").

Figure 3A:
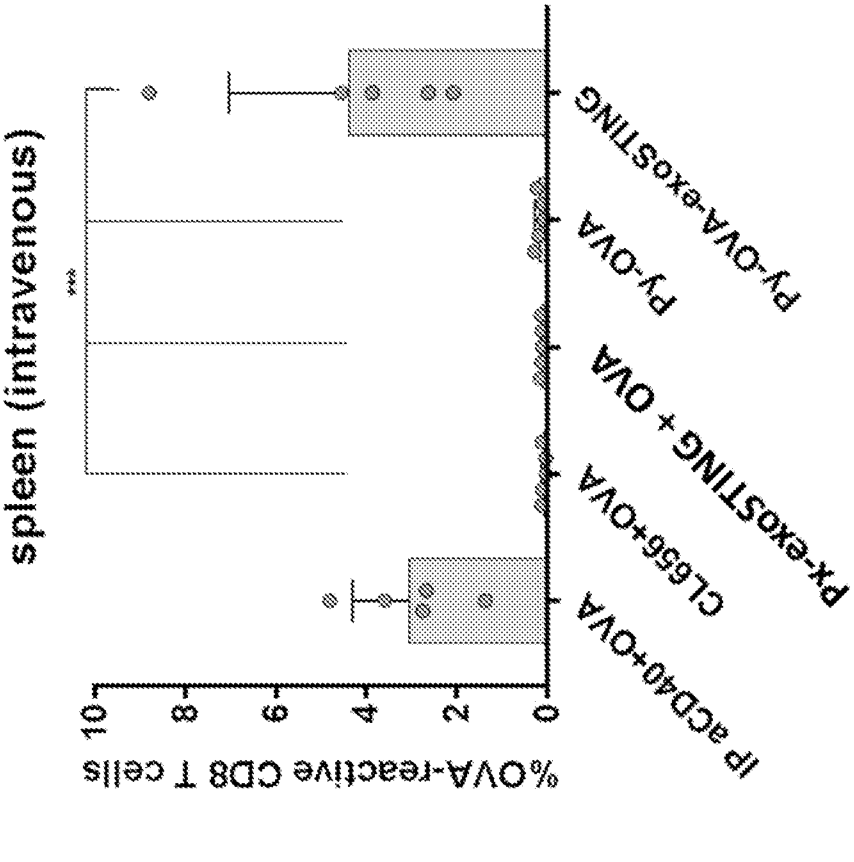
FIGS. 3A and 3B show the ability of an engineered-EV, e.g., exosome, comprising both OVA-Scaffold Y and loaded with STING agonist (“Py-OVA-exoSTING”) to induce OVA-specific CD8 T cell immune response after intravenous administration into naïve C57/BL6 mice. The induction of OVA-specific CD8 T cell immune response is shown both in the spleen (FIG. 3A) and in pooled peripheral blood mononuclear cells (PBMCs) (FIG. 3B). The following constructs were used as controls: (i) anti-CD40 antibody in combination with soluble OVA protein (not part of an EV, e.g., exosome) (“IP aCD40+OVA”); (ii) cAIM(PS)2 Difluor (Rp/Sp) (“CL656”; STING agonist) in combination with soluble OVA protein (not part of an EV, e.g., exosome) (“CL656+OVA”); (iii) EV, e.g., exosome overexpressing Scaffold X, loaded with STING agonist in combination with soluble OVA protein (OVA is not part of the EV, e.g., exosome) (“Px-exoSTING+OVA”); and (iv) EV, e.g., exosome, expressing only OVA-Scaffold Y fusion protein (“Py-OVA”). Data are shown both individually and as mean±S.D. “***” indicates $p<0.0005$ by one-way ANOVA.
Figure 3B:
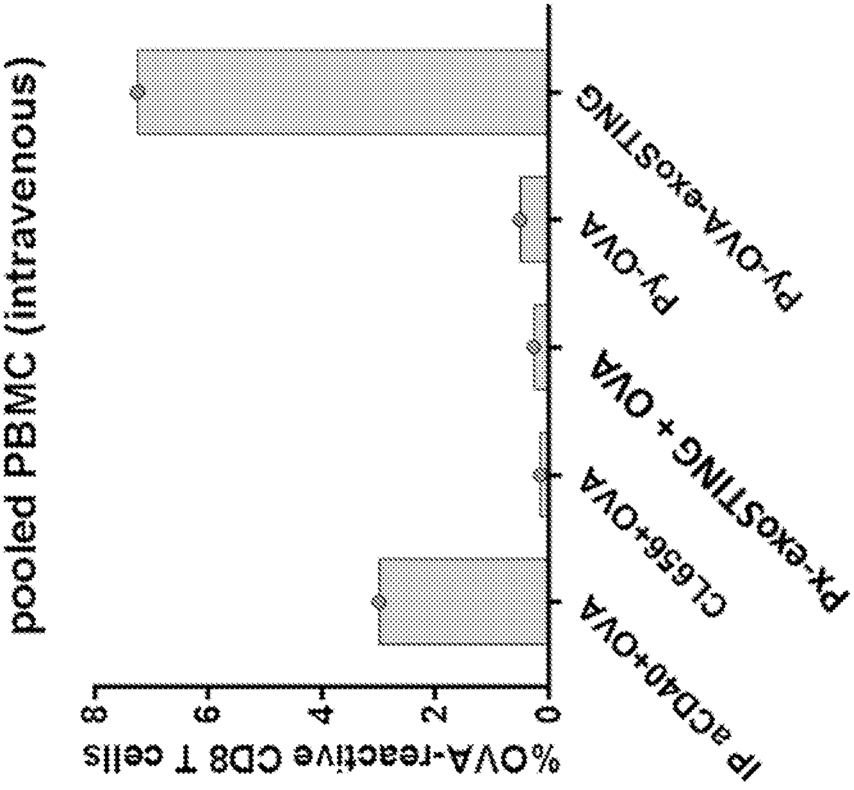
Figure 4B:
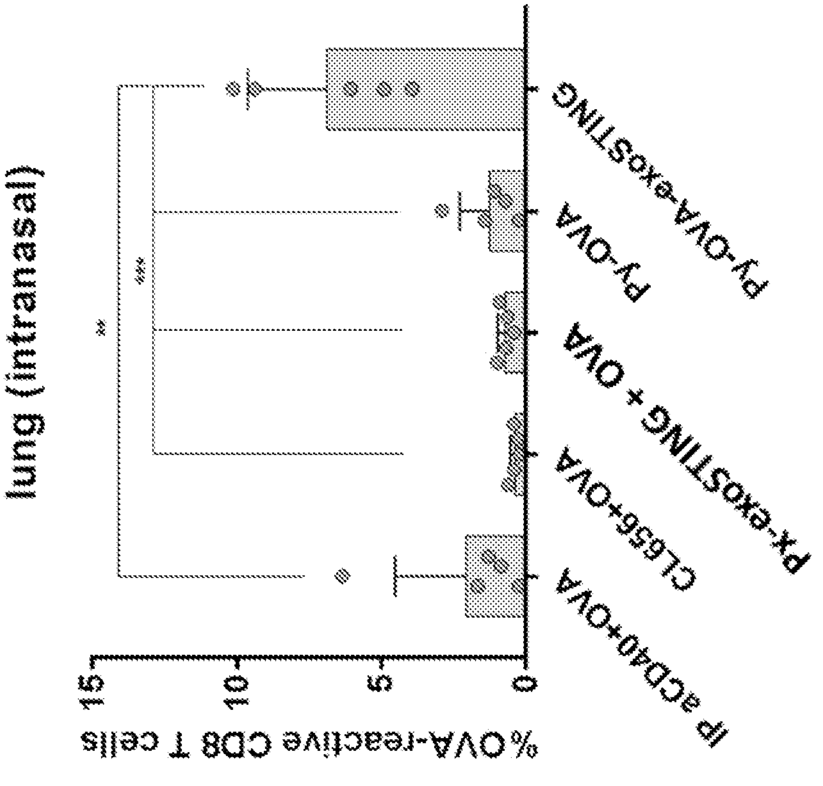
FIGS. 4A and 4B show the ability of an engineered-EV, e.g., exosome comprising both OVA-Scaffold Y and loaded with STING-agonist (“Py-OVA-exoSTING”) to induce OVA-specific CD8 T cell immune response after intranasal administration into naïve C57/BL6 mice. The induction of OVA-specific CD8 T cell immune response is shown both in the spleen (FIG. 4A) and in the lung (FIG. 4B). The following constructs were used as controls: (i) anti-CD40 antibody in combination with soluble OVA protein (not part of an EV, e.g., exosome); (ii) cAIM(PS)2 Difluor (Rp/Sp) ("CL656"; STING agonist) in combination with soluble OVA protein ("CL656+OVA"); (iii) EV, e.g., exosome over-expressing Scaffold X, loaded with STING-agonist in combination with soluble OVA protein (OVA is not part of the EV, e.g., exosome) ("Px-exoSTING+OVA"); and (iv) EV, e.g., exosome, expressing only OVA-Scaffold Y fusion protein ("Py-OVA"). Data are shown both individually and as mean±S.D. "" indicates $p<0.005$ by one way ANOVA. "*" indicates $p<0.0005$ by one-way ANOVA.
Figure 4A:
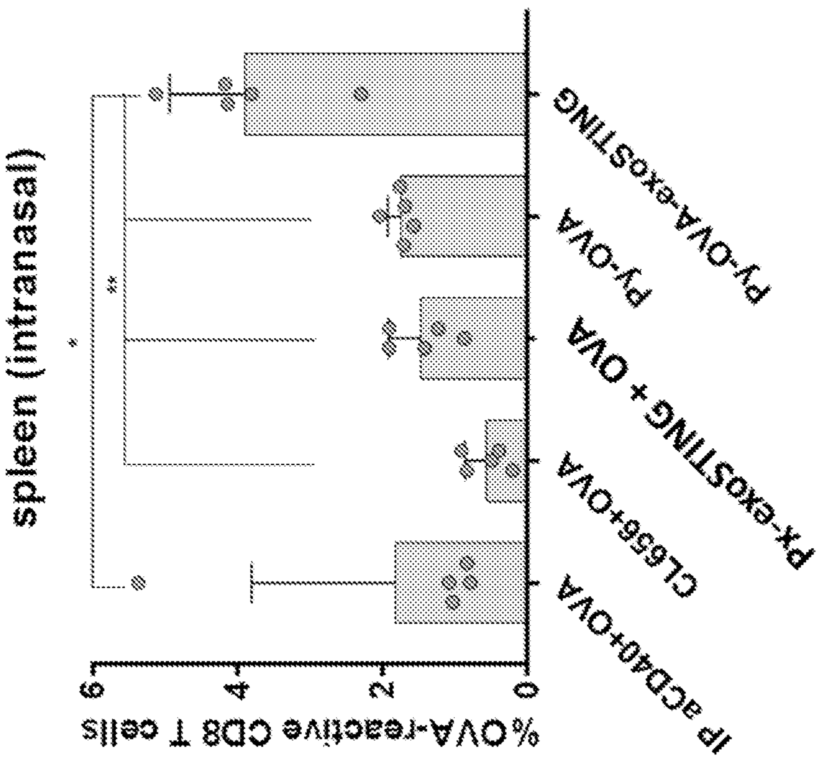
Figure 5B:
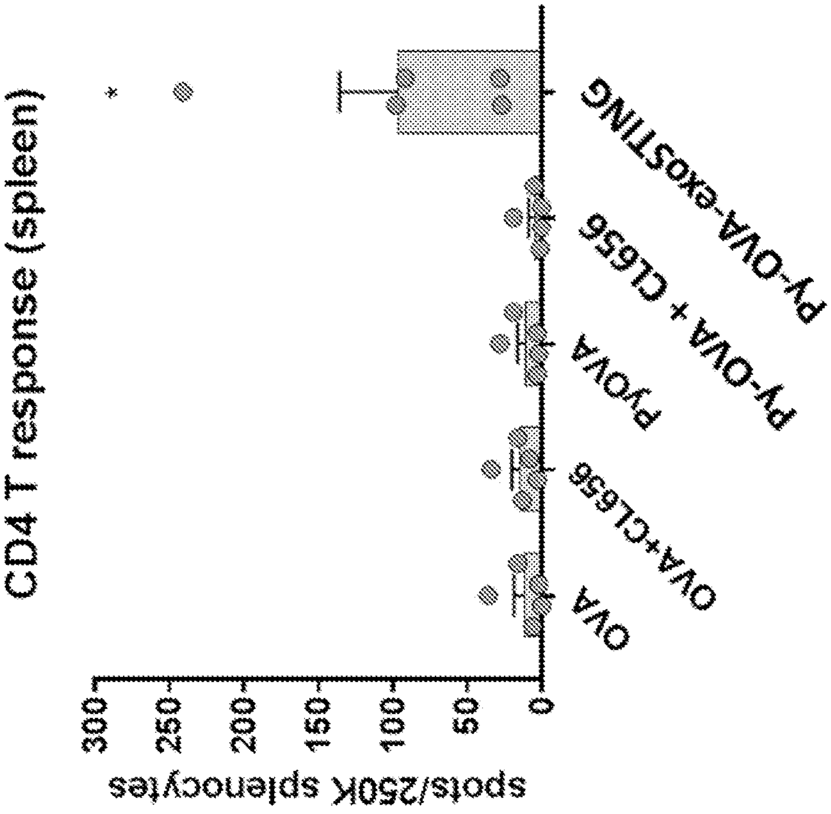
FIGS. 5A and 5B show a comparison of OVA-specific T cell response in the spleen of mice after intranasal administration of an engineered-EV, e.g., exosome comprising both OVA-Scaffold Y and loaded with STING agonist ("Py-OVA-exoSTING"). OVA-specific T cell responses were measured using an IFN-γ ELISPOT analysis one week post administration.
Figure 5A:
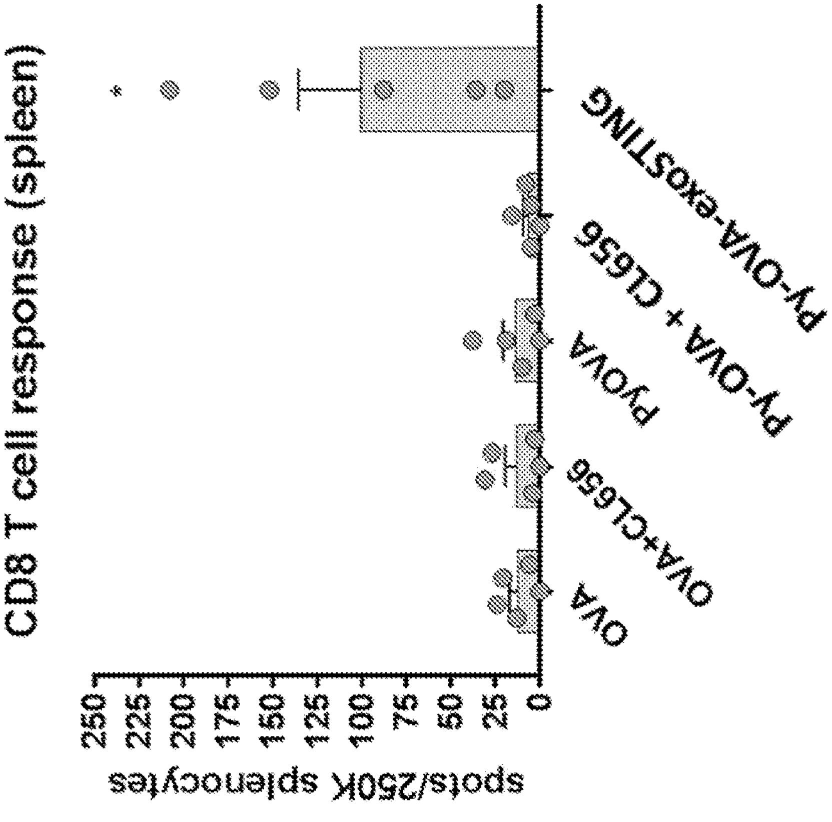

As shown in FIGS. 3A and 3B, among the different treatment groups, animals that received intravenous administration of the Py-OVA-exoSTING exosome had the greatest number of OVA-specific CD8 T cells both in the spleen and in PBMC. Similar results were observed when the different treatment regiments were administered intranasally. (See FIGS. 4A and 4B for flow cytometry analysis and FIGS. 5A and 5B for ELISPOT results). These results demonstrate that the exosomes disclosed herein (i.e., comprising both OVA-Scaffold Y and loaded with a STING agonist) can be used to induce robust immune responses against antigens of interest (e.g., tumor or microbial antigen).

Example 3: Efficacy of Engineered-Exosomes to Induce Immune Tolerance

To assess the tolerogenic potential of exosomes disclosed herein, engineered-exosomes comprising antigens associated with autoimmune diseases (e.g., beta-cell proteins (type I diabetes), myelin oligodendrocyte glycoprotein (MOG, multiple sclerosis), or synovial proteins (rheumatoid arthritis)) will be constructed. As in Example 2, the antigen will be linked to a Scaffold Y protein described herein. Some of the engineered-exosomes will further comprise immune modulators in the NFkB inhibition class such as rapamycin and/or its derivatives. These immune modulators will be expressed in the exosome linked to a Scaffold X protein (e.g., those described herein) or loaded exogenously into exosomes.

The above-engineered exosomes will be administered to an experimental animal model for delayed type hypersensitivity (DTH) or experimental autoimmune encephalomyelitis (EAE). Then, the tolerogenic/regulatory T cell responses to the target antigen will be assessed in the animals using assays, such as flow cytometry and ELISPOT assay.

Example 4: Comparison of Engineered-Exosomes to Other Antigen-Adjuvant Combinations in Inducing Immune Response The ability of the engineered-exosomes disclosed herein (e.g., see Example 2) to induce OVA-specific immune response (both T and B cells) will be compared to other known antigen-adjuvant combinations. Specifically, a direct head-to-head comparison will be conducted against the following antigen-adjuvant combinations: vaccination with soluble OVA (antigen) and Monophosphoryl Lipid A (MPLA), squalene in water emulsions (AddaVax™), saponin based vaccines (Quil-A®), incomplete Freund's adjuvant (IFA), and/or Polyinosinic-polycytidylic acid (poly I:C).

The following endpoints will be analyzed: (i) distribution of T cell subsets induced, i.e. % OVA-reactive CD8 and CD4 T cells one week after a single administration as well as one week after a boost administration (two doses, two weeks a part); (ii) T cell effector analysis: same as above, but examining the types of T cell responses in the CD4 and CD8 compartment. Time points would be identical to above, and the analysis would be intracellular cytokine staining (ICS) by flow; and (iii) humoral responses one week after boost administration ($2^{nd}$ dose): This would be analysis of serum for OVA-specific antibodies and antibody class, by ELISA or Bio-Layer Interferometry (BLI), as well as flow based analysis of B cell reactivity to biotinylated, whole OVA antigen.

Example 5: Dose Response Analysis of Luminal Antigens

A dose response analysis will be conducted to determine the lowest amount of antigen required for the engineered-exosomes disclosed herein to mount an effective immune response. The study will compare a Py-OVA:Py-GFP mixture (i.e., exosome expressing OVA and GFP, both linked to Scaffold Y protein) loaded with equal amounts of CL656, and decreasing amounts of Py-OVA with increasing amounts of Py-GFP. See TABLE 10 (below).

TABLE 10

Make-up of different exosomes to be tested

| Py-OVA ng | Py-GFP ng | CL656 | total exosomes ng |
|---|---|---|---|
| 150 | 50 | 100 | 200 |
| 100 | 100 | | |
| 50 | 150 | | |

As described in Example 2, approximately a week after the administration, animals will be sacrificed and antigen-specific immune response will be assessed in various tissues (e.g., spleen, lung, blood) using flow cytometry and/or ELISPOT assay.

Example 6: Effect of Route of Administration on Inducing Immune Response

Data will compare several doses of Py-OVA-exoSTING (see Example 2) following intranasal, intravenous, subcutaneous, intraperitoneal, and intramuscular administration. Endpoint analysis will include splenic and circulating (PBMC) OVA-reactive CD4 and CD8 T cells one week after a single and double (two weeks apart) administration.

Example 7: Induction of Mucosal Homing

To assess the ability of the exosomes disclosed herein to induce immune response within mucosal tissues, Py-OVA-exoSTING (see Example 2) will be administered intranasally to female mice. After one or two doses, female mice will be challenged by induction of intravaginal administration of MPLA and squalene. 5 days after intravaginal challenge, genital tracts will be harvested and assessed for recruitment of OVA-specific CD4 and CD8 T cells.

Example 8: Tissue Resident Memory T Cell Responses Following Intravenous or Intranasal Vaccination To better characterize the ability of the engineered-exosomes disclosed herein to induce circulating and/or tissue-resident memory T cells, Py-OVA-exoSTING will be administered to animals as described in Example 2. One week post administration, the lung (from animals that received intranasal administration) and/or the liver (from animals that received intravenous administration) will be processed and analyzed for circulating and/or tissue-resident memory T cells.

Example 9: Therapeutic Vaccination Against Human Herpes Virus 2 (HSV2)

A mouse model of HSV2 infection, wherein the animals have genital HSV2 infection, will be treated intranasally with one of the following: (i) an exosome expressing HSV2 antigen linked to Scaffold Y and loaded with a STING agonist ("Py-HSV2-exoSTING"), (ii) an exosome expressing OVA antigen linked to Scaffold Y and loaded with a STING agonist ("Py-OVA-exoSTING"), or ACYCLOVIR™. The Py-HSV2-exoSTING construct will express two to three different HSV2 antigens. Endpoints will measure viral shedding and paralysis after 1 or 2 (biweekly) doses of the different treatment regiments.

Example 10: Prophylactic Vaccination Against Human Herpes Virus 2 (HSV2)

Using the exosome constructs described in Example 9, naïve mice will be vaccinated intranasally one or two times (bi-weekly) and intravaginally challenged with HSV2 one week after final administration. Endpoints will include measurements of viral shedding and paralysis through three weeks post challenge.

Example 11: Therapeutic Vaccination Against Mice Bearing EG7-OVA Tumors

Mice will be inoculated with subcutaneous EG7-OVA tumors. When tumors reach 50 $mm^3$, mice will be vaccinated intranasally, intravenously, or subcutaneously with Py-OVA-exoSTING (see Example 2) or appropriate controls. Endpoints will be measurement of tumor growth expressed as tumor growth inhibition (TGI).

Example 12: Vaccination with CD40L-Px:Py-OVA-exoSTING Compared to Py-OVA-exoSTING The ability of Py-OVA-exoSTING (see Example 2) to induce immune response will be directly compared to an exosome expressing (i) CD40L linked to a Scaffold X, (ii) OVA linked to a Scaffold Y, and (iii) loaded with STING agonist ("CD40L-Px:Py-OVA-exoSTING"). The exosomes will be administered to naïve animals and then OVA-specific T cell response will be assessed in various tissues approximately one week after administration, as described in Example 2.

Example 13: Vaccination with Anti-Clec9a EVs (e.g., Exosomes)

The ability of an OVA-expressing EV (e.g., exosome) loaded with STING agonist and expressing anti-Clec9a moiety ("anti-Clec9a EVs") to induce immune response will also be assessed in an animal model. FIG. 6 provides a schematic of a proposed experimental design. Animals will be treated with one of the following: (i) OVA-expressing EVs (e.g., exosomes) loaded with STING agonist and expressing a control isotype antibody; (ii) OVA-expressing EVs (e.g., exosomes) expressing a control isotype antibody alone; (iii) OVA-expressing EVs (e.g., exosomes) loaded with STING agonist and expressing anti-Clec9a targeting moiety; (iv) OVA-expressing EVs (e.g., exosomes) expressing anti-Clec9a targeting moiety but not loaded with STING agonist; and (v) EVs (e.g., exosomes) expressing OVA alone. The different treatment regimens will be administered intranasally. Then, some of the animals will be sacrificed and OVA-specific T cell responses will be assessed in the spleen and lung. Some of the animals will receive a second administration of the EVs (e.g., exosomes) approximately 14 days after the initial administration. OVA-specific T cell responses will be further assessed after the boost.

Example 14: Vaccination with Anti-EBV BZLF1 EVs (e.g. Exosomes)

Figure 8:
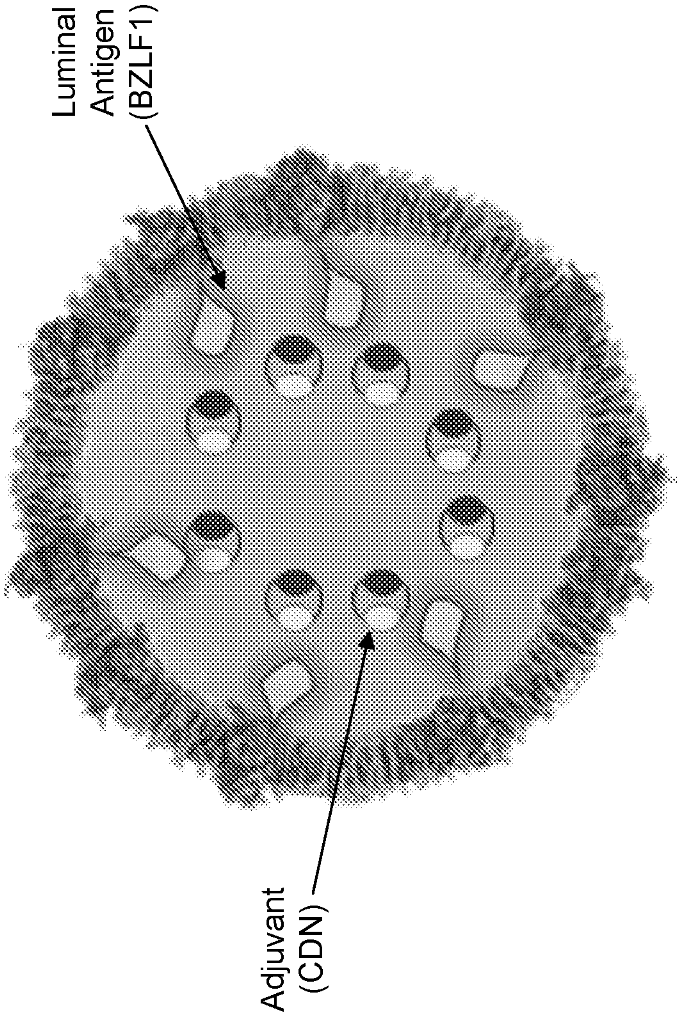
FIG. 8 illustrate the use of EBV BZLF1 as a targeting antigen for post-transplant lymphoproliferative disease in EBV-transplant patients.

The ability of an EV (e.g., exosome) loaded with an Epstein Barr Virus (EBV) BZLF1 antigen to induce an immune response will in assessed in an animal model according to the methods and experimental designs disclosed above (e.g., replacing an antigen disclosed above with BZLF1). FIG. 8 shows an schematic representation of an EV, e.g., an exosome, containing the BZLF1 antigen attached to the luminal surface of the EV membrane.

Example 15: Efficacy of Engineered-Exosomes to Induce Effector and Memory T Cells (Spleen)

To further characterize the T cell response observed after immunization with an exosome disclosed herein (see Example 2), the ability of the exosomes to induce both effector and memory T cells was observed in mice. Briefly, mice were subcutaneously administered with an engineered-exosome expressing OVA-Scaffold Y and loaded with the STING agonist CL656 ("Py-OVA exoVACC"). Control animals received one of the following: (i) soluble OVA ("OVA"), (ii) soluble OVA+CL656 ("OVA+STING"), (iii) exosome expressing only OVA-Scaffold Y fusion protein ("PyOVA"), (iv) exosome expressing only OVA-Scaffold Y fusion protein+soluble CL656 (i.e., the STING agonist is not loaded into the exosomes) ("PyOVA+STING"), and (v) soluble OVA+alum adjuvant ("OVA+Alum").

Two weeks after administration, some of the animals were sacrificed and the frequency of OVA-specific T cells (both CD4+ and CD4+ T cells) in the spleen was assessed using an IFN-γ ELISPOT assay. To induce IFN-γ production, the splenocytes were stimulated in vitro with OVA peptides specific for CD4+ and CD8+ T cells. The remaining animals were boosted (i.e., immunized again) with the same treatment regimen. Then, at day 28 post initial immunization (or day 14 after the boost), the animals were sacrificed and the frequency of OVA-specific T cells (both CD4+ and CD4+ T cells) in the spleen was also assessed using an IFN-γ ELISPOT assay.

Figure 9A:
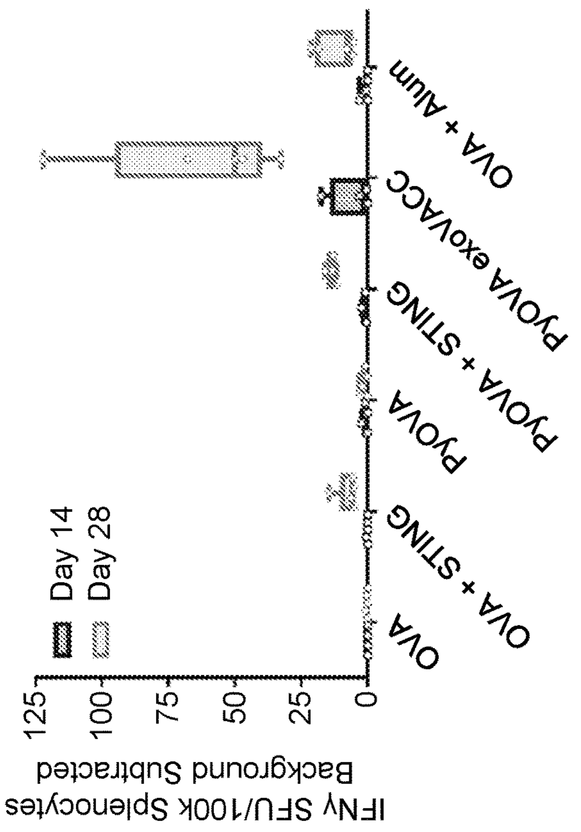
FIGS. 9A and 9B provide a comparison of the number of CD4+ (FIG. 9A) and CD8+ (FIG. 9B) T cells from wild-type mice immunized with soluble or exosomal OVA with or without STING adjuvant. Wild-type mice were immunized with soluble OVA (Ovalbumin); soluble OVA+CL656 (STING agonist); PyOVA (exosomal luminal expression of OVA fused to BASP1); PyOVA+soluble CL656; PyOVA exoVacc (PyOVA exosomes loaded with CL656); or soluble OVA+alum adjuvant, as indicated (FIGS. 9A and 9B). Antigen-specific cells were identified by IFN-g expression and data expressed as the number of IFN-g positive spot forming units (SFU) per 100,000 splenocytes after subtracting for background (non-antigen-specific activation) (x-axis, FIGS. 9A and 9B). "Day 14" represent the number of CD4+ and CD8+ T cells observed in the animals after a single immunization. "Day 28" represent the number of CD4+ and CD8+ T cells observed in the animals after a boost with a second administration.
Figure 9B:
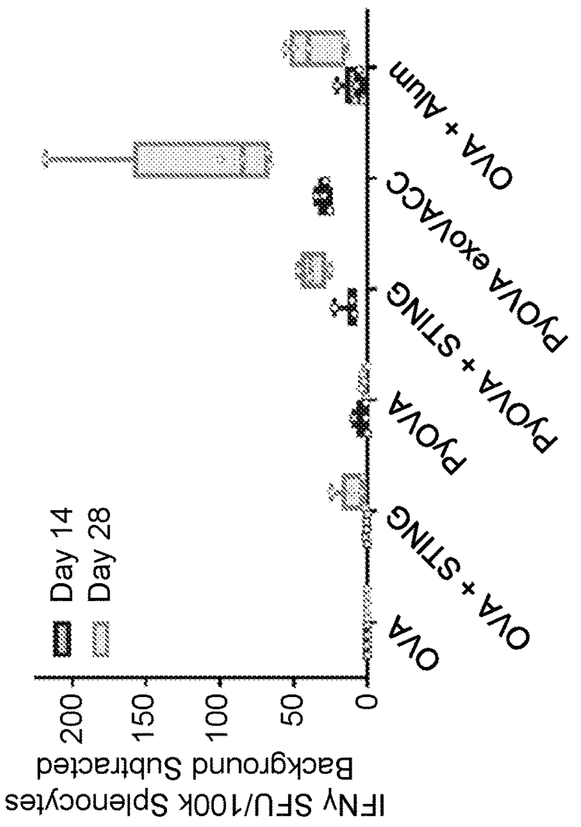

As shown in FIGS. 9A and 9B, after a single subcutaneous administration, animals that received the Py-OVA exoVACC exosome had the greatest number of OVA-specific CD4+ and CD8+ T cells in the spleen. This increase in CD4+ and CD8+ T cell numbers increased further after the boost in animals that received the Py-OVA exoVACC exosome.

The above data are in agreement with the results from Example 2 and further demonstrate that the exosomes disclosed herein (e.g., engineered-exosome expressing OVA-Scaffold Y and loaded with the STING agonist CL656) can be used to induce robust effector and memory T cells against an antigen of interest (e.g., tumor or microbial antigens) even when administered subcutaneously.

Example 16: Efficacy of Engineered-Exosomes to Induce Effector and Memory T Cells (Lung)

To assess whether the results from Example 15 are also observed in other tissues (e.g., mucosal tissues), an engineered-exosome expressing OVA-Scaffold Y and loaded with the STING agonist CL656 ("Py-OVA exoVACC") was administered to mice via intranasal administration. At day 7 post immunization, some of the animals were sacrificed and the frequency of OVA-specific CD8+ T cells was assessed in the lung using flow cytometry. The remaining mice were instead boosted with a second administration of Py-OVA exoVACC. These animals were sacrificed a week later (i.e., day 14 post initial immunization) and the frequency of OVA-specific CD8+ T cells was assessed in the lung using flow cytometry. At both time points, OVA-specific CD8+ T cells were further categorized as effector memory (CD44+ and CD62L−) or resident memory (CD44+, CD62L−, and CD103+) T cells.

Figure 10:
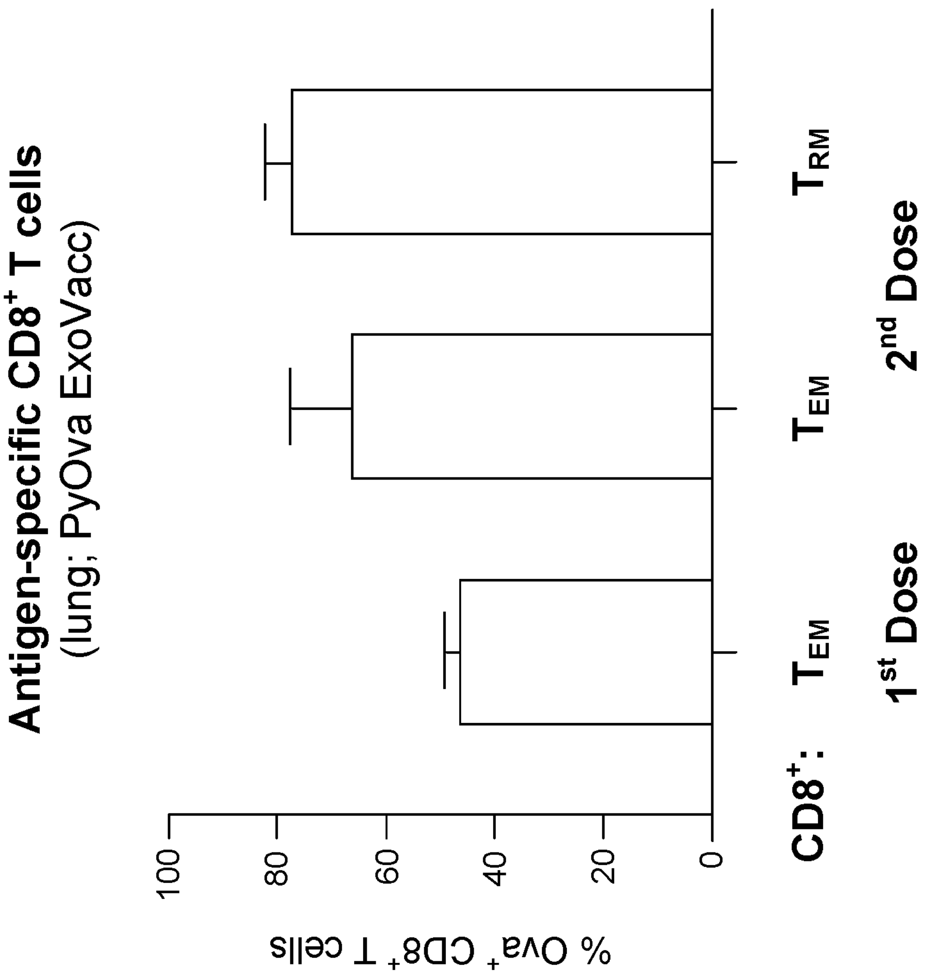
FIG. 10 shows the number of OVA-specific CD8+ T cells in the lung of mice treated with an exosome disclosed herein (e.g., expressing OVA-Scaffold Y and loaded with the STING agonist CL656). "1$^{st}$ Dose" represents the number of effector memory ($T_{EM}$) CD8+ T cells observed after a single administration of the exosome. "2$^{nd}$ Dose" represents the number of effector memory and/or resident memory ($T_{RM}$) CD8+ T cells observed after a boost with a second administration.

As shown in FIG. 10, after a single intranasal administration of Py-OVA exoVACC, robust OVA-specific effector memory CD8+ T cells were observed in the lungs of the treated animals. After a boost, the number of OVA-specific CD8+ T cells increased further, resulting in robust effector and memory CD8+ T cells.

To assess whether the EVs (e.g., exosomes) disclosed herein can also mount a robust resident memory CD4+ T cells, mice were administered via intranasal administration one of the following: (i) soluble OVA ("OVA"), (ii) exosome expressing only OVA-Scaffold Y fusion protein ("PyOVA"), (iii) exosome expressing OVA-Scaffold Y and loaded with the STING agonist CL656 ("Py-OVA exoVACC"), (iv) soluble OVA+soluble poly I:C ("OVA+poly I:C"), and (v) exosome expressing only OVA-Scaffold Y fusion protein+soluble poly I:C ("PyOVA+poly I:C"). At day 7 post initial immunization, the animals received a second administration of the same treatment. Animals were then sacrificed a week later (i.e., day 14 post initial immunization) and the frequency of OVA-specific CD8+ T cells was assessed in the lung using flow cytometry.

Figure 13B:
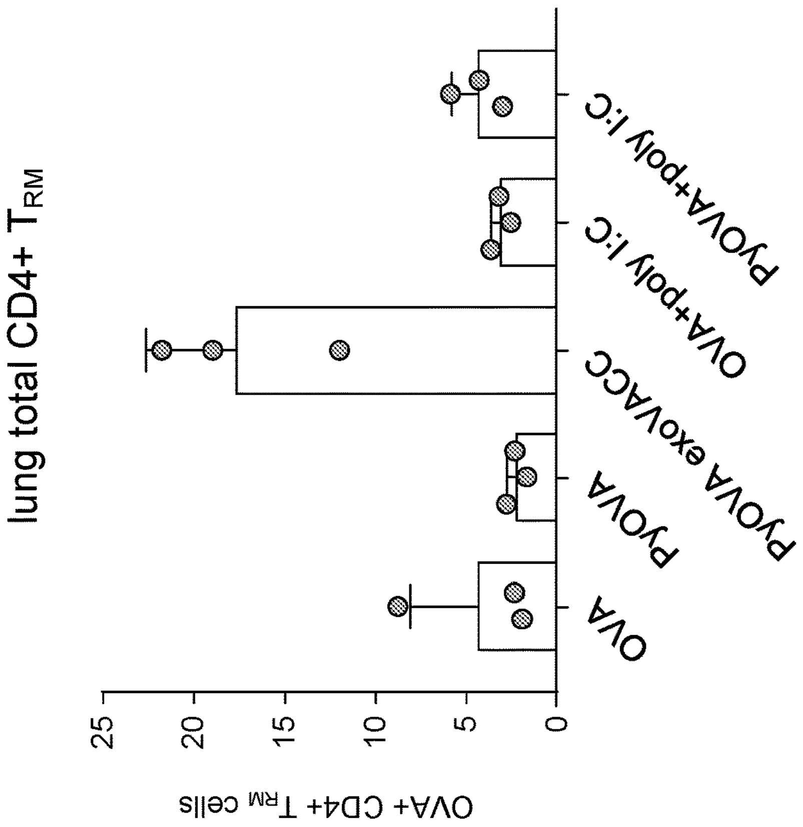
FIGS. 13A, 13B, and 13C show the induction of OVA-specific resident memory ($T_{RM}$) CD8+ T cells (FIG. 13A) and CD4+ T cells (FIG. 13B) in the lungs of mice that received two administrations of an exosome expressing OVA-Scaffold Y and loaded with the STING agonist CL656 ("Py-OVA exoVACC"). Control animals received one of the following: (i) soluble OVA ("OVA"), (ii) exosome expressing only OVA-Scaffold Y fusion protein ("PyOVA"), (iii) soluble OVA+soluble poly I:C ("OVA+poly I:C"), and (iv) exosome expressing only OVA-Scaffold Y fusion protein+soluble poly I:C ("PyOVA+poly I:C").
Figure 13A:
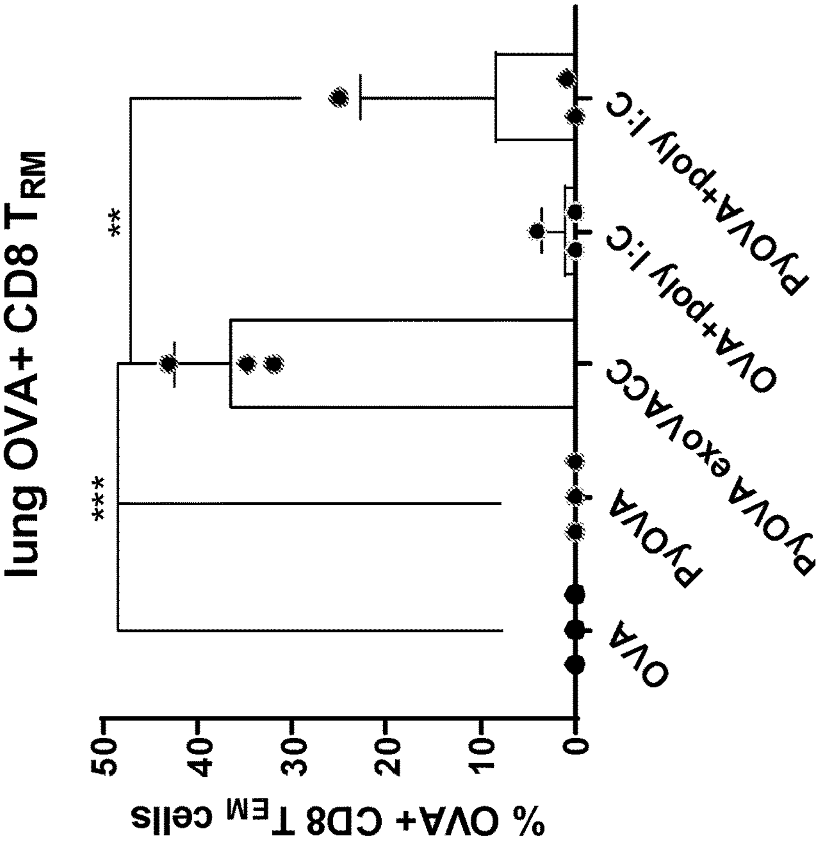
Figure 13C:
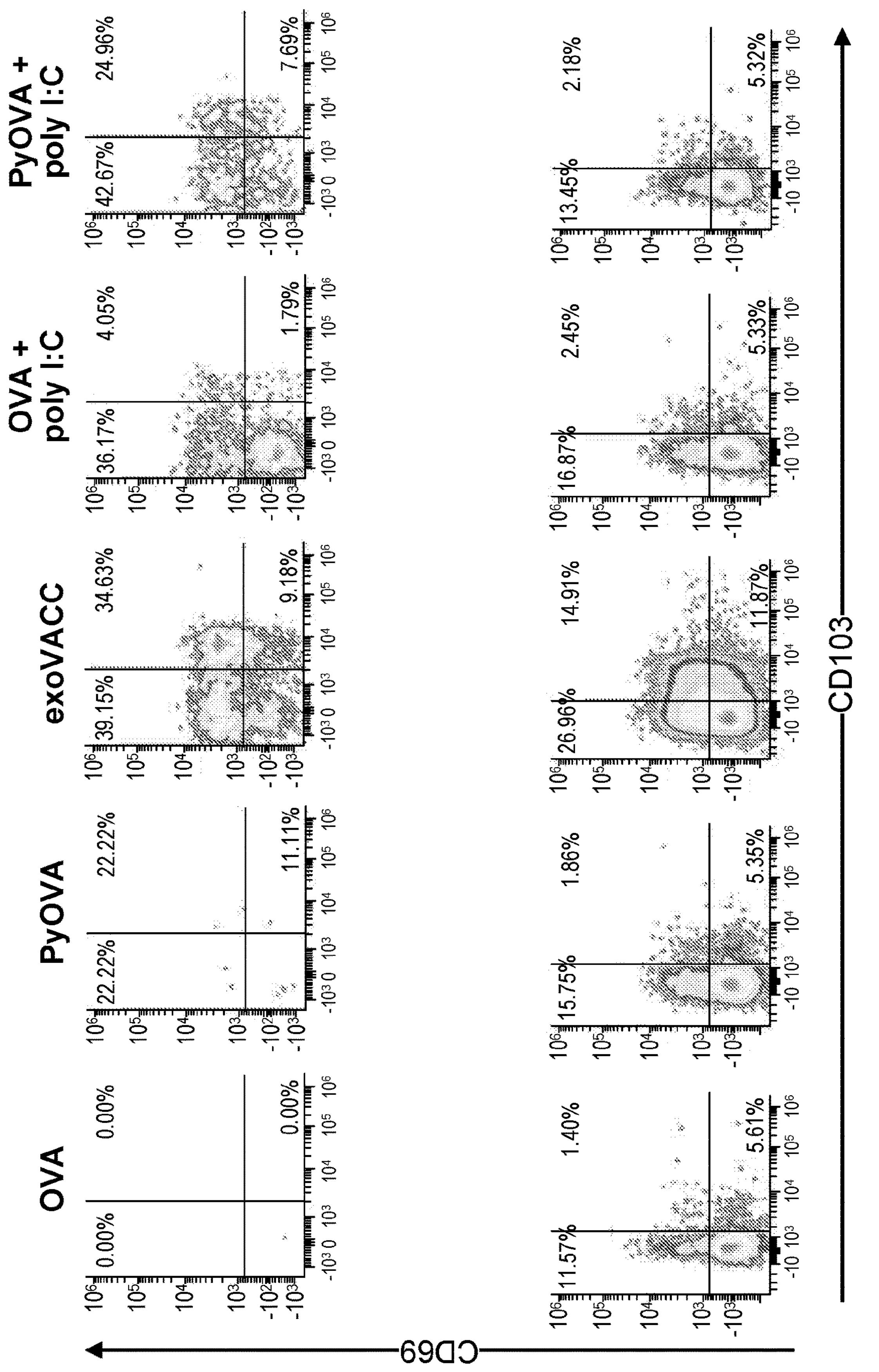

In agreement with the above results, animals that were treated with Py-OVA exoVACC exhibited robust resident memory CD8+ T cells within the lung (FIGS. 13A, 13B, and 13C). Similar results were observed for resident memory CD4+ T cells.

Collectively, the above data further demonstrate the effectiveness of the exosomes disclosed herein (e.g., engineered-exosome expressing OVA-Scaffold Y and loaded with the STING agonist CL656) to induce robust effector and memory T cells (both CD8+ and CD4+), including in mucosal tissues (e.g., lung).

Example 17: Analysis of the Tropism of Anti-Clec9a Expressing EVs (e.g., Exosomes)

Further to Example 13 described above, EVs (e.g., exosomes) were engineered to express an anti-Clec9a antibody fragment linked to a Scaffold X protein on their surface ("anti-Clec9a EV"). As in the earlier Examples, the anti-Clec9a EVs were loaded with the STING agonist CL656.

Figure 11A:
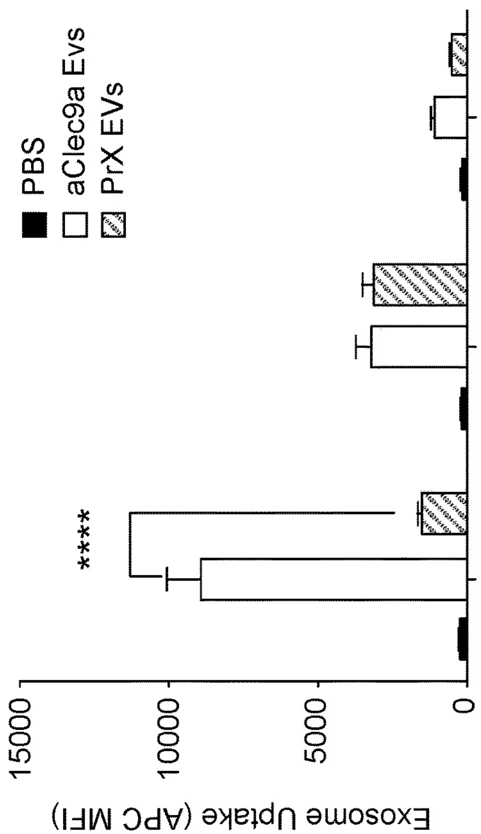
FIGS. 11A and 11B show the effect of expressing anti-Clec9a binding moiety in an EV (e.g., exosome) disclosed herein.

The anti-Clec9a EVs were administered to mice and their cell-specific tropism was assessed. Control animals received either PBS alone ("PBS") or an exosome expressing Scaffold X protein alone ("PrX EVs"). As shown in FIG. 11A, there was a preferential uptake of the anti-Clec9a EVs by the conventional dendritic cell 1 ("cDC1") population within the spleen. Among the other dendritic cells analyzed (i.e., conventional DC 2 ("cDC2") and plasmacyotid DC ("pDC")), there was no noticeable difference in the uptake of the anti-Clec9a EV compared to the control exosome (PrX EVs).

Figure 11B:
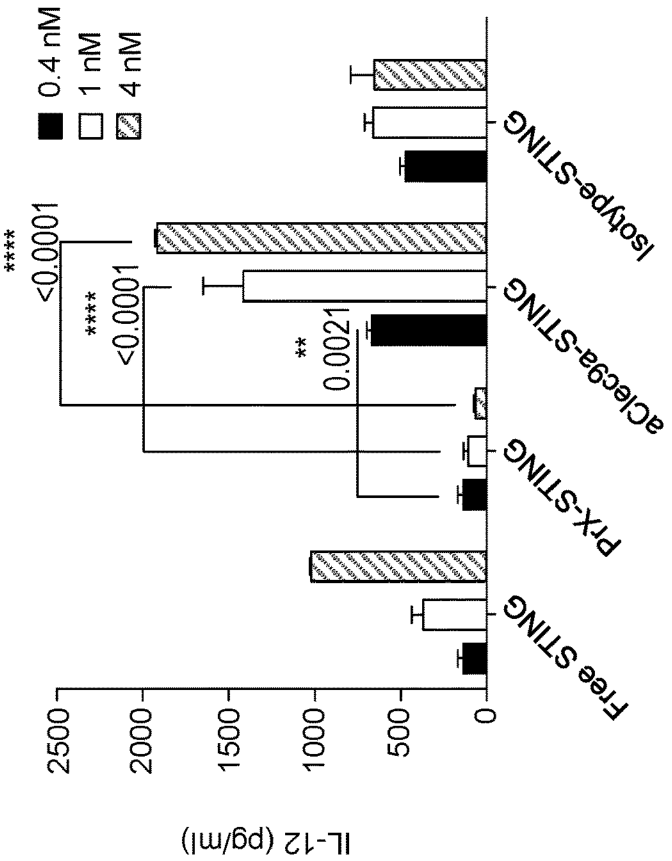

Next, to further assess the effect of the enhanced tropism of the anti-Clec9a EVs to cDC1, splenic dendritic cells (isolated from wild-type mice) were stimulated in vitro with anti-Clec9a EVs, and STING activity within the DCs was assessed. The DCs were stimulated with varying concentrations of the anti-Clec9a EVs (i.e., 0.4 nM, 1 nM, or 4 nM). DCs in the control groups were stimulated with one of the following: (i) soluble STING agonist ("free STING"), (ii) EVs (e.g., exosomes) expressing Scaffold X protein alone (i.e., no anti-Clec9a antibody fragment) and loaded with the STING agonist ("PrX-STING"), and (iii) EVs (e.g., exosomes) expressing a non-relevant antibody and loaded with the STING agonist ("Isotype-STING"). STING activity was assessed by measuring the amount of IL-12 produced by the different DCs. As shown in FIG. 11B, isolated DCs treated with anti-Clec9a EV produced much greater amount of IL-12 compared to the other groups, including DCs treated with PrX-STING.

The above results demonstrate that EVs (e.g., exosomes) expressing anti-Clec9a targeting moieties can preferentially target Clec9a-expressing cells, such as cDC1, and that this enhanced tropism can help increase dendritic cell activation. Such abilities can be useful in the context of vaccination, as described in the present disclosure.

Example 18: Effect of Route of Administration on Inducing Immune Response

Further to Example 6 provided above, the effect of administration route on the ability of the EVs (e.g., exosomes) disclosed herein to induce an immune response was further assessed. Briefly, an engineered-exosome expressing OVA-Scaffold Y and loaded with the STING agonist CL656 ("Py-OVA exoVACC") (1 μg OVA) was administered to mice via one of the following administration routes: (i) intravenous ("IV"), (ii) intranasal ("IN"), and (iii) subcutaneous ("SQ"). As a comparison, some of the mice received a subcutaneous administration of soluble OVA in a commercially available formulation (ADDAVAX™, InvioGen) ("SubQ AV"). At day 7 post immunization, all the animals were sacrificed, splenocytes isolated, and the frequency of OVA-specific effector memory CD8+ T cells (CD44+ and CD62L−) was assessed via flow cytometry.

Figure 12A:
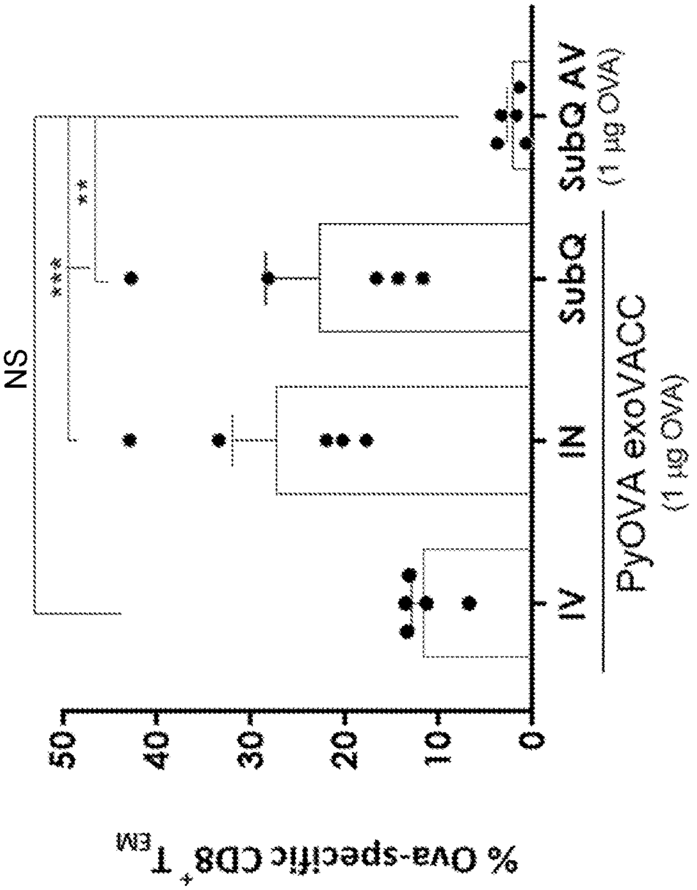
FIGS. 12A and 12B show the effect of administration route on the induction of OVA-specific CD8$^{+}$ $T_{EM}$ cells by an engineered-exosome expressing OVA-Scaffold Y and loaded with the STING agonist CL656 ("Py-OVA exoVACC"). The administration routes shown include: (i) intravenous ("IV"), (ii) intranasal ("IN"), and (iii) subcutaneous ("SQ"). "SubQ AV" corresponds to animals treated with soluble OVA in a commercially available formulation (ADDAVAX™, InvioGen) ("SubQ AV").
Figure 12B:
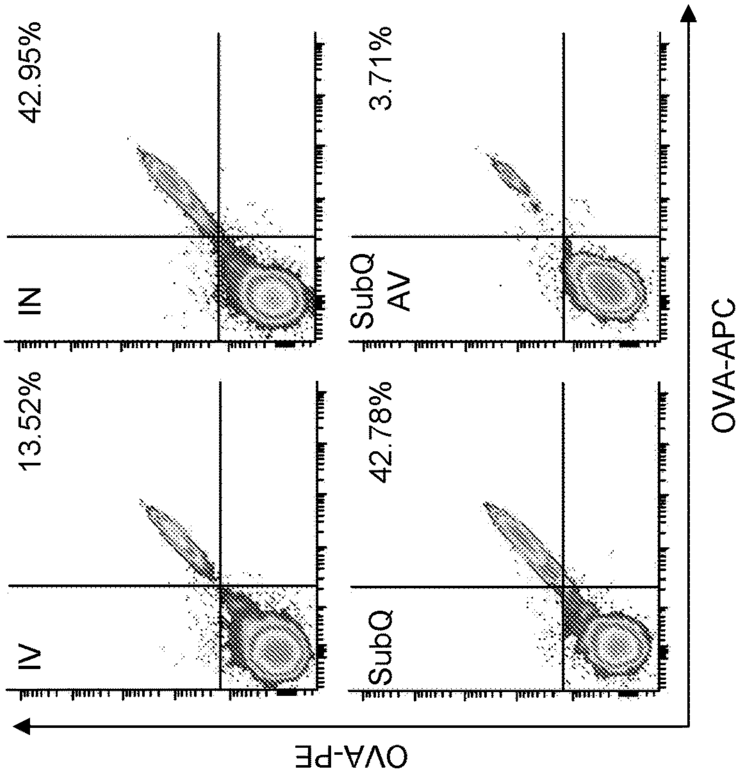

As shown in FIGS. 12A and 12B, regardless of the administration route, Py-OVA exoVACC was able to induce robust OVA-specific effector memory CD8+ T cells in the animals, particularly when compared to OVA delivered using the commercially available formulation. These results further confirm the efficacy of EVs (e.g., exosomes) disclosed herein and demonstrate that the EVs could be used to induce robust immune response regardless of the route of administration.

Example 19: Anti-Tumor Effects of Py-OVA exoVACC EVs (e.g., Exosomes)

Further to Example 11 provided above, the ability of the EVs (e.g., exosomes) disclosed herein to induce an anti-tumor immune response was assessed in a mouse model. Briefly, mice were treated with one of the following: (i) exosome expressing OVA-Scaffold Y and loaded with the STING agonist CL656 ("Py-OVA exoVACC") via intranasal administration ("exoVACC (IN)"), (ii) exosome expressing OVA-Scaffold Y and loaded with the STING agonist CL656 (Py-OVA exoVACC) via subcutaneous administration ("exoVACC (SQ)"), (iii) soluble OVA+soluble poly I:C via intranasal administration ("OVA+poly I:C (IN)"), and (iv) soluble OVA+soluble poly I:C via subcutaneous administration ("OVA+poly I:C (IN)"). See FIG. 14A. Untreated or PBS-only treated animals were used as controls. Then, at day 7 post immunization, EG7-OVA tumor cells were subcutaneously implanted into all the animals. Then, both tumor volume and survival of the animals were monitored over a course of at least 30 days.

Figure 14B:
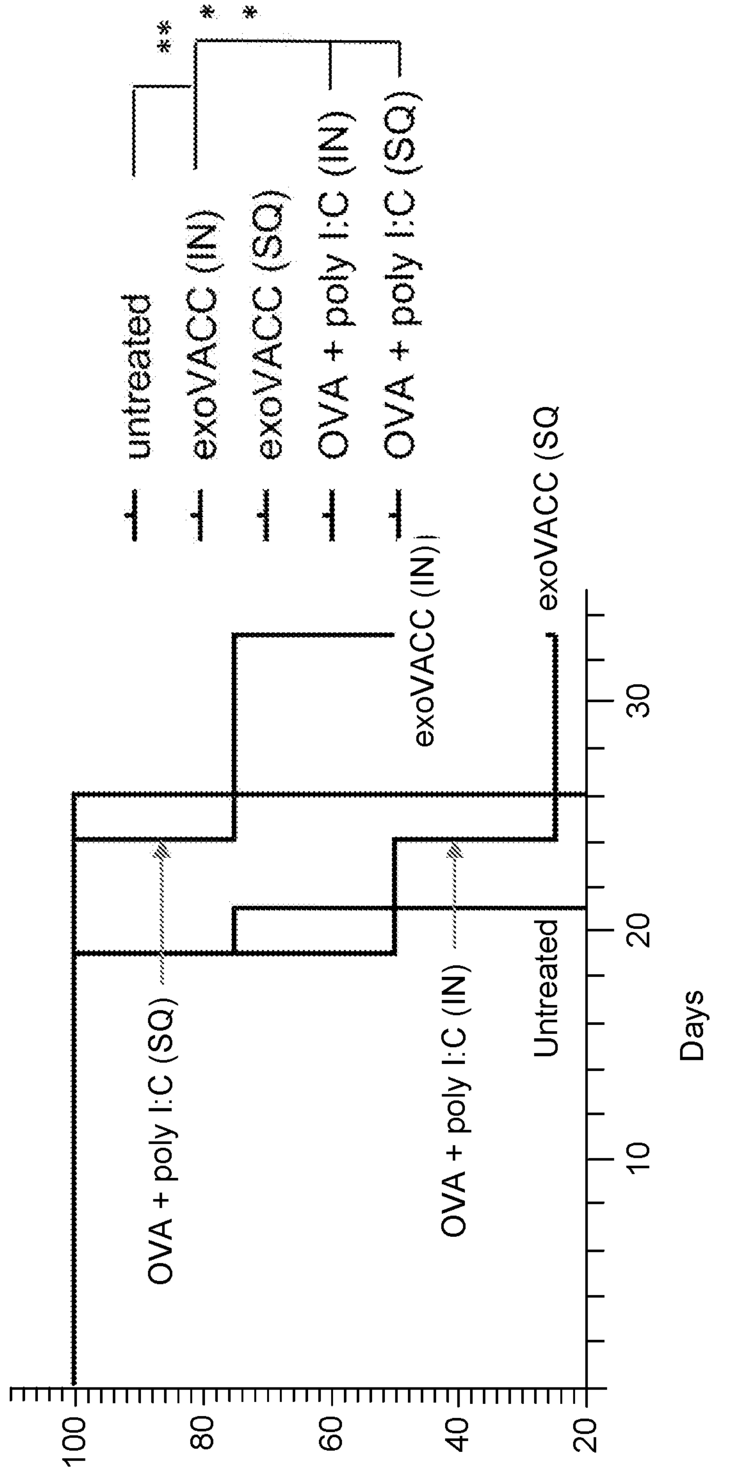
Figure 14C:
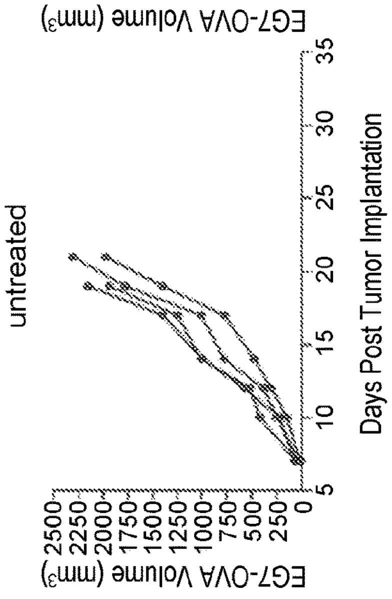
Figure 14D:
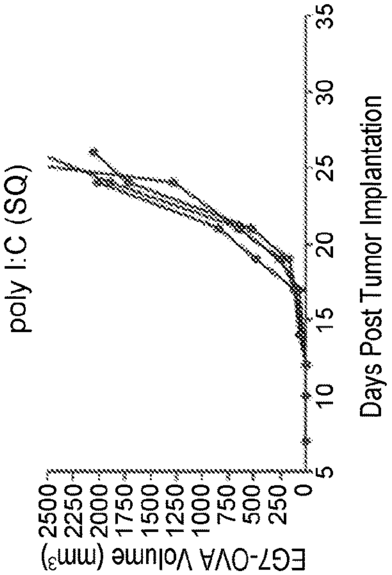
Figure 14E:
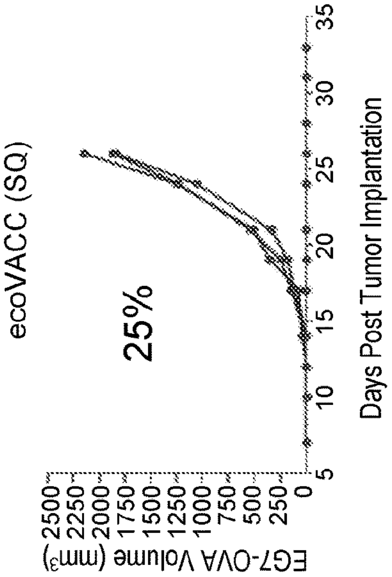
Figure 14F:
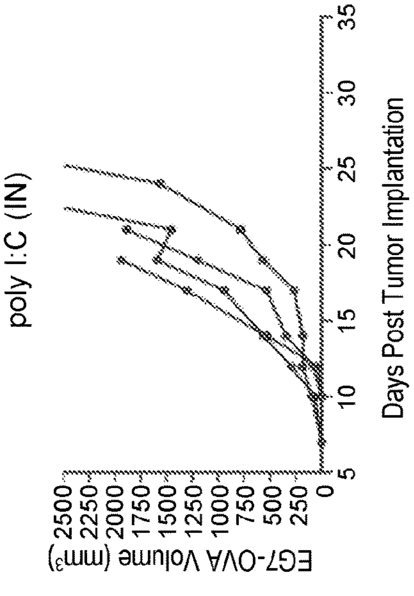
Figure 14G:
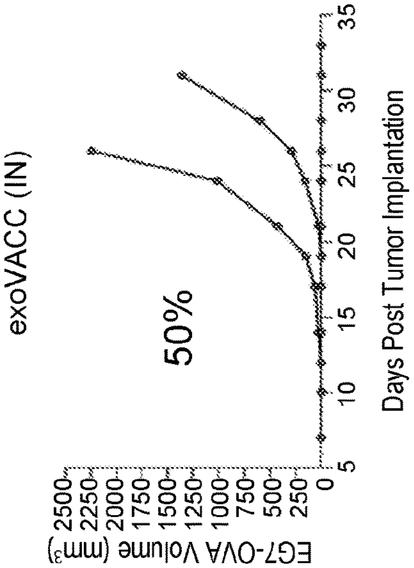
Figure 14H:
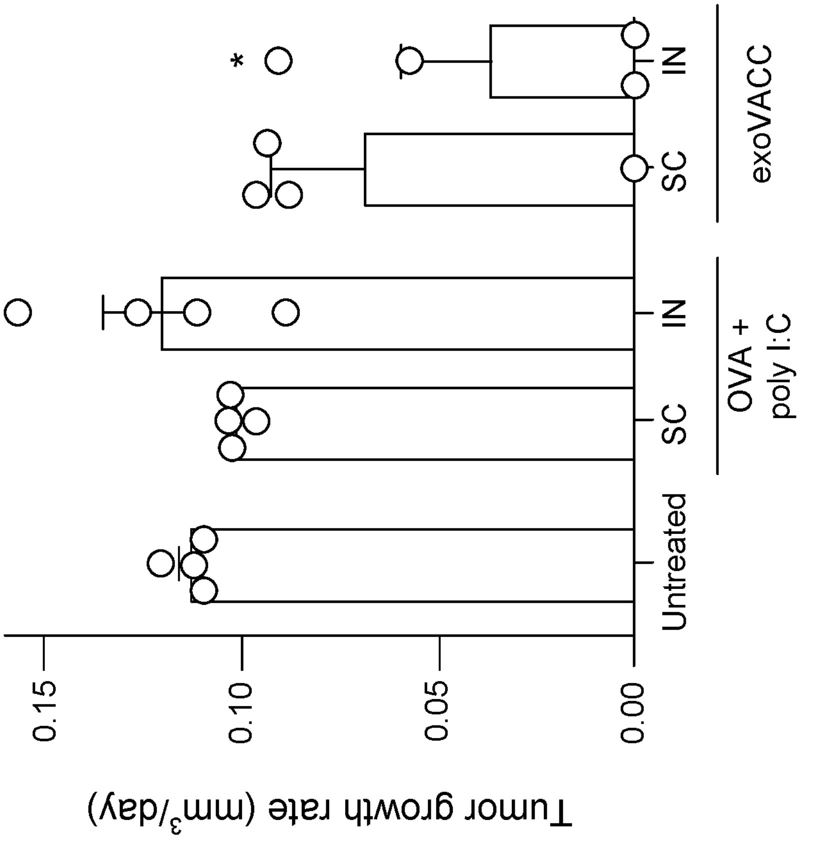
Figure 14I:
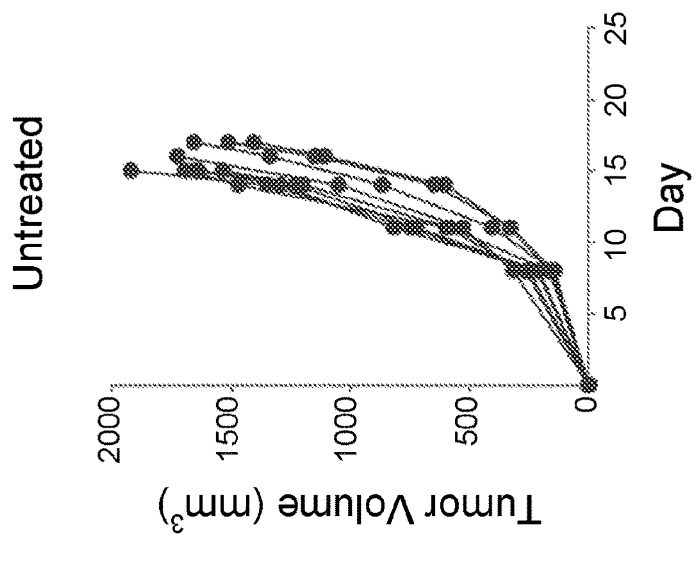
Figure 14J:
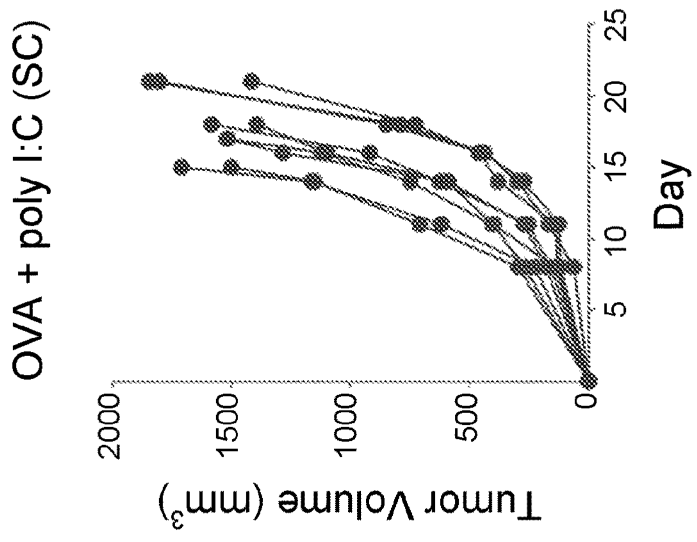
Figure 14K:
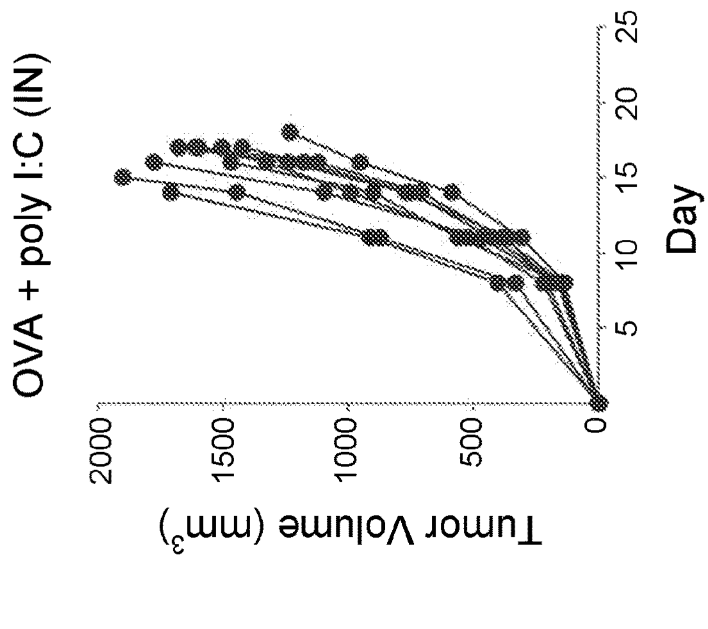
Figure 14M:
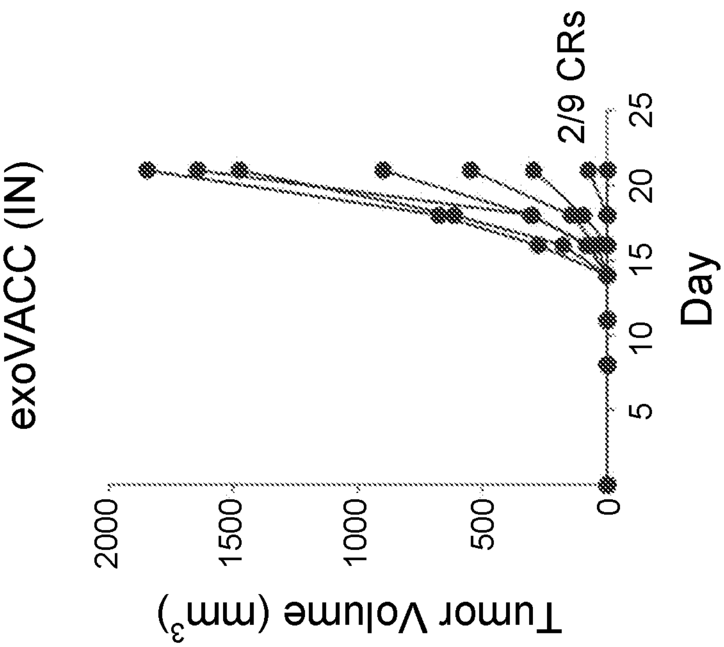
Figure 14L:
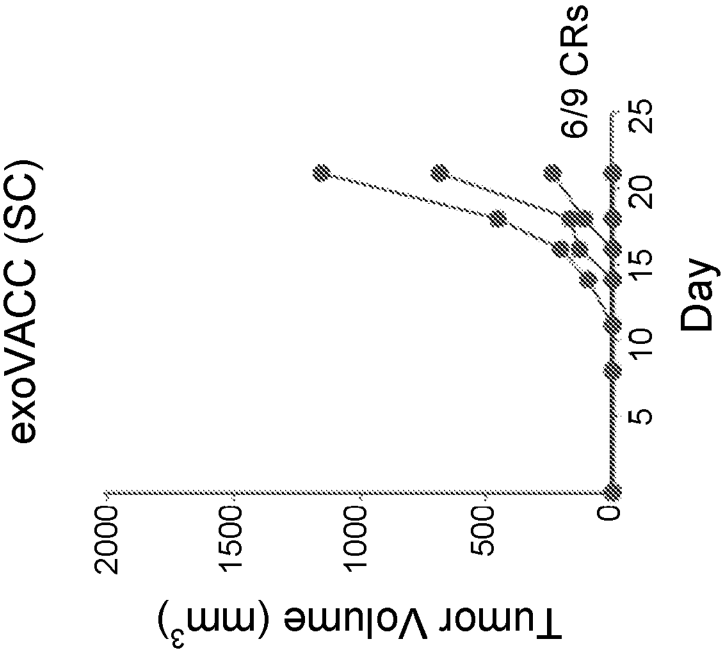
Figure 14N:
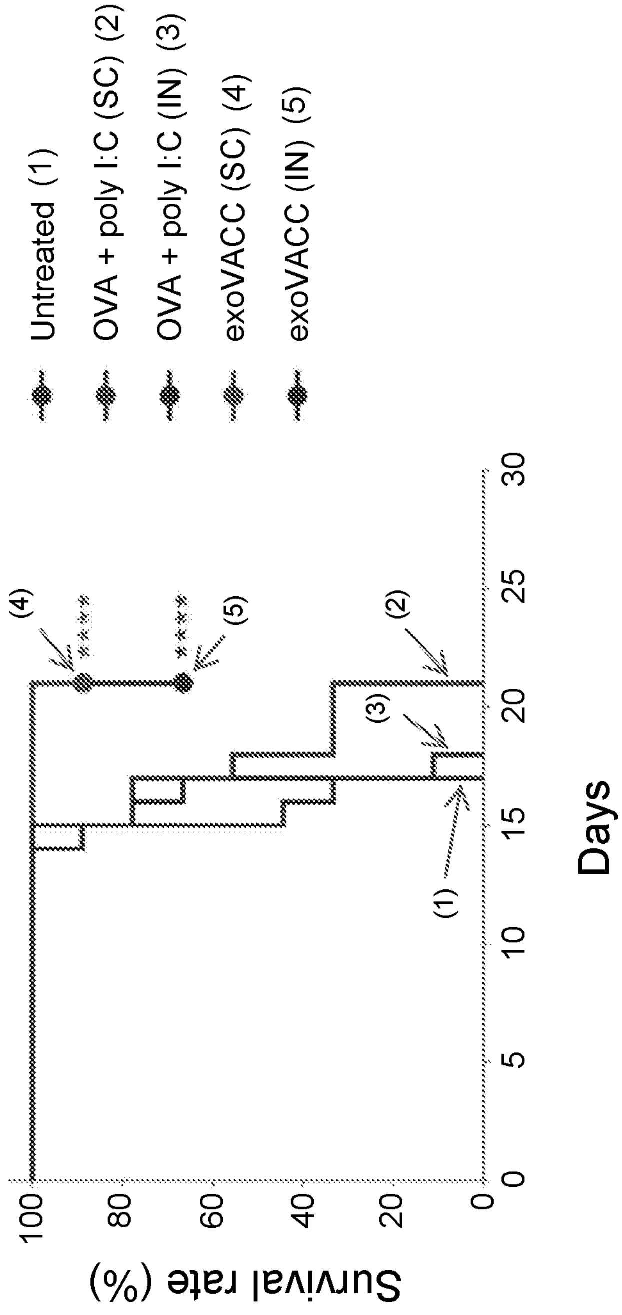

As shown in FIGS. 14B, 14C, 14D, and 14F, animals that were either untreated or treated with OVA+poly I:C (both intranasal and subcutaneous administration) failed to control the tumor and succumbed to the disease by about day 30 post tumor implantation. However, in animals that received an administration of exoVACC, improved anti-tumor immune response was observed. For the exoVACC (SQ) group, 25% of the animals effectively controlled the tumor and survived to the end of the experiment (FIGS. 14B and 14E). For the exoVACC (IN) group, 50% of the animals mounted an effective anti-tumor immune response against the EG7-tumor cells (FIGS. 14B and 14G). As shown in FIG. 14H, the improved anti-tumor immune response correlated with a decrease in the rate of tumor growth. In a separate independent experiment, greater percentage of animals from both the exoVACC (SQ) group and the exoVACC (IN) group controlled tumor growth and survived the entire duration of the experiment (see FIGS. 14L, 14M, and 14N).

The above results demonstrate that the EVs (e.g., exosomes) disclosed herein could be used as a vaccine for the treatment of certain cancers.

Figure 15F:
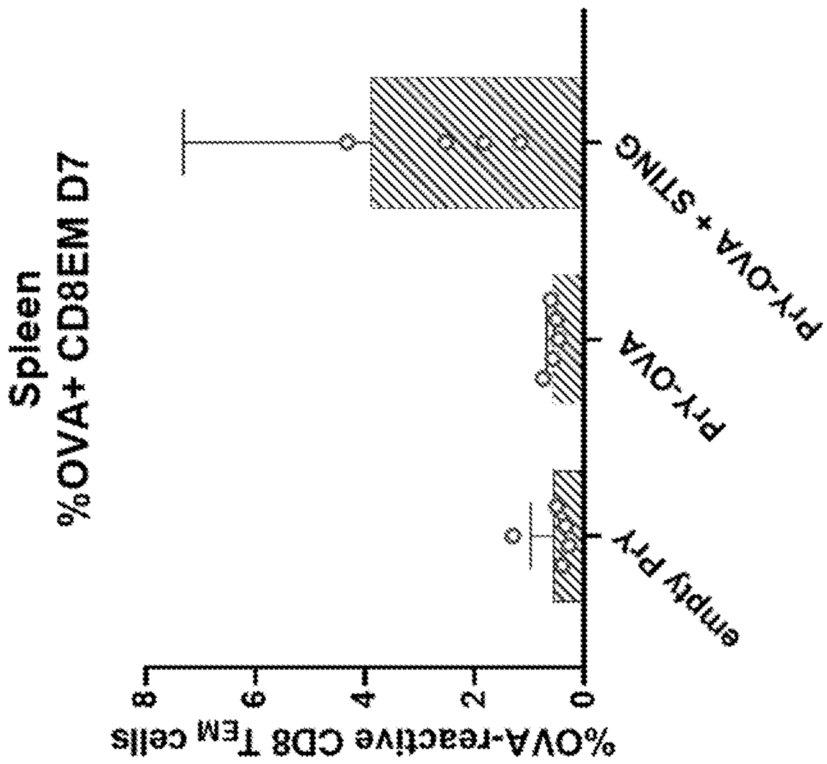
Figure 15E:
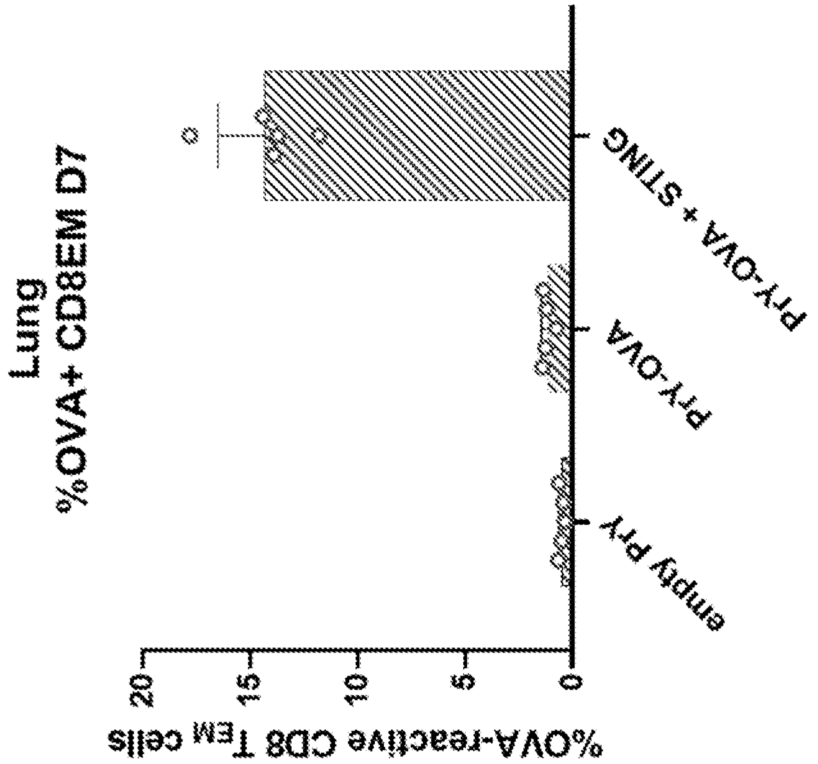

Example 20: Ability of Py-OVA exoVACC EVs (e.g., Exosomes) to Induce Antigen-Specific T Cells in Mesenteric Lymph Nodes after Intranasal Administration To further assess the ability of the EVs (e.g., exosomes) disclosed herein to induce a mucosal immune response, the frequency of antigen-specific T cells in mesenteric lymph nodes (i.e., gut draining lymph nodes) was assessed after intranasal administration of Py-OVA exoVACC (i.e., engineered-exosome expressing OVA-Scaffold Y and loaded with the STING agonist CL656) (see "Group 5" in FIG. 15A). The control animals received one of the following: (i) empty (i.e., no OVA antigen) exosome expressing Scaffold Y alone ("Group 1"); (ii) soluble OVA ("Group 2"); (iii) soluble OVA+soluble STING agonist ("Group 3"); or (iv) exosome expressing only OVA-Scaffold Y fusion protein ("Group 4"). At day 7 post-vaccination, the animals were sacrificed and the frequency of OVA-specific CD8+ T cells was assessed using both IFN-γ ELISPOT and/or flow cytometry.

As shown in FIGS. 15B, 15C, 15E, and 15F (and in agreement with the earlier results—see, e.g., Example 2), animals that received an intranasal administration of the Py-OVA exoVACC had significantly greater number of OVA-specific CD4+ and OVA-specific CD8+ T cells in both the spleen and the lung, compared to the control animals (e.g., Group 1 and Group 4). In the mesenteric lymph nodes, no significant differences were observed for CD4+ T cells among the different treatment groups (see FIG. 15D, left bar in each of the groups). However, a significant increase in the number of OVA-specific CD8+ T cells was observed in the mesenteric lymph nodes of animals treated with Py-OVA exoVACC (see FIG. 15D, right bar in each of the groups). These results confirm that the EVs (e.g., exosomes) disclosed herein (e.g., comprising OVA-Scaffold Y and loaded with STING agonist) can be useful in inducing robust mucosal immune response when administered intranasally.

Example 21: Efficacy of Scaffold X-Engineered EVs (e.g., Exosomes) Comprising Antigen and STING Agonist in Inducing Antigen-Specific T Cell Responses To further assess the ability of the EVs (e.g., exosomes) disclosed herein to induce immune response, engineered EVs (e.g., exosomes) overexpressing Scaffold X ("Scaffold X-engineered EVs") were generated (see, e.g., Example 1). CD8 peptide (Lama4) and/or CD4 peptide (Itgb1) containing maleimide linker were cross-linked to the Scaffold X expressed on the surface of the engineered EVs. The CD8 peptide had the following structure: (maleimide linker)-QKISFFDGFE<u>V</u>GFNFRTLQPNGLLFYYT (SEQ ID NO: 379). The underlined amino acid indicates a mutation. The bolded residues represent the CD8+ T cell epitope. The CD4 peptide had the following structure: (maleimide linker)-WFYFTYSVNG<u>Y</u>NEAIVHVVETPD (SEQ ID NO: 380). The underlined amino acid indicates a mutation. The CD4+ T cell epitope was unknown. The Scaffold X-engineered EVs were further loaded with a STING agonist (CL656). The Scaffold X-engineered EVs were then administered to mice as shown in FIG. 16A. Briefly, the animals received one of the following: (i) PBS alone (i.e., no EV) (Group 1); (ii) Scaffold X-engineered EVs expressing the CD8 peptide (Lama4) alone (Group 2); (iii) Scaffold X-engineered EVs expressing the CD4 peptide (Itgb1) alone (Group 3); and (iv) Scaffold X-engineered EVs expressing both the CD4 peptide and the CD8 peptide. The Scaffold X-engineered EVs were administered to the animals via subcutaneous administration at a dose that would result in the animals receiving the same amount of STING agonist. Each of the animals received total of two doses (one week between doses) of the relevant treatment regimen. At day 7 post the second administration, the animals were sacrificed and the frequency of antigen-specific CD4+ and CD8+ T cells in the spleen was assessed using IFN-γ ELISPOT.

Figure 16B:
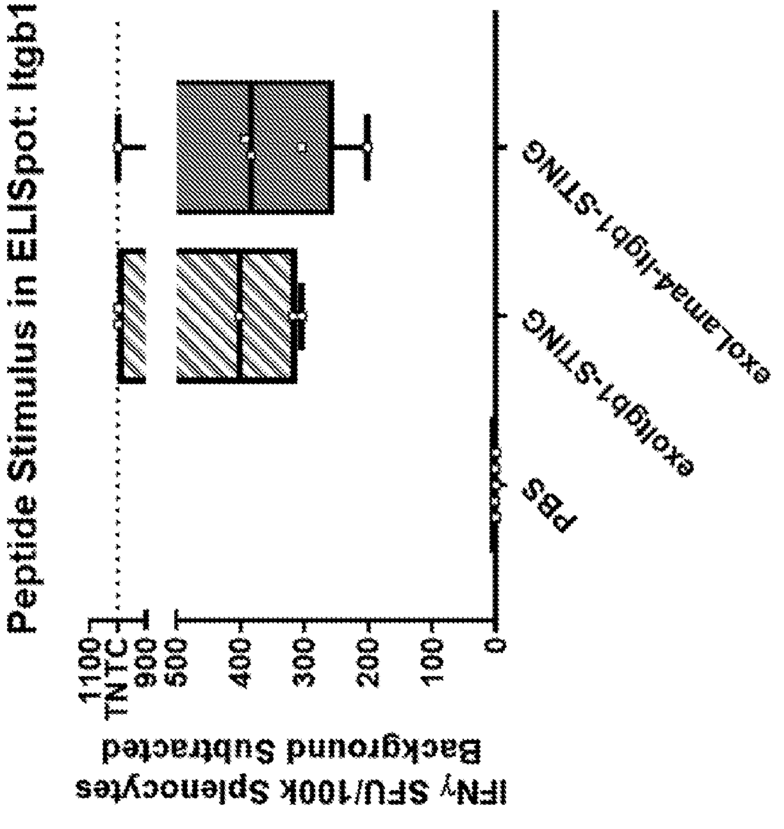
Figure 16C:
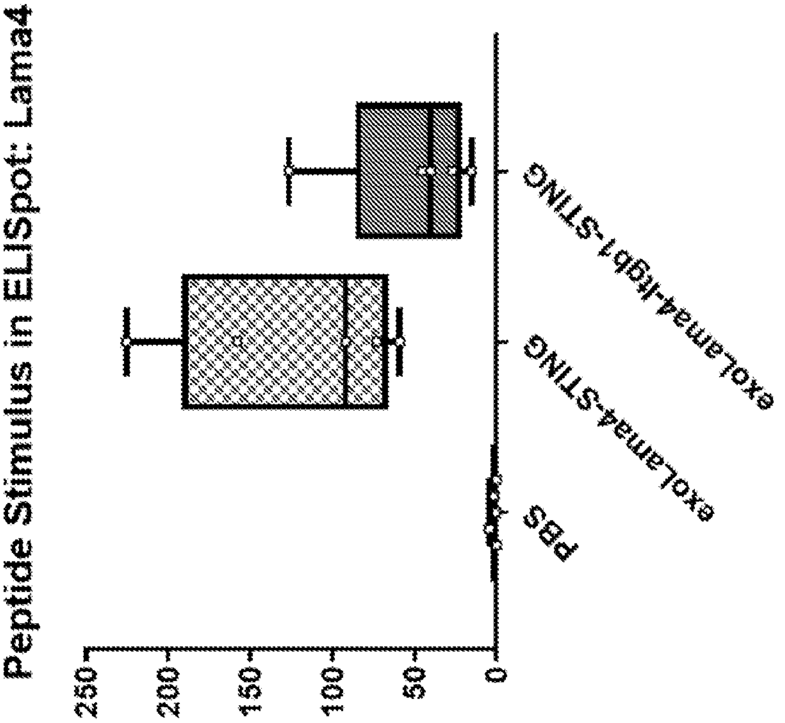
Figure 18B:
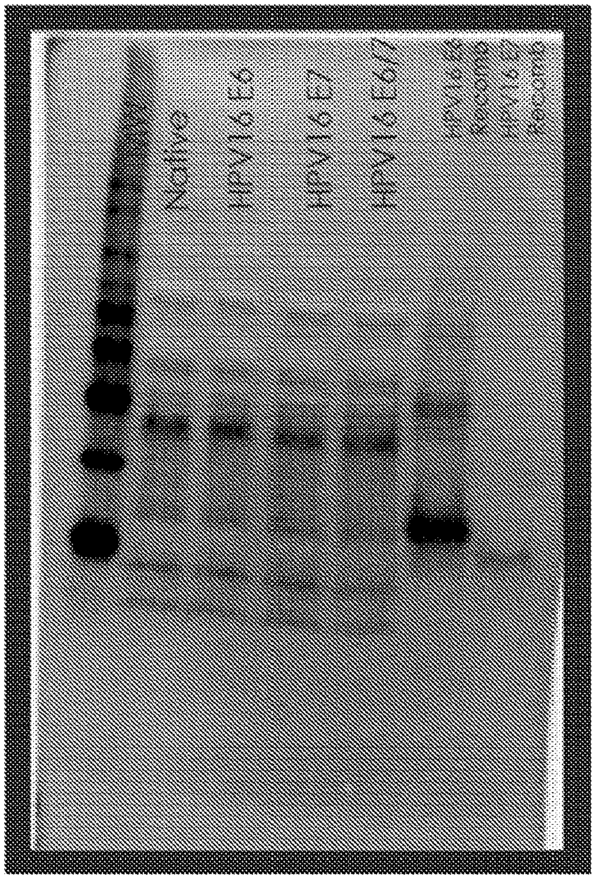
FIGS. 18A, 18B, 18C, 18D, 18E, 18F, 18G, 18H, 18I, 18J, 18K, and 18L show the expression of E6 and E7 proteins of HPV16 and HPV18 in the surface-engineered EVs (e.g., exosomes) disclosed herein, as measured by Western Blot.
Figure 18A:
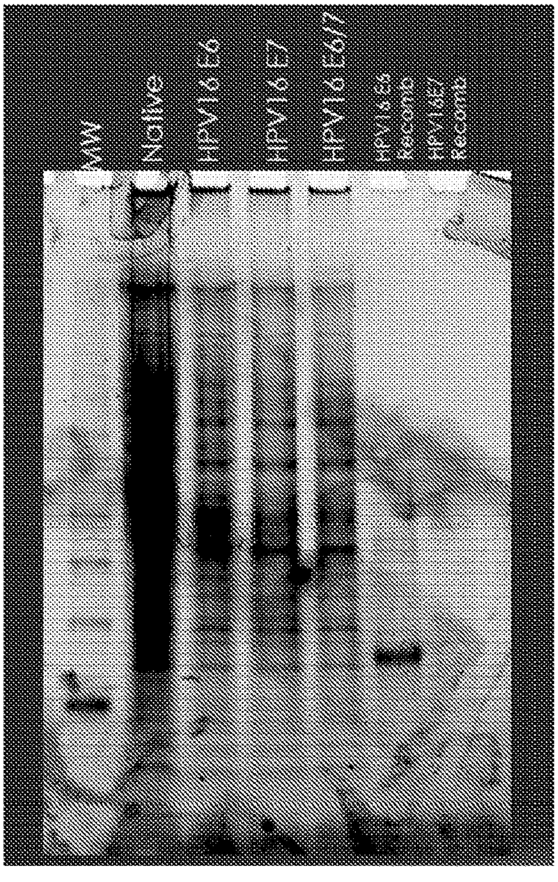
Figure 18D:
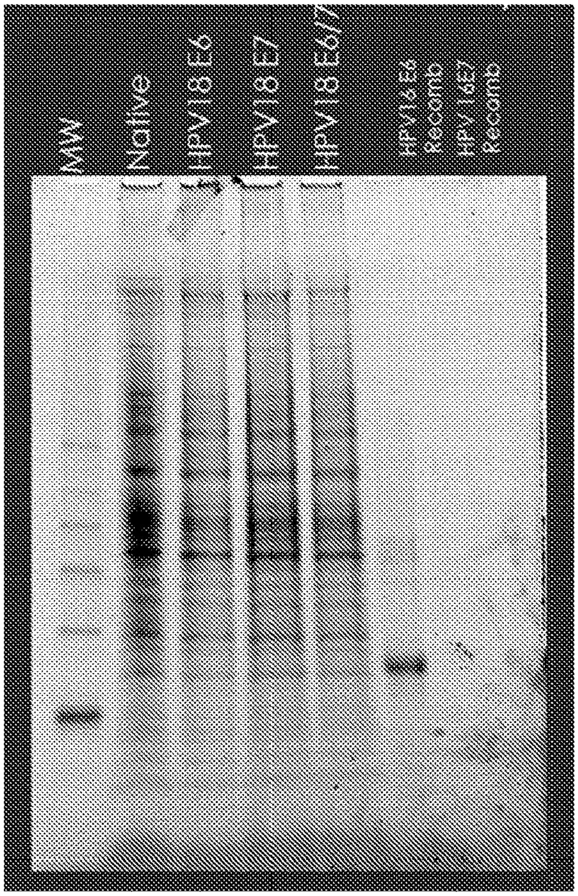
Figure 18C:
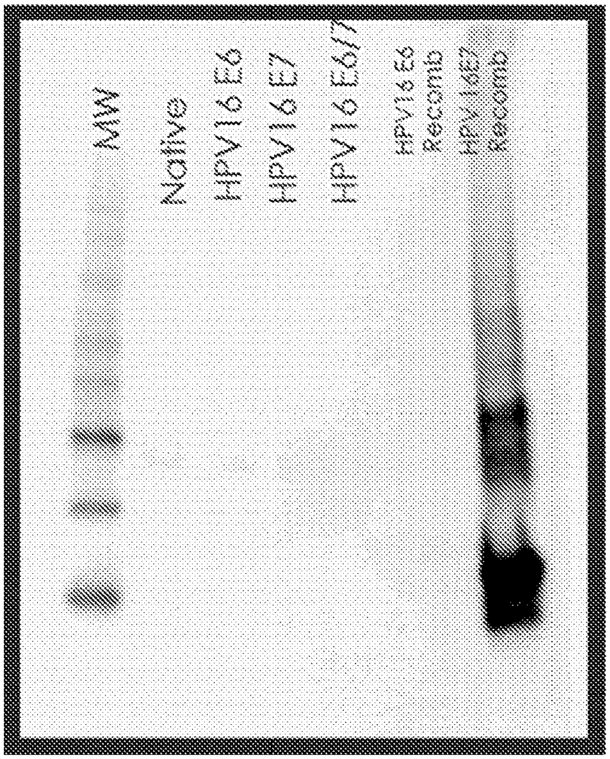
Figure 18E:
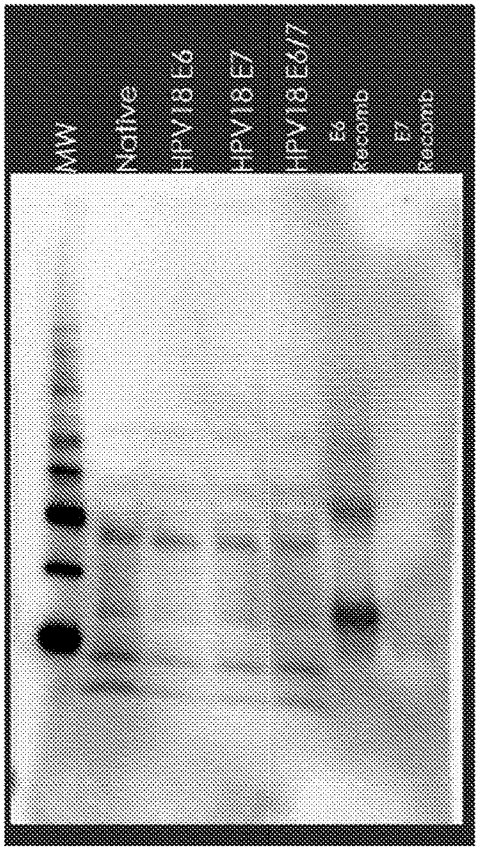
Figure 18F:
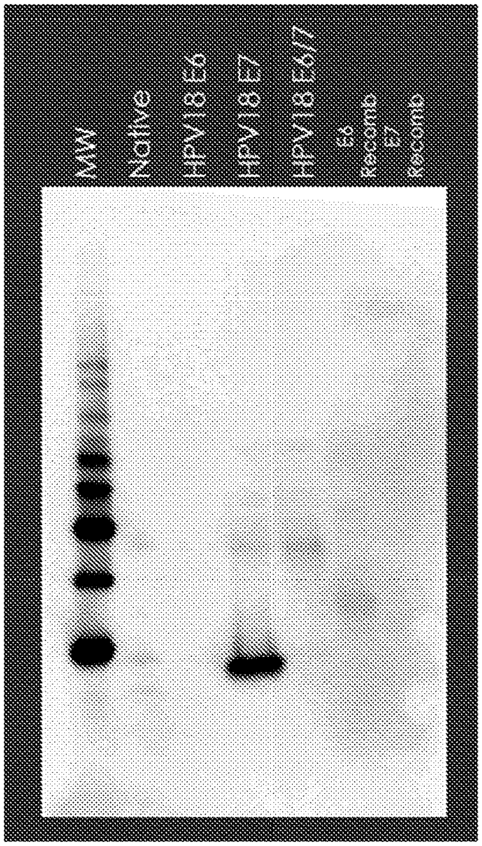
Figure 18H:
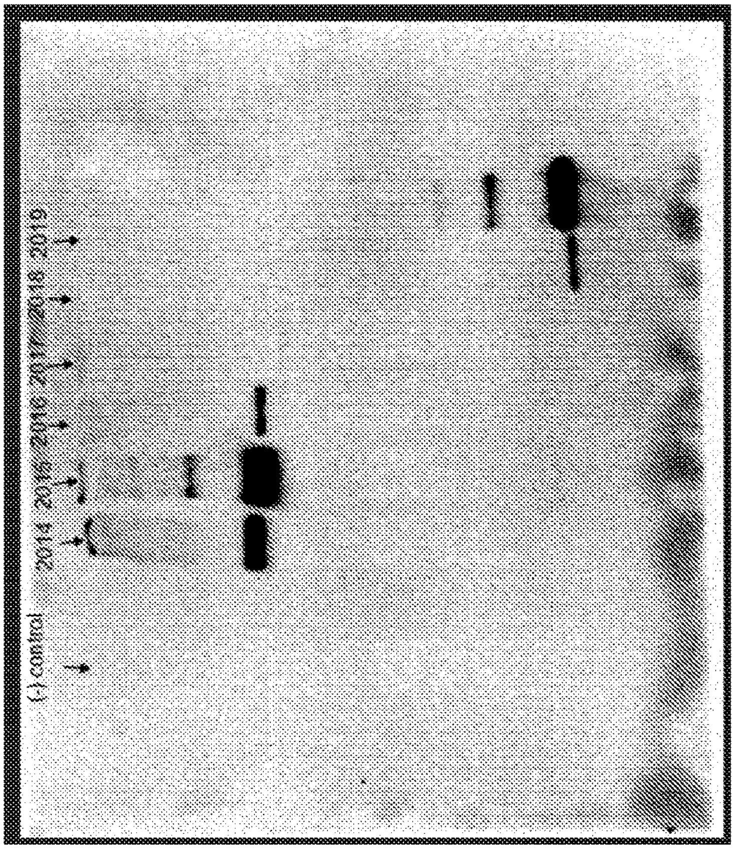
Figure 18G:
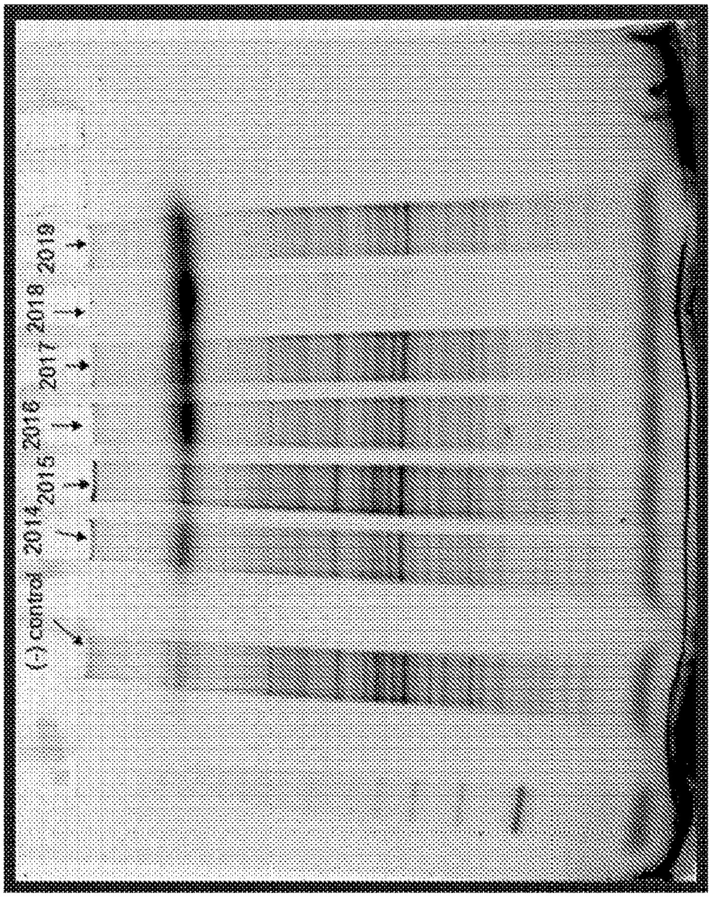
Figure 18J:
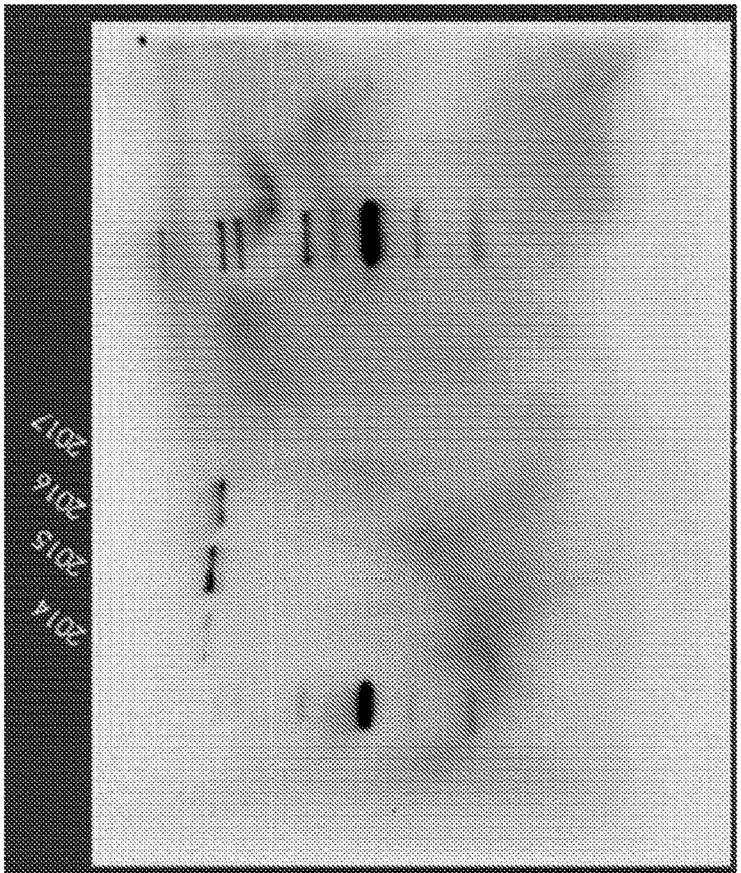
Figure 18I:
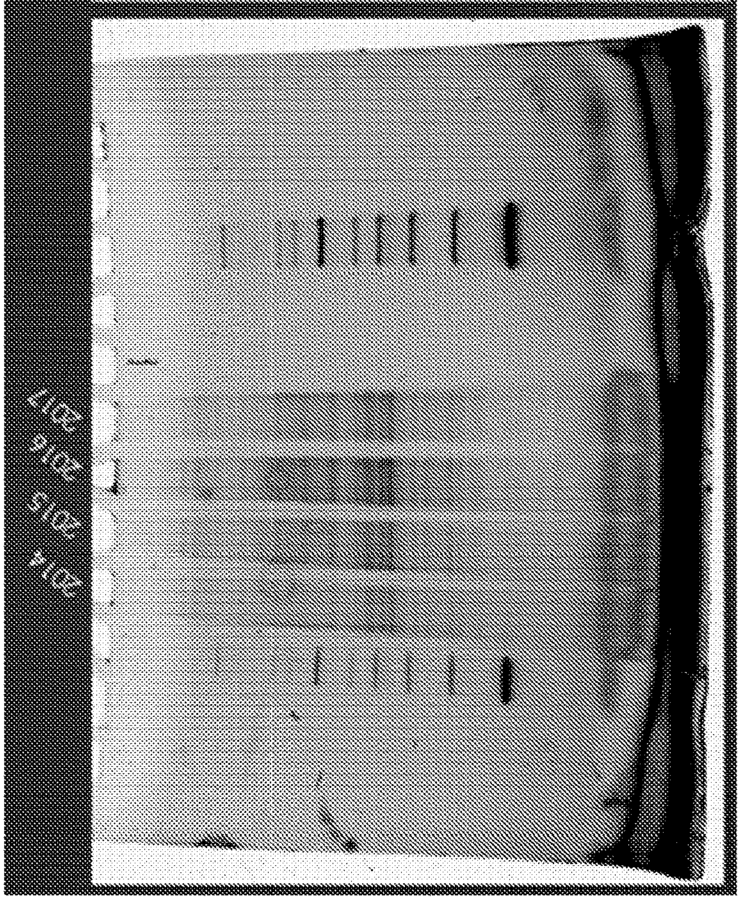
Figure 18L:
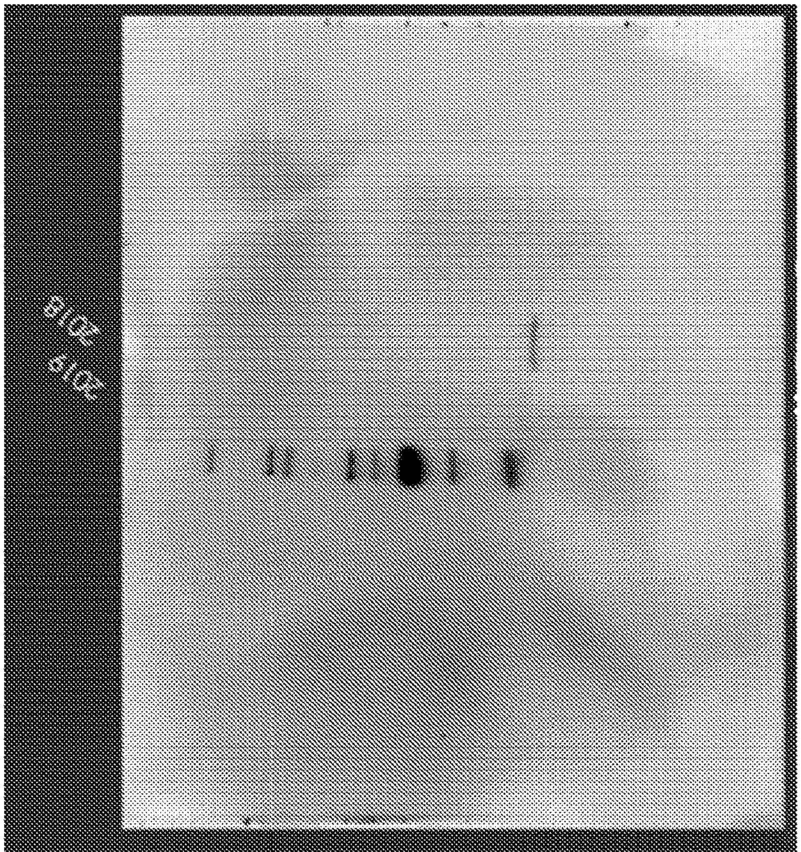
Figure 18K:
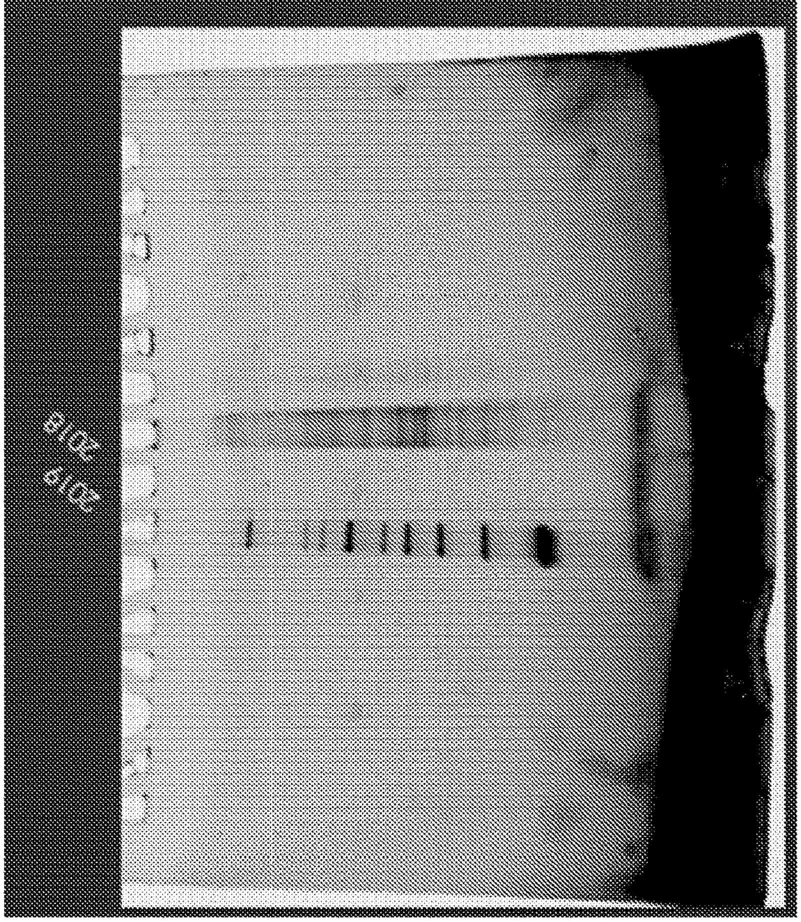

As shown in FIGS. 16B and 16C, robust Itgb1-specific CD8+ T cells and Lama4-specific CD4+ T cells were detected in animals from Group 2 (i.e., received Scaffold X-engineered EVs expressing the CD8 peptide alone) and Group 3 (i.e., received Scaffold X-engineered EVs expressing the CD4 peptide alone), respectively. Similarly, administering the Scaffold X-engineered EVs expressing both the CD4 peptide and the CD8 peptide to the animals resulted in strong antigen-specific CD8+ T cell and CD4+ T cell immune responses.

The results further confirm that the EVs (e.g., exosomes) disclosed herein can be used to induce robust immune responses against antigens of interest (e.g., tumor). The results also demonstrate the ability of the EVs (e.g., exosomes) disclosed herein to induce immune responses to multiple antigens, e.g., by expressing multiple antigens on the EVs.

Example 22: Efficacy of Scaffold X-Engineered EVs (e.g., Exosomes) Comprising Antigen and CpG Adjuvant in Inducing Antigen-Specific T Cell Responses To further assess the vaccine capabilities of the EVs (e.g., exosomes) disclosed herein, engineered EVs (e.g., exosomes) overexpressing Scaffold X ("Scaffold X-engineered EVs") were again generated (see, e.g., Example 1). CD8 peptide (Lama4) and/or CD4 peptide (Itgb1) containing maleimide linker were again cross-linked to the Scaffold X expressed on the surface of the engineered EVs as described in Example 21. In the current Example, the Scaffold X-engineered EVs were further loaded with CpG (i.e., a TLR9 agonist) instead of STING agonist. The Scaffold X-engineered EVs were then administered to mice as shown in FIG. 17A. Briefly, the animals received one of the following: (i) control EV (i.e., EV expressing Scaffold X alone) ("Empty PrX exos") (Group 1); (ii) Scaffold X-engineered EVs expressing the CD8 peptide (Lama4) alone ("exo-Lama4-CpG") (Group 2); and (iii) Scaffold X-engineered EVs expressing both the CD8 peptide (Lama4) and the CD4 peptide (Itgb1) ("exoItgb1-Lama4-CpG") (Group 3). Each of the animals received two doses (one week between doses) of the relevant treatment regimen. And, at day 7 post second administration, the animals were sacrificed and the frequency of antigen-specific CD4+ and CD8+ T cells in the spleen was assessed using IFN-γ ELISPOT.

As shown in FIGS. 17B and 17C, treating the animals with the Scaffold X-engineered EVs expressing Lama4 alone ("exoLama4-CpG") resulted in the induction of a strong CD8+ T cell response specific for Lama4 (see FIG. FIG. 17C) but not to the Itgb1 peptide (see FIG. 17B). This result demonstrates the specificity of the CD8+ T cell response induced by the Scaffold X-engineered EVs. And, in agreement with the results provided in Example 21, Scaffold X-engineered EVs expressing both Lama4 and Itgb1 were able to induce robust T cell responses against both antigens. These results further suggest that the EVs (e.g., exosomes) disclosed herein could be useful in inducing immune responses against variety of antigens.

Example 23: Expression of HPV Antigens in Surface-Engineered EVs (e.g., Exosomes)

To further assess the ability to express different antigens in the EVs (e.g., exosomes) of the present disclosure, 293SF cells were transfected to express the E6 and/or E7 proteins of HPV16 or HPV18. Briefly, the cells were transfected with a plasmid encoding one of the following full length proteins: (i) HPV16 E6, (ii) HPV16 E7, (iii) HPV16 E6/E7, (iv) HPV18 E6, (v) HPV18 E7, and (vi) HPV18 E6/E7. Approximately 72 hours after the media change, cells were harvested and lysates were made from each of the transfected groups. Untransfected cells were used as negative control. Then, about 5 μL of each of the lysates were loaded on PAGE gel and blotted with the following antibodies: (i) HPV16/18 anti-E6 (AbCam, cat. #ab70), (ii) HPV16 anti-E7 (AbCam, cat. #1b30731), and (iii) HPV18 anti-E7 (AbCam, cat. #ab100953).

FIGS. 18A-18F provide the results. As shown, except perhaps for cells transfected with a plasmid encoding the HPV18 E7 protein, the transfected cells failed to express the full length HPV16 or HPV18 proteins as measured by Western Blot. This result suggested that at least the full length HPV16 E6, HPV16, and HPV18 E6 are not expressed in transient.

To address the above issue, a split protein expression strategy was used. Briefly, the 158 amino acid long HPV E6 protein was split in half at an unstructured region in the middle. This generated two peptides fragments: (i) the N-terminal nE6 (1-88aa) and (ii) the C-terminal cE6 (89-158aa). The codon optimized DNA sequences encoding the nE6 and the cE6 peptides fragments were used to assemble constructs expressing the split HPV E6 fused to Scaffold X (e.g., PTGFRN) at the N- or C-terminus and Scaffold Y at the C-terminus, respectively. The following plasmids were generated, which were used to transfect the 293SF cells: (i) pUC57-Kan-AAVS1HR-CAGGS-PTGFRN-FLAG-coHPV16nE6 ("pCB-2014"), (ii) pUC57-Kan-AAVS1HR-CAGGS-PTGFRN-FLAG-coHPV16cE6 ("pCB-2015"), (iii) pUC57-Kan-AAVS1HR-CAGGS-coHPV16nE6-FLAG-PTGFRN ("pCB-2016"), (iv) pUC57-Kan-AAVS1HR-CAGGS-coHPV16cE6-FLAG-PTGFRN ("pCB-2017"), (v) pUC57-Kan-AAVS1HR-CAGGS-PrY-FLAG-coHPV16nE6 ("pCB-2018"), and (vi) pUC57-Kan-AAVS1HR-CAGGS-PrY-FLAG-coHPV16cE6 ("pCB-2019"). (See Table 11, below). Then, the expression of the E6 and E7 proteins of HPV16 and HPV18 was assessed by Western Blot (as described above) and using an anti-FLAG antibody.

TABLE 11

Description of HPV Plasmids

| Name | Construct | Insert | Antigen |
|---|---|---|---|
| pCB-2014 | pUC57-Kan-AAVS1HR-CAGGS-PTGFRN-FLAG-coHPV16nE6 | PrX-FLAG-HPV-nE6 | nE6: N-terminal fragment of HPV16 E6 (1-88aa) |
| pCB-2015 | pUC57-Kan-AAVS1HR-CAGGS-PTGFRN-FLAG-coHPV16cE6 | PrX-FLAG-HPV-cE6 | cE6: C-terminal fragment of HPV16 E6 (89-158aa) |
| pCB-2016 | pUC57-Kan-AAVS1HR-CAGGS-coHPV16nE6-FLAG-PTGFRN | HPV-nE6-FLAG-PrX | nE6: N-terminal fragment of HPV16 E6 (1-88aa) |
| pCB-2017 | pUC57-Kan-AAVS1HR-CAGGS-coHPV16cE6-FLAG-PTGFRN | HPV-cE6-FLAG-PrX | cE6: C-terminal fragment of HPV16 E6 (89-158aa) |

TABLE 11-continued

| Description of HPV Plasmids | | | |
|---|---|---|---|
| Name | Construct | Insert | Antigen |
| pCB-2018 | pUC57-Kan-AAVS1HR-CAGGS-PrY-FLAG-coHPV16nE6 | PrY-FLAG-HPV-nE6 | nE6: N-terminal fragment of HPV16 E6 (1-88aa) |
| pCB-2019 | pUC57-Kan-AAVS1HR-CAGGS-PrY-FLAG-coHPV16cE6 | PrY-FLAG-HPV-cE6 | cE6: C-terminal fragment of HPV16 E6 (89-158aa) |

As shown in FIGS. 18G-18L, with the split protein expression strategy, each of the HPV proteins tested (i.e., HPV16 E6, HPV16 E7, HPV18 E6, and HPV18 E7) were expressed in both transient and stable cell lysates.

These results further confirm that the EVs (e.g., exosomes) disclosed herein can be engineered to express wide range of antigens, including different HPV proteins.

Example 24: Efficacy of Scaffold X-Engineered EVs (e.g., Exosomes) Comprising an Anti-Clec9a Targeting Moiety in Inducing an Antigen-Specific Immune Response Further to Examples 13 and 17 above, ability of an aCLEC9A-Px-OVA exoVACC to induce an antigen-specific immune response was assessed in an animal model. The aCLEC9A-Px-OVA exoVACC is an EV (e.g., exosome) loaded with a STING agonist and engineered to express the following: (i) aCLEC9A-Px (i.e., an anti-Clec9a antibody fragment linked to a Scaffold X) and (ii) OVA-Py (i.e., OVA linked to a Scaffold Y). Briefly, as shown in FIG. 19A, mice received one of the following: (i) OVA-expressing EVs (e.g., exosomes) loaded with STING agonist and expressing a control isotype antibody ("IgG-Px-OVA exoVACC") (Group 1), (ii) aCLEC9A-Px-OVA exoVACC (Group 2), and (iii) OVA-expressing EVs (e.g., exosomes) loaded with STING agonist (i.e., does not express Scaffold X) ("PyOVA exoVACC") (Group 3). Some of the animals received a single dose and then sacrificed a week later. Other animals received a second dose (one week after the first dose) and then sacrificed a week after the second dose. Splenocytes were harvested from the sacrificed animals and then, OVA-specific CD8+ T cells were analyzed using flow cytometry.

As shown in FIG. 19B, after a single administration of the EVs, there was no significant difference in the number of OVA-specific CD8+ effector memory T cells in the spleen. However, after a second dose, the number of OVA-specific CD8+ effector memory T cells in the spleen was significantly higher in animals treated with aCLEC9A-Px-OVA exoVACC (see FIG. 19C). This result highlights the benefits of expressing a targeting moiety (e.g., anti-Clec9a antibody fragment) in designing EVs (e.g., exosomes) for the treatment of diseases and disorders.

Example 25: Efficacy of Engineered-EVs (e.g., Exosomes) to Induce Antigen-Specific Antibody Response To determine whether EVs (e.g., exosomes) disclosed herein are also capable of inducing a robust humoral immune response, the ability of EVs (e.g., exosomes) to induce antigen-specific antibodies was observed in mice. Briefly, mice were intranasally administered with an engineered-exosome expressing OVA-Scaffold Y and loaded with the STING agonist CL656 ("Py-OVA exoVACC"). Control animals received one of the following: (i) soluble OVA ("OVA") (intranasally), (ii) soluble OVA+CL656 ("OVA+STING") (intranasally), (iii) exosome expressing only OVA-Scaffold Y fusion protein ("PyOVA") (intranasally), (iv) exosome expressing only OVA-Scaffold Y fusion protein+soluble CL656 (i.e., the STING agonist is not loaded into the exosomes) ("PyOVA+STING") (intranasally), and (v) soluble OVA+alum adjuvant ("OVA+Alum") (subcutaneously) (see FIG. 20A). Each of the treatment regiments were administered for a total of two doses (two weeks apart between doses). Then, two weeks after the last administration, sera was collected from the animals and the amount of OVA-specific IgG1 and IgA antibodies was determined using an ELISA assay.

As seen in FIGS. 20A and 20B, EVs (e.g., exosomes) comprising OVA-Scaffold Y (i.e., antigen) and a STING agonist (i.e., adjuvant) were able to induce both antigen-specific IgG1 and IgA in the sera. This result demonstrates that the EVs (e.g., exosomes) disclosed herein are capable of inducing both antigen-specific cell-mediated and antibody-mediated immune responses after administration.

Figure 21:
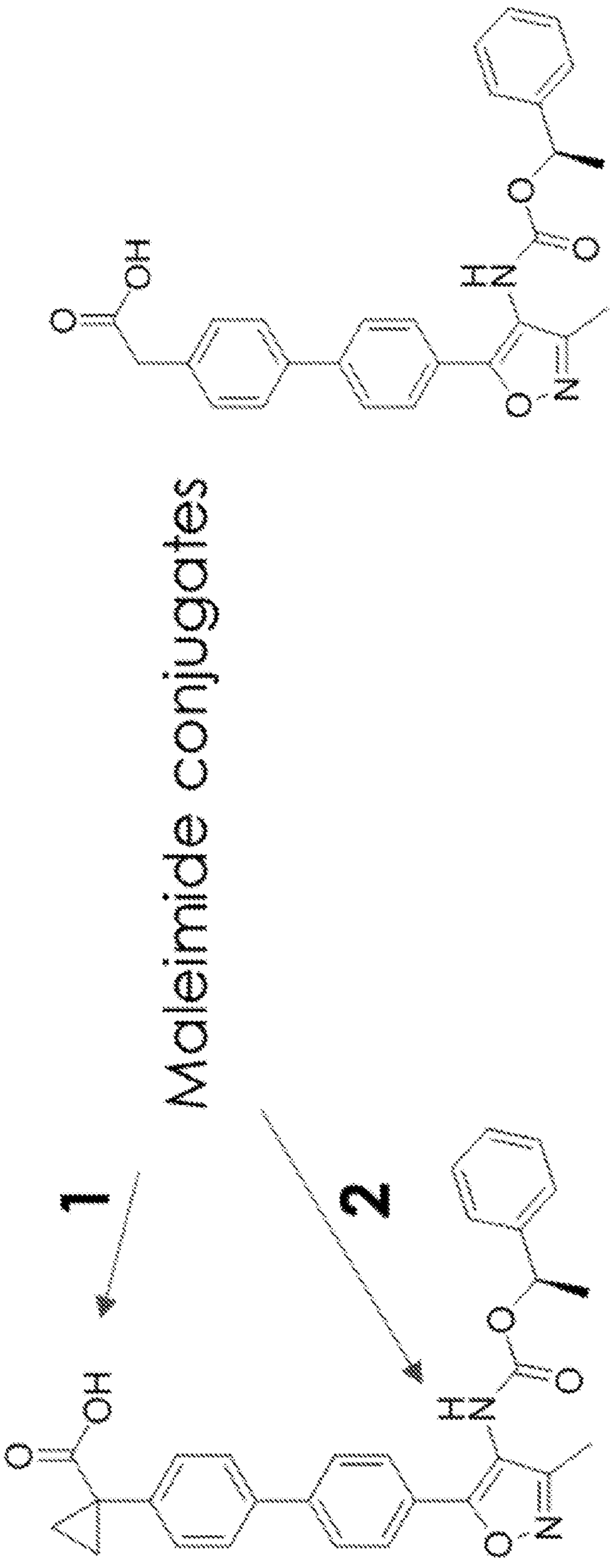
FIG. 21 shows the chemical structures of AM152 (Cyclopropanecarboxylic acid, 1-[4'-[3-methyl-4-[[[(1R)-1-phenylethoxy]carbonyl]amino]-5-isoxazolyl][1,1'-biphenyl]-4-yl]-) and AM095 (1,1'-Biphenyl]-4-acetic acid, 4'-[3-methyl-4-[[[(1R)-1-phenylethoxy]carbonyl]amino]-5-isoxazolyl[ ]-). Arrows labeled 1 and 2 indicate locations (carboxylic acid and carbamate) suitable for derivation to introduce a maleimide reactive group. The corresponding sites indicated in AM152 are also present in AM095.

Example 26: Surface-Engineered EVs (e.g., Exosomes) Comprising an LPA-1 Inhibitor As described herein, EVs (e.g., exosomes) of the present disclosure can be engineered to express an LPA-1 inhibitor on the surface of the EVs. Non-limiting examples of LPA-1 inhibitors that can be used with the present disclosure include AM152 and AM095. The chemical structures of AM152 and AM095 are presented in FIG. 21. The figure shows that maleimide-containing reagents can be conjugated to the carboxylic acid and/or carbamate groups of AM152. The same approach could be used to derivatize AM095 since the same reactive groups are present in AM095.

Figure 22:
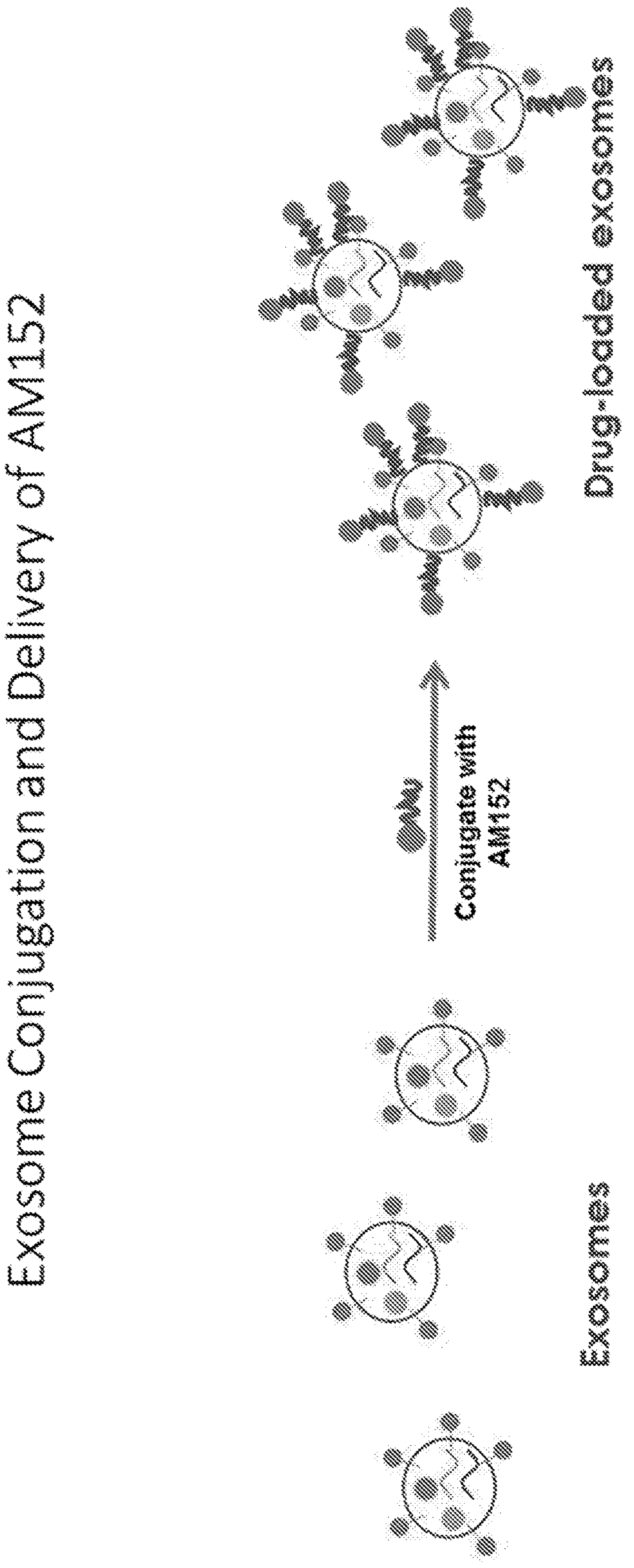
FIG. 22 provides a schematic representation showing the conjugation of an LPA1 antagonist (AM152) to exosomes, to yield a population of exosomes containing a plurality of LPA1 antagonist molecules on their surface.

LPA-1 inhibitors such as AM095 and AM152 can be conjugated to the surface of EVs (e.g., exosomes) using the methods disclosed herein. The results would be an EV (e.g., exosome) comprising a plurality of inhibitors on the surface of the EV. See FIG. 22.

Figure 23:
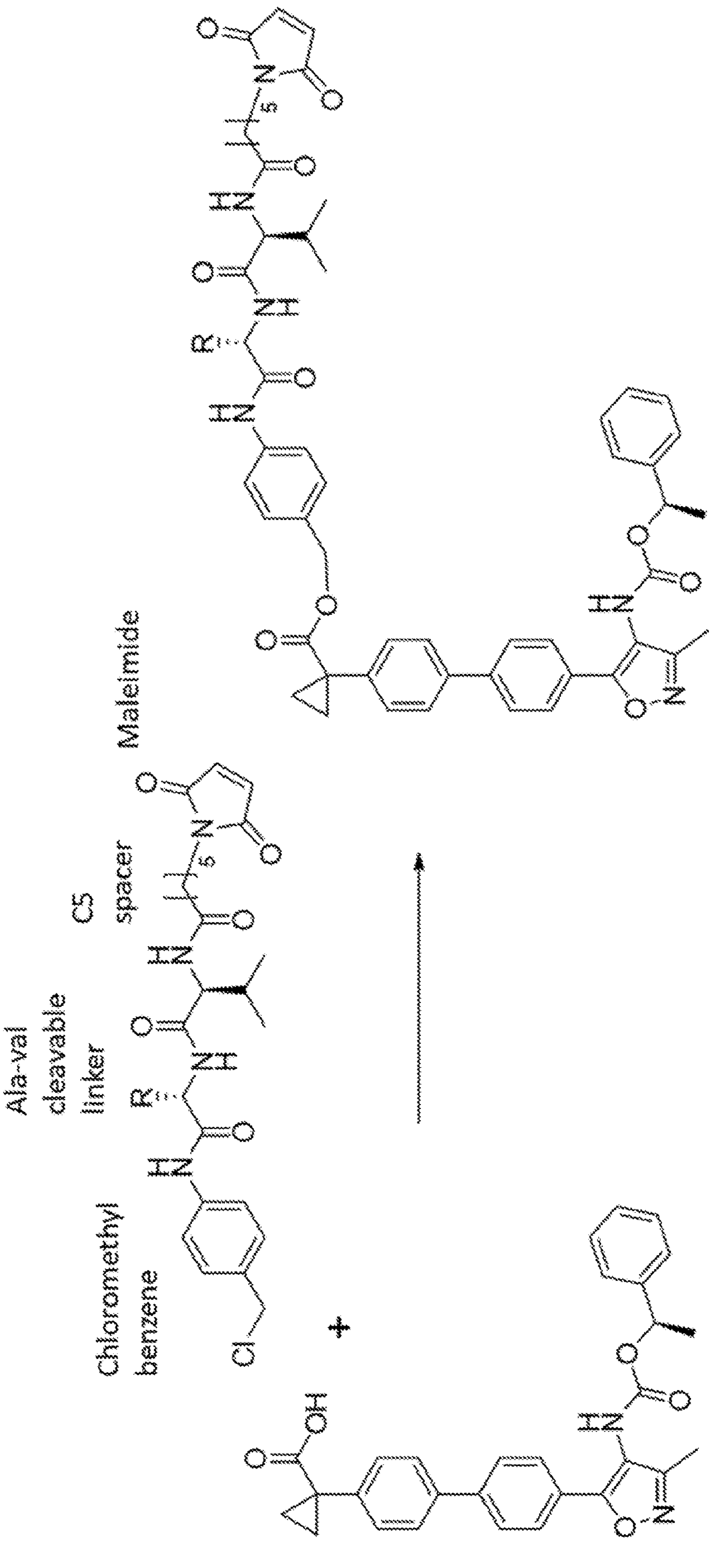
FIG. 23 shows an example of how a maleimide reactive group can be added to AM152 via its carboxylic acid group. The example shows the maleimide group as part of a reactive complex comprising an ala-val cleavable linker and a C5 spacer interposed between the maleimide group and the carboxylic acid-reactive chloromethyl benzene group.
Figure 24:
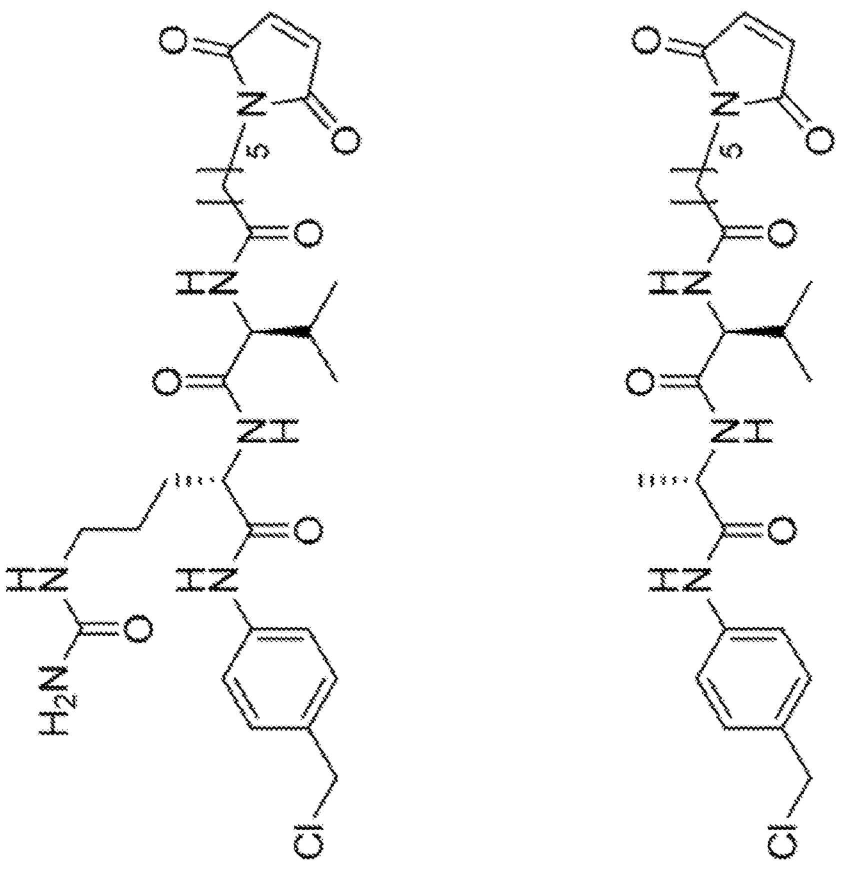
FIG. 24 shows two exemplary reagents that can be used to derivatize AM152. The top reagent comprises (i) a chloromethyl benzene group that can react with the carboxylic acid group of AM152 and (ii) a maleimide group; and interposed between them are a cleavable cit-val dipeptide and a C5 spacer. The bottom reagent comprises (i) a chloromethyl benzene group that can react with the carboxylic acid group of AM152 and (ii) a maleimide group, and interposed between them are a cleavable ala-val dipeptide and a C5 spacer.

FIG. 23 shows an example of how a maleimide reactive group can be added to AM152 via the acid group. The example shows the maleimide group as part of a complex comprising an ala-val cleavable linker interposed between the maleimide group and the carboxylic acid-reactive chloromethyl benzene group. FIG. 24 shows two exemplary reagents that can be used to derivatize AM152. The top reagent comprises (i) a chloromethyl benzene group that can react with the carboxylic acid group of AM152 and (ii) a maleimide group; and interposed between them are a cleavable cit-val dipeptide and a C5 spacer. The bottom reagent comprises (i) a chloromethyl benzene group that can react with the carboxylic acid group of AM152 and (ii) a maleimide group, and interposed between them are a cleavable ala-val dipeptide and a C5 spacer. The maleimide group would be subsequently used to attach the AM152 (or AM095), e.g., to a scaffold moiety either directly or indirectly via one or more spacers or linkers (e.g., disclosed herein).

Figure 25:
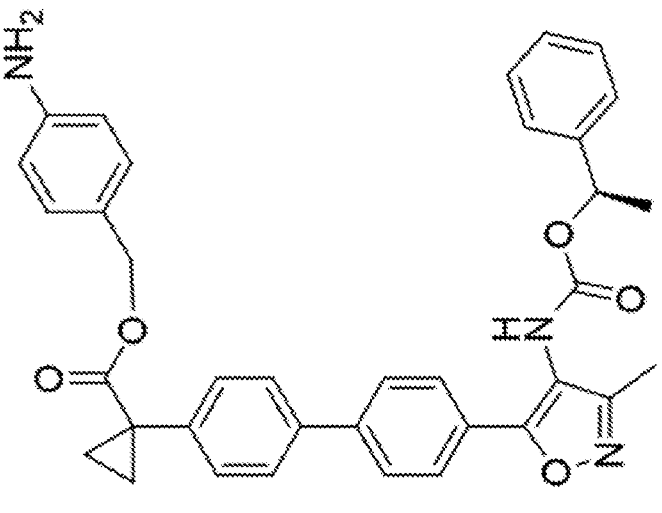
FIG. 25 shows the product that would result from cleaving the cit-val or ala-val dipeptide (e.g., by cathepsin B) in the conjugation product. The product, an AM152 aniline ester, could be further processed by an endogenous esterase to yield the free acid AM152 product.

FIG. 25 shows the product that would result from cleaving the cit-val or ala-val dipeptide (e.g., by cathepsin B) in the conjugation product. The product, an AM152 aniline ester, could be further processed by an endogenous esterase to yield the free acid AM152 product.

Figure 27:
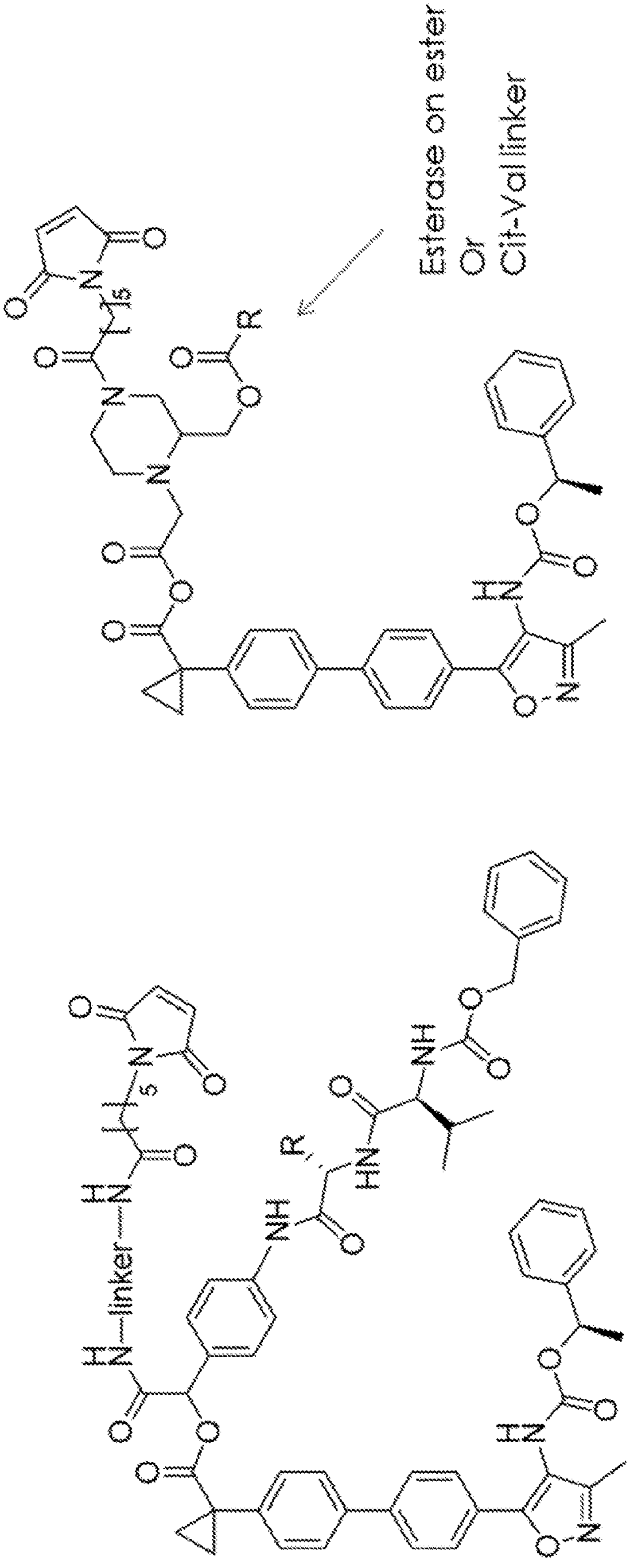

FIG. 26 shows several AM152 derivatives comprising a free maleimide group and different combinations of spacers. Additional derivatives are shown in FIG. 27.

Figure 28:
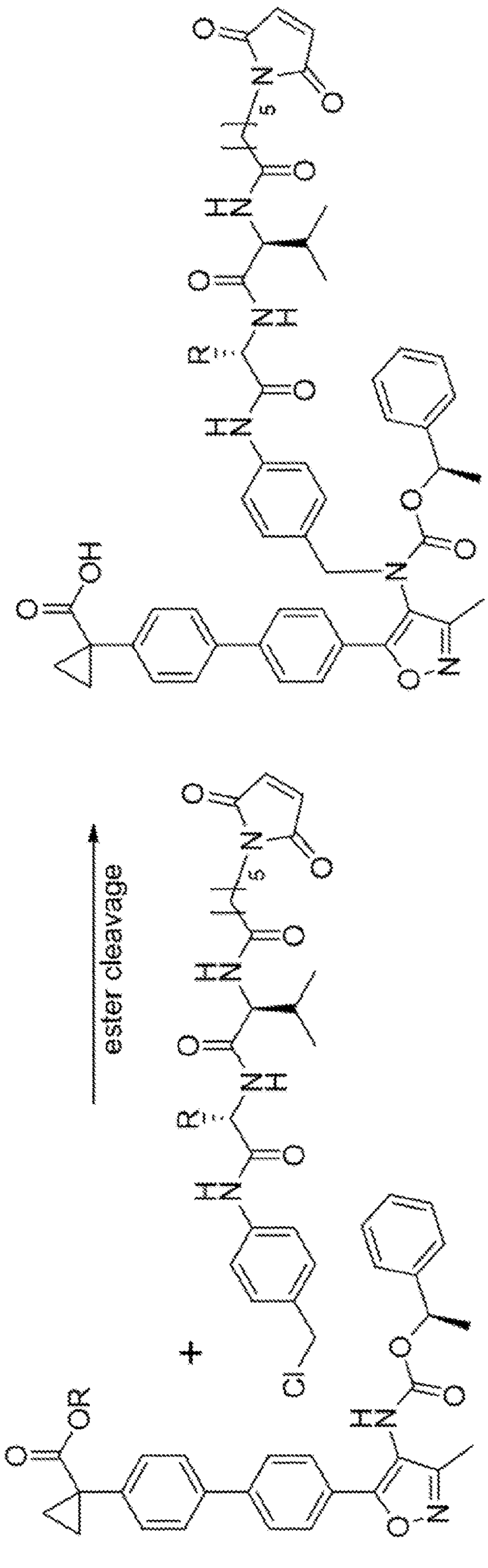
FIG. 28 shows that after protection of the carboxylic acid group, it is possible to use the same reagents used to derivatize the carboxylic acid group to derivatize AM152 at its carbamate group. The resulting product would be subsequently deprotected to free the carboxylic acid group.

FIG. 28 shows that after protection of the carboxylic acid group, it is possible to use the same reagents used to derivatize the carboxylic acid group to derivatize AM152 at its carbamate group. The resulting product would be subsequently deprotected to free the carboxylic acid group.

Figure 29:
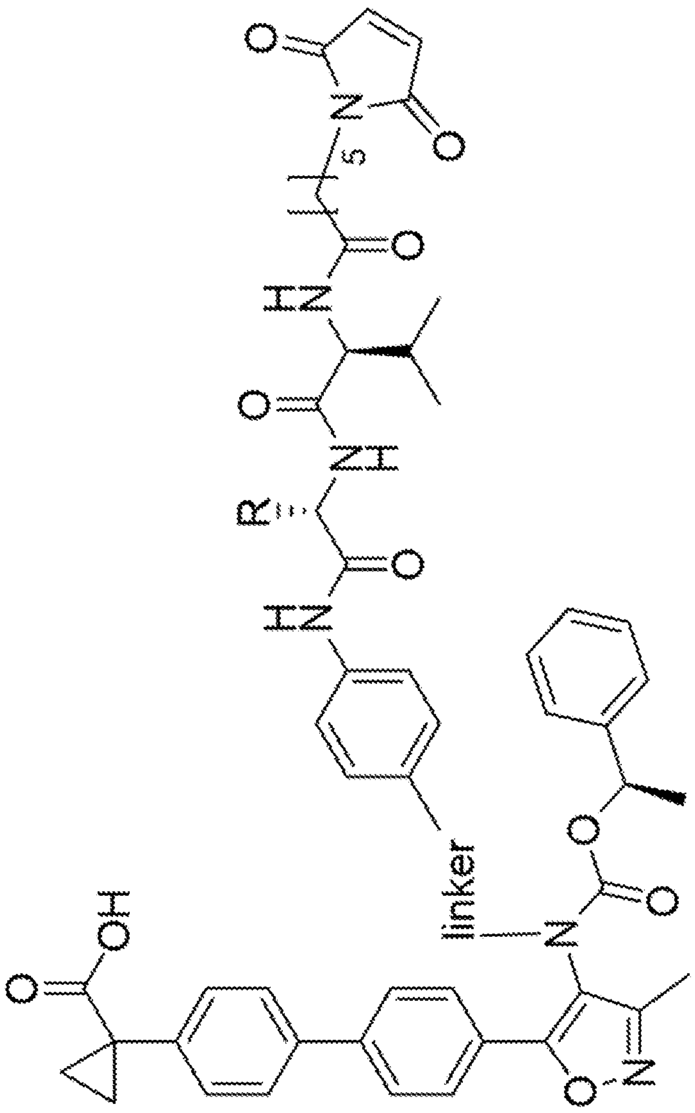
FIG. 29 shows illustrates an example in which the complex with the maleimide group is attached to the carbamate group of AM152 via a linker. Suitable linkers include any of the linkers disclosed in the present specification.

FIG. 29 illustrates an example in which the complex with the maleimide group is attached to the carbamate group of AM152 via a linker. Suitable linkers include any of the linkers disclosed in the present specification.

The processes disclosed in this example relate to the generation of an AM152 or AM095 derivative comprising a free maleimide reactive group, which could subsequently react with a scaffold moiety either directly or indirectly via one or more spacers or linkers. As a result, the AM152 or AM095 would be attached to the external surface of the EV, e.g., an exosome.

Figure 30:
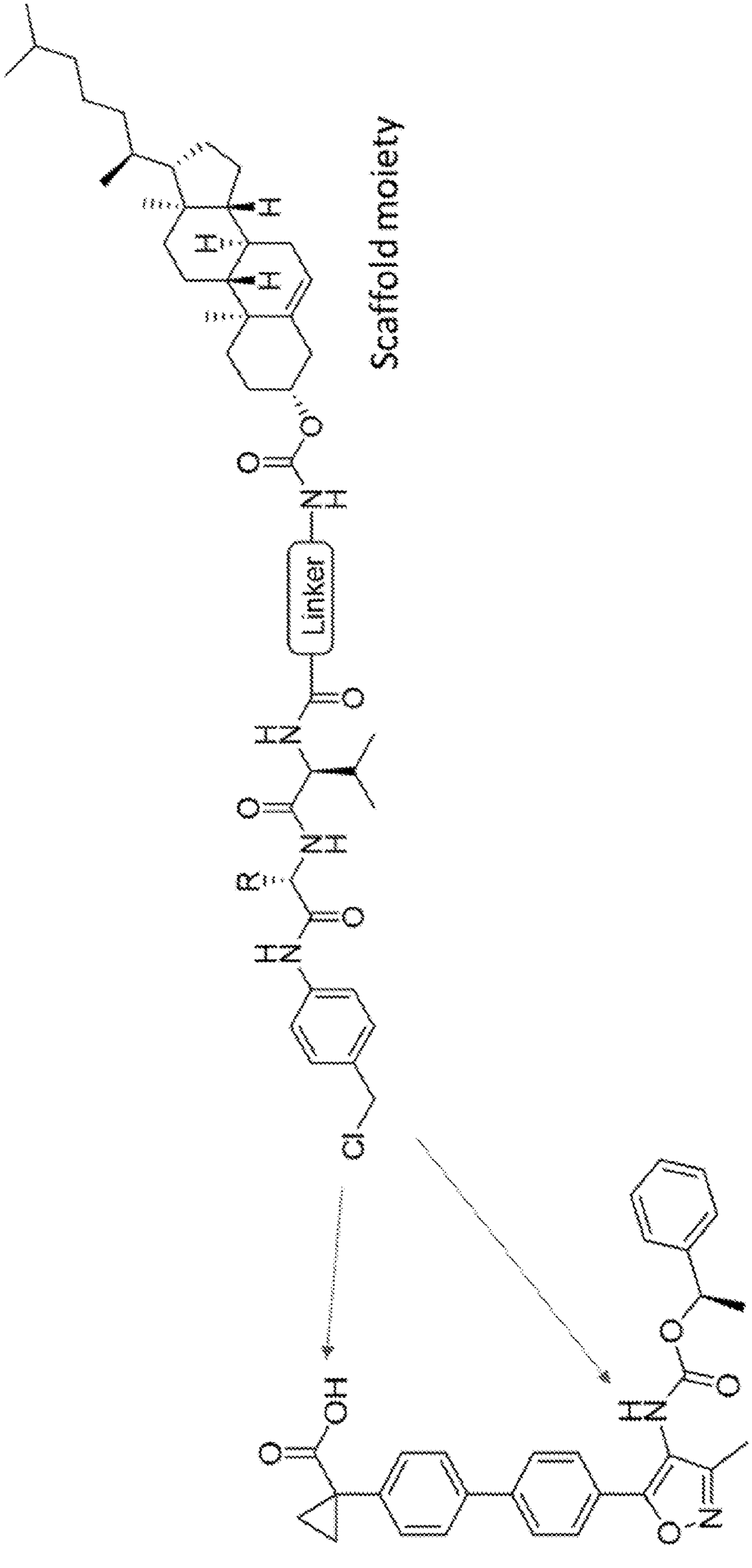
FIG. 30 shows that AM152 can be attached to a derivatized anchoring moiety instead of being derivatized and subsequently attached to an anchoring moiety via the reactive maleimide group.

However, the invention could also be practiced by derivatizing an anchoring moiety first, e.g., with a bifunctional group comprising maleimide, and then reacting the derivatized anchoring moiety, e.g., having a free chloromethyl benzene group, with either the carboxylic acid or the carbamate group of AM152, as shown in FIG. 30.

In some aspects, conjugating AM152 (or AM095) to the surface of EV, e.g., exosomes, improves at least one beneficial property of unconjugated AM152 (or AM095) and/or decreases at least one deleterious property of unconjugated AM152 or AM095 (e.g., toxicity, such as gall bladder toxicity and/or liver toxicity). In some aspects, conjugating AM152 (or AM095) to an EV, e.g., an exosome, improves the efficacy of AM512 or AM095 (compared to free AM152 or free AM095) in the treatment of a fibrotic disease, e.g., lung fibrosis, such as IPF.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific aspects have been illustrated and described, the above specification is not restrictive. It will be appreciated that various changes can be made without departing from the spirit and scope of the invention(s). Many variations will become apparent to those skilled in the art upon review of this specification.

What is claimed is:

1. An isolated extracellular vesicle (EV) comprising (i) an antigen, (ii) a first scaffold moiety, and (iii) an adjuvant,
   wherein the first scaffold moiety comprises a prostaglandin F2 receptor negative regulator (PTGFRN) protein or a fragment thereof.

2. The EV of claim 1, which comprises (i) at least 2 different antigens; (ii) at least 2 different adjuvants; or (iii) both (i) and (ii).

3. The EV of claim 1, which further comprises a second scaffold moiety.

4. The EV of claim 3, wherein the antigen, the adjuvant, or both the antigen and the adjuvant are linked to the first scaffold moiety, second scaffold moiety, or both.

5. The EV of claim 3, wherein the second scaffold moiety comprises a Scaffold Y or a Scaffold X.

6. The EV of claim 5, wherein: (i) the Scaffold X is selected from a prostaglandin F2 receptor negative regulator (the PTGFRN protein); basigin (BSG protein); immunoglobulin superfamily member 2 (IGSF2 protein); immunoglobulin superfamily member 3 (IGSF3 protein); immunoglobulin superfamily member 8 (IGSF8 protein); integrin beta-1 (ITGB1 protein); integrin alpha-4 (ITGA4 protein); 4F2 cell-surface antigen heavy chain (SLC3A2 protein); ATP transporter protein, or a fragment thereof, or any combination thereof; (ii) the Scaffold Y is selected from a myristoylated alanine rich Protein Kinase C substrate (MARCKS protein); myristoylated alanine rich Protein Kinase C substrate like 1 (MARCKSL1 protein); brain acid soluble protein 1 (BASP1 protein), or a fragment thereof, or any combination thereof; or (iii) both (i) and (ii).

7. The EV of claim 3, wherein:
   (a) the antigen is linked to the first scaffold moiety on the luminal surface of the EV, and the adjuvant is linked to the second scaffold moiety on the luminal surface of the EV;
   (b) the antigen is linked to the first scaffold moiety on the luminal surface of the EV, and the adjuvant is linked directly to the luminal surface of the EV;
   (c) the antigen is linked to the first scaffold moiety on the luminal surface of the EV, and the adjuvant is in the lumen of the EV;
   (d) the antigen is linked to the first scaffold moiety on the luminal surface of the EV, and the adjuvant is linked to the second scaffold moiety on the exterior surface of the EV;
   (e) the antigen is linked to the first scaffold moiety on the luminal surface of the EV, and the adjuvant is linked directly to the exterior surface of the EV;
   (f) the antigen is linked to the first scaffold moiety on the exterior surface of the EV, and the adjuvant is linked to the second scaffold moiety on the luminal surface of the EV surface;
   (g) the antigen is linked to the first scaffold moiety on the exterior surface of the EV, and the adjuvant is linked directly to the luminal surface of the EV;
   (h) the antigen is linked to the first scaffold moiety on the exterior surface of the EV, and the adjuvant is in the lumen of the EV;
   (i) the antigen is linked to the first scaffold moiety on the exterior surface of the EV, and the adjuvant is linked to the second scaffold moiety on the exterior surface of the EV;
   (j) the antigen is linked to the first scaffold moiety on the exterior surface of the EV, and the adjuvant is linked directly to the exterior surface of the EV;
   (k) the antigen is in the lumen of the EV, and the adjuvant is linked to the first scaffold moiety on the luminal surface of the EV;
   (l) the antigen is in the lumen of the EV, and the adjuvant is linked to the first scaffold moiety on the exterior surface of the EV;
   (m) the antigen is linked directly to the luminal surface of the EV, and the adjuvant is linked to the first scaffold moiety on the luminal surface of the EV;
   (n) the antigen is linked directly to the luminal surface of the EV, and the adjuvant is linked to a first scaffold moiety on the exterior surface of the EV;
   (o) the antigen is linked directly to the exterior surface of the EV, and the adjuvant is linked to the first scaffold moiety on the luminal surface of the EV; or
   (p) the antigen is linked directly to the exterior surface of the EV, and the adjuvant is linked to the first scaffold moiety on the exterior surface of the EV.

8. The EV of claim 6, wherein: (i) the Scaffold X is a PTGFRN protein or a fragment thereof; (ii) the Scaffold Y is a BASP1 protein or a fragment thereof; or (iii) both (i) and (ii).

9. The EV of claim 5, wherein: (i) the Scaffold X comprises an amino acid sequence set forth in SEQ ID NO: 33; (ii) the Scaffold Y comprises an amino acid sequence set forth in any one of SEQ ID NOs: 49-155 and 246-256; or (iii) both (i) and (ii).

10. The EV of claim 1, which further comprises an immune modulator; targeting moiety; or both.

11. An isolated extracellular vesicle (EV) comprising (i) an antigen, (ii) a first scaffold moiety and (iii) an immune modulator, wherein the first scaffold moiety comprises a prostaglandin F2 receptor negative regulator (PTGFRN) protein or a fragment thereof.

12. The EV of claim 11, further comprising an adjuvant, targeting moiety, or both.

13. The EV of claim 1, which is an exosome.

14. A pharmaceutical composition comprising the EV of claim 1 and a pharmaceutically acceptable carrier.

15. A cell that produces the EV of claim 1.

16. An EV-drug conjugate comprising the EV of claim 1.

17. A method of making EVs comprising culturing the cell of claim 15 under a suitable condition and obtaining the EVs.

18. A method of inducing an immune response in a subject in need thereof comprising administering the EV of claim 1 to the subject.

19. A method of preventing or treating a disease in a subject in need thereof, comprising administering the EV of claim 1, wherein the disease is associated with the antigen.

* * * * *

SEQUENCE LISTING

```
<160> NUMBER OF SEQ ID NOS: 380

<210> SEQ ID NO 1
<211> LENGTH: 879
<212> TYPE: PRT
<213> ORGANISM: Homo sapiens

<400> SEQUENCE: 1

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160
```

-continued

```
Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
```

```
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875


<210> SEQ ID NO 2
<211> LENGTH: 731
<212> TYPE: PRT
<213> ORGANISM: Homo sapiens

<400> SEQUENCE: 2

Pro Ser Ala Arg Pro Pro Pro Ser Leu Ser Leu Arg Glu Gly Glu Pro
1               5                   10                  15

Phe Glu Leu Arg Cys Thr Ala Ala Ser Ala Ser Pro Leu His Thr His
            20                  25                  30

Leu Ala Leu Leu Trp Glu Val His Arg Gly Pro Ala Arg Arg Ser Val
        35                  40                  45

Leu Ala Leu Thr His Glu Gly Arg Phe His Pro Gly Leu Gly Tyr Glu
    50                  55                  60

Gln Arg Tyr His Ser Gly Asp Val Arg Leu Asp Thr Val Gly Ser Asp
65                  70                  75                  80
```

-continued

```
Ala Tyr Arg Leu Ser Val Ser Arg Ala Leu Ser Ala Asp Gln Gly Ser
                85                  90                  95

Tyr Arg Cys Ile Val Ser Glu Trp Ile Ala Glu Gln Gly Asn Trp Gln
            100                 105                 110

Glu Ile Gln Glu Lys Ala Val Glu Val Ala Thr Val Val Ile Gln Pro
        115                 120                 125

Ser Val Leu Arg Ala Ala Val Pro Lys Asn Val Ser Val Ala Glu Gly
    130                 135                 140

Lys Glu Leu Asp Leu Thr Cys Asn Ile Thr Thr Asp Arg Ala Asp Asp
145                 150                 155                 160

Val Arg Pro Glu Val Thr Trp Ser Phe Ser Arg Met Pro Asp Ser Thr
                165                 170                 175

Leu Pro Gly Ser Arg Val Leu Ala Arg Leu Asp Arg Asp Ser Leu Val
            180                 185                 190

His Ser Ser Pro His Val Ala Leu Ser His Val Asp Ala Arg Ser Tyr
        195                 200                 205

His Leu Leu Val Arg Asp Val Ser Lys Glu Asn Ser Gly Tyr Tyr Tyr
    210                 215                 220

Cys His Val Ser Leu Trp Ala Pro Gly His Asn Arg Ser Trp His Lys
225                 230                 235                 240

Val Ala Glu Ala Val Ser Ser Pro Ala Gly Val Gly Val Thr Trp Leu
                245                 250                 255

Glu Pro Asp Tyr Gln Val Tyr Leu Asn Ala Ser Lys Val Pro Gly Phe
            260                 265                 270

Ala Asp Asp Pro Thr Glu Leu Ala Cys Arg Val Val Asp Thr Lys Ser
        275                 280                 285

Gly Glu Ala Asn Val Arg Phe Thr Val Ser Trp Tyr Tyr Arg Met Asn
    290                 295                 300

Arg Arg Ser Asp Asn Val Val Thr Ser Glu Leu Leu Ala Val Met Asp
305                 310                 315                 320

Gly Asp Trp Thr Leu Lys Tyr Gly Glu Arg Ser Lys Gln Arg Ala Gln
                325                 330                 335

Asp Gly Asp Phe Ile Phe Ser Lys Glu His Thr Asp Thr Phe Asn Phe
            340                 345                 350

Arg Ile Gln Arg Thr Thr Glu Glu Asp Arg Gly Asn Tyr Tyr Cys Val
        355                 360                 365

Val Ser Ala Trp Thr Lys Gln Arg Asn Asn Ser Trp Val Lys Ser Lys
    370                 375                 380

Asp Val Phe Ser Lys Pro Val Asn Ile Phe Trp Ala Leu Glu Asp Ser
385                 390                 395                 400

Val Leu Val Val Lys Ala Arg Gln Pro Lys Pro Phe Phe Ala Ala Gly
                405                 410                 415

Asn Thr Phe Glu Met Thr Cys Lys Val Ser Ser Lys Asn Ile Lys Ser
            420                 425                 430

Pro Arg Tyr Ser Val Leu Ile Met Ala Glu Lys Pro Val Gly Asp Leu
        435                 440                 445

Ser Ser Pro Asn Glu Thr Lys Tyr Ile Ile Ser Leu Asp Gln Asp Ser
    450                 455                 460

Val Val Lys Leu Glu Asn Trp Thr Asp Ala Ser Arg Val Asp Gly Val
465                 470                 475                 480

Val Leu Glu Lys Val Gln Glu Asp Glu Phe Arg Tyr Arg Met Tyr Gln
                485                 490                 495

Thr Gln Val Ser Asp Ala Gly Leu Tyr Arg Cys Met Val Thr Ala Trp
```

```
            500                 505                 510

Ser Pro Val Arg Gly Ser Leu Trp Arg Glu Ala Ala Thr Ser Leu Ser
        515                 520                 525

Asn Pro Ile Glu Ile Asp Phe Gln Thr Ser Gly Pro Ile Phe Asn Ala
    530                 535                 540

Ser Val His Ser Asp Thr Pro Ser Val Ile Arg Gly Asp Leu Ile Lys
545                 550                 555                 560

Leu Phe Cys Ile Ile Thr Val Glu Gly Ala Ala Leu Asp Pro Asp Asp
                565                 570                 575

Met Ala Phe Asp Val Ser Trp Phe Ala Val His Ser Phe Gly Leu Asp
            580                 585                 590

Lys Ala Pro Val Leu Leu Ser Ser Leu Asp Arg Lys Gly Ile Val Thr
        595                 600                 605

Thr Ser Arg Arg Asp Trp Lys Ser Asp Leu Ser Leu Glu Arg Val Ser
    610                 615                 620

Val Leu Glu Phe Leu Leu Gln Val His Gly Ser Glu Asp Gln Asp Phe
625                 630                 635                 640

Gly Asn Tyr Tyr Cys Ser Val Thr Pro Trp Val Lys Ser Pro Thr Gly
                645                 650                 655

Ser Trp Gln Lys Glu Ala Glu Ile His Ser Lys Pro Val Phe Ile Thr
            660                 665                 670

Val Lys Met Asp Val Leu Asn Ala Phe Lys Tyr Pro Leu Leu Ile Gly
        675                 680                 685

Val Gly Leu Ser Thr Val Ile Gly Leu Leu Ser Cys Leu Ile Gly Tyr
    690                 695                 700

Cys Ser Ser His Trp Cys Cys Lys Lys Glu Val Gln Glu Thr Arg Arg
705                 710                 715                 720

Glu Arg Arg Arg Leu Met Ser Met Glu Met Asp
                725                 730


<210> SEQ ID NO 3
<211> LENGTH: 611
<212> TYPE: PRT
<213> ORGANISM: Homo sapiens

<400> SEQUENCE: 3

Val Ala Thr Val Val Ile Gln Pro Ser Val Leu Arg Ala Ala Val Pro
1               5                   10                  15

Lys Asn Val Ser Val Ala Glu Gly Lys Glu Leu Asp Leu Thr Cys Asn
            20                  25                  30

Ile Thr Thr Asp Arg Ala Asp Asp Val Arg Pro Glu Val Thr Trp Ser
        35                  40                  45

Phe Ser Arg Met Pro Asp Ser Thr Leu Pro Gly Ser Arg Val Leu Ala
    50                  55                  60

Arg Leu Asp Arg Asp Ser Leu Val His Ser Ser Pro His Val Ala Leu
65                  70                  75                  80

Ser His Val Asp Ala Arg Ser Tyr His Leu Leu Val Arg Asp Val Ser
                85                  90                  95

Lys Glu Asn Ser Gly Tyr Tyr Tyr Cys His Val Ser Leu Trp Ala Pro
            100                 105                 110

Gly His Asn Arg Ser Trp His Lys Val Ala Glu Ala Val Ser Ser Pro
        115                 120                 125

Ala Gly Val Gly Val Thr Trp Leu Glu Pro Asp Tyr Gln Val Tyr Leu
    130                 135                 140
```

-continued

```
Asn Ala Ser Lys Val Pro Gly Phe Ala Asp Asp Pro Thr Glu Leu Ala
145                 150                 155                 160

Cys Arg Val Val Asp Thr Lys Ser Gly Glu Ala Asn Val Arg Phe Thr
                165                 170                 175

Val Ser Trp Tyr Tyr Arg Met Asn Arg Arg Ser Asp Asn Val Val Thr
            180                 185                 190

Ser Glu Leu Leu Ala Val Met Asp Gly Asp Trp Thr Leu Lys Tyr Gly
        195                 200                 205

Glu Arg Ser Lys Gln Arg Ala Gln Asp Gly Asp Phe Ile Phe Ser Lys
    210                 215                 220

Glu His Thr Asp Thr Phe Asn Phe Arg Ile Gln Arg Thr Thr Glu Glu
225                 230                 235                 240

Asp Arg Gly Asn Tyr Tyr Cys Val Val Ser Ala Trp Thr Lys Gln Arg
                245                 250                 255

Asn Asn Ser Trp Val Lys Ser Lys Asp Val Phe Ser Lys Pro Val Asn
            260                 265                 270

Ile Phe Trp Ala Leu Glu Asp Ser Val Leu Val Val Lys Ala Arg Gln
        275                 280                 285

Pro Lys Pro Phe Phe Ala Ala Gly Asn Thr Phe Glu Met Thr Cys Lys
    290                 295                 300

Val Ser Ser Lys Asn Ile Lys Ser Pro Arg Tyr Ser Val Leu Ile Met
305                 310                 315                 320

Ala Glu Lys Pro Val Gly Asp Leu Ser Ser Pro Asn Glu Thr Lys Tyr
                325                 330                 335

Ile Ile Ser Leu Asp Gln Asp Ser Val Val Lys Leu Glu Asn Trp Thr
            340                 345                 350

Asp Ala Ser Arg Val Asp Gly Val Val Leu Glu Lys Val Gln Glu Asp
        355                 360                 365

Glu Phe Arg Tyr Arg Met Tyr Gln Thr Gln Val Ser Asp Ala Gly Leu
    370                 375                 380

Tyr Arg Cys Met Val Thr Ala Trp Ser Pro Val Arg Gly Ser Leu Trp
385                 390                 395                 400

Arg Glu Ala Ala Thr Ser Leu Ser Asn Pro Ile Glu Ile Asp Phe Gln
                405                 410                 415

Thr Ser Gly Pro Ile Phe Asn Ala Ser Val His Ser Asp Thr Pro Ser
            420                 425                 430

Val Ile Arg Gly Asp Leu Ile Lys Leu Phe Cys Ile Ile Thr Val Glu
        435                 440                 445

Gly Ala Ala Leu Asp Pro Asp Asp Met Ala Phe Asp Val Ser Trp Phe
    450                 455                 460

Ala Val His Ser Phe Gly Leu Asp Lys Ala Pro Val Leu Leu Ser Ser
465                 470                 475                 480

Leu Asp Arg Lys Gly Ile Val Thr Thr Ser Arg Arg Asp Trp Lys Ser
                485                 490                 495

Asp Leu Ser Leu Glu Arg Val Ser Val Leu Glu Phe Leu Leu Gln Val
            500                 505                 510

His Gly Ser Glu Asp Gln Asp Phe Gly Asn Tyr Tyr Cys Ser Val Thr
        515                 520                 525

Pro Trp Val Lys Ser Pro Thr Gly Ser Trp Gln Lys Glu Ala Glu Ile
    530                 535                 540

His Ser Lys Pro Val Phe Ile Thr Val Lys Met Asp Val Leu Asn Ala
545                 550                 555                 560

Phe Lys Tyr Pro Leu Leu Ile Gly Val Gly Leu Ser Thr Val Ile Gly
```

```
                565                 570                 575

Leu Leu Ser Cys Leu Ile Gly Tyr Cys Ser Ser His Trp Cys Cys Lys
            580                 585                 590

Lys Glu Val Gln Glu Thr Arg Arg Glu Arg Arg Arg Leu Met Ser Met
        595                 600                 605

Glu Met Asp
    610


<210> SEQ ID NO 4
<211> LENGTH: 485
<212> TYPE: PRT
<213> ORGANISM: homo sapien

<400> SEQUENCE: 4

Ser Pro Ala Gly Val Gly Val Thr Trp Leu Glu Pro Asp Tyr Gln Val
1               5                   10                  15

Tyr Leu Asn Ala Ser Lys Val Pro Gly Phe Ala Asp Asp Pro Thr Glu
            20                  25                  30

Leu Ala Cys Arg Val Val Asp Thr Lys Ser Gly Glu Ala Asn Val Arg
        35                  40                  45

Phe Thr Val Ser Trp Tyr Tyr Arg Met Asn Arg Arg Ser Asp Asn Val
    50                  55                  60

Val Thr Ser Glu Leu Leu Ala Val Met Asp Gly Asp Trp Thr Leu Lys
65                  70                  75                  80

Tyr Gly Glu Arg Ser Lys Gln Arg Ala Gln Asp Gly Asp Phe Ile Phe
                85                  90                  95

Ser Lys Glu His Thr Asp Thr Phe Asn Phe Arg Ile Gln Arg Thr Thr
            100                 105                 110

Glu Glu Asp Arg Gly Asn Tyr Tyr Cys Val Val Ser Ala Trp Thr Lys
        115                 120                 125

Gln Arg Asn Asn Ser Trp Val Lys Ser Lys Asp Val Phe Ser Lys Pro
    130                 135                 140

Val Asn Ile Phe Trp Ala Leu Glu Asp Ser Val Leu Val Val Lys Ala
145                 150                 155                 160

Arg Gln Pro Lys Pro Phe Phe Ala Ala Gly Asn Thr Phe Glu Met Thr
                165                 170                 175

Cys Lys Val Ser Ser Lys Asn Ile Lys Ser Pro Arg Tyr Ser Val Leu
            180                 185                 190

Ile Met Ala Glu Lys Pro Val Gly Asp Leu Ser Ser Pro Asn Glu Thr
        195                 200                 205

Lys Tyr Ile Ile Ser Leu Asp Gln Asp Ser Val Val Lys Leu Glu Asn
    210                 215                 220

Trp Thr Asp Ala Ser Arg Val Asp Gly Val Val Leu Glu Lys Val Gln
225                 230                 235                 240

Glu Asp Glu Phe Arg Tyr Arg Met Tyr Gln Thr Gln Val Ser Asp Ala
                245                 250                 255

Gly Leu Tyr Arg Cys Met Val Thr Ala Trp Ser Pro Val Arg Gly Ser
            260                 265                 270

Leu Trp Arg Glu Ala Ala Thr Ser Leu Ser Asn Pro Ile Glu Ile Asp
        275                 280                 285

Phe Gln Thr Ser Gly Pro Ile Phe Asn Ala Ser Val His Ser Asp Thr
    290                 295                 300

Pro Ser Val Ile Arg Gly Asp Leu Ile Lys Leu Phe Cys Ile Ile Thr
305                 310                 315                 320
```

-continued

```
Val Glu Gly Ala Ala Leu Asp Pro Asp Asp Met Ala Phe Asp Val Ser
                325                 330                 335

Trp Phe Ala Val His Ser Phe Gly Leu Asp Lys Ala Pro Val Leu Leu
            340                 345                 350

Ser Ser Leu Asp Arg Lys Gly Ile Val Thr Thr Ser Arg Arg Asp Trp
        355                 360                 365

Lys Ser Asp Leu Ser Leu Glu Arg Val Ser Val Leu Glu Phe Leu Leu
    370                 375                 380

Gln Val His Gly Ser Glu Asp Gln Asp Phe Gly Asn Tyr Tyr Cys Ser
385                 390                 395                 400

Val Thr Pro Trp Val Lys Ser Pro Thr Gly Ser Trp Gln Lys Glu Ala
                405                 410                 415

Glu Ile His Ser Lys Pro Val Phe Ile Thr Val Lys Met Asp Val Leu
            420                 425                 430

Asn Ala Phe Lys Tyr Pro Leu Leu Ile Gly Val Gly Leu Ser Thr Val
        435                 440                 445

Ile Gly Leu Leu Ser Cys Leu Ile Gly Tyr Cys Ser Ser His Trp Cys
    450                 455                 460

Cys Lys Lys Glu Val Gln Glu Thr Arg Arg Glu Arg Arg Arg Leu Met
465                 470                 475                 480

Ser Met Glu Met Asp
                485


<210> SEQ ID NO 5
<211> LENGTH: 343
<212> TYPE: PRT
<213> ORGANISM: Homo sapiens

<400> SEQUENCE: 5

Lys Pro Val Asn Ile Phe Trp Ala Leu Glu Asp Ser Val Leu Val Val
1               5                   10                  15

Lys Ala Arg Gln Pro Lys Pro Phe Phe Ala Ala Gly Asn Thr Phe Glu
            20                  25                  30

Met Thr Cys Lys Val Ser Ser Lys Asn Ile Lys Ser Pro Arg Tyr Ser
        35                  40                  45

Val Leu Ile Met Ala Glu Lys Pro Val Gly Asp Leu Ser Ser Pro Asn
    50                  55                  60

Glu Thr Lys Tyr Ile Ile Ser Leu Asp Gln Asp Ser Val Val Lys Leu
65                  70                  75                  80

Glu Asn Trp Thr Asp Ala Ser Arg Val Asp Gly Val Val Leu Glu Lys
                85                  90                  95

Val Gln Glu Asp Glu Phe Arg Tyr Arg Met Tyr Gln Thr Gln Val Ser
            100                 105                 110

Asp Ala Gly Leu Tyr Arg Cys Met Val Thr Ala Trp Ser Pro Val Arg
        115                 120                 125

Gly Ser Leu Trp Arg Glu Ala Ala Thr Ser Leu Ser Asn Pro Ile Glu
    130                 135                 140

Ile Asp Phe Gln Thr Ser Gly Pro Ile Phe Asn Ala Ser Val His Ser
145                 150                 155                 160

Asp Thr Pro Ser Val Ile Arg Gly Asp Leu Ile Lys Leu Phe Cys Ile
                165                 170                 175

Ile Thr Val Glu Gly Ala Ala Leu Asp Pro Asp Asp Met Ala Phe Asp
            180                 185                 190

Val Ser Trp Phe Ala Val His Ser Phe Gly Leu Asp Lys Ala Pro Val
        195                 200                 205
```

```
Leu Leu Ser Ser Leu Asp Arg Lys Gly Ile Val Thr Thr Ser Arg Arg
    210                 215                 220

Asp Trp Lys Ser Asp Leu Ser Leu Glu Arg Val Ser Val Leu Glu Phe
225                 230                 235                 240

Leu Leu Gln Val His Gly Ser Glu Asp Gln Asp Phe Gly Asn Tyr Tyr
                245                 250                 255

Cys Ser Val Thr Pro Trp Val Lys Ser Pro Thr Gly Ser Trp Gln Lys
            260                 265                 270

Glu Ala Glu Ile His Ser Lys Pro Val Phe Ile Thr Val Lys Met Asp
        275                 280                 285

Val Leu Asn Ala Phe Lys Tyr Pro Leu Leu Ile Gly Val Gly Leu Ser
    290                 295                 300

Thr Val Ile Gly Leu Leu Ser Cys Leu Ile Gly Tyr Cys Ser Ser His
305                 310                 315                 320

Trp Cys Cys Lys Lys Glu Val Gln Glu Thr Arg Arg Glu Arg Arg Arg
                325                 330                 335

Leu Met Ser Met Glu Met Asp
            340


<210> SEQ ID NO 6
<211> LENGTH: 217
<212> TYPE: PRT
<213> ORGANISM: Homo sapiens

<400> SEQUENCE: 6

Val Arg Gly Ser Leu Trp Arg Glu Ala Ala Thr Ser Leu Ser Asn Pro
1               5                   10                  15

Ile Glu Ile Asp Phe Gln Thr Ser Gly Pro Ile Phe Asn Ala Ser Val
            20                  25                  30

His Ser Asp Thr Pro Ser Val Ile Arg Gly Asp Leu Ile Lys Leu Phe
        35                  40                  45

Cys Ile Ile Thr Val Glu Gly Ala Ala Leu Asp Pro Asp Asp Met Ala
    50                  55                  60

Phe Asp Val Ser Trp Phe Ala Val His Ser Phe Gly Leu Asp Lys Ala
65                  70                  75                  80

Pro Val Leu Leu Ser Ser Leu Asp Arg Lys Gly Ile Val Thr Thr Ser
                85                  90                  95

Arg Arg Asp Trp Lys Ser Asp Leu Ser Leu Glu Arg Val Ser Val Leu
            100                 105                 110

Glu Phe Leu Leu Gln Val His Gly Ser Glu Asp Gln Asp Phe Gly Asn
        115                 120                 125

Tyr Tyr Cys Ser Val Thr Pro Trp Val Lys Ser Pro Thr Gly Ser Trp
    130                 135                 140

Gln Lys Glu Ala Glu Ile His Ser Lys Pro Val Phe Ile Thr Val Lys
145                 150                 155                 160

Met Asp Val Leu Asn Ala Phe Lys Tyr Pro Leu Leu Ile Gly Val Gly
                165                 170                 175

Leu Ser Thr Val Ile Gly Leu Leu Ser Cys Leu Ile Gly Tyr Cys Ser
            180                 185                 190

Ser His Trp Cys Cys Lys Lys Glu Val Gln Glu Thr Arg Arg Glu Arg
        195                 200                 205

Arg Arg Leu Met Ser Met Glu Met Asp
    210                 215
```

<210> SEQ ID NO 7
<211> LENGTH: 66
<212> TYPE: PRT
<213> ORGANISM: homo sapiens

<400> SEQUENCE: 7

```
Ser Lys Pro Val Phe Ile Thr Val Lys Met Asp Val Leu Asn Ala Phe
1               5                   10                  15

Lys Tyr Pro Leu Leu Ile Gly Val Gly Leu Ser Thr Val Ile Gly Leu
            20                  25                  30

Leu Ser Cys Leu Ile Gly Tyr Cys Ser Ser His Trp Cys Cys Lys Lys
        35                  40                  45

Glu Val Gln Glu Thr Arg Arg Glu Arg Arg Arg Leu Met Ser Met Glu
    50                  55                  60

Met Asp
65
```

<210> SEQ ID NO 8
<211> LENGTH: 21
<212> TYPE: PRT
<213> ORGANISM: Homo sapiens

<400> SEQUENCE: 8

```
Met Gly Arg Leu Ala Ser Arg Pro Leu Leu Leu Ala Leu Leu Ser Leu
1               5                   10                  15

Ala Leu Cys Arg Gly
            20
```

<210> SEQ ID NO 9
<211> LENGTH: 385
<212> TYPE: PRT
<213> ORGANISM: Homo sapiens

<400> SEQUENCE: 9

```
Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190
```

```
Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
    370                 375                 380

Ser
385
```

<210> SEQ ID NO 10
<211> LENGTH: 247
<212> TYPE: PRT
<213> ORGANISM: Homo sapiens

<400> SEQUENCE: 10

```
Pro Gly Thr Val Phe Thr Thr Val Glu Asp Leu Gly Ser Lys Ile Leu
1               5                   10                  15

Leu Thr Cys Ser Leu Asn Asp Ser Ala Thr Glu Val Thr Gly His Arg
            20                  25                  30

Trp Leu Lys Gly Gly Val Val Leu Lys Glu Asp Ala Leu Pro Gly Gln
        35                  40                  45

Lys Thr Glu Phe Lys Val Asp Ser Asp Asp Gln Trp Gly Glu Tyr Ser
    50                  55                  60

Cys Val Phe Leu Pro Glu Pro Met Gly Thr Ala Asn Ile Gln Leu His
65                  70                  75                  80

Gly Pro Pro Arg Val Lys Ala Val Lys Ser Ser Glu His Ile Asn Glu
                85                  90                  95

Gly Glu Thr Ala Met Leu Val Cys Lys Ser Glu Ser Val Pro Pro Val
            100                 105                 110

Thr Asp Trp Ala Trp Tyr Lys Ile Thr Asp Ser Glu Asp Lys Ala Leu
        115                 120                 125

Met Asn Gly Ser Glu Ser Arg Phe Phe Val Ser Ser Ser Gln Gly Arg
    130                 135                 140

Ser Glu Leu His Ile Glu Asn Leu Asn Met Glu Ala Asp Pro Gly Gln
145                 150                 155                 160

Tyr Arg Cys Asn Gly Thr Ser Ser Lys Gly Ser Asp Gln Ala Ile Ile
```

-continued

```
                165                 170                 175

Thr Leu Arg Val Arg Ser His Leu Ala Ala Leu Trp Pro Phe Leu Gly
            180                 185                 190

Ile Val Ala Glu Val Leu Val Leu Val Thr Ile Ile Phe Ile Tyr Glu
        195                 200                 205

Lys Arg Arg Lys Pro Glu Asp Val Leu Asp Asp Asp Ala Gly Ser
    210                 215                 220

Ala Pro Leu Lys Ser Ser Gly Gln His Gln Asn Asp Lys Gly Lys Asn
225                 230                 235                 240

Val Arg Gln Arg Asn Ser Ser
                245


<210> SEQ ID NO 11
<211> LENGTH: 168
<212> TYPE: PRT
<213> ORGANISM: Homo sapiens

<400> SEQUENCE: 11

His Gly Pro Pro Arg Val Lys Ala Val Lys Ser Ser Glu His Ile Asn
1               5                   10                  15

Glu Gly Glu Thr Ala Met Leu Val Cys Lys Ser Glu Ser Val Pro Pro
            20                  25                  30

Val Thr Asp Trp Ala Trp Tyr Lys Ile Thr Asp Ser Glu Asp Lys Ala
        35                  40                  45

Leu Met Asn Gly Ser Glu Ser Arg Phe Phe Val Ser Ser Ser Gln Gly
    50                  55                  60

Arg Ser Glu Leu His Ile Glu Asn Leu Asn Met Glu Ala Asp Pro Gly
65                  70                  75                  80

Gln Tyr Arg Cys Asn Gly Thr Ser Ser Lys Gly Ser Asp Gln Ala Ile
                85                  90                  95

Ile Thr Leu Arg Val Arg Ser His Leu Ala Ala Leu Trp Pro Phe Leu
            100                 105                 110

Gly Ile Val Ala Glu Val Leu Val Leu Val Thr Ile Ile Phe Ile Tyr
        115                 120                 125

Glu Lys Arg Arg Lys Pro Glu Asp Val Leu Asp Asp Asp Asp Ala Gly
    130                 135                 140

Ser Ala Pro Leu Lys Ser Ser Gly Gln His Gln Asn Asp Lys Gly Lys
145                 150                 155                 160

Asn Val Arg Gln Arg Asn Ser Ser
                165


<210> SEQ ID NO 12
<211> LENGTH: 66
<212> TYPE: PRT
<213> ORGANISM: homo sapiens

<400> SEQUENCE: 12

Ser His Leu Ala Ala Leu Trp Pro Phe Leu Gly Ile Val Ala Glu Val
1               5                   10                  15

Leu Val Leu Val Thr Ile Ile Phe Ile Tyr Glu Lys Arg Arg Lys Pro
            20                  25                  30

Glu Asp Val Leu Asp Asp Asp Asp Ala Gly Ser Ala Pro Leu Lys Ser
        35                  40                  45

Ser Gly Gln His Gln Asn Asp Lys Gly Lys Asn Val Arg Gln Arg Asn
    50                  55                  60

Ser Ser
```

65

<210> SEQ ID NO 13
<211> LENGTH: 18
<212> TYPE: PRT
<213> ORGANISM: homo sapiens

<400> SEQUENCE: 13

Met Ala Ala Ala Leu Phe Val Leu Leu Gly Phe Ala Leu Leu Gly Thr
1 5 10 15

His Gly

<210> SEQ ID NO 14
<211> LENGTH: 613
<212> TYPE: PRT
<213> ORGANISM: homo sapiens

<400> SEQUENCE: 14

Met Gly Ala Leu Arg Pro Thr Leu Leu Pro Pro Ser Leu Pro Leu Leu
1 5 10 15

Leu Leu Leu Met Leu Gly Met Gly Cys Trp Ala Arg Glu Val Leu Val
20 25 30

Pro Glu Gly Pro Leu Tyr Arg Val Ala Gly Thr Ala Val Ser Ile Ser
35 40 45

Cys Asn Val Thr Gly Tyr Glu Gly Pro Ala Gln Gln Asn Phe Glu Trp
50 55 60

Phe Leu Tyr Arg Pro Glu Ala Pro Asp Thr Ala Leu Gly Ile Val Ser
65 70 75 80

Thr Lys Asp Thr Gln Phe Ser Tyr Ala Val Phe Lys Ser Arg Val Val
85 90 95

Ala Gly Glu Val Gln Val Gln Arg Leu Gln Gly Asp Ala Val Val Leu
100 105 110

Lys Ile Ala Arg Leu Gln Ala Gln Asp Ala Gly Ile Tyr Glu Cys His
115 120 125

Thr Pro Ser Thr Asp Thr Arg Tyr Leu Gly Ser Tyr Ser Gly Lys Val
130 135 140

Glu Leu Arg Val Leu Pro Asp Val Leu Gln Val Ser Ala Ala Pro Pro
145 150 155 160

Gly Pro Arg Gly Arg Gln Ala Pro Thr Ser Pro Pro Arg Met Thr Val
165 170 175

His Glu Gly Gln Glu Leu Ala Leu Gly Cys Leu Ala Arg Thr Ser Thr
180 185 190

Gln Lys His Thr His Leu Ala Val Ser Phe Gly Arg Ser Val Pro Glu
195 200 205

Ala Pro Val Gly Arg Ser Thr Leu Gln Glu Val Val Gly Ile Arg Ser
210 215 220

Asp Leu Ala Val Glu Ala Gly Ala Pro Tyr Ala Glu Arg Leu Ala Ala
225 230 235 240

Gly Glu Leu Arg Leu Gly Lys Glu Gly Thr Asp Arg Tyr Arg Met Val
245 250 255

Val Gly Gly Ala Gln Ala Gly Asp Ala Gly Thr Tyr His Cys Thr Ala
260 265 270

Ala Glu Trp Ile Gln Asp Pro Asp Gly Ser Trp Ala Gln Ile Ala Glu
275 280 285

Lys Arg Ala Val Leu Ala His Val Asp Val Gln Thr Leu Ser Ser Gln
290 295 300

```
Leu Ala Val Thr Val Gly Pro Gly Glu Arg Arg Ile Gly Pro Gly Glu
305                 310                 315                 320

Pro Leu Glu Leu Leu Cys Asn Val Ser Gly Ala Leu Pro Pro Ala Gly
                325                 330                 335

Arg His Ala Ala Tyr Ser Val Gly Trp Glu Met Ala Pro Ala Gly Ala
            340                 345                 350

Pro Gly Pro Gly Arg Leu Val Ala Gln Leu Asp Thr Glu Gly Val Gly
        355                 360                 365

Ser Leu Gly Pro Gly Tyr Glu Gly Arg His Ile Ala Met Glu Lys Val
    370                 375                 380

Ala Ser Arg Thr Tyr Arg Leu Arg Leu Glu Ala Ala Arg Pro Gly Asp
385                 390                 395                 400

Ala Gly Thr Tyr Arg Cys Leu Ala Lys Ala Tyr Val Arg Gly Ser Gly
                405                 410                 415

Thr Arg Leu Arg Glu Ala Ala Ser Ala Arg Ser Arg Pro Leu Pro Val
            420                 425                 430

His Val Arg Glu Glu Gly Val Val Leu Glu Ala Val Ala Trp Leu Ala
        435                 440                 445

Gly Gly Thr Val Tyr Arg Gly Glu Thr Ala Ser Leu Leu Cys Asn Ile
    450                 455                 460

Ser Val Arg Gly Gly Pro Pro Gly Leu Arg Leu Ala Ala Ser Trp Trp
465                 470                 475                 480

Val Glu Arg Pro Glu Asp Gly Glu Leu Ser Ser Val Pro Ala Gln Leu
                485                 490                 495

Val Gly Gly Val Gly Gln Asp Gly Val Ala Glu Leu Gly Val Arg Pro
            500                 505                 510

Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
    530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
            580                 585                 590

Val Thr Gly Ala Thr Val Leu Gly Thr Ile Thr Cys Cys Phe Met Lys
        595                 600                 605

Arg Leu Arg Lys Arg
    610
```

<210> SEQ ID NO 15
<211> LENGTH: 456
<212> TYPE: PRT
<213> ORGANISM: homo sapiens

<400> SEQUENCE: 15

```
Ala Pro Pro Gly Pro Arg Gly Arg Gln Ala Pro Thr Ser Pro Pro Arg
1               5                   10                  15

Met Thr Val His Glu Gly Gln Glu Leu Ala Leu Gly Cys Leu Ala Arg
            20                  25                  30

Thr Ser Thr Gln Lys His Thr His Leu Ala Val Ser Phe Gly Arg Ser
        35                  40                  45

Val Pro Glu Ala Pro Val Gly Arg Ser Thr Leu Gln Glu Val Val Gly
```

```
    50                  55                  60

Ile Arg Ser Asp Leu Ala Val Glu Ala Gly Ala Pro Tyr Ala Glu Arg
65                  70                  75                  80

Leu Ala Ala Gly Glu Leu Arg Leu Gly Lys Glu Gly Thr Asp Arg Tyr
                85                  90                  95

Arg Met Val Val Gly Gly Ala Gln Ala Gly Asp Ala Gly Thr Tyr His
            100                 105                 110

Cys Thr Ala Ala Glu Trp Ile Gln Asp Pro Asp Gly Ser Trp Ala Gln
        115                 120                 125

Ile Ala Glu Lys Arg Ala Val Leu Ala His Val Asp Val Gln Thr Leu
    130                 135                 140

Ser Ser Gln Leu Ala Val Thr Val Gly Pro Gly Glu Arg Arg Ile Gly
145                 150                 155                 160

Pro Gly Glu Pro Leu Glu Leu Leu Cys Asn Val Ser Gly Ala Leu Pro
                165                 170                 175

Pro Ala Gly Arg His Ala Ala Tyr Ser Val Gly Trp Glu Met Ala Pro
            180                 185                 190

Ala Gly Ala Pro Gly Pro Gly Arg Leu Val Ala Gln Leu Asp Thr Glu
        195                 200                 205

Gly Val Gly Ser Leu Gly Pro Gly Tyr Glu Gly Arg His Ile Ala Met
    210                 215                 220

Glu Lys Val Ala Ser Arg Thr Tyr Arg Leu Arg Leu Glu Ala Ala Arg
225                 230                 235                 240

Pro Gly Asp Ala Gly Thr Tyr Arg Cys Leu Ala Lys Ala Tyr Val Arg
                245                 250                 255

Gly Ser Gly Thr Arg Leu Arg Glu Ala Ala Ser Ala Arg Ser Arg Pro
            260                 265                 270

Leu Pro Val His Val Arg Glu Glu Gly Val Val Leu Glu Ala Val Ala
        275                 280                 285

Trp Leu Ala Gly Gly Thr Val Tyr Arg Gly Glu Thr Ala Ser Leu Leu
    290                 295                 300

Cys Asn Ile Ser Val Arg Gly Gly Pro Pro Gly Leu Arg Leu Ala Ala
305                 310                 315                 320

Ser Trp Trp Val Glu Arg Pro Glu Asp Gly Glu Leu Ser Ser Val Pro
                325                 330                 335

Ala Gln Leu Val Gly Gly Val Gly Gln Asp Gly Val Ala Glu Leu Gly
            340                 345                 350

Val Arg Pro Gly Gly Gly Pro Val Ser Val Glu Leu Val Gly Pro Arg
        355                 360                 365

Ser His Arg Leu Arg Leu His Ser Leu Gly Pro Glu Asp Glu Gly Val
    370                 375                 380

Tyr His Cys Ala Pro Ser Ala Trp Val Gln His Ala Asp Tyr Ser Trp
385                 390                 395                 400

Tyr Gln Ala Gly Ser Ala Arg Ser Gly Pro Val Thr Val Tyr Pro Tyr
                405                 410                 415

Met His Ala Leu Asp Thr Leu Phe Val Pro Leu Leu Val Gly Thr Gly
            420                 425                 430

Val Ala Leu Val Thr Gly Ala Thr Val Leu Gly Thr Ile Thr Cys Cys
        435                 440                 445

Phe Met Lys Arg Leu Arg Lys Arg
    450                 455

<210> SEQ ID NO 16
```

-continued

<211> LENGTH: 320
<212> TYPE: PRT
<213> ORGANISM: Homo sapiens

<400> SEQUENCE: 16

```
Ala His Val Asp Val Gln Thr Leu Ser Ser Gln Leu Ala Val Thr Val
1               5                   10                  15

Gly Pro Gly Glu Arg Arg Ile Gly Pro Gly Glu Pro Leu Glu Leu Leu
            20                  25                  30

Cys Asn Val Ser Gly Ala Leu Pro Pro Ala Gly Arg His Ala Ala Tyr
        35                  40                  45

Ser Val Gly Trp Glu Met Ala Pro Ala Gly Ala Pro Gly Pro Gly Arg
    50                  55                  60

Leu Val Ala Gln Leu Asp Thr Glu Gly Val Gly Ser Leu Gly Pro Gly
65                  70                  75                  80

Tyr Glu Gly Arg His Ile Ala Met Glu Lys Val Ala Ser Arg Thr Tyr
                85                  90                  95

Arg Leu Arg Leu Glu Ala Ala Arg Pro Gly Asp Ala Gly Thr Tyr Arg
            100                 105                 110

Cys Leu Ala Lys Ala Tyr Val Arg Gly Ser Gly Thr Arg Leu Arg Glu
        115                 120                 125

Ala Ala Ser Ala Arg Ser Arg Pro Leu Pro Val His Val Arg Glu Glu
    130                 135                 140

Gly Val Val Leu Glu Ala Val Ala Trp Leu Ala Gly Gly Thr Val Tyr
145                 150                 155                 160

Arg Gly Glu Thr Ala Ser Leu Leu Cys Asn Ile Ser Val Arg Gly Gly
                165                 170                 175

Pro Pro Gly Leu Arg Leu Ala Ala Ser Trp Trp Val Glu Arg Pro Glu
            180                 185                 190

Asp Gly Glu Leu Ser Ser Val Pro Ala Gln Leu Val Gly Gly Val Gly
        195                 200                 205

Gln Asp Gly Val Ala Glu Leu Gly Val Arg Pro Gly Gly Gly Pro Val
    210                 215                 220

Ser Val Glu Leu Val Gly Pro Arg Ser His Arg Leu Arg Leu His Ser
225                 230                 235                 240

Leu Gly Pro Glu Asp Glu Gly Val Tyr His Cys Ala Pro Ser Ala Trp
                245                 250                 255

Val Gln His Ala Asp Tyr Ser Trp Tyr Gln Ala Gly Ser Ala Arg Ser
            260                 265                 270

Gly Pro Val Thr Val Tyr Pro Tyr Met His Ala Leu Asp Thr Leu Phe
        275                 280                 285

Val Pro Leu Leu Val Gly Thr Gly Val Ala Leu Val Thr Gly Ala Thr
    290                 295                 300

Val Leu Gly Thr Ile Thr Cys Cys Phe Met Lys Arg Leu Arg Lys Arg
305                 310                 315                 320
```

<210> SEQ ID NO 17
<211> LENGTH: 179
<212> TYPE: PRT
<213> ORGANISM: homo sapiens

<400> SEQUENCE: 17

```
Arg Glu Glu Gly Val Val Leu Glu Ala Val Ala Trp Leu Ala Gly Gly
1               5                   10                  15

Thr Val Tyr Arg Gly Glu Thr Ala Ser Leu Leu Cys Asn Ile Ser Val
            20                  25                  30
```

```
Arg Gly Gly Pro Pro Gly Leu Arg Leu Ala Ala Ser Trp Trp Val Glu
        35                  40                  45

Arg Pro Glu Asp Gly Glu Leu Ser Ser Val Pro Ala Gln Leu Val Gly
    50                  55                  60

Gly Val Gly Gln Asp Gly Val Ala Glu Leu Gly Val Arg Pro Gly Gly
65                  70                  75                  80

Gly Pro Val Ser Val Glu Leu Val Gly Pro Arg Ser His Arg Leu Arg
                85                  90                  95

Leu His Ser Leu Gly Pro Glu Asp Glu Gly Val Tyr His Cys Ala Pro
            100                 105                 110

Ser Ala Trp Val Gln His Ala Asp Tyr Ser Trp Tyr Gln Ala Gly Ser
        115                 120                 125

Ala Arg Ser Gly Pro Val Thr Val Tyr Pro Tyr Met His Ala Leu Asp
    130                 135                 140

Thr Leu Phe Val Pro Leu Leu Val Gly Thr Gly Val Ala Leu Val Thr
145                 150                 155                 160

Gly Ala Thr Val Leu Gly Thr Ile Thr Cys Cys Phe Met Lys Arg Leu
                165                 170                 175

Arg Lys Arg


<210> SEQ ID NO 18
<211> LENGTH: 24
<212> TYPE: PRT
<213> ORGANISM: Homo sapiens

<400> SEQUENCE: 18

Val Ala Leu Val Thr Gly Ala Thr Val Leu Gly Thr Ile Thr Cys Cys
1               5                   10                  15

Phe Met Lys Arg Leu Arg Lys Arg
            20


<210> SEQ ID NO 19
<211> LENGTH: 27
<212> TYPE: PRT
<213> ORGANISM: Homo sapiens

<400> SEQUENCE: 19

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala
            20                  25


<210> SEQ ID NO 20
<211> LENGTH: 1195
<212> TYPE: PRT
<213> ORGANISM: homo sapiens

<400> SEQUENCE: 20

Met Lys Cys Phe Phe Pro Val Leu Ser Cys Leu Ala Val Leu Gly Val
1               5                   10                  15

Val Ser Ala Gln Arg Gln Val Thr Val Gln Glu Gly Pro Leu Tyr Arg
            20                  25                  30

Thr Glu Gly Ser His Ile Thr Ile Trp Cys Asn Val Ser Gly Tyr Gln
        35                  40                  45

Gly Pro Ser Glu Gln Asn Phe Gln Trp Ser Ile Tyr Leu Pro Ser Ser
    50                  55                  60

Pro Glu Arg Glu Val Gln Ile Val Ser Thr Met Asp Ser Ser Phe Pro
```

-continued

```
65                  70                  75                  80

Tyr Ala Ile Tyr Thr Gln Arg Val Arg Gly Gly Lys Ile Phe Ile Glu
                85                  90                  95

Arg Val Gln Gly Asn Ser Thr Leu Leu His Ile Thr Asp Leu Gln Ala
            100                 105                 110

Arg Asp Ala Gly Glu Tyr Glu Cys His Thr Pro Ser Thr Asp Lys Gln
        115                 120                 125

Tyr Phe Gly Ser Tyr Ser Ala Lys Met Asn Leu Val Val Ile Pro Asp
    130                 135                 140

Ser Leu Gln Thr Thr Ala Met Pro Gln Thr Leu His Arg Val Glu Gln
145                 150                 155                 160

Asp Pro Leu Glu Leu Thr Cys Glu Val Ala Ser Glu Thr Ile Gln His
                165                 170                 175

Ser His Leu Ser Val Ala Trp Leu Arg Gln Lys Val Gly Glu Lys Pro
            180                 185                 190

Val Glu Val Ile Ser Leu Ser Arg Asp Phe Met Leu His Ser Ser Ser
        195                 200                 205

Glu Tyr Ala Gln Arg Gln Ser Leu Gly Glu Val Arg Leu Asp Lys Leu
    210                 215                 220

Gly Arg Thr Thr Phe Arg Leu Thr Ile Phe His Leu Gln Pro Ser Asp
225                 230                 235                 240

Gln Gly Glu Phe Tyr Cys Glu Ala Ala Glu Trp Ile Gln Asp Pro Asp
                245                 250                 255

Gly Ser Trp Tyr Ala Met Thr Arg Lys Arg Ser Glu Gly Ala Val Val
            260                 265                 270

Asn Val Gln Pro Thr Asp Lys Glu Phe Thr Val Arg Leu Glu Thr Glu
        275                 280                 285

Lys Arg Leu His Thr Val Gly Glu Pro Val Glu Phe Arg Cys Ile Leu
    290                 295                 300

Glu Ala Gln Asn Val Pro Asp Arg Tyr Phe Ala Val Ser Trp Ala Phe
305                 310                 315                 320

Asn Ser Ser Leu Ile Ala Thr Met Gly Pro Asn Ala Val Pro Val Leu
                325                 330                 335

Asn Ser Glu Phe Ala His Arg Glu Ala Arg Gly Gln Leu Lys Val Ala
            340                 345                 350

Lys Glu Ser Asp Ser Val Phe Val Leu Lys Ile Tyr His Leu Arg Gln
        355                 360                 365

Glu Asp Ser Gly Lys Tyr Asn Cys Arg Val Thr Glu Arg Glu Lys Thr
    370                 375                 380

Val Thr Gly Glu Phe Ile Asp Lys Glu Ser Lys Arg Pro Lys Asn Ile
385                 390                 395                 400

Pro Ile Ile Val Leu Pro Leu Lys Ser Ser Ile Ser Val Glu Val Ala
                405                 410                 415

Ser Asn Ala Ser Val Ile Leu Glu Gly Glu Asp Leu Arg Phe Ser Cys
            420                 425                 430

Ser Val Arg Thr Ala Gly Arg Pro Gln Gly Arg Phe Ser Val Ile Trp
        435                 440                 445

Gln Leu Val Asp Arg Gln Asn Arg Arg Ser Asn Ile Met Trp Leu Asp
    450                 455                 460

Arg Asp Gly Thr Val Gln Pro Gly Ser Ser Tyr Trp Glu Arg Ser Ser
465                 470                 475                 480

Phe Gly Gly Val Gln Met Glu Gln Val Gln Pro Asn Ser Phe Ser Leu
                485                 490                 495
```

-continued

```
Gly Ile Phe Asn Ser Arg Lys Glu Asp Glu Gly Gln Tyr Glu Cys His
            500                 505                 510

Val Thr Glu Trp Val Arg Ala Val Asp Gly Glu Trp Gln Ile Val Gly
        515                 520                 525

Glu Arg Arg Ala Ser Thr Pro Ile Ser Ile Thr Ala Leu Glu Met Gly
    530                 535                 540

Phe Ala Val Thr Ala Ile Ser Arg Thr Pro Gly Val Thr Tyr Ser Asp
545                 550                 555                 560

Ser Phe Asp Leu Gln Cys Ile Ile Lys Pro His Tyr Pro Ala Trp Val
                565                 570                 575

Pro Val Ser Val Thr Trp Arg Phe Gln Pro Val Gly Thr Val Glu Phe
            580                 585                 590

His Asp Leu Val Thr Phe Thr Arg Asp Gly Gly Val Gln Trp Gly Asp
        595                 600                 605

Arg Ser Ser Ser Phe Arg Thr Arg Thr Ala Ile Glu Lys Ala Glu Ser
    610                 615                 620

Ser Asn Asn Val Arg Leu Ser Ile Ser Arg Ala Ser Asp Thr Glu Ala
625                 630                 635                 640

Gly Lys Tyr Gln Cys Val Ala Glu Leu Trp Arg Lys Asn Tyr Asn Asn
                645                 650                 655

Thr Trp Thr Arg Leu Ala Glu Arg Thr Ser Asn Leu Leu Glu Ile Arg
            660                 665                 670

Val Leu Gln Pro Val Thr Lys Leu Gln Val Ser Lys Ser Lys Arg Thr
        675                 680                 685

Leu Thr Leu Val Glu Asn Lys Pro Ile Gln Leu Asn Cys Ser Val Lys
    690                 695                 700

Ser Gln Thr Ser Gln Asn Ser His Phe Ala Val Leu Trp Tyr Val His
705                 710                 715                 720

Lys Pro Ser Asp Ala Asp Gly Lys Leu Ile Leu Lys Thr Thr His Asn
                725                 730                 735

Ser Ala Phe Glu Tyr Gly Thr Tyr Ala Glu Glu Glu Gly Leu Arg Ala
            740                 745                 750

Arg Leu Gln Phe Glu Arg His Val Ser Gly Gly Leu Phe Ser Leu Thr
        755                 760                 765

Val Gln Arg Ala Glu Val Ser Asp Ser Gly Ser Tyr Tyr Cys His Val
    770                 775                 780

Glu Glu Trp Leu Leu Ser Pro Asn Tyr Ala Trp Tyr Lys Leu Ala Glu
785                 790                 795                 800

Glu Val Ser Gly Arg Thr Glu Val Thr Val Lys Gln Pro Asp Ser Arg
                805                 810                 815

Leu Arg Leu Ser Gln Ala Gln Gly Asn Leu Ser Val Leu Glu Thr Arg
            820                 825                 830

Gln Val Gln Leu Glu Cys Val Val Leu Asn Arg Thr Ser Ile Thr Ser
        835                 840                 845

Gln Leu Met Val Glu Trp Phe Val Trp Lys Pro Asn His Pro Glu Arg
    850                 855                 860

Glu Thr Val Ala Arg Leu Ser Arg Asp Ala Thr Phe His Tyr Gly Glu
865                 870                 875                 880

Gln Ala Ala Lys Asn Asn Leu Lys Gly Arg Leu His Leu Glu Ser Pro
                885                 890                 895

Ser Pro Gly Val Tyr Arg Leu Phe Ile Gln Asn Val Ala Val Gln Asp
            900                 905                 910
```

-continued

```
Ser Gly Thr Tyr Ser Cys His Val Glu Glu Trp Leu Pro Ser Pro Ser
        915                 920                 925

Gly Met Trp Tyr Lys Arg Ala Glu Asp Thr Ala Gly Gln Thr Ala Leu
    930                 935                 940

Thr Val Met Arg Pro Asp Ala Ser Leu Gln Val Asp Thr Val Val Pro
945                 950                 955                 960

Asn Ala Thr Val Ser Glu Lys Ala Ala Phe Gln Leu Asp Cys Ser Ile
                965                 970                 975

Val Ser Arg Ser Ser Gln Asp Ser Arg Phe Ala Val Ala Trp Tyr Ser
            980                 985                 990

Leu Arg Thr Lys Ala Gly Gly Lys  Arg Ser Ser Pro Gly  Leu Glu Glu
        995                 1000                 1005

Gln Glu  Glu Glu Arg Glu Glu  Glu Glu Glu Glu Glu  Glu Asp Asp
    1010                 1015                 1020

Asp Asp  Asp Asp Pro Thr Glu  Arg Thr Ala Leu Leu  Ser Val Gly
    1025                 1030                 1035

Pro Asp  Ala Val Phe Gly Pro  Glu Gly Ser Pro Trp  Glu Gly Arg
    1040                 1045                 1050

Leu Arg  Phe Gln Arg Leu Ser  Pro Val Leu Tyr Arg  Leu Thr Val
    1055                 1060                 1065

Leu Gln  Ala Ser Pro Gln Asp  Thr Gly Asn Tyr Ser  Cys His Val
    1070                 1075                 1080

Glu Glu  Trp Leu Pro Ser Pro  Gln Lys Glu Trp Tyr  Arg Leu Thr
    1085                 1090                 1095

Glu Glu  Glu Ser Ala Pro Ile  Gly Ile Arg Val Leu  Asp Thr Ser
    1100                 1105                 1110

Pro Thr  Leu Gln Ser Ile Ile  Cys Ser Asn Asp Ala  Leu Phe Tyr
    1115                 1120                 1125

Phe Val  Phe Phe Tyr Pro Phe  Pro Ile Phe Gly Ile  Leu Ile Ile
    1130                 1135                 1140

Thr Ile  Leu Leu Val Arg Phe  Lys Ser Arg Asn Ser  Ser Lys Asn
    1145                 1150                 1155

Ser Asp  Gly Lys Asn Gly Val  Pro Leu Leu Trp Ile  Lys Glu Pro
    1160                 1165                 1170

His Leu  Asn Tyr Ser Pro Thr  Cys Leu Glu Pro Pro  Val Leu Ser
    1175                 1180                 1185

Ile His  Pro Gly Ala Ile Asp
    1190                 1195
```

<210> SEQ ID NO 21
<211> LENGTH: 798
<212> TYPE: PRT
<213> ORGANISM: homo sapiens

<400> SEQUENCE: 21

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80
```

-continued

```
Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495
```

Gly Arg His Cys Glu Cys Ser Thr Asp Glu Val Asn Ser Glu Asp Met
500 505 510

Asp Ala Tyr Cys Arg Lys Glu Asn Ser Ser Glu Ile Cys Ser Asn Asn
515 520 525

Gly Glu Cys Val Cys Gly Gln Cys Val Cys Arg Lys Arg Asp Asn Thr
530 535 540

Asn Glu Ile Tyr Ser Gly Lys Phe Cys Glu Cys Asp Asn Phe Asn Cys
545 550 555 560

Asp Arg Ser Asn Gly Leu Ile Cys Gly Gly Asn Gly Val Cys Lys Cys
565 570 575

Arg Val Cys Glu Cys Asn Pro Asn Tyr Thr Gly Ser Ala Cys Asp Cys
580 585 590

Ser Leu Asp Thr Ser Thr Cys Glu Ala Ser Asn Gly Gln Ile Cys Asn
595 600 605

Gly Arg Gly Ile Cys Glu Cys Gly Val Cys Lys Cys Thr Asp Pro Lys
610 615 620

Phe Gln Gly Gln Thr Cys Glu Met Cys Gln Thr Cys Leu Gly Val Cys
625 630 635 640

Ala Glu His Lys Glu Cys Val Gln Cys Arg Ala Phe Asn Lys Gly Glu
645 650 655

Lys Lys Asp Thr Cys Thr Gln Glu Cys Ser Tyr Phe Asn Ile Thr Lys
660 665 670

Val Glu Ser Arg Asp Lys Leu Pro Gln Pro Val Gln Pro Asp Pro Val
675 680 685

Ser His Cys Lys Glu Lys Asp Val Asp Asp Cys Trp Phe Tyr Phe Thr
690 695 700

Tyr Ser Val Asn Gly Asn Asn Glu Val Met Val His Val Val Glu Asn
705 710 715 720

Pro Glu Cys Pro Thr Gly Pro Asp Ile Ile Pro Ile Val Ala Gly Val
725 730 735

Val Ala Gly Ile Val Leu Ile Gly Leu Ala Leu Leu Leu Ile Trp Lys
740 745 750

Leu Leu Met Ile Ile His Asp Arg Arg Glu Phe Ala Lys Phe Glu Lys
755 760 765

Glu Lys Met Asn Ala Lys Trp Asp Thr Gly Glu Asn Pro Ile Tyr Lys
770 775 780

Ser Ala Val Thr Thr Val Val Asn Pro Lys Tyr Glu Gly Lys
785 790 795

<210> SEQ ID NO 22
<211> LENGTH: 1032
<212> TYPE: PRT
<213> ORGANISM: homo sapiens

<400> SEQUENCE: 22

Met Ala Trp Glu Ala Arg Arg Glu Pro Gly Pro Arg Arg Ala Ala Val
1 5 10 15

Arg Glu Thr Val Met Leu Leu Leu Cys Leu Gly Val Pro Thr Gly Arg
20 25 30

Pro Tyr Asn Val Asp Thr Glu Ser Ala Leu Leu Tyr Gln Gly Pro His
35 40 45

Asn Thr Leu Phe Gly Tyr Ser Val Val Leu His Ser His Gly Ala Asn
50 55 60

Arg Trp Leu Leu Val Gly Ala Pro Thr Ala Asn Trp Leu Ala Asn Ala
65 70 75 80

```
Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495
```

```
Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

Ser Pro Gln Thr Asp Lys Leu Phe Asn Ile Leu Asp Val Gln Thr Thr
        835                 840                 845

Thr Gly Glu Cys His Phe Glu Asn Tyr Gln Arg Val Cys Ala Leu Glu
    850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
```

```
        915                 920                 925

Asp Glu Thr Ser Ala Leu Lys Phe Glu Ile Arg Ala Thr Gly Phe Pro
    930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
            980                 985                 990

Leu Leu Ile Ser Tyr Val Met Trp  Lys Ala Gly Phe Phe  Lys Arg Gln
        995                 1000                1005

Tyr Lys  Ser Ile Leu Gln Glu  Glu Asn Arg Arg Asp  Ser Trp Ser
    1010                1015                1020

Tyr Ile  Asn Ser Lys Ser Asn  Asp Asp
    1025                1030


<210> SEQ ID NO 23
<211> LENGTH: 660
<212> TYPE: PRT
<213> ORGANISM: homo sapiens

<400> SEQUENCE: 23

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Leu Gly Ser His Cys Val Ala Gln Thr Gly
        35                  40                  45

Leu Glu Leu Leu Ala Ser Gly Asp Pro Leu Pro Ser Ala Ser Gln Asn
    50                  55                  60

Ala Glu Met Ile Glu Thr Gly Ser Asp Cys Val Thr Gln Ala Gly Leu
65                  70                  75                  80

Gln Leu Leu Ala Ser Ser Asp Pro Pro Ala Leu Ala Ser Lys Asn Ala
                85                  90                  95

Glu Val Thr Glu Thr Gly Phe His His Val Ser Gln Ala Asp Ile Glu
            100                 105                 110

Phe Leu Thr Ser Ile Asp Pro Thr Ala Ser Ala Ser Gly Ser Ala Gly
        115                 120                 125

Ile Thr Gly Thr Met Ser Gln Asp Thr Glu Val Asp Met Lys Glu Val
    130                 135                 140

Glu Leu Asn Glu Leu Glu Pro Glu Lys Gln Pro Met Asn Ala Ala Ser
145                 150                 155                 160

Gly Ala Ala Met Ser Leu Ala Gly Ala Glu Lys Asn Gly Leu Val Lys
                165                 170                 175

Ile Lys Val Ala Glu Asp Glu Ala Glu Ala Ala Ala Ala Ala Lys Phe
            180                 185                 190

Thr Gly Leu Ser Lys Glu Glu Leu Leu Lys Val Ala Gly Ser Pro Gly
        195                 200                 205

Trp Val Arg Thr Arg Trp Ala Leu Leu Leu Leu Phe Trp Leu Gly Trp
    210                 215                 220

Leu Gly Met Leu Ala Gly Ala Val Val Ile Ile Val Arg Ala Pro Arg
225                 230                 235                 240

Cys Arg Glu Leu Pro Ala Gln Lys Trp Trp His Thr Gly Ala Leu Tyr
                245                 250                 255
```

-continued

```
Arg Ile Gly Asp Leu Gln Ala Phe Gln Gly His Gly Ala Gly Asn Leu
            260                 265                 270

Ala Gly Leu Lys Gly Arg Leu Asp Tyr Leu Ser Ser Leu Lys Val Lys
        275                 280                 285

Gly Leu Val Leu Gly Pro Ile His Lys Asn Gln Lys Asp Asp Val Ala
    290                 295                 300

Gln Thr Asp Leu Leu Gln Ile Asp Pro Asn Phe Gly Ser Lys Glu Asp
305                 310                 315                 320

Phe Asp Ser Leu Leu Gln Ser Ala Lys Lys Lys Ser Ile Arg Val Ile
                325                 330                 335

Leu Asp Leu Thr Pro Asn Tyr Arg Gly Glu Asn Ser Trp Phe Ser Thr
            340                 345                 350

Gln Val Asp Thr Val Ala Thr Lys Val Lys Asp Ala Leu Glu Phe Trp
        355                 360                 365

Leu Gln Ala Gly Val Asp Gly Phe Gln Val Arg Asp Ile Glu Asn Leu
    370                 375                 380

Lys Asp Ala Ser Ser Phe Leu Ala Glu Trp Gln Asn Ile Thr Lys Gly
385                 390                 395                 400

Phe Ser Glu Asp Arg Leu Leu Ile Ala Gly Thr Asn Ser Ser Asp Leu
                405                 410                 415

Gln Gln Ile Leu Ser Leu Leu Glu Ser Asn Lys Asp Leu Leu Leu Thr
            420                 425                 430

Ser Ser Tyr Leu Ser Asp Ser Gly Ser Thr Gly Glu His Thr Lys Ser
        435                 440                 445

Leu Val Thr Gln Tyr Leu Asn Ala Thr Gly Asn Arg Trp Cys Ser Trp
    450                 455                 460

Ser Leu Ser Gln Ala Arg Leu Leu Thr Ser Phe Leu Pro Ala Gln Leu
465                 470                 475                 480

Leu Arg Leu Tyr Gln Leu Met Leu Phe Thr Leu Pro Gly Thr Pro Val
                485                 490                 495

Phe Ser Tyr Gly Asp Glu Ile Gly Leu Asp Ala Ala Ala Leu Pro Gly
            500                 505                 510

Gln Pro Met Glu Ala Pro Val Met Leu Trp Asp Glu Ser Ser Phe Pro
        515                 520                 525

Asp Ile Pro Gly Ala Val Ser Ala Asn Met Thr Val Lys Gly Gln Ser
    530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
            580                 585                 590

Arg Phe Leu Val Val Leu Asn Phe Gly Asp Val Gly Leu Ser Ala Gly
        595                 600                 605

Leu Gln Ala Ser Asp Leu Pro Ala Ser Ala Ser Leu Pro Ala Lys Ala
    610                 615                 620

Asp Leu Leu Leu Ser Thr Gln Pro Gly Arg Glu Glu Gly Ser Pro Leu
625                 630                 635                 640

Glu Leu Glu Arg Leu Lys Leu Glu Pro His Glu Gly Leu Leu Leu Arg
                645                 650                 655

Phe Pro Tyr Ala
            660
```

<210> SEQ ID NO 24
<211> LENGTH: 1023
<212> TYPE: PRT
<213> ORGANISM: homo sapiens

<400> SEQUENCE: 24

```
Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Glu Pro Gln Asn Asp
        115                 120                 125

Asn Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
    210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
        275                 280                 285

Glu His Phe Ile His Ile Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
    370                 375                 380
```

-continued

```
Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Leu Cys Cys
    450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510

Arg Ile Leu Asp Arg Cys Ser Ser Ile Leu Leu His Gly Lys Glu Gln
        515                 520                 525

Pro Leu Asp Glu Glu Leu Lys Asp Ala Phe Gln Asn Ala Tyr Leu Glu
    530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
    610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
        675                 680                 685

Val Phe Ala Arg Thr Ser Pro Gln Gln Lys Leu Ile Ile Val Glu Gly
    690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
```

```
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val  Tyr Asp Glu Val Arg  Lys Leu Ile
        995                 1000                1005

Ile Arg  Arg Arg Pro Gly Gly  Trp Val Glu Lys Glu  Thr Tyr Tyr
    1010                1015                1020


<210> SEQ ID NO 25
<211> LENGTH: 1020
<212> TYPE: PRT
<213> ORGANISM: homo sapiens

<400> SEQUENCE: 25

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
            20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
            100                 105                 110

Tyr Gly Ile Gln Ala Ala Met Glu Asp Glu Pro Ser Asn Asp Asn Leu
        115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160
```

-continued

```
Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
            180                 185                 190

Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
    210                 215                 220

Arg Ser Pro Glu Phe Thr His Glu Asn Pro Leu Glu Thr Arg Asn Ile
225                 230                 235                 240

Cys Phe Phe Ser Thr Asn Cys Val Glu Gly Thr Ala Arg Gly Ile Val
                245                 250                 255

Ile Ala Thr Gly Asp Arg Thr Val Met Gly Arg Ile Ala Thr Leu Ala
            260                 265                 270

Ser Gly Leu Glu Val Gly Arg Thr Pro Ile Ala Met Glu Ile Glu His
        275                 280                 285

Phe Ile Gln Leu Ile Thr Gly Val Ala Val Phe Leu Gly Val Ser Phe
    290                 295                 300

Phe Val Leu Ser Leu Ile Leu Gly Tyr Ser Trp Leu Glu Ala Val Ile
305                 310                 315                 320

Phe Leu Ile Gly Ile Ile Val Ala Asn Val Pro Glu Gly Leu Leu Ala
                325                 330                 335

Thr Val Thr Val Cys Leu Thr Leu Thr Ala Lys Arg Met Ala Arg Lys
            340                 345                 350

Asn Cys Leu Val Lys Asn Leu Glu Ala Val Glu Thr Leu Gly Ser Thr
        355                 360                 365

Ser Thr Ile Cys Ser Asp Lys Thr Gly Thr Leu Thr Gln Asn Arg Met
    370                 375                 380

Thr Val Ala His Met Trp Phe Asp Asn Gln Ile His Glu Ala Asp Thr
385                 390                 395                 400

Thr Glu Asp Gln Ser Gly Ala Thr Phe Asp Lys Arg Ser Pro Thr Trp
                405                 410                 415

Thr Ala Leu Ser Arg Ile Ala Gly Leu Cys Asn Arg Ala Val Phe Lys
            420                 425                 430

Ala Gly Gln Glu Asn Ile Ser Val Ser Lys Arg Asp Thr Ala Gly Asp
        435                 440                 445

Ala Ser Glu Ser Ala Leu Leu Lys Cys Ile Glu Leu Ser Cys Gly Ser
    450                 455                 460

Val Arg Lys Met Arg Asp Arg Asn Pro Lys Val Ala Glu Ile Pro Phe
465                 470                 475                 480

Asn Ser Thr Asn Lys Tyr Gln Leu Ser Ile His Glu Arg Glu Asp Ser
                485                 490                 495

Pro Gln Ser His Val Leu Val Met Lys Gly Ala Pro Glu Arg Ile Leu
            500                 505                 510

Asp Arg Cys Ser Thr Ile Leu Val Gln Gly Lys Glu Ile Pro Leu Asp
        515                 520                 525

Lys Glu Met Gln Asp Ala Phe Gln Asn Ala Tyr Met Glu Leu Gly Gly
    530                 535                 540

Leu Gly Glu Arg Val Leu Gly Phe Cys Gln Leu Asn Leu Pro Ser Gly
545                 550                 555                 560

Lys Phe Pro Arg Gly Phe Lys Phe Asp Thr Asp Glu Leu Asn Phe Pro
                565                 570                 575

Thr Glu Lys Leu Cys Phe Val Gly Leu Met Ser Met Ile Asp Pro Pro
```

```
            580                 585                 590

Arg Ala Ala Val Pro Asp Ala Val Gly Lys Cys Arg Ser Ala Gly Ile
        595                 600                 605

Lys Val Ile Met Val Thr Gly Asp His Pro Ile Thr Ala Lys Ala Ile
    610                 615                 620

Ala Lys Gly Val Gly Ile Ile Ser Glu Gly Asn Glu Thr Val Glu Asp
625                 630                 635                 640

Ile Ala Ala Arg Leu Asn Ile Pro Met Ser Gln Val Asn Pro Arg Glu
                645                 650                 655

Ala Lys Ala Cys Val Val His Gly Ser Asp Leu Lys Asp Met Thr Ser
            660                 665                 670

Glu Gln Leu Asp Glu Ile Leu Lys Asn His Thr Glu Ile Val Phe Ala
        675                 680                 685

Arg Thr Ser Pro Gln Gln Lys Leu Ile Ile Val Glu Gly Cys Gln Arg
    690                 695                 700

Gln Gly Ala Ile Val Ala Val Thr Gly Asp Gly Val Asn Asp Ser Pro
705                 710                 715                 720

Ala Leu Lys Lys Ala Asp Ile Gly Ile Ala Met Gly Ile Ser Gly Ser
                725                 730                 735

Asp Val Ser Lys Gln Ala Ala Asp Met Ile Leu Leu Asp Asp Asn Phe
            740                 745                 750

Ala Ser Ile Val Thr Gly Val Glu Glu Gly Arg Leu Ile Phe Asp Asn
        755                 760                 765

Leu Lys Lys Ser Ile Ala Tyr Thr Leu Thr Ser Asn Ile Pro Glu Ile
    770                 775                 780

Thr Pro Phe Leu Leu Phe Ile Ile Ala Asn Ile Pro Leu Pro Leu Gly
785                 790                 795                 800

Thr Val Thr Ile Leu Cys Ile Asp Leu Gly Thr Asp Met Val Pro Ala
                805                 810                 815

Ile Ser Leu Ala Tyr Glu Ala Ala Glu Ser Asp Ile Met Lys Arg Gln
            820                 825                 830

Pro Arg Asn Ser Gln Thr Asp Lys Leu Val Asn Glu Arg Leu Ile Ser
        835                 840                 845

Met Ala Tyr Gly Gln Ile Gly Met Ile Gln Ala Leu Gly Gly Phe Phe
    850                 855                 860

Thr Tyr Phe Val Ile Leu Ala Glu Asn Gly Phe Leu Pro Ser Arg Leu
865                 870                 875                 880

Leu Gly Ile Arg Leu Asp Trp Asp Asp Arg Thr Met Asn Asp Leu Glu
                885                 890                 895

Asp Ser Tyr Gly Gln Glu Trp Thr Tyr Glu Gln Arg Lys Val Val Glu
            900                 905                 910

Phe Thr Cys His Thr Ala Phe Phe Ala Ser Ile Val Val Val Gln Trp
        915                 920                 925

Ala Asp Leu Ile Ile Cys Lys Thr Arg Arg Asn Ser Val Phe Gln Gln
    930                 935                 940

Gly Met Lys Asn Lys Ile Leu Ile Phe Gly Leu Leu Glu Glu Thr Ala
945                 950                 955                 960

Leu Ala Ala Phe Leu Ser Tyr Cys Pro Gly Met Gly Val Ala Leu Arg
                965                 970                 975

Met Tyr Pro Leu Lys Val Thr Trp Trp Phe Cys Ala Phe Pro Tyr Ser
            980                 985                 990

Leu Leu Ile Phe Ile Tyr Asp Glu  Val Arg Lys Leu Ile  Leu Arg Arg
        995                 1000                 1005
```

```
Tyr Pro  Gly Gly Trp Val Glu  Lys Glu Thr Tyr Tyr
    1010                 1015                1020


<210> SEQ ID NO 26
<211> LENGTH: 1026
<212> TYPE: PRT
<213> ORGANISM: homo sapiens

<400> SEQUENCE: 26

Met Gly Ser Gly Gly Ser Asp Ser Tyr Arg Ile Ala Thr Ser Gln Asp
1               5                   10                  15

Lys Lys Asp Asp Lys Asp Ser Pro Lys Lys Asn Lys Gly Lys Glu Arg
            20                  25                  30

Arg Asp Leu Asp Asp Leu Lys Lys Glu Val Ala Met Thr Glu His Lys
        35                  40                  45

Met Ser Val Glu Glu Val Cys Arg Lys Tyr Asn Thr Asp Cys Val Gln
    50                  55                  60

Gly Leu Thr His Ser Lys Ala Gln Glu Ile Leu Ala Arg Asp Gly Pro
65                  70                  75                  80

Asn Ala Leu Thr Pro Pro Pro Thr Thr Pro Glu Trp Val Lys Phe Cys
                85                  90                  95

Arg Gln Leu Phe Gly Gly Phe Ser Ile Leu Leu Trp Ile Gly Ala Ile
            100                 105                 110

Leu Cys Phe Leu Ala Tyr Gly Ile Gln Ala Gly Thr Glu Asp Asp Pro
        115                 120                 125

Ser Gly Asp Asn Leu Tyr Leu Gly Ile Val Leu Ala Ala Val Val Ile
    130                 135                 140

Ile Thr Gly Cys Phe Ser Tyr Tyr Gln Glu Ala Lys Ser Ser Lys Ile
145                 150                 155                 160

Met Glu Ser Phe Lys Asn Met Val Pro Gln Gln Ala Leu Val Ile Arg
                165                 170                 175

Glu Gly Glu Lys Met Gln Val Asn Ala Glu Glu Val Val Val Gly Asp
            180                 185                 190

Leu Val Glu Ile Lys Gly Gly Asp Arg Val Pro Ala Asp Leu Arg Ile
        195                 200                 205

Ile Ser Ala His Gly Cys Lys Val Asp Asn Ser Ser Leu Thr Gly Glu
    210                 215                 220

Ser Glu Pro Gln Thr Arg Ser Pro Asp Cys Thr His Asp Asn Pro Leu
225                 230                 235                 240

Glu Thr Arg Asn Ile Thr Phe Phe Ser Thr Asn Cys Val Glu Gly Thr
                245                 250                 255

Ala Arg Gly Val Val Val Ala Thr Gly Asp Arg Thr Val Met Gly Arg
            260                 265                 270

Ile Ala Thr Leu Ala Ser Gly Leu Glu Val Gly Lys Thr Pro Ile Ala
        275                 280                 285

Ile Glu Ile Glu His Phe Ile Gln Leu Ile Thr Gly Val Ala Val Phe
    290                 295                 300

Leu Gly Val Ser Phe Phe Ile Leu Ser Leu Ile Leu Gly Tyr Thr Trp
305                 310                 315                 320

Leu Glu Ala Val Ile Phe Leu Ile Gly Ile Ile Val Ala Asn Val Pro
                325                 330                 335

Glu Gly Leu Leu Ala Thr Val Thr Val Cys Leu Thr Leu Thr Ala Lys
            340                 345                 350

Arg Met Ala Arg Lys Asn Cys Leu Val Lys Asn Leu Glu Ala Val Glu
```

-continued

```
        355                 360                 365

Thr Leu Gly Ser Thr Ser Thr Ile Cys Ser Asp Lys Thr Gly Thr Leu
    370                 375                 380

Thr Gln Asn Arg Met Thr Val Ala His Met Trp Phe Asp Asn Gln Ile
385                 390                 395                 400

His Glu Ala Asp Thr Thr Glu Asp Gln Ser Gly Thr Ser Phe Asp Lys
                405                 410                 415

Ser Ser His Thr Trp Val Ala Leu Ser His Ile Ala Gly Leu Cys Asn
            420                 425                 430

Arg Ala Val Phe Lys Gly Gly Gln Asp Asn Ile Pro Val Leu Lys Arg
        435                 440                 445

Asp Val Ala Gly Asp Ala Ser Glu Ser Ala Leu Leu Lys Cys Ile Glu
    450                 455                 460

Leu Ser Ser Gly Ser Val Lys Leu Met Arg Glu Arg Asn Lys Lys Val
465                 470                 475                 480

Ala Glu Ile Pro Phe Asn Ser Thr Asn Lys Tyr Gln Leu Ser Ile His
                485                 490                 495

Glu Thr Glu Asp Pro Asn Asp Asn Arg Tyr Leu Leu Val Met Lys Gly
            500                 505                 510

Ala Pro Glu Arg Ile Leu Asp Arg Cys Ser Thr Ile Leu Leu Gln Gly
        515                 520                 525

Lys Glu Gln Pro Leu Asp Glu Glu Met Lys Glu Ala Phe Gln Asn Ala
    530                 535                 540

Tyr Leu Glu Leu Gly Gly Leu Gly Glu Arg Val Leu Gly Phe Cys His
545                 550                 555                 560

Tyr Tyr Leu Pro Glu Glu Gln Phe Pro Lys Gly Phe Ala Phe Asp Cys
                565                 570                 575

Asp Asp Val Asn Phe Thr Thr Asp Asn Leu Cys Phe Val Gly Leu Met
            580                 585                 590

Ser Met Ile Asp Pro Pro Arg Ala Ala Val Pro Asp Ala Val Gly Lys
        595                 600                 605

Cys Arg Ser Ala Gly Ile Lys Val Ile Met Val Thr Gly Asp His Pro
    610                 615                 620

Ile Thr Ala Lys Ala Ile Ala Lys Gly Val Gly Ile Ile Ser Glu Gly
625                 630                 635                 640

Asn Glu Thr Val Glu Asp Ile Ala Ala Arg Leu Asn Ile Pro Val Ser
                645                 650                 655

Gln Val Asn Pro Arg Asp Ala Lys Ala Cys Val Ile His Gly Thr Asp
            660                 665                 670

Leu Lys Asp Phe Thr Ser Glu Gln Ile Asp Glu Ile Leu Gln Asn His
        675                 680                 685

Thr Glu Ile Val Phe Ala Arg Thr Ser Pro Gln Gln Lys Leu Ile Ile
    690                 695                 700

Val Glu Gly Cys Gln Arg Gln Gly Ala Ile Val Ala Val Thr Gly Asp
705                 710                 715                 720

Gly Val Asn Asp Ser Pro Ala Leu Lys Lys Ala Asp Ile Gly Val Ala
                725                 730                 735

Met Gly Ile Ala Gly Ser Asp Val Ser Lys Gln Ala Ala Asp Met Ile
            740                 745                 750

Leu Leu Asp Asp Asn Phe Ala Ser Ile Val Thr Gly Val Glu Glu Gly
        755                 760                 765

Arg Leu Ile Phe Asp Asn Leu Lys Lys Ser Ile Ala Tyr Thr Leu Thr
    770                 775                 780
```

```
Ser Asn Ile Pro Glu Ile Thr Pro Phe Leu Leu Phe Ile Met Ala Asn
785                 790                 795                 800

Ile Pro Leu Pro Leu Gly Thr Ile Thr Ile Leu Cys Ile Asp Leu Gly
                805                 810                 815

Thr Asp Met Val Pro Ala Ile Ser Leu Ala Tyr Glu Ala Ala Glu Ser
            820                 825                 830

Asp Ile Met Lys Arg Gln Pro Arg Asn Pro Arg Thr Asp Lys Leu Val
        835                 840                 845

Asn Glu Arg Leu Ile Ser Met Ala Tyr Gly Gln Ile Gly Met Ile Gln
    850                 855                 860

Ala Leu Gly Gly Phe Phe Ser Tyr Phe Val Ile Leu Ala Glu Asn Gly
865                 870                 875                 880

Phe Leu Pro Gly Asn Leu Val Gly Ile Arg Leu Asn Trp Asp Asp Arg
                885                 890                 895

Thr Val Asn Asp Leu Glu Asp Ser Tyr Gly Gln Gln Trp Thr Tyr Glu
            900                 905                 910

Gln Arg Lys Val Val Glu Phe Thr Cys His Thr Ala Phe Phe Val Ser
        915                 920                 925

Ile Val Val Val Gln Trp Ala Asp Leu Ile Ile Cys Lys Thr Arg Arg
    930                 935                 940

Asn Ser Val Phe Gln Gln Gly Met Lys Asn Lys Ile Leu Ile Phe Gly
945                 950                 955                 960

Leu Phe Glu Glu Thr Ala Leu Ala Ala Phe Leu Ser Tyr Cys Pro Gly
                965                 970                 975

Met Asp Val Ala Leu Arg Met Tyr Pro Leu Lys Pro Ser Trp Trp Phe
            980                 985                 990

Cys Ala Phe Pro Tyr Ser Phe Leu  Ile Phe Val Tyr Asp  Glu Ile Arg
        995                 1000                1005

Lys Leu  Ile Leu Arg Arg Asn  Pro Gly Gly Trp Val  Glu Lys Glu
    1010                1015                1020

Thr Tyr  Tyr
    1025


<210> SEQ ID NO 27
<211> LENGTH: 1029
<212> TYPE: PRT
<213> ORGANISM: Homo sapiens

<400> SEQUENCE: 27

Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Lys Met Val Lys
            20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Pro Thr Thr Pro Glu
                85                  90                  95

Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
```

-continued

```
        115                 120                 125

Phe Asn Glu Glu Pro Thr Lys Asp Asn Leu Tyr Leu Ser Ile Val Leu
    130                 135                 140

Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
                165                 170                 175

Ala Leu Val Ile Arg Gly Gly Glu Lys Met Gln Ile Asn Val Gln Glu
            180                 185                 190

Val Val Leu Gly Asp Leu Val Glu Ile Lys Gly Gly Asp Arg Val Pro
        195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
        275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu
            340                 345                 350

Thr Leu Thr Ala Lys Arg Met Ala Arg Lys Asn Cys Leu Val Lys Asn
        355                 360                 365

Leu Glu Ala Val Glu Thr Leu Gly Ser Thr Ser Thr Ile Cys Ser Asp
    370                 375                 380

Lys Thr Gly Thr Leu Thr Gln Asn Arg Met Thr Val Ala His Met Trp
385                 390                 395                 400

Phe Asp Met Thr Val Tyr Glu Ala Asp Thr Thr Glu Glu Gln Thr Gly
                405                 410                 415

Lys Thr Phe Thr Lys Ser Ser Asp Thr Trp Phe Met Leu Ala Arg Ile
            420                 425                 430

Ala Gly Leu Cys Asn Arg Ala Asp Phe Lys Ala Asn Gln Glu Ile Leu
        435                 440                 445

Pro Ile Ala Lys Arg Ala Thr Thr Gly Asp Ala Ser Glu Ser Ala Leu
    450                 455                 460

Leu Lys Phe Ile Glu Gln Ser Tyr Ser Ser Val Ala Glu Met Arg Glu
465                 470                 475                 480

Lys Asn Pro Lys Val Ala Glu Ile Pro Phe Asn Ser Thr Asn Lys Tyr
                485                 490                 495

Gln Met Ser Ile His Leu Arg Glu Asp Ser Ser Gln Thr His Val Leu
            500                 505                 510

Met Met Lys Gly Ala Pro Glu Arg Ile Leu Glu Phe Cys Ser Thr Phe
        515                 520                 525

Leu Leu Asn Gly Gln Glu Tyr Ser Met Asn Asp Glu Met Lys Glu Ala
    530                 535                 540
```

```
Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
                565                 570                 575

Phe Asn Thr Asp Glu Ile Asn Phe Pro Met Asp Asn Leu Cys Phe Val
            580                 585                 590

Gly Leu Ile Ser Met Ile Asp Pro Pro Arg Ala Ala Val Pro Asp Ala
        595                 600                 605

Val Ser Lys Cys Arg Ser Ala Gly Ile Lys Val Ile Met Val Thr Gly
    610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Glu Val Ala Ala Arg Leu Lys Ile
                645                 650                 655

Pro Ile Ser Lys Val Asp Ala Ser Ala Ala Lys Ala Ile Val Val His
            660                 665                 670

Gly Ala Glu Leu Lys Asp Ile Gln Ser Lys Gln Leu Asp Gln Ile Leu
        675                 680                 685

Gln Asn His Pro Glu Ile Val Phe Ala Arg Thr Ser Pro Gln Gln Lys
    690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
            740                 745                 750

Asp Met Ile Leu Leu Asp Asp Asn Phe Ala Ser Ile Val Thr Gly Val
        755                 760                 765

Glu Glu Gly Arg Leu Ile Phe Asp Asn Leu Lys Lys Ser Ile Met Tyr
    770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
            820                 825                 830

Ala Glu Ser Asp Ile Met Lys Arg Leu Pro Arg Asn Pro Lys Thr Asp
        835                 840                 845

Asn Leu Val Asn His Arg Leu Ile Gly Met Ala Tyr Gly Gln Ile Gly
    850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
            900                 905                 910

Thr Tyr Glu Gln Arg Lys Val Val Glu Phe Thr Cys Gln Thr Ala Phe
        915                 920                 925

Phe Val Thr Ile Val Val Val Gln Trp Ala Asp Leu Ile Ile Ser Lys
    930                 935                 940

Thr Arg Arg Asn Ser Leu Phe Gln Gln Gly Met Arg Asn Lys Val Leu
945                 950                 955                 960
```

```
Ile Phe Gly Ile Leu Glu Glu Thr Leu Leu Ala Ala Phe Leu Ser Tyr
                965                 970                 975

Thr Pro Gly Met Asp Val Ala Leu Arg Met Tyr Pro Leu Lys Ile Thr
            980                 985                 990

Trp Trp Leu Cys Ala Ile Pro Tyr  Ser Ile Leu Ile Phe  Val Tyr Asp
        995                 1000                 1005

Glu Ile  Arg Lys Leu Leu Ile  Arg Gln His Pro Asp  Gly Trp Val
    1010                 1015                 1020

Glu Arg  Glu Thr Tyr Tyr
    1025


<210> SEQ ID NO 28
<211> LENGTH: 279
<212> TYPE: PRT
<213> ORGANISM: homo sapiens

<400> SEQUENCE: 28

Met Thr Lys Asn Glu Lys Lys Ser Leu Asn Gln Ser Leu Ala Glu Trp
1               5                   10                  15

Lys Leu Phe Ile Tyr Asn Pro Thr Thr Gly Glu Phe Leu Gly Arg Thr
            20                  25                  30

Ala Lys Ser Trp Gly Leu Ile Leu Leu Phe Tyr Leu Val Phe Tyr Gly
        35                  40                  45

Phe Leu Ala Ala Leu Phe Ser Phe Thr Met Trp Val Met Leu Gln Thr
    50                  55                  60

Leu Asn Asp Glu Val Pro Lys Tyr Arg Asp Gln Ile Pro Ser Pro Gly
65                  70                  75                  80

Leu Met Val Phe Pro Lys Pro Val Thr Ala Leu Glu Tyr Thr Phe Ser
                85                  90                  95

Arg Ser Asp Pro Thr Ser Tyr Ala Gly Tyr Ile Glu Asp Leu Lys Lys
            100                 105                 110

Phe Leu Lys Pro Tyr Thr Leu Glu Glu Gln Lys Asn Leu Thr Val Cys
        115                 120                 125

Pro Asp Gly Ala Leu Phe Glu Gln Lys Gly Pro Val Tyr Val Ala Cys
    130                 135                 140

Gln Phe Pro Ile Ser Leu Leu Gln Ala Cys Ser Gly Met Asn Asp Pro
145                 150                 155                 160

Asp Phe Gly Tyr Ser Gln Gly Asn Pro Cys Ile Leu Val Lys Met Asn
                165                 170                 175

Arg Ile Ile Gly Leu Lys Pro Glu Gly Val Pro Arg Ile Asp Cys Val
            180                 185                 190

Ser Lys Asn Glu Asp Ile Pro Asn Val Ala Val Tyr Pro His Asn Gly
        195                 200                 205

Met Ile Asp Leu Lys Tyr Phe Pro Tyr Tyr Gly Lys Lys Leu His Val
    210                 215                 220

Gly Tyr Leu Gln Pro Leu Val Ala Val Gln Val Ser Phe Ala Pro Asn
225                 230                 235                 240

Asn Thr Gly Lys Glu Val Thr Val Glu Cys Lys Ile Asp Gly Ser Ala
                245                 250                 255

Asn Leu Lys Ser Gln Asp Asp Arg Asp Lys Phe Leu Gly Arg Val Met
            260                 265                 270

Phe Lys Ile Thr Ala Arg Ala
        275


<210> SEQ ID NO 29
```

<211> LENGTH: 1258
<212> TYPE: PRT
<213> ORGANISM: Homo sapiens

<400> SEQUENCE: 29

Met Gly Asp Met Ala Asn Asn Ser Val Ala Tyr Ser Gly Val Lys Asn
1               5                   10                  15

Ser Leu Lys Glu Ala Asn His Asp Gly Asp Phe Gly Ile Thr Leu Ala
            20                  25                  30

Glu Leu Arg Ala Leu Met Glu Leu Arg Ser Thr Asp Ala Leu Arg Lys
        35                  40                  45

Ile Gln Glu Ser Tyr Gly Asp Val Tyr Gly Ile Cys Thr Lys Leu Lys
    50                  55                  60

Thr Ser Pro Asn Glu Gly Leu Ser Gly Asn Pro Ala Asp Leu Glu Arg
65                  70                  75                  80

Arg Glu Ala Val Phe Gly Lys Asn Phe Ile Pro Pro Lys Lys Pro Lys
                85                  90                  95

Thr Phe Leu Gln Leu Val Trp Glu Ala Leu Gln Asp Val Thr Leu Ile
            100                 105                 110

Ile Leu Glu Ile Ala Ala Ile Val Ser Leu Gly Leu Ser Phe Tyr Gln
        115                 120                 125

Pro Pro Glu Gly Asp Asn Ala Leu Cys Gly Glu Val Ser Val Gly Glu
    130                 135                 140

Glu Glu Gly Glu Gly Glu Thr Gly Trp Ile Glu Gly Ala Ala Ile Leu
145                 150                 155                 160

Leu Ser Val Val Cys Val Val Leu Val Thr Ala Phe Asn Asp Trp Ser
                165                 170                 175

Lys Glu Lys Gln Phe Arg Gly Leu Gln Ser Arg Ile Glu Gln Glu Gln
            180                 185                 190

Lys Phe Thr Val Ile Arg Gly Gly Gln Val Ile Gln Ile Pro Val Ala
        195                 200                 205

Asp Ile Thr Val Gly Asp Ile Ala Gln Val Lys Tyr Gly Asp Leu Leu
    210                 215                 220

Pro Ala Asp Gly Ile Leu Ile Gln Gly Asn Asp Leu Lys Ile Asp Glu
225                 230                 235                 240

Ser Ser Leu Thr Gly Glu Ser Asp His Val Lys Lys Ser Leu Asp Lys
                245                 250                 255

Asp Pro Leu Leu Leu Ser Gly Thr His Val Met Glu Gly Ser Gly Arg
            260                 265                 270

Met Val Val Thr Ala Val Gly Val Asn Ser Gln Thr Gly Ile Ile Phe
        275                 280                 285

Thr Leu Leu Gly Ala Gly Gly Glu Glu Glu Glu Lys Lys Asp Glu Lys
    290                 295                 300

Lys Lys Glu Lys Lys Asn Lys Lys Gln Asp Gly Ala Ile Glu Asn Arg
305                 310                 315                 320

Asn Lys Ala Lys Ala Gln Asp Gly Ala Ala Met Glu Met Gln Pro Leu
                325                 330                 335

Lys Ser Glu Glu Gly Gly Asp Gly Asp Glu Lys Asp Lys Lys Lys Ala
            340                 345                 350

Asn Leu Pro Lys Lys Glu Lys Ser Val Leu Gln Gly Lys Leu Thr Lys
        355                 360                 365

Leu Ala Val Gln Ile Gly Lys Ala Gly Leu Leu Met Ser Ala Ile Thr
    370                 375                 380

Val Ile Ile Leu Val Leu Tyr Phe Val Ile Asp Thr Phe Trp Val Gln

-continued

```
385                 390                 395                 400

Lys Arg Pro Trp Leu Ala Glu Cys Thr Pro Ile Tyr Ile Gln Tyr Phe
                405                 410                 415

Val Lys Phe Phe Ile Ile Gly Val Thr Val Leu Val Val Ala Val Pro
            420                 425                 430

Glu Gly Leu Pro Leu Ala Val Thr Ile Ser Leu Ala Tyr Ser Val Lys
        435                 440                 445

Lys Met Met Lys Asp Asn Asn Leu Val Arg His Leu Asp Ala Cys Glu
    450                 455                 460

Thr Met Gly Asn Ala Thr Ala Ile Cys Ser Asp Lys Thr Gly Thr Leu
465                 470                 475                 480

Thr Met Asn Arg Met Thr Val Val Gln Ala Tyr Ile Asn Glu Lys His
                485                 490                 495

Tyr Lys Lys Val Pro Glu Pro Glu Ala Ile Pro Pro Asn Ile Leu Ser
            500                 505                 510

Tyr Leu Val Thr Gly Ile Ser Val Asn Cys Ala Tyr Thr Ser Lys Ile
        515                 520                 525

Leu Pro Pro Glu Lys Glu Gly Gly Leu Pro Arg His Val Gly Asn Lys
    530                 535                 540

Thr Glu Cys Ala Leu Leu Gly Leu Leu Leu Asp Leu Lys Arg Asp Tyr
545                 550                 555                 560

Gln Asp Val Arg Asn Glu Ile Pro Glu Glu Ala Leu Tyr Lys Val Tyr
                565                 570                 575

Thr Phe Asn Ser Val Arg Lys Ser Met Ser Thr Val Leu Lys Asn Ser
            580                 585                 590

Asp Gly Ser Tyr Arg Ile Phe Ser Lys Gly Ala Ser Glu Ile Ile Leu
        595                 600                 605

Lys Lys Cys Phe Lys Ile Leu Ser Ala Asn Gly Glu Ala Lys Val Phe
    610                 615                 620

Arg Pro Arg Asp Arg Asp Asp Ile Val Lys Thr Val Ile Glu Pro Met
625                 630                 635                 640

Ala Ser Glu Gly Leu Arg Thr Ile Cys Leu Ala Phe Arg Asp Phe Pro
                645                 650                 655

Ala Gly Glu Pro Glu Pro Glu Trp Asp Asn Glu Asn Asp Ile Val Thr
            660                 665                 670

Gly Leu Thr Cys Ile Ala Val Val Gly Ile Glu Asp Pro Val Arg Pro
        675                 680                 685

Glu Val Pro Asp Ala Ile Lys Lys Cys Gln Arg Ala Gly Ile Thr Val
    690                 695                 700

Arg Met Val Thr Gly Asp Asn Ile Asn Thr Ala Arg Ala Ile Ala Thr
705                 710                 715                 720

Lys Cys Gly Ile Leu His Pro Gly Glu Asp Phe Leu Cys Leu Glu Gly
                725                 730                 735

Lys Asp Phe Asn Arg Arg Ile Arg Asn Glu Lys Gly Glu Ile Glu Gln
            740                 745                 750

Glu Arg Ile Asp Lys Ile Trp Pro Lys Leu Arg Val Leu Ala Arg Ser
        755                 760                 765

Ser Pro Thr Asp Lys His Thr Leu Val Lys Gly Ile Ile Asp Ser Thr
    770                 775                 780

Val Ser Asp Gln Arg Gln Val Val Ala Val Thr Gly Asp Gly Thr Asn
785                 790                 795                 800

Asp Gly Pro Ala Leu Lys Lys Ala Asp Val Gly Phe Ala Met Gly Ile
                805                 810                 815
```

```
Ala Gly Thr Asp Val Ala Lys Glu Ala Ser Asp Ile Ile Leu Thr Asp
            820                 825                 830

Asp Asn Phe Thr Ser Ile Val Lys Ala Val Met Trp Gly Arg Asn Val
        835                 840                 845

Tyr Asp Ser Ile Ser Lys Phe Leu Gln Phe Gln Leu Thr Val Asn Val
    850                 855                 860

Val Ala Val Ile Val Ala Phe Thr Gly Ala Cys Ile Thr Gln Asp Ser
865                 870                 875                 880

Pro Leu Lys Ala Val Gln Met Leu Trp Val Asn Leu Ile Met Asp Thr
                885                 890                 895

Leu Ala Ser Leu Ala Leu Ala Thr Glu Pro Pro Thr Glu Ser Leu Leu
            900                 905                 910

Leu Arg Lys Pro Tyr Gly Arg Asn Lys Pro Leu Ile Ser Arg Thr Met
        915                 920                 925

Met Lys Asn Ile Leu Gly His Ala Phe Tyr Gln Leu Val Val Val Phe
    930                 935                 940

Thr Leu Leu Phe Ala Gly Glu Lys Phe Phe Asp Ile Asp Ser Gly Arg
945                 950                 955                 960

Asn Ala Pro Leu His Ala Pro Pro Ser Glu His Tyr Thr Ile Val Phe
                965                 970                 975

Asn Thr Phe Val Leu Met Gln Leu Phe Asn Glu Ile Asn Ala Arg Lys
            980                 985                 990

Ile His Gly Glu Arg Asn Val Phe  Glu Gly Ile Phe Asn  Asn Ala Ile
        995                 1000                1005

Phe Cys  Thr Ile Val Leu Gly  Thr Phe Val Val Gln  Ile Ile Ile
    1010                1015                1020

Val Gln  Phe Gly Gly Lys Pro  Phe Ser Cys Ser Glu  Leu Ser Ile
    1025                1030                1035

Glu Gln  Trp Leu Trp Ser Ile  Phe Leu Gly Met Gly  Thr Leu Leu
    1040                1045                1050

Trp Gly  Gln Leu Ile Ser Thr  Ile Pro Thr Ser Arg  Leu Lys Phe
    1055                1060                1065

Leu Lys  Glu Ala Gly His Gly  Thr Gln Lys Glu Glu  Ile Pro Glu
    1070                1075                1080

Glu Glu  Leu Ala Glu Asp Val  Glu Glu Ile Asp His  Ala Glu Arg
    1085                1090                1095

Glu Leu  Arg Arg Gly Gln Ile  Leu Trp Phe Arg Gly  Leu Asn Arg
    1100                1105                1110

Ile Gln  Thr Gln Met Asp Val  Val Asn Ala Phe Gln  Ser Gly Ser
    1115                1120                1125

Ser Ile  Gln Gly Ala Leu Arg  Arg Gln Pro Ser Ile  Ala Ser Gln
    1130                1135                1140

His His  Asp Val Thr Asn Ile  Ser Thr Pro Thr His  Ile Arg Val
    1145                1150                1155

Val Asn  Ala Phe Arg Ser Ser  Leu Tyr Glu Gly Leu  Glu Lys Pro
    1160                1165                1170

Glu Ser  Arg Ser Ser Ile His  Asn Phe Met Thr His  Pro Glu Phe
    1175                1180                1185

Arg Ile  Glu Asp Ser Glu Pro  His Ile Pro Leu Ile  Asp Asp Thr
    1190                1195                1200

Asp Ala  Glu Asp Asp Ala Pro  Thr Lys Arg Asn Ser  Ser Pro Pro
    1205                1210                1215
```

```
Pro Ser  Pro Asn Lys Asn Asn  Asn Ala Val Asp Ser  Gly Ile His
    1220                 1225                1230

Leu Thr  Ile Glu Met Asn Lys  Ser Ala Thr Ser Ser  Ser Pro Gly
    1235                 1240                1245

Ser Pro  Leu His Ser Leu Glu  Thr Ser Leu
    1250                 1255


<210> SEQ ID NO 30
<211> LENGTH: 1272
<212> TYPE: PRT
<213> ORGANISM: Homo sapiens

<400> SEQUENCE: 30

Met Gly Asp Met Thr Asn Ser Asp Phe Tyr Ser Lys Asn Gln Arg Asn
1               5                   10                  15

Glu Ser Ser His Gly Gly Glu Phe Gly Cys Thr Met Glu Glu Leu Arg
            20                  25                  30

Ser Leu Met Glu Leu Arg Gly Thr Glu Ala Val Val Lys Ile Lys Glu
        35                  40                  45

Thr Tyr Gly Asp Thr Glu Ala Ile Cys Arg Arg Leu Lys Thr Ser Pro
    50                  55                  60

Val Glu Gly Leu Pro Gly Thr Ala Pro Asp Leu Glu Lys Arg Lys Gln
65                  70                  75                  80

Ile Phe Gly Gln Asn Phe Ile Pro Pro Lys Lys Pro Lys Thr Phe Leu
                85                  90                  95

Gln Leu Val Trp Glu Ala Leu Gln Asp Val Thr Leu Ile Ile Leu Glu
            100                 105                 110

Ile Ala Ala Ile Ile Ser Leu Gly Leu Ser Phe Tyr His Pro Pro Gly
        115                 120                 125

Glu Gly Asn Glu Gly Cys Ala Thr Ala Gln Gly Gly Ala Glu Asp Glu
    130                 135                 140

Gly Glu Ala Glu Ala Gly Trp Ile Glu Gly Ala Ala Ile Leu Leu Ser
145                 150                 155                 160

Val Ile Cys Val Val Leu Val Thr Ala Phe Asn Asp Trp Ser Lys Glu
                165                 170                 175

Lys Gln Phe Arg Gly Leu Gln Ser Arg Ile Glu Gln Glu Gln Lys Phe
            180                 185                 190

Thr Val Val Arg Ala Gly Gln Val Val Gln Ile Pro Val Ala Glu Ile
        195                 200                 205

Val Val Gly Asp Ile Ala Gln Val Lys Tyr Gly Asp Leu Leu Pro Ala
    210                 215                 220

Asp Gly Leu Phe Ile Gln Gly Asn Asp Leu Lys Ile Asp Glu Ser Ser
225                 230                 235                 240

Leu Thr Gly Glu Ser Asp Gln Val Arg Lys Ser Val Asp Lys Asp Pro
                245                 250                 255

Met Leu Leu Ser Gly Thr His Val Met Glu Gly Ser Gly Arg Met Leu
            260                 265                 270

Val Thr Ala Val Gly Val Asn Ser Gln Thr Gly Ile Ile Phe Thr Leu
        275                 280                 285

Leu Gly Ala Gly Gly Glu Glu Glu Glu Lys Lys Asp Lys Lys Gly Val
    290                 295                 300

Lys Lys Gly Asp Gly Leu Gln Leu Pro Ala Ala Asp Gly Ala Ala Ala
305                 310                 315                 320

Ser Asn Ala Ala Asp Ser Ala Asn Ala Ser Leu Val Asn Gly Lys Met
                325                 330                 335
```

```
Gln Asp Gly Asn Val Asp Ala Ser Gln Ser Lys Ala Lys Gln Gln Asp
            340                 345                 350

Gly Ala Ala Ala Met Glu Met Gln Pro Leu Lys Ser Ala Glu Gly Gly
        355                 360                 365

Asp Ala Asp Asp Arg Lys Lys Ala Ser Met His Lys Lys Glu Lys Ser
    370                 375                 380

Val Leu Gln Gly Lys Leu Thr Lys Leu Ala Val Gln Ile Gly Lys Ala
385                 390                 395                 400

Gly Leu Val Met Ser Ala Ile Thr Val Ile Ile Leu Val Leu Tyr Phe
                405                 410                 415

Thr Val Asp Thr Phe Val Val Asn Lys Lys Pro Trp Leu Pro Glu Cys
            420                 425                 430

Thr Pro Val Tyr Val Gln Tyr Phe Val Lys Phe Phe Ile Ile Gly Val
        435                 440                 445

Thr Val Leu Val Val Ala Val Pro Glu Gly Leu Pro Leu Ala Val Thr
    450                 455                 460

Ile Ser Leu Ala Tyr Ser Val Lys Lys Met Met Lys Asp Asn Asn Leu
465                 470                 475                 480

Val Arg His Leu Asp Ala Cys Glu Thr Met Gly Asn Ala Thr Ala Ile
                485                 490                 495

Cys Ser Asp Lys Thr Gly Thr Leu Thr Thr Asn Arg Met Thr Val Val
            500                 505                 510

Gln Ala Tyr Val Gly Asp Val His Tyr Lys Glu Ile Pro Asp Pro Ser
        515                 520                 525

Ser Ile Asn Thr Lys Thr Met Glu Leu Leu Ile Asn Ala Ile Ala Ile
    530                 535                 540

Asn Ser Ala Tyr Thr Thr Lys Ile Leu Pro Pro Glu Lys Glu Gly Ala
545                 550                 555                 560

Leu Pro Arg Gln Val Gly Asn Lys Thr Glu Cys Gly Leu Leu Gly Phe
                565                 570                 575

Val Leu Asp Leu Lys Gln Asp Tyr Glu Pro Val Arg Ser Gln Met Pro
            580                 585                 590

Glu Glu Lys Leu Tyr Lys Val Tyr Thr Phe Asn Ser Val Arg Lys Ser
        595                 600                 605

Met Ser Thr Val Ile Lys Leu Pro Asp Glu Ser Phe Arg Met Tyr Ser
    610                 615                 620

Lys Gly Ala Ser Glu Ile Val Leu Lys Lys Cys Cys Lys Ile Leu Asn
625                 630                 635                 640

Gly Ala Gly Glu Pro Arg Val Phe Arg Pro Arg Asp Arg Asp Glu Met
                645                 650                 655

Val Lys Lys Val Ile Glu Pro Met Ala Cys Asp Gly Leu Arg Thr Ile
            660                 665                 670

Cys Val Ala Tyr Arg Asp Phe Pro Ser Ser Pro Glu Pro Asp Trp Asp
        675                 680                 685

Asn Glu Asn Asp Ile Leu Asn Glu Leu Thr Cys Ile Cys Val Val Gly
    690                 695                 700

Ile Glu Asp Pro Val Arg Pro Glu Val Pro Glu Ala Ile Arg Lys Cys
705                 710                 715                 720

Gln Arg Ala Gly Ile Thr Val Arg Met Val Thr Gly Asp Asn Ile Asn
                725                 730                 735

Thr Ala Arg Ala Ile Ala Ile Lys Cys Gly Ile Ile His Pro Gly Glu
            740                 745                 750
```

```
Asp Phe Leu Cys Leu Glu Gly Lys Glu Phe Asn Arg Arg Ile Arg Asn
        755                 760                 765

Glu Lys Gly Glu Ile Glu Gln Glu Arg Ile Asp Lys Ile Trp Pro Lys
    770                 775                 780

Leu Arg Val Leu Ala Arg Ser Ser Pro Thr Asp Lys His Thr Leu Val
785                 790                 795                 800

Lys Gly Ile Ile Asp Ser Thr His Thr Glu Gln Arg Gln Val Val Ala
                805                 810                 815

Val Thr Gly Asp Gly Thr Asn Asp Gly Pro Ala Leu Lys Lys Ala Asp
            820                 825                 830

Val Gly Phe Ala Met Gly Ile Ala Gly Thr Asp Val Ala Lys Glu Ala
        835                 840                 845

Ser Asp Ile Ile Leu Thr Asp Asp Asn Phe Ser Ser Ile Val Lys Ala
    850                 855                 860

Val Met Trp Gly Arg Asn Val Tyr Asp Ser Ile Ser Lys Phe Leu Gln
865                 870                 875                 880

Phe Gln Leu Thr Val Asn Val Val Ala Val Ile Val Ala Phe Thr Gly
                885                 890                 895

Ala Cys Ile Thr Gln Asp Ser Pro Leu Lys Ala Val Gln Met Leu Trp
            900                 905                 910

Val Asn Leu Ile Met Asp Thr Phe Ala Ser Leu Ala Leu Ala Thr Glu
        915                 920                 925

Pro Pro Thr Glu Thr Leu Leu Leu Arg Lys Pro Tyr Gly Arg Asn Lys
    930                 935                 940

Pro Leu Ile Ser Arg Thr Met Met Lys Asn Ile Leu Gly His Ala Val
945                 950                 955                 960

Tyr Gln Leu Ala Leu Ile Phe Thr Leu Leu Phe Val Gly Glu Lys Met
                965                 970                 975

Phe Gln Ile Asp Ser Gly Arg Asn Ala Pro Leu His Ser Pro Pro Ser
            980                 985                 990

Glu His Tyr Thr Ile Ile Phe Asn  Thr Phe Val Met Met  Gln Leu Phe
        995                 1000                 1005

Asn Glu  Ile Asn Ala Arg Lys  Ile His Gly Glu Arg  Asn Val Phe
    1010                 1015                 1020

Asp Gly  Ile Phe Arg Asn Pro  Ile Phe Cys Thr Ile  Val Leu Gly
    1025                 1030                 1035

Thr Phe  Ala Ile Gln Ile Val  Ile Val Gln Phe Gly  Gly Lys Pro
    1040                 1045                 1050

Phe Ser  Cys Ser Pro Leu Gln  Leu Asp Gln Trp Met  Trp Cys Ile
    1055                 1060                 1065

Phe Ile  Gly Leu Gly Glu Leu  Val Trp Gly Gln Val  Ile Ala Thr
    1070                 1075                 1080

Ile Pro  Thr Ser Arg Leu Lys  Phe Leu Lys Glu Ala  Gly Arg Leu
    1085                 1090                 1095

Thr Gln  Lys Glu Glu Ile Pro  Glu Glu Glu Leu Asn  Glu Asp Val
    1100                 1105                 1110

Glu Glu  Ile Asp His Ala Glu  Arg Glu Leu Arg Arg  Gly Gln Ile
    1115                 1120                 1125

Leu Trp  Phe Arg Gly Leu Asn  Arg Ile Gln Thr Gln  Ile Glu Val
    1130                 1135                 1140

Val Asn  Thr Phe Lys Ser Gly  Ala Ser Phe Gln Gly  Ala Leu Arg
    1145                 1150                 1155

Arg Gln  Ser Ser Val Thr Ser  Gln Ser Gln Asp Ile  Arg Val Val
```

```
    1160                1165                1170

Lys Ala  Phe Arg Ser Ser Leu  Tyr Glu Gly Leu Glu  Lys Pro Glu
    1175                1180                1185

Ser Arg  Thr Ser Ile His Asn  Phe Met Ala His Pro  Glu Phe Arg
    1190                1195                1200

Ile Glu  Asp Ser Gln Pro His  Ile Pro Leu Ile Asp  Asp Thr Asp
    1205                1210                1215

Leu Glu  Glu Asp Ala Ala Leu  Lys Gln Asn Ser Ser  Pro Pro Ser
    1220                1225                1230

Ser Leu  Asn Lys Asn Asn Ser  Ala Ile Asp Ser Gly  Ile Asn Leu
    1235                1240                1245

Thr Thr  Asp Thr Ser Lys Ser  Ala Thr Ser Ser Ser  Pro Gly Ser
    1250                1255                1260

Pro Ile  His Ser Leu Glu Thr  Ser Leu
    1265                1270


<210> SEQ ID NO 31
<211> LENGTH: 1241
<212> TYPE: PRT
<213> ORGANISM: Homo sapiens

<400> SEQUENCE: 31

Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175

Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205

Gly Asp Ile Ala Gln Val Lys Tyr Gly Asp Leu Leu Pro Ala Asp Gly
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
                245                 250                 255
```

-continued

```
Leu Ser Gly Thr His Val Met Glu Gly Ser Gly Arg Met Val Val Thr
            260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Lys Gly Lys Lys Gln
    290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
                325                 330                 335

Lys Asp Lys Lys Ala Val Lys Val Pro Lys Lys Glu Lys Ser Val Leu
            340                 345                 350

Gln Gly Lys Leu Thr Arg Leu Ala Val Gln Ile Gly Lys Ala Gly Leu
        355                 360                 365

Leu Met Ser Ala Leu Thr Val Phe Ile Leu Ile Leu Tyr Phe Val Ile
    370                 375                 380

Asp Asn Phe Val Ile Asn Arg Arg Pro Trp Leu Pro Glu Cys Thr Pro
385                 390                 395                 400

Ile Tyr Ile Gln Tyr Phe Val Lys Phe Phe Ile Ile Gly Ile Thr Val
                405                 410                 415

Leu Val Val Ala Val Pro Glu Gly Leu Pro Leu Ala Val Thr Ile Ser
            420                 425                 430

Leu Ala Tyr Ser Val Lys Lys Met Met Lys Asp Asn Asn Leu Val Arg
        435                 440                 445

His Leu Asp Ala Cys Glu Thr Met Gly Asn Ala Thr Ala Ile Cys Ser
    450                 455                 460

Asp Lys Thr Gly Thr Leu Thr Met Asn Arg Met Thr Val Val Gln Ala
465                 470                 475                 480

Tyr Ile Gly Gly Ile His Tyr Arg Gln Ile Pro Ser Pro Asp Val Phe
                485                 490                 495

Leu Pro Lys Val Leu Asp Leu Ile Val Asn Gly Ile Ser Ile Asn Ser
            500                 505                 510

Ala Tyr Thr Ser Lys Ile Leu Pro Pro Glu Lys Glu Gly Gly Leu Pro
        515                 520                 525

Arg Gln Val Gly Asn Lys Thr Glu Cys Ala Leu Leu Gly Phe Val Thr
    530                 535                 540

Asp Leu Lys Gln Asp Tyr Gln Ala Val Arg Asn Glu Val Pro Glu Glu
545                 550                 555                 560

Lys Leu Tyr Lys Val Tyr Thr Phe Asn Ser Val Arg Lys Ser Met Ser
                565                 570                 575

Thr Val Ile Arg Asn Pro Asn Gly Gly Phe Arg Met Tyr Ser Lys Gly
            580                 585                 590

Ala Ser Glu Ile Ile Leu Arg Lys Cys Asn Arg Ile Leu Asp Arg Lys
        595                 600                 605

Gly Glu Ala Val Pro Phe Lys Asn Lys Asp Arg Asp Asp Met Val Arg
    610                 615                 620

Thr Val Ile Glu Pro Met Ala Cys Asp Gly Leu Arg Thr Ile Cys Ile
625                 630                 635                 640

Ala Tyr Arg Asp Phe Asp Asp Thr Glu Pro Ser Trp Asp Asn Glu Asn
                645                 650                 655

Glu Ile Leu Thr Glu Leu Thr Cys Ile Ala Val Val Gly Ile Glu Asp
            660                 665                 670

Pro Val Arg Pro Glu Val Pro Asp Ala Ile Ala Lys Cys Lys Gln Ala
```

```
        675                 680                 685

Gly Ile Thr Val Arg Met Val Thr Gly Asp Asn Ile Asn Thr Ala Arg
    690                 695                 700

Ala Ile Ala Thr Lys Cys Gly Ile Leu Thr Pro Gly Asp Asp Phe Leu
705                 710                 715                 720

Cys Leu Glu Gly Lys Glu Phe Asn Arg Leu Ile Arg Asn Glu Lys Gly
                725                 730                 735

Glu Val Glu Gln Glu Lys Leu Asp Lys Ile Trp Pro Lys Leu Arg Val
            740                 745                 750

Leu Ala Arg Ser Ser Pro Thr Asp Lys His Thr Leu Val Lys Gly Ile
        755                 760                 765

Ile Asp Ser Thr Val Gly Glu His Arg Gln Val Val Ala Val Thr Gly
    770                 775                 780

Asp Gly Thr Asn Asp Gly Pro Ala Leu Lys Lys Ala Asp Val Gly Phe
785                 790                 795                 800

Ala Met Gly Ile Ala Gly Thr Asp Val Ala Lys Glu Ala Ser Asp Ile
                805                 810                 815

Ile Leu Thr Asp Asp Asn Phe Thr Ser Ile Val Lys Ala Val Met Trp
            820                 825                 830

Gly Arg Asn Val Tyr Asp Ser Ile Ser Lys Phe Leu Gln Phe Gln Leu
        835                 840                 845

Thr Val Asn Val Val Ala Val Ile Val Ala Phe Thr Gly Ala Cys Ile
    850                 855                 860

Thr Gln Asp Ser Pro Leu Lys Ala Val Gln Met Leu Trp Val Asn Leu
865                 870                 875                 880

Ile Met Asp Thr Phe Ala Ser Leu Ala Leu Ala Thr Glu Pro Pro Thr
                885                 890                 895

Glu Ser Leu Leu Lys Arg Arg Pro Tyr Gly Arg Asn Lys Pro Leu Ile
            900                 905                 910

Ser Arg Thr Met Met Lys Asn Ile Leu Gly His Ala Phe Tyr Gln Leu
        915                 920                 925

Ile Val Ile Phe Ile Leu Val Phe Ala Gly Glu Lys Phe Phe Asp Ile
    930                 935                 940

Asp Ser Gly Arg Lys Ala Pro Leu His Ser Pro Pro Ser Gln His Tyr
945                 950                 955                 960

Thr Ile Val Phe Asn Thr Phe Val Leu Met Gln Leu Phe Asn Glu Ile
                965                 970                 975

Asn Ser Arg Lys Ile His Gly Glu Lys Asn Val Phe Ser Gly Ile Tyr
            980                 985                 990

Arg Asn Ile Ile Phe Cys Ser Val  Val Leu Gly Thr Phe  Ile Cys Gln
        995                 1000                1005

Ile Phe  Ile Val Glu Phe Gly  Gly Lys Pro Phe Ser  Cys Thr Ser
    1010                1015                1020

Leu Ser  Leu Ser Gln Trp Leu  Trp Cys Leu Phe Ile  Gly Ile Gly
    1025                1030                1035

Glu Leu  Leu Trp Gly Gln Phe  Ile Ser Ala Ile Pro  Thr Arg Ser
    1040                1045                1050

Leu Lys  Phe Leu Lys Glu Ala  Gly His Gly Thr Thr  Lys Glu Glu
    1055                1060                1065

Ile Thr  Lys Asp Ala Glu Gly  Leu Asp Glu Ile Asp  His Ala Glu
    1070                1075                1080

Met Glu  Leu Arg Arg Gly Gln  Ile Leu Trp Phe Arg  Gly Leu Asn
    1085                1090                1095
```

```
Arg Ile  Gln Thr Gln Ile Asp  Val Ile Asn Thr Phe  Gln Thr Gly
    1100                 1105                 1110

Ala Ser  Phe Lys Gly Val Leu  Arg Arg Gln Asn Met  Gly Gln His
    1115                 1120                 1125

Leu Asp  Val Lys Leu Val Pro  Ser Ser Ser Tyr Ile  Lys Val Val
    1130                 1135                 1140

Lys Ala  Phe His Ser Ser Leu  His Glu Ser Ile Gln  Lys Pro Tyr
    1145                 1150                 1155

Asn Gln  Lys Ser Ile His Ser  Phe Met Thr His Pro  Glu Phe Ala
    1160                 1165                 1170

Ile Glu  Glu Glu Leu Pro Arg  Thr Pro Leu Leu Asp  Glu Glu Glu
    1175                 1180                 1185

Glu Glu  Asn Pro Asp Lys Ala  Ser Lys Phe Gly Thr  Arg Val Leu
    1190                 1195                 1200

Leu Leu  Asp Gly Glu Val Thr  Pro Tyr Ala Asn Thr  Asn Asn Asn
    1205                 1210                 1215

Ala Val  Asp Cys Asn Gln Val  Gln Leu Pro Gln Ser  Asp Ser Ser
    1220                 1225                 1230

Leu Gln  Ser Leu Glu Thr Ser  Val
    1235                 1240


<210> SEQ ID NO 32
<211> LENGTH: 1241
<212> TYPE: PRT
<213> ORGANISM: homo sapiens

<400> SEQUENCE: 32

Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175

Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205

Gly Asp Ile Ala Gln Val Lys Tyr Gly Asp Leu Leu Pro Ala Asp Gly
```

-continued

```
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
                245                 250                 255

Leu Ser Gly Thr His Val Met Glu Gly Ser Gly Arg Met Val Val Thr
            260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Lys Gly Lys Lys Gln
    290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
                325                 330                 335

Lys Asp Lys Lys Ala Val Lys Val Pro Lys Lys Glu Lys Ser Val Leu
            340                 345                 350

Gln Gly Lys Leu Thr Arg Leu Ala Val Gln Ile Gly Lys Ala Gly Leu
        355                 360                 365

Leu Met Ser Ala Leu Thr Val Phe Ile Leu Ile Leu Tyr Phe Val Ile
    370                 375                 380

Asp Asn Phe Val Ile Asn Arg Arg Pro Trp Leu Pro Glu Cys Thr Pro
385                 390                 395                 400

Ile Tyr Ile Gln Tyr Phe Val Lys Phe Phe Ile Ile Gly Ile Thr Val
                405                 410                 415

Leu Val Val Ala Val Pro Glu Gly Leu Pro Leu Ala Val Thr Ile Ser
            420                 425                 430

Leu Ala Tyr Ser Val Lys Lys Met Met Lys Asp Asn Asn Leu Val Arg
        435                 440                 445

His Leu Asp Ala Cys Glu Thr Met Gly Asn Ala Thr Ala Ile Cys Ser
    450                 455                 460

Asp Lys Thr Gly Thr Leu Thr Met Asn Arg Met Thr Val Val Gln Ala
465                 470                 475                 480

Tyr Ile Gly Gly Ile His Tyr Arg Gln Ile Pro Ser Pro Asp Val Phe
                485                 490                 495

Leu Pro Lys Val Leu Asp Leu Ile Val Asn Gly Ile Ser Ile Asn Ser
            500                 505                 510

Ala Tyr Thr Ser Lys Ile Leu Pro Pro Glu Lys Glu Gly Gly Leu Pro
        515                 520                 525

Arg Gln Val Gly Asn Lys Thr Glu Cys Ala Leu Leu Gly Phe Val Thr
    530                 535                 540

Asp Leu Lys Gln Asp Tyr Gln Ala Val Arg Asn Glu Val Pro Glu Glu
545                 550                 555                 560

Lys Leu Tyr Lys Val Tyr Thr Phe Asn Ser Val Arg Lys Ser Met Ser
                565                 570                 575

Thr Val Ile Arg Asn Pro Asn Gly Gly Phe Arg Met Tyr Ser Lys Gly
            580                 585                 590

Ala Ser Glu Ile Ile Leu Arg Lys Cys Asn Arg Ile Leu Asp Arg Lys
        595                 600                 605

Gly Glu Ala Val Pro Phe Lys Asn Lys Asp Arg Asp Asp Met Val Arg
    610                 615                 620

Thr Val Ile Glu Pro Met Ala Cys Asp Gly Leu Arg Thr Ile Cys Ile
625                 630                 635                 640
```

```
Ala Tyr Arg Asp Phe Asp Asp Thr Glu Pro Ser Trp Asp Asn Glu Asn
                645                 650                 655

Glu Ile Leu Thr Glu Leu Thr Cys Ile Ala Val Val Gly Ile Glu Asp
            660                 665                 670

Pro Val Arg Pro Glu Val Pro Asp Ala Ile Ala Lys Cys Lys Gln Ala
        675                 680                 685

Gly Ile Thr Val Arg Met Val Thr Gly Asp Asn Ile Asn Thr Ala Arg
    690                 695                 700

Ala Ile Ala Thr Lys Cys Gly Ile Leu Thr Pro Gly Asp Asp Phe Leu
705                 710                 715                 720

Cys Leu Glu Gly Lys Glu Phe Asn Arg Leu Ile Arg Asn Glu Lys Gly
                725                 730                 735

Glu Val Glu Gln Glu Lys Leu Asp Lys Ile Trp Pro Lys Leu Arg Val
            740                 745                 750

Leu Ala Arg Ser Ser Pro Thr Asp Lys His Thr Leu Val Lys Gly Ile
        755                 760                 765

Ile Asp Ser Thr Val Gly Glu His Arg Gln Val Val Ala Val Thr Gly
    770                 775                 780

Asp Gly Thr Asn Asp Gly Pro Ala Leu Lys Lys Ala Asp Val Gly Phe
785                 790                 795                 800

Ala Met Gly Ile Ala Gly Thr Asp Val Ala Lys Glu Ala Ser Asp Ile
                805                 810                 815

Ile Leu Thr Asp Asp Asn Phe Thr Ser Ile Val Lys Ala Val Met Trp
            820                 825                 830

Gly Arg Asn Val Tyr Asp Ser Ile Ser Lys Phe Leu Gln Phe Gln Leu
        835                 840                 845

Thr Val Asn Val Val Ala Val Ile Val Ala Phe Thr Gly Ala Cys Ile
    850                 855                 860

Thr Gln Asp Ser Pro Leu Lys Ala Val Gln Met Leu Trp Val Asn Leu
865                 870                 875                 880

Ile Met Asp Thr Phe Ala Ser Leu Ala Leu Ala Thr Glu Pro Pro Thr
                885                 890                 895

Glu Ser Leu Leu Lys Arg Arg Pro Tyr Gly Arg Asn Lys Pro Leu Ile
            900                 905                 910

Ser Arg Thr Met Met Lys Asn Ile Leu Gly His Ala Phe Tyr Gln Leu
        915                 920                 925

Ile Val Ile Phe Ile Leu Val Phe Ala Gly Glu Lys Phe Phe Asp Ile
    930                 935                 940

Asp Ser Gly Arg Lys Ala Pro Leu His Ser Pro Pro Ser Gln His Tyr
945                 950                 955                 960

Thr Ile Val Phe Asn Thr Phe Val Leu Met Gln Leu Phe Asn Glu Ile
                965                 970                 975

Asn Ser Arg Lys Ile His Gly Glu Lys Asn Val Phe Ser Gly Ile Tyr
            980                 985                 990

Arg Asn Ile Ile Phe Cys Ser Val  Val Leu Gly Thr Phe  Ile Cys Gln
        995                 1000                1005

Ile Phe  Ile Val Glu Phe Gly  Gly Lys Pro Phe Ser  Cys Thr Ser
    1010                1015                1020

Leu Ser  Leu Ser Gln Trp Leu  Trp Cys Leu Phe Ile  Gly Ile Gly
    1025                1030                1035

Glu Leu  Leu Trp Gly Gln Phe  Ile Ser Ala Ile Pro  Thr Arg Ser
    1040                1045                1050
```

```
Leu Lys  Phe Leu Lys Glu Ala  Gly His Gly Thr Thr  Lys Glu Glu
    1055                 1060                 1065

Ile Thr  Lys Asp Ala Glu Gly  Leu Asp Glu Ile Asp  His Ala Glu
    1070                 1075                 1080

Met Glu  Leu Arg Arg Gly Gln  Ile Leu Trp Phe Arg  Gly Leu Asn
    1085                 1090                 1095

Arg Ile  Gln Thr Gln Ile Asp  Val Ile Asn Thr Phe  Gln Thr Gly
    1100                 1105                 1110

Ala Ser  Phe Lys Gly Val Leu  Arg Arg Gln Asn Met  Gly Gln His
    1115                 1120                 1125

Leu Asp  Val Lys Leu Val Pro  Ser Ser Ser Tyr Ile  Lys Val Val
    1130                 1135                 1140

Lys Ala  Phe His Ser Ser Leu  His Glu Ser Ile Gln  Lys Pro Tyr
    1145                 1150                 1155

Asn Gln  Lys Ser Ile His Ser  Phe Met Thr His Pro  Glu Phe Ala
    1160                 1165                 1170

Ile Glu  Glu Glu Leu Pro Arg  Thr Pro Leu Leu Asp  Glu Glu Glu
    1175                 1180                 1185

Glu Glu  Asn Pro Asp Lys Ala  Ser Lys Phe Gly Thr  Arg Val Leu
    1190                 1195                 1200

Leu Leu  Asp Gly Glu Val Thr  Pro Tyr Ala Asn Thr  Asn Asn Asn
    1205                 1210                 1215

Ala Val  Asp Cys Asn Gln Val  Gln Leu Pro Gln Ser  Asp Ser Ser
    1220                 1225                 1230

Leu Gln  Ser Leu Glu Thr Ser  Val
    1235                 1240


<210> SEQ ID NO 33
<211> LENGTH: 193
<212> TYPE: PRT
<213> ORGANISM: homo sapiens

<400> SEQUENCE: 33

Gly Pro Ile Phe Asn Ala Ser Val His Ser Asp Thr Pro Ser Val Ile
1               5                   10                  15

Arg Gly Asp Leu Ile Lys Leu Phe Cys Ile Ile Thr Val Glu Gly Ala
            20                  25                  30

Ala Leu Asp Pro Asp Asp Met Ala Phe Asp Val Ser Trp Phe Ala Val
        35                  40                  45

His Ser Phe Gly Leu Asp Lys Ala Pro Val Leu Leu Ser Ser Leu Asp
    50                  55                  60

Arg Lys Gly Ile Val Thr Thr Ser Arg Arg Asp Trp Lys Ser Asp Leu
65                  70                  75                  80

Ser Leu Glu Arg Val Ser Val Leu Glu Phe Leu Leu Gln Val His Gly
                85                  90                  95

Ser Glu Asp Gln Asp Phe Gly Asn Tyr Tyr Cys Ser Val Thr Pro Trp
            100                 105                 110

Val Lys Ser Pro Thr Gly Ser Trp Gln Lys Glu Ala Glu Ile His Ser
        115                 120                 125

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160

Ser Cys Leu Ile Gly Tyr Cys Ser Ser His Trp Cys Cys Lys Lys Glu
                165                 170                 175
```

```
Val Gln Glu Thr Arg Arg Glu Arg Arg Arg Leu Met Ser Met Glu Met
            180                 185                 190

Asp


<210> SEQ ID NO 34
<211> LENGTH: 1021
<212> TYPE: PRT
<213> ORGANISM: homo sapiens

<400> SEQUENCE: 34

Met Ala Gly Ile Ser Tyr Val Ala Ser Phe Phe Leu Leu Leu Thr Lys
1               5                   10                  15

Leu Ser Ile Gly Gln Arg Glu Val Thr Val Gln Lys Gly Pro Leu Phe
            20                  25                  30

Arg Ala Glu Gly Tyr Pro Val Ser Ile Gly Cys Asn Val Thr Gly His
        35                  40                  45

Gln Gly Pro Ser Glu Gln His Phe Gln Trp Ser Val Tyr Leu Pro Thr
    50                  55                  60

Asn Pro Thr Gln Glu Val Gln Ile Ile Ser Thr Lys Asp Ala Ala Phe
65                  70                  75                  80

Ser Tyr Ala Val Tyr Thr Gln Arg Val Arg Ser Gly Asp Val Tyr Val
                85                  90                  95

Glu Arg Val Gln Gly Asn Ser Val Leu Leu His Ile Ser Lys Leu Gln
            100                 105                 110

Met Lys Asp Ala Gly Glu Tyr Glu Cys His Thr Pro Asn Thr Asp Glu
        115                 120                 125

Lys Tyr Tyr Gly Ser Tyr Ser Ala Lys Thr Asn Leu Ile Val Ile Pro
    130                 135                 140

Asp Thr Leu Ser Ala Thr Met Ser Ser Gln Thr Leu Gly Lys Glu Glu
145                 150                 155                 160

Gly Glu Pro Leu Ala Leu Thr Cys Glu Ala Ser Lys Ala Thr Ala Gln
                165                 170                 175

His Thr His Leu Ser Val Thr Trp Tyr Leu Thr Gln Asp Gly Gly Gly
            180                 185                 190

Ser Gln Ala Thr Glu Ile Ile Ser Leu Ser Lys Asp Phe Ile Leu Val
        195                 200                 205

Pro Gly Pro Leu Tyr Thr Glu Arg Phe Ala Ala Ser Asp Val Gln Leu
    210                 215                 220

Asn Lys Leu Gly Pro Thr Thr Phe Arg Leu Ser Ile Glu Arg Leu Gln
225                 230                 235                 240

Ser Ser Asp Gln Gly Gln Leu Phe Cys Glu Ala Thr Glu Trp Ile Gln
                245                 250                 255

Asp Pro Asp Glu Thr Trp Met Phe Ile Thr Lys Lys Gln Thr Asp Gln
            260                 265                 270

Thr Thr Leu Arg Ile Gln Pro Ala Val Lys Asp Phe Gln Val Asn Ile
        275                 280                 285

Thr Ala Asp Ser Leu Phe Ala Glu Gly Lys Pro Leu Glu Leu Val Cys
    290                 295                 300

Leu Val Val Ser Ser Gly Arg Asp Pro Gln Leu Gln Gly Ile Trp Phe
305                 310                 315                 320

Phe Asn Gly Thr Glu Ile Ala His Ile Asp Ala Gly Gly Val Leu Gly
                325                 330                 335

Leu Lys Asn Asp Tyr Lys Glu Arg Ala Ser Gln Gly Glu Leu Gln Val
            340                 345                 350
```

-continued

```
Ser Lys Leu Gly Pro Lys Ala Phe Ser Leu Lys Ile Phe Ser Leu Gly
        355                 360                 365

Pro Glu Asp Glu Gly Ala Tyr Arg Cys Val Val Ala Glu Val Met Lys
    370                 375                 380

Thr Arg Thr Gly Ser Trp Gln Val Leu Gln Arg Lys Gln Ser Pro Asp
385                 390                 395                 400

Ser His Val His Leu Arg Lys Pro Ala Ala Arg Ser Val Val Met Ser
                405                 410                 415

Thr Lys Asn Lys Gln Gln Val Val Trp Glu Gly Glu Thr Leu Ala Phe
            420                 425                 430

Leu Cys Lys Ala Gly Gly Ala Glu Ser Pro Leu Ser Val Ser Trp Trp
        435                 440                 445

His Ile Pro Arg Asp Gln Thr Gln Pro Glu Phe Val Ala Gly Met Gly
    450                 455                 460

Gln Asp Gly Ile Val Gln Leu Gly Ala Ser Tyr Gly Val Pro Ser Tyr
465                 470                 475                 480

His Gly Asn Thr Arg Leu Glu Lys Met Asp Trp Ala Thr Phe Gln Leu
                485                 490                 495

Glu Ile Thr Phe Thr Ala Ile Thr Asp Ser Gly Thr Tyr Glu Cys Arg
            500                 505                 510

Val Ser Glu Lys Ser Arg Asn Gln Ala Arg Asp Leu Ser Trp Thr Gln
        515                 520                 525

Lys Ile Ser Val Thr Val Lys Ser Leu Glu Ser Ser Leu Gln Val Ser
    530                 535                 540

Leu Met Ser Arg Gln Pro Gln Val Met Leu Thr Asn Thr Phe Asp Leu
545                 550                 555                 560

Ser Cys Val Val Arg Ala Gly Tyr Ser Asp Leu Lys Val Pro Leu Thr
                565                 570                 575

Val Thr Trp Gln Phe Gln Pro Ala Ser Ser His Ile Phe His Gln Leu
            580                 585                 590

Ile Arg Ile Thr His Asn Gly Thr Ile Glu Trp Gly Asn Phe Leu Ser
        595                 600                 605

Arg Phe Gln Lys Lys Thr Lys Val Ser Gln Ser Leu Phe Arg Ser Gln
    610                 615                 620

Leu Leu Val His Asp Ala Thr Glu Glu Glu Thr Gly Val Tyr Gln Cys
625                 630                 635                 640

Glu Val Glu Val Tyr Asp Arg Asn Ser Leu Tyr Asn Asn Arg Pro Pro
                645                 650                 655

Arg Ala Ser Ala Ile Ser His Pro Leu Arg Ile Ala Val Thr Leu Pro
            660                 665                 670

Glu Ser Lys Leu Lys Val Asn Ser Arg Ser Gln Val Gln Glu Leu Ser
        675                 680                 685

Ile Asn Ser Asn Thr Asp Ile Glu Cys Ser Ile Leu Ser Arg Ser Asn
    690                 695                 700

Gly Asn Leu Gln Leu Ala Ile Ile Trp Tyr Phe Ser Pro Val Ser Thr
705                 710                 715                 720

Asn Ala Ser Trp Leu Lys Ile Leu Glu Met Asp Gln Thr Asn Val Ile
                725                 730                 735

Lys Thr Gly Asp Glu Phe His Thr Pro Gln Arg Lys Gln Lys Phe His
            740                 745                 750

Thr Glu Lys Val Ser Gln Asp Leu Phe Gln Leu His Ile Leu Asn Val
        755                 760                 765
```

-continued

```
Glu Asp Ser Asp Arg Gly Lys Tyr His Cys Ala Val Glu Glu Trp Leu
    770                 775                 780

Leu Ser Thr Asn Gly Thr Trp His Lys Leu Gly Glu Lys Lys Ser Gly
785                 790                 795                 800

Leu Thr Glu Leu Lys Leu Lys Pro Thr Gly Ser Lys Val Arg Val Ser
                805                 810                 815

Lys Val Tyr Trp Thr Glu Asn Val Thr Glu His Arg Glu Val Ala Ile
            820                 825                 830

Arg Cys Ser Leu Glu Ser Val Gly Ser Ser Ala Thr Leu Tyr Ser Val
        835                 840                 845

Met Trp Tyr Trp Asn Arg Glu Asn Ser Gly Ser Lys Leu Leu Val His
    850                 855                 860

Leu Gln His Asp Gly Leu Leu Glu Tyr Gly Glu Glu Gly Leu Arg Arg
865                 870                 875                 880

His Leu His Cys Tyr Arg Ser Ser Ser Thr Asp Phe Val Leu Lys Leu
                885                 890                 895

His Gln Val Glu Met Glu Asp Ala Gly Met Tyr Trp Cys Arg Val Ala
            900                 905                 910

Glu Trp Gln Leu His Gly His Pro Ser Lys Trp Ile Asn Gln Ala Ser
        915                 920                 925

Asp Glu Ser Gln Arg Met Val Leu Thr Val Leu Pro Ser Glu Pro Thr
    930                 935                 940

Leu Pro Ser Arg Ile Cys Ser Ser Ala Pro Leu Leu Tyr Phe Leu Phe
945                 950                 955                 960

Ile Cys Pro Phe Val Leu Leu Leu Leu Leu Leu Ile Ser Leu Leu Cys
                965                 970                 975

Leu Tyr Trp Lys Ala Arg Lys Leu Ser Thr Leu Arg Ser Asn Thr Arg
            980                 985                 990

Lys Glu Lys Ala Leu Trp Val Asp  Leu Lys Glu Ala Gly  Gly Val Thr
        995                 1000                1005

Thr Asn  Arg Arg Glu Asp Glu  Glu Glu Asp Glu Gly  Asn
    1010                1015                1020
```

<210> SEQ ID NO 35
<211> LENGTH: 20
<212> TYPE: PRT
<213> ORGANISM: homo sapiens

<400> SEQUENCE: 35

```
Met Ala Gly Ile Ser Tyr Val Ala Ser Phe Phe Leu Leu Leu Thr Lys
1               5                   10                  15

Leu Ser Ile Gly
            20
```

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
cgttggcagt ccgccttaac 20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
catagtcact gacgttgcag 20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ttgtggagct tgcaagcacc 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gttctttatg tggagctcca 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tatcccttgc tgatcggcgt 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gctgcagtac ccgatgagac 20

<210> SEQ ID NO 42
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 42

```
Glu His Ser Ala Gly Gly Gly Gly Ser Asp Tyr Lys Asp Asp Asp Asp
1               5                   10                  15

Lys Gly Gly Gly Gly Ser Leu Ser Asn Pro Ile Glu Ile Asp Phe Gln
            20                  25                  30

Thr Ser Gly Pro Ile Phe
        35
```

<210> SEQ ID NO 43
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 43

Glu His Ser Ala Gly Gly Gly Gly Ser Asp Tyr Lys Asp Asp Asp Asp
1               5                   10                  15

Lys Gly Gly Gly Gly Ser Ile Glu Ile Asp Phe Gln Thr Ser Gly Pro
            20                  25                  30

Ile Phe

<210> SEQ ID NO 44
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 44

Glu His Ser Ala Gly Gly Gly Gly Ser Asp Tyr Lys Asp Asp Asp Asp
1               5                   10                  15

Lys Gly Gly Gly Gly Ser Phe Gln Thr Ser Gly Pro Ile Phe
            20                  25                  30

<210> SEQ ID NO 45
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 45

Glu His Ser Ala Gly Gly Gly Gly Ser Asp Tyr Lys Asp Asp Asp Asp
1               5                   10                  15

Lys Gly Gly Gly Gly Ser Gly Pro Ile Phe
            20                  25

<210> SEQ ID NO 46
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 46

Phe Ile Thr Val Lys Met Asp Thr Leu Asp Pro Arg Ser Phe Leu Leu
1               5                   10                  15

Arg Asn Pro Asn Asp Lys Tyr Glu Pro Phe Trp Glu Asp Glu Glu Lys
            20                  25                  30

Asn Glu Ser Gly Ser Asp Lys Thr His Thr
        35                  40

<210> SEQ ID NO 47
<211> LENGTH: 332
<212> TYPE: PRT
<213> ORGANISM: Homo sapiens

<400> SEQUENCE: 47

Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala

```
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Ala Gly Ser Gly Ala Ala
65                  70                  75                  80

Ser Pro Ser Ala Ala Glu Lys Gly Glu Pro Ala Ala Ala Ala Ala Pro
                85                  90                  95

Glu Ala Gly Ala Ser Pro Val Glu Lys Glu Ala Pro Ala Glu Gly Glu
            100                 105                 110

Ala Ala Glu Pro Gly Ser Pro Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Ala Glu Ala Gly
        195                 200                 205

Ala Ala Ser Gly Glu Gln Ala Ala Ala Pro Gly Glu Glu Ala Ala Ala
    210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Pro Gly
        275                 280                 285

Ala Pro Pro Glu Gln Glu Ala Ala Pro Ala Glu Glu Pro Ala Ala Ala
    290                 295                 300

Ala Ala Ser Ser Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330


<210> SEQ ID NO 48
<211> LENGTH: 195
<212> TYPE: PRT
<213> ORGANISM: Homo sapiens

<400> SEQUENCE: 48

Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
            20                  25                  30

His Val Lys Ser Asn Gly Asp Leu Ser Pro Lys Gly Glu Gly Glu Ser
        35                  40                  45

Pro Pro Val Asn Gly Thr Asp Glu Ala Ala Gly Ala Thr Gly Asp Ala
    50                  55                  60

Ile Glu Pro Ala Pro Pro Ser Gln Gly Ala Glu Ala Lys Gly Glu Val
65                  70                  75                  80
```

```
Pro Pro Lys Glu Thr Pro Lys Lys Lys Lys Lys Phe Ser Phe Lys Lys
                85                  90                  95

Pro Phe Lys Leu Ser Gly Leu Ser Phe Lys Arg Asn Arg Lys Glu Gly
            100                 105                 110

Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
    130                 135                 140

Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195
```

<210> SEQ ID NO 49
<211> LENGTH: 227
<212> TYPE: PRT
<213> ORGANISM: Homo sapiens

<400> SEQUENCE: 49

```
Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala Ala
        115                 120                 125

Pro Ala Glu Ser Ala Ala Pro Ala Ala Gly Glu Glu Pro Ser Lys Glu
    130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
    210                 215                 220

Val Lys Glu
225
```

<210> SEQ ID NO 50

<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala
20 25 30

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu
20 25

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Met Gly Gly Lys Leu Ser Lys Lys Lys Lys Gly Tyr Asn Val Asn Asp
1 5 10 15

Glu Lys Ala Lys Glu Lys Asp Lys
20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Met Gly Gly Lys Leu Ser Lys Lys Lys Lys Gly Tyr Asn Val Asn Asp
1 5 10 15

Glu Lys Ala Lys Glu
20

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Met Gly Gly Lys Leu Ser Lys Lys Lys Lys Gly Tyr Asn Val Asn Asp
1 5 10 15

Glu Lys

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Met Gly Gly Lys Leu Ser Lys Lys Lys Lys Gly Tyr Asn Val Asn
1 5 10 15

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Met Gly Gly Lys Leu Ser Lys Lys Lys Lys Gly Tyr
1 5 10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Met Gly Gly Lys Leu Ser Lys Lys Lys Lys Gly
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Met Gly Gly Lys Leu Ser Lys Lys Lys Lys
1 5 10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Met Gly Gly Lys Leu Ser Lys Lys Lys
1 5

<210> SEQ ID NO 60
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 60

Met Gly Gly Lys Leu Ser Lys Lys
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Gly Gly Lys Leu Ser Lys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Gly Gly Lys Leu Ala Lys Lys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Gly Gly Lys Phe Ser Lys Lys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Gly Gly Lys Phe Ala Lys Lys
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Gly Gly Lys Ser Ser Lys Lys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Met Gly Gly Lys Ser Ala Lys Lys
1 5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Met Gly Gly Lys Gln Ser Lys Lys
1 5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Met Gly Gly Lys Gln Ala Lys Lys
1 5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Met Gly Gly Gln Leu Ser Lys Lys
1 5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Met Gly Gly Gln Leu Ala Lys Lys
1 5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Met Gly Gly Gln Phe Ser Lys Lys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Gly Gly Gln Phe Ala Lys Lys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Gly Gly Gln Ser Ser Lys Lys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met Gly Gly Gln Ser Ala Lys Lys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Gly Gly Gln Gln Ser Lys Lys
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Gly Gly Gln Gln Ala Lys Lys
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Met Gly Ala Lys Leu Ser Lys Lys
1 5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Met Gly Ala Lys Leu Ala Lys Lys
1 5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Met Gly Ala Lys Phe Ser Lys Lys
1 5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Met Gly Ala Lys Phe Ala Lys Lys
1 5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Met Gly Ala Lys Ser Ser Lys Lys
1 5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Met Gly Ala Lys Ser Ala Lys Lys
1 5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Met Gly Ala Lys Gln Ser Lys Lys
1 5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Met Gly Ala Lys Gln Ala Lys Lys
1 5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Met Gly Ala Gln Leu Ser Lys Lys
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Met Gly Ala Gln Leu Ala Lys Lys
1 5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Met Gly Ala Gln Phe Ser Lys Lys
1 5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Met Gly Ala Gln Phe Ala Lys Lys
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Gly Ala Gln Ser Ser Lys Lys
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Gly Ala Gln Ser Ala Lys Lys
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Gly Ala Gln Gln Ser Lys Lys
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Met Gly Ala Gln Gln Ala Lys Lys
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met Gly Ser Lys Leu Ser Lys Lys
1               5

<210> SEQ ID NO 94
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 94

Met Gly Ser Lys Leu Ala Lys Lys
1 5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Met Gly Ser Lys Phe Ser Lys Lys
1 5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Met Gly Ser Lys Phe Ala Lys Lys
1 5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Met Gly Ser Lys Ser Ser Lys Lys
1 5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Met Gly Ser Lys Ser Ala Lys Lys
1 5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Met Gly Ser Lys Gln Ser Lys Lys
1 5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Met Gly Ser Lys Gln Ala Lys Lys
1 5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Met Gly Ser Gln Leu Ser Lys Lys
1 5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Met Gly Ser Gln Leu Ala Lys Lys
1 5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Met Gly Ser Gln Phe Ser Lys Lys
1 5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Met Gly Ser Gln Phe Ala Lys Lys
1 5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 105

Met Gly Ser Gln Ser Ser Lys Lys
1               5


<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Gly Ser Gln Ser Ala Lys Lys
1               5


<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Met Gly Ser Gln Gln Ser Lys Lys
1               5


<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met Gly Ser Gln Gln Ala Lys Lys
1               5


<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Met Gly Gly Lys Leu Ala Lys
1               5


<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Met Gly Gly Lys Phe Ser Lys
1               5


<210> SEQ ID NO 111
<211> LENGTH: 7
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Met Gly Gly Lys Phe Ala Lys
1 5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Met Gly Gly Lys Ser Ser Lys
1 5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Met Gly Gly Lys Ser Ala Lys
1 5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Met Gly Gly Lys Gln Ser Lys
1 5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Met Gly Gly Lys Gln Ala Lys
1 5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Met Gly Gly Gln Leu Ser Lys 1 5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Met Gly Gly Gln Leu Ala Lys
1 5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Met Gly Gly Gln Phe Ser Lys
1 5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Met Gly Gly Gln Phe Ala Lys
1 5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Met Gly Gly Gln Ser Ser Lys
1 5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Met Gly Gly Gln Ser Ala Lys
1 5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Met Gly Gly Gln Gln Ser Lys
1 5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Met Gly Gly Gln Gln Ala Lys
1 5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Met Gly Ala Lys Leu Ser Lys
1 5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Met Gly Ala Lys Leu Ala Lys
1 5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Met Gly Ala Lys Phe Ser Lys
1 5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Met Gly Ala Lys Phe Ala Lys
1 5

<210> SEQ ID NO 128

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Met Gly Ala Lys Ser Ser Lys
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Met Gly Ala Lys Ser Ala Lys
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Met Gly Ala Lys Gln Ser Lys
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Gly Ala Lys Gln Ala Lys
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Gly Ala Gln Leu Ser Lys
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Met Gly Ala Gln Leu Ala Lys
1 5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Met Gly Ala Gln Phe Ser Lys
1 5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Met Gly Ala Gln Phe Ala Lys
1 5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Met Gly Ala Gln Ser Ser Lys
1 5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Met Gly Ala Gln Ser Ala Lys
1 5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Met Gly Ala Gln Gln Ser Lys
1 5

<210> SEQ ID NO 139
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 139

Met Gly Ala Gln Gln Ala Lys
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Gly Ser Lys Leu Ser Lys
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Met Gly Ser Lys Leu Ala Lys
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Met Gly Ser Lys Phe Ser Lys
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Met Gly Ser Lys Phe Ala Lys
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Gly Ser Lys Ser Ser Lys
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Met Gly Ser Lys Ser Ala Lys
1 5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Met Gly Ser Lys Gln Ser Lys
1 5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Met Gly Ser Lys Gln Ala Lys
1 5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Met Gly Ser Gln Leu Ser Lys
1 5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Met Gly Ser Gln Leu Ala Lys
1 5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Met Gly Ser Gln Phe Ser Lys
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Met Gly Ser Gln Phe Ala Lys
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Met Gly Ser Gln Ser Ser Lys
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Met Gly Ser Gln Ser Ala Lys
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Met Gly Ser Gln Gln Ser Lys
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Met Gly Ser Gln Gln Ala Lys
1               5

<210> SEQ ID NO 156
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 156

Met Gly Ala Lys Leu Ser Lys Lys Lys
1               5


<210> SEQ ID NO 157
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Ser Gly
            20                  25                  30

Gly Ser Gly Gly Ser Asp Tyr Lys Asp Asp Asp Asp Lys Gly Gly Gly
        35                  40                  45

Ser Gly Met Ala Ser Asn Phe Thr Gln Phe Val Leu Val Asp Asn Gly
    50                  55                  60

Gly Thr Gly Asp Val Thr Val Ala Pro Ser Asn Phe Ala Asn Gly Ile
65                  70                  75                  80

Ala Glu Trp Ile Ser Ser Asn Ser Arg Ser Gln Ala Tyr Lys Val Thr
                85                  90                  95

Cys Ser Val Arg Gln Ser Ser Ala Gln Asn Arg Lys Tyr Thr Ile Lys
            100                 105                 110

Val Glu Val Pro Lys Gly Ala Trp Arg Ser Tyr Leu Asn Met Glu Leu
        115                 120                 125

Thr Ile Pro Ile Phe Ala Thr Asn Ser Asp Cys Glu Leu Ile Val Lys
    130                 135                 140

Ala Met Gln Gly Leu Leu Lys Asp Gly Asn Pro Ile Pro Ser Ala Ile
145                 150                 155                 160

Ala Ala Asn Ser Gly Ile Tyr
                165


<210> SEQ ID NO 158
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Ser Gly
            20                  25                  30

Gly Ser Gly Gly Ser Asp Tyr Lys Asp Asp Asp Asp Lys Gly Gly Gly
        35                  40                  45

Ser Gly Met Ala Ser Asn Phe Thr Gln Phe Val Leu Val Asp Asn Gly
    50                  55                  60

Gly Thr Gly Asp Val Thr Val Ala Pro Ser Asn Phe Ala Asn Gly Ile
65                  70                  75                  80
```

Ala Glu Trp Ile Ser Ser Asn Ser Arg Ser Gln Ala Tyr Lys Val Thr
85 90 95

Cys Ser Val Arg Gln Ser Ser Ala Gln Lys Arg Lys Tyr Thr Ile Lys
100 105 110

Val Glu Val Pro Lys Gly Ala Trp Arg Ser Tyr Leu Asn Met Glu Leu
115 120 125

Thr Ile Pro Ile Phe Ala Thr Asn Ser Asp Cys Glu Leu Ile Val Lys
130 135 140

Ala Met Gln Gly Leu Leu Lys Asp Gly Asn Pro Ile Pro Ser Ala Ile
145 150 155 160

Ala Ala Asn Ser Gly Ile Tyr
165

<210> SEQ ID NO 159
<211> LENGTH: 296
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Gly
20 25 30

Gly Ser Gly Gly Ser Asp Tyr Lys Asp Asp Asp Asp Lys Gly Gly Gly
35 40 45

Ser Gly Met Ala Ser Asn Phe Thr Gln Phe Val Leu Val Asp Asn Gly
50 55 60

Gly Thr Gly Asp Val Thr Val Ala Pro Ser Asn Phe Ala Asn Gly Ile
65 70 75 80

Ala Glu Trp Ile Ser Ser Asn Ser Arg Ser Gln Ala Tyr Lys Val Thr
85 90 95

Cys Ser Val Arg Gln Ser Ser Ala Gln Asn Arg Lys Tyr Thr Ile Lys
100 105 110

Val Glu Val Pro Lys Gly Ala Trp Arg Ser Tyr Leu Asn Met Glu Leu
115 120 125

Thr Ile Pro Ile Phe Ala Thr Asn Ser Asp Cys Glu Leu Ile Val Lys
130 135 140

Ala Met Gln Gly Leu Leu Lys Asp Gly Asn Pro Ile Pro Ser Ala Ile
145 150 155 160

Ala Ala Asn Ser Gly Ile Tyr Gly Ser Gly Gly Ser Gly Gly Ser Gly
165 170 175

Gly Ser Gly Met Ala Ser Asn Phe Thr Gln Phe Val Leu Val Asp Asn
180 185 190

Gly Gly Thr Gly Asp Val Thr Val Ala Pro Ser Asn Phe Ala Asn Gly
195 200 205

Ile Ala Glu Trp Ile Ser Ser Asn Ser Arg Ser Gln Ala Tyr Lys Val
210 215 220

Thr Cys Ser Val Arg Gln Ser Ser Ala Gln Asn Arg Lys Tyr Thr Ile
225 230 235 240

Lys Val Glu Val Pro Lys Gly Ala Trp Arg Ser Tyr Leu Asn Met Glu
245 250 255

Leu Thr Ile Pro Ile Phe Ala Thr Asn Ser Asp Cys Glu Leu Ile Val
260 265 270

```
Lys Ala Met Gln Gly Leu Leu Lys Asp Gly Asn Pro Ile Pro Ser Ala
        275                 280                 285

Ile Ala Ala Asn Ser Gly Ile Tyr
    290                 295


<210> SEQ ID NO 160
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Ser Gly
            20                  25                  30

Gly Ser Gly Gly Ser Asp Tyr Lys Asp Asp Asp Asp Lys Gly Gly Gly
        35                  40                  45

Ser Gly Met Ala Ser Asn Phe Thr Gln Phe Val Leu Val Asp Asn Gly
    50                  55                  60

Gly Thr Gly Asp Val Thr Val Ala Pro Ser Asn Phe Ala Asn Gly Ile
65                  70                  75                  80

Ala Glu Trp Ile Ser Ser Asn Ser Arg Ser Gln Ala Tyr Lys Val Thr
                85                  90                  95

Cys Ser Val Arg Gln Ser Ser Ala Gln Lys Arg Lys Tyr Thr Ile Lys
            100                 105                 110

Val Glu Val Pro Lys Gly Ala Trp Arg Ser Tyr Leu Asn Met Glu Leu
        115                 120                 125

Thr Ile Pro Ile Phe Ala Thr Asn Ser Asp Cys Glu Leu Ile Val Lys
    130                 135                 140

Ala Met Gln Gly Leu Leu Lys Asp Gly Asn Pro Ile Pro Ser Ala Ile
145                 150                 155                 160

Ala Ala Asn Ser Gly Ile Tyr Gly Ser Gly Gly Ser Gly Gly Ser Gly
                165                 170                 175

Gly Ser Gly Met Ala Ser Asn Phe Thr Gln Phe Val Leu Val Asp Asn
            180                 185                 190

Gly Gly Thr Gly Asp Val Thr Val Ala Pro Ser Asn Phe Ala Asn Gly
        195                 200                 205

Ile Ala Glu Trp Ile Ser Ser Asn Ser Arg Ser Gln Ala Tyr Lys Val
    210                 215                 220

Thr Cys Ser Val Arg Gln Ser Ser Ala Gln Lys Arg Lys Tyr Thr Ile
225                 230                 235                 240

Lys Val Glu Val Pro Lys Gly Ala Trp Arg Ser Tyr Leu Asn Met Glu
                245                 250                 255

Leu Thr Ile Pro Ile Phe Ala Thr Asn Ser Asp Cys Glu Leu Ile Val
            260                 265                 270

Lys Ala Met Gln Gly Leu Leu Lys Asp Gly Asn Pro Ile Pro Ser Ala
        275                 280                 285

Ile Ala Ala Asn Ser Gly Ile Tyr
    290                 295


<210> SEQ ID NO 161
<211> LENGTH: 680
<212> TYPE: RNA
```

<213> ORGANISM: Artificial Sequence
<220> FEATURE:
<223> OTHER INFORMATION: Description of Artificial Sequence: Synthetic
polynucleotide

<400> SEQUENCE: 161
augaagccca ccgagaacaa cgaagacuuc aacaucgugg ccguggccag caacuucgcg 60
accacggauc ucgaugcuga ccgcgggaag uugcccggca agaagcugcc gcuggaggug 120
cucaaagagu uggaagccaa ugcccggaaa gcuggcugca ccaggggcug ucugaucugc 180
cugucccaca ucaagugcac gcccaagaug aagaaguuca ucccaggacg cugccacacc 240
uacgaaggcg acaaagaguc cgcacagggc ggcauaggcg aggcgaucgu cgacauuccu 300
gagauuccug gguucaagga cuuggagccc uuggagcagu ucaucgcaca ggucgaucug 360
uguguggacu gcacaacugg cugccucaaa gggcuugcca acgugcagug uucugaccug 420
cucaagaagu ggcugccgca acgcugugcg accuuugcca gcaagaucca gggccaggug 480
gacaagauca agggggccgg uggugacuaa ggauccaucg auaagcuuca ucgaaacaug 540
aggaucaccc auaucugcag ucgacaucga aacaugagga ucacccaugu cugcagucga 600
caucgaaaca ugaggaucac ccaugucugc agucgacauc gaaacaugag gaucacccau 660
gucugcaguc gacaucgaaa 680

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any Naturally Occuring Amino Acid

<400> SEQUENCE: 162

Met Gly Xaa Lys Leu Ser Lys Lys Lys
1 5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: See specification as filed for detailed
description of substitutions and preferred embodiments

<400> SEQUENCE: 163

Met Gly Xaa Lys Leu Ser Lys Lys Lys
1 5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)

<223> OTHER INFORMATION: Gly, Ala, or Ser
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (5)..(5)
<223> OTHER INFORMATION: Leu, Phe, Ser, or Gln
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (6)..(6)
<223> OTHER INFORMATION: Ser or Ala, See specification as filed for
      detailed description of substitutions and preferred embodiments

<400> SEQUENCE: 164

Met Gly Xaa Xaa Xaa Xaa Lys Lys
1               5

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tggaggtgct caaagagttg                                                   20

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ttgggcgtgc acttgat                                                      17

<210> SEQ ID NO 167
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
gggcattggc ttc                                                          13

<210> SEQ ID NO 168
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Ser Ala
            20                  25                  30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 169
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

Met Ala Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 170
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Met Gly Ala Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 171
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Met Ala Ala Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 172
<211> LENGTH: 57

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Ser Ala Gly Gly Gly
            20                  25                  30

Gly Ser Asp Tyr Lys Asp Asp Asp Asp Lys Gly Gly Gly Gly Ser Val
        35                  40                  45

Ser Lys Gly Glu Glu Leu Phe Thr Gly
    50                  55
```

<210> SEQ ID NO 173
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

```
Met Gly Gly Lys Leu Ser Lys Lys Lys Lys Gly Tyr Asn Val Asn Asp
1               5                   10                  15

Glu Lys Ala Lys Glu Lys Asp Lys Ser Ala Gly Gly Gly Gly Ser Asp
            20                  25                  30

Tyr Lys Asp Asp Asp Asp Lys Gly Gly Gly Gly Ser Val Ser Lys Gly
        35                  40                  45

Glu Glu Leu Phe Thr Gly
    50
```

<210> SEQ ID NO 174
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

```
Met Gly Gly Lys Leu Ser Lys Lys Lys Lys Gly Tyr Asn Val Asn Asp
1               5                   10                  15

Glu Lys Ala Lys Glu Ser Ala Gly Gly Gly Gly Ser Asp Tyr Lys Asp
            20                  25                  30

Asp Asp Asp Lys Gly Gly Gly Gly Ser Val Ser Lys Gly Glu Glu Leu
        35                  40                  45

Phe Thr Gly
    50
```

<210> SEQ ID NO 175
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

```
Met Gly Gly Lys Leu Ser Lys Lys Lys Lys Gly Tyr Asn Val Asn Asp
1               5                   10                  15
```

```
Glu Lys Ser Ala Gly Gly Gly Gly Ser Asp Tyr Lys Asp Asp Asp Asp
            20                  25                  30

Lys Gly Gly Gly Gly Ser Val Ser Lys Gly Glu Glu Leu Phe Thr Gly
        35                  40                  45


<210> SEQ ID NO 176
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Gly Gly Lys Leu Ser Lys Lys Lys Lys Gly Tyr Asn Val Asn Ser
1               5                   10                  15

Ala Gly Gly Gly Gly Ser Asp Tyr Lys Asp Asp Asp Asp Lys Gly Gly
            20                  25                  30

Gly Gly Ser Val Ser Lys Gly Glu Glu Leu Phe Thr Gly
        35                  40                  45


<210> SEQ ID NO 177
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Gly Gly Lys Leu Ser Lys Lys Lys Lys Gly Tyr Ser Ala Gly Gly
1               5                   10                  15

Gly Gly Ser Asp Tyr Lys Asp Asp Asp Asp Lys Gly Gly Gly Gly Ser
            20                  25                  30

Val Ser Lys Gly Glu Glu Leu Phe Thr Gly
        35                  40


<210> SEQ ID NO 178
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Gly Gly Lys Leu Ser Lys Lys Lys Ser Ala Gly Gly Gly Gly Ser
1               5                   10                  15

Asp Tyr Lys Asp Asp Asp Asp Lys Gly Gly Gly Gly Ser Val Ser Lys
            20                  25                  30

Gly Glu Glu Leu Phe Thr Gly
        35


<210> SEQ ID NO 179
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Gly Gly Lys Leu Ser Ser Ala Gly Gly Gly Gly Ser Asp Tyr Lys
```

1 5 10 15

Asp Asp Asp Asp Lys Gly Gly Gly Gly Ser Val Ser Lys Gly Glu Glu
20 25 30

Leu Phe Thr Gly
35

<210> SEQ ID NO 180
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Met Gly Gly Ser Ala Gly Gly Gly Gly Ser Asp Tyr Lys Asp Asp Asp
1 5 10 15

Asp Lys Gly Gly Gly Gly Ser Val Ser Lys Gly Glu Glu Leu Phe Thr
20 25 30

Gly

<210> SEQ ID NO 181
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly
50

<210> SEQ ID NO 182
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Met Gly Gly Lys Leu Ser Lys Lys Lys Lys Gly Tyr Ser Ala Gly Gly
1 5 10 15

Gly Gly Ser Asp Tyr Lys Asp Asp Asp Asp Lys Gly Gly Gly Gly Ser
20 25 30

Val Ser Lys Gly
35

<210> SEQ ID NO 183
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 183

Met Gly Gly Lys Leu Ser Lys Lys Lys Lys Gly Ser Ala Gly Gly Gly
1 5 10 15

Gly Ser Asp Tyr Lys Asp Asp Asp Asp Lys Gly Gly Gly Gly Ser Val
20 25 30

Ser Lys Gly
35

<210> SEQ ID NO 184
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

Met Gly Gly Lys Leu Ser Lys Lys Lys Lys Ser Ala Gly Gly Gly Gly
1 5 10 15

Ser Asp Tyr Lys Asp Asp Asp Asp Lys Gly Gly Gly Gly Ser Val Ser
20 25 30

Lys Gly

<210> SEQ ID NO 185
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

Met Gly Gly Lys Leu Ser Lys Lys Lys Ser Ala Gly Gly Gly Gly Ser
1 5 10 15

Asp Tyr Lys Asp Asp Asp Asp Lys Gly Gly Gly Gly Ser Val Ser Lys
20 25 30

Gly

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

Met Gly Gly Lys Leu Ser Lys Lys Ser Ala Gly Gly Gly Gly Ser Asp
1 5 10 15

Tyr Lys Asp Asp Asp Asp Lys Gly Gly Gly Gly Ser Val Ser Lys Gly
20 25 30

<210> SEQ ID NO 187
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Met Gly Gly Lys Leu Ser Lys Ser Ala Gly Gly Gly Gly Ser Asp Tyr
1 5 10 15

```
Lys Asp Asp Asp Asp Lys Gly Gly Gly Gly Ser Val Ser Lys Gly
            20                  25                  30


<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Gly Gly Lys Leu Ser Ser Ala Gly Gly Gly Gly Ser Asp Tyr Lys
1               5                   10                  15

Asp Asp Asp Asp Lys Gly Gly Gly Gly Ser Val Ser Lys Gly
            20                  25                  30


<210> SEQ ID NO 189
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Gly Gly Lys Leu Asp Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30


<210> SEQ ID NO 190
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Gly Gly Lys Leu Ala Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30


<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Gly Gly Lys Gln Ser Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30


<210> SEQ ID NO 192
<211> LENGTH: 30
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 192

Met Gly Ala Lys Lys Lys Lys Lys Arg Phe Ser Phe Lys Lys Ser Phe
1 5 10 15

Lys Leu Ser Gly Phe Ser Phe Lys Lys Asn Lys Lys Glu Ala
20 25 30

<210> SEQ ID NO 193
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

Met Ala Ala Lys Lys Lys Lys Lys Arg Phe Ser Phe Lys Lys Ser Phe
1 5 10 15

Lys Leu Ser Gly Phe Ser Phe Lys Lys Asn Lys Lys Glu Ala
20 25 30

<210> SEQ ID NO 194
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Met Gly Ala Lys Lys Ser Lys Lys Arg Phe Ser Phe Lys Lys Ser Phe
1 5 10 15

Lys Leu Ser Gly Phe Ser Phe Lys Lys Asn Lys Lys Glu Ala
20 25 30

<210> SEQ ID NO 195
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Met Gly Ala Lys Lys Ala Lys Lys Arg Phe Ser Phe Lys Lys Pro Phe
1 5 10 15

Lys Leu Ser Gly Phe Ser Phe Lys Lys Asn Lys Lys Glu Ala
20 25 30

<210> SEQ ID NO 196
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

Met Gly Gly Lys Leu Ser Lys Lys Lys Lys Ser Ala Gly Gly Ser Gly
1 5 10 15

Gly Ser Thr Ser Gly Ser Gly Asp Tyr Lys Asp Asp Asp Asp Lys Gly
20 25 30

Ser Gly Phe Glu Met Asp Gln Val Gln Leu Val Glu Ser Gly Gly Ala

-continued

```
        35                  40                  45

Leu Val Gln Pro Gly Gly Ser Leu Arg Leu Ser Cys Ala Ala Ser Gly
    50                  55                  60

Phe Pro Val Asn Arg Tyr Ser Met Arg Trp Tyr Arg Gln Ala Pro Gly
65                  70                  75                  80

Lys Glu Arg Glu Trp Val Ala Gly Met Ser Ser Ala Gly Asp Arg Ser
                85                  90                  95

Ser Tyr Glu Asp Ser Val Lys Gly Arg Phe Thr Ile Ser Arg Asp Asp
            100                 105                 110

Ala Arg Asn Thr Val Tyr Leu Gln Met Asn Ser Leu Lys Pro Glu Asp
        115                 120                 125

Thr Ala Val Tyr Tyr Cys Asn Val Asn Val Gly Phe Glu Tyr Trp Gly
    130                 135                 140

Gln Gly Thr Gln Val Thr Val Ser Ser
145                 150


<210> SEQ ID NO 197
<211> LENGTH: 4
<212> TYPE: PRT
<213> ORGANISM: Artificial Sequence
<220> FEATURE:
<223> OTHER INFORMATION: Peptide Linker

<400> SEQUENCE: 197

Gly Gly Gly Gly
1


<210> SEQ ID NO 198
<211> LENGTH: 7
<212> TYPE: PRT
<213> ORGANISM: Artificial Sequence
<220> FEATURE:
<223> OTHER INFORMATION: Peptide Linker

<400> SEQUENCE: 198

Ser Gly Gly Ser Gly Gly Ser
1               5


<210> SEQ ID NO 199
<211> LENGTH: 15
<212> TYPE: PRT
<213> ORGANISM: Artificial Sequence
<220> FEATURE:
<223> OTHER INFORMATION: Peptide Linker

<400> SEQUENCE: 199

Gly Gly Ser Gly Gly Ser Gly Gly Ser Gly Gly Ser Gly Gly Gly
1               5                   10                  15


<210> SEQ ID NO 200
<211> LENGTH: 16
<212> TYPE: PRT
<213> ORGANISM: Artificial Sequence
<220> FEATURE:
<223> OTHER INFORMATION: Peptide Linker

<400> SEQUENCE: 200

Gly Gly Ser Gly Gly Ser Gly Gly Gly Gly Ser Gly Gly Gly Gly Ser
1               5                   10                  15


<210> SEQ ID NO 201
<211> LENGTH: 18
<212> TYPE: PRT
```

<213> ORGANISM: Artificial Sequence
<220> FEATURE:
<223> OTHER INFORMATION: Peptide Linker

<400> SEQUENCE: 201

Gly Gly Ser Gly Gly Ser Gly Gly Ser Gly Gly Ser Gly Gly Ser Gly
1               5                   10                  15

Gly Ser

<210> SEQ ID NO 202
<211> LENGTH: 15
<212> TYPE: PRT
<213> ORGANISM: Artificial Sequence
<220> FEATURE:
<223> OTHER INFORMATION: Peptide Linker

<400> SEQUENCE: 202

Gly Gly Gly Gly Ser Gly Gly Gly Gly Ser Gly Gly Gly Gly Ser
1               5                   10                  15

<210> SEQ ID NO 203
<211> LENGTH: 5
<212> TYPE: PRT
<213> ORGANISM: Artificial Sequence
<220> FEATURE:
<223> OTHER INFORMATION: Peptide Linker
<220> FEATURE:
<221> NAME/KEY: MISC_FEATURE
<223> OTHER INFORMATION: X can be an integer from 1-100
<220> FEATURE:
<221> NAME/KEY: misc_feature
<222> LOCATION: (5)..(5)
<223> OTHER INFORMATION: X can be any integer from 1-100

<400> SEQUENCE: 203

Gly Gly Gly Ser Xaa
1               5

<210> SEQ ID NO 204
<211> LENGTH: 10
<212> TYPE: PRT
<213> ORGANISM: Artificial Sequence
<220> FEATURE:
<223> OTHER INFORMATION: Peptide Linker
<220> FEATURE:
<221> NAME/KEY: MISC_FEATURE
<222> LOCATION: (4)..(4)
<223> OTHER INFORMATION: X can be any integer from 1-100
<220> FEATURE:
<221> NAME/KEY: MISC_FEATURE
<222> LOCATION: (10)..(10)
<223> OTHER INFORMATION: X can be any integer from 1-100

<400> SEQUENCE: 204

Gly Gly Ser Xaa Gly Gly Gly Gly Ser Xaa
1               5                   10

<210> SEQ ID NO 205
<211> LENGTH: 4
<212> TYPE: PRT
<213> ORGANISM: Artificial Sequence
<220> FEATURE:
<223> OTHER INFORMATION: Effector Domain Sequence

<400> SEQUENCE: 205

Lys Lys Lys Lys
1

<210> SEQ ID NO 206
<211> LENGTH: 5
<212> TYPE: PRT
<213> ORGANISM: Artificial Sequence
<220> FEATURE:
<223> OTHER INFORMATION: Effector Domain Sequence

<400> SEQUENCE: 206

Lys Lys Lys Lys Lys
1               5

<210> SEQ ID NO 207
<211> LENGTH: 4
<212> TYPE: PRT
<213> ORGANISM: Artificial Sequence
<220> FEATURE:
<223> OTHER INFORMATION: Effector Domain Sequence

<400> SEQUENCE: 207

Arg Arg Arg Arg
1

<210> SEQ ID NO 208
<211> LENGTH: 5
<212> TYPE: PRT
<213> ORGANISM: Artificial Sequence
<220> FEATURE:
<223> OTHER INFORMATION: Effector Domain Sequence

<400> SEQUENCE: 208

Arg Arg Arg Arg Arg
1               5

<210> SEQ ID NO 209
<211> LENGTH: 4
<212> TYPE: PRT
<213> ORGANISM: Artificial Sequence
<220> FEATURE:
<223> OTHER INFORMATION: Effector Domain Sequence
<220> FEATURE:
<221> NAME/KEY: misc_feature
<222> LOCATION: (1)..(4)
<223> OTHER INFORMATION: Xaa can be Lys or Arg

<400> SEQUENCE: 209

Xaa Xaa Xaa Xaa
1

<210> SEQ ID NO 210
<211> LENGTH: 5
<212> TYPE: PRT
<213> ORGANISM: Artificial Sequence
<220> FEATURE:
<223> OTHER INFORMATION: Effector Domain Sequence
<220> FEATURE:
<221> NAME/KEY: misc_feature
<222> LOCATION: (1)..(5)
<223> OTHER INFORMATION: Xaa can be Lys or Arg

<400> SEQUENCE: 210

Xaa Xaa Xaa Xaa Xaa
1               5

<210> SEQ ID NO 211
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 211

Gly Gly Lys Leu Ser Lys Lys
1               5

<210> SEQ ID NO 212
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 212

Gly Ala Lys Leu Ser Lys Lys
1               5

<210> SEQ ID NO 213
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 213

Gly Gly Lys Gln Ser Lys Lys
1               5

<210> SEQ ID NO 214
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 214

Gly Gly Lys Leu Ala Lys Lys
1               5

<210> SEQ ID NO 215
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 215

Gly Gly Lys Leu Ser Lys
1               5

<210> SEQ ID NO 216
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 216

Gly Ala Lys Leu Ser Lys
1               5

<210> SEQ ID NO 217
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 217

Gly Gly Lys Gln Ser Lys
1               5

<210> SEQ ID NO 218
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 218

Gly Gly Lys Leu Ala Lys
1               5

<210> SEQ ID NO 219
<211> LENGTH: 4
<212> TYPE: PRT
<213> ORGANISM: Artificial Sequence
<220> FEATURE:
<223> OTHER INFORMATION: N Terminus Domain Sequence

<400> SEQUENCE: 219

Lys Lys Lys Gly
1

<210> SEQ ID NO 220
<211> LENGTH: 5
<212> TYPE: PRT
<213> ORGANISM: Artificial Sequence
<220> FEATURE:
<223> OTHER INFORMATION: N Terminus Domain Sequence

<400> SEQUENCE: 220

Lys Lys Lys Gly Tyr
1               5

<210> SEQ ID NO 221
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 221

Lys Lys Lys Gly Tyr Asn
1               5

<210> SEQ ID NO 222
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 222

Lys Lys Lys Gly Tyr Asn Val
1               5

<210> SEQ ID NO 223
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 223

```
Lys Lys Lys Gly Tyr Asn Val Asn
1               5


<210> SEQ ID NO 224
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 224

Lys Lys Lys Gly Tyr Ser
1               5


<210> SEQ ID NO 225
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 225

Lys Lys Lys Gly Tyr Gly
1               5


<210> SEQ ID NO 226
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 226

Lys Lys Lys Gly Tyr Gly Gly
1               5


<210> SEQ ID NO 227
<211> LENGTH: 5
<212> TYPE: PRT
<213> ORGANISM: Artificial Sequence
<220> FEATURE:
<223> OTHER INFORMATION: N Terminus Domain Sequence

<400> SEQUENCE: 227

Lys Lys Lys Gly Ser
1               5


<210> SEQ ID NO 228
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 228

Lys Lys Lys Gly Ser Gly
1               5


<210> SEQ ID NO 229
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 229
```

Lys Lys Lys Gly Ser Gly Ser
1 5

<210> SEQ ID NO 230
<211> LENGTH: 4
<212> TYPE: PRT
<213> ORGANISM: Artificial Sequence
<220> FEATURE:
<223> OTHER INFORMATION: N Terminus Domain Sequence

<400> SEQUENCE: 230

Lys Lys Lys Ser
1

<210> SEQ ID NO 231
<211> LENGTH: 5
<212> TYPE: PRT
<213> ORGANISM: Artificial Sequence
<220> FEATURE:
<223> OTHER INFORMATION: N Terminus Domain Sequence

<400> SEQUENCE: 231

Lys Lys Lys Ser Gly
1 5

<210> SEQ ID NO 232
<211> LENGTH: 6
<212> TYPE: PRT
<213> ORGANISM: Artificial Sequence
<220> FEATURE:
<223> OTHER INFORMATION: N Terminus Domain Sequence

<400> SEQUENCE: 232

Lys Lys Lys Ser Gly Gly
1 5

<210> SEQ ID NO 233
<211> LENGTH: 7
<212> TYPE: PRT
<213> ORGANISM: Artificial Sequence
<220> FEATURE:
<223> OTHER INFORMATION: N Terminus Domain Sequence

<400> SEQUENCE: 233

Lys Lys Lys Ser Gly Gly Ser
1 5

<210> SEQ ID NO 234
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 234

Lys Lys Lys Ser Gly Gly Ser Gly
1 5

<210> SEQ ID NO 235
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 235

Lys Lys Ser Gly Gly Ser Gly Gly 1 5

<210> SEQ ID NO 236
<211> LENGTH: 10
<212> TYPE: PRT
<213> ORGANISM: Artificial Sequence
<220> FEATURE:
<223> OTHER INFORMATION: N Terminus Domain Sequence

<400> SEQUENCE: 236

Lys Lys Lys Ser Gly Gly Ser Gly Gly Ser
1 5 10

<210> SEQ ID NO 237
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 237

Lys Arg Phe Ser Phe Lys Lys Ser
1 5

<210> SEQ ID NO 238
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 238

Gly Gly Lys Leu Ser Lys Lys Lys
1 5

<210> SEQ ID NO 239
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 239

Gly Gly Lys Leu Ser Lys Lys Ser
1 5

<210> SEQ ID NO 240
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 240

Gly Ala Lys Leu Ser Lys Lys Lys
1 5

<210> SEQ ID NO 241
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 241

Gly Ala Lys Leu Ser Lys Lys Ser
1 5

<210> SEQ ID NO 242
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 242

Gly Gly Lys Gln Ser Lys Lys Lys
1               5

<210> SEQ ID NO 243
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 243

Gly Gly Lys Gln Ser Lys Lys Ser
1               5

<210> SEQ ID NO 244
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 244

Gly Gly Lys Leu Ala Lys Lys Lys
1               5

<210> SEQ ID NO 245
<211> LENGTH: 8
<212> TYPE: PRT
<213> ORGANISM: Artificial Sequence
<220> FEATURE:
<223> OTHER INFORMATION: N Terminus Domain Sequence

<400> SEQUENCE: 245

Gly Gly Lys Leu Ala Lys Lys Ser
1               5

<210> SEQ ID NO 246
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 246

Gly Gly Lys Leu Ser Lys Lys Lys Lys Gly Tyr Asn Val Asn
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 247

Gly Ala Lys Leu Ser Lys Lys Lys Lys Gly Tyr Asn Val Asn
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 248

Gly Gly Lys Gln Ser Lys Lys Lys Lys Gly Tyr Asn Val Asn
1 5 10

<210> SEQ ID NO 249
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 249

Gly Gly Lys Leu Ala Lys Lys Lys Lys Gly Tyr Asn Val Asn
1 5 10

<210> SEQ ID NO 250
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 250

Gly Gly Lys Leu Ser Lys Lys Lys Lys Gly Tyr Ser Gly Gly
1 5 10

<210> SEQ ID NO 251
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 251

Gly Gly Lys Leu Ser Lys Lys Lys Lys Gly Ser Gly Gly Ser
1 5 10

<210> SEQ ID NO 252
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 252

Gly Gly Lys Leu Ser Lys Lys Lys Lys Ser Gly Gly Ser Gly
1 5 10

<210> SEQ ID NO 253
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 253

Gly Gly Lys Leu Ser Lys Lys Lys Ser Gly Gly Ser Gly Gly
1 5 10

<210> SEQ ID NO 254
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 254

Gly Gly Lys Leu Ser Lys Lys Ser Gly Gly Ser Gly Gly Ser
1 5 10

<210> SEQ ID NO 255
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 255

Gly Gly Lys Leu Ser Lys Ser Gly Gly Ser Gly Gly Ser Val
1 5 10

<210> SEQ ID NO 256
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 256

Gly Ala Lys Lys Ser Lys Lys Arg Phe Ser Phe Lys Lys Ser
1 5 10

<210> SEQ ID NO 257
<211> LENGTH: 29
<212> TYPE: PRT
<213> ORGANISM: Artificial Sequence
<220> FEATURE:
<223> OTHER INFORMATION: Scaffold Y Sequence

<400> SEQUENCE: 257

Gly Gly Lys Leu Ser Lys Lys Lys Lys Gly Tyr Asn Val Asn Asp Glu
1 5 10 15

Lys Ala Lys Glu Lys Asp Lys Lys Ala Glu Gly Ala Ala
20 25

<210> SEQ ID NO 258
<211> LENGTH: 28
<212> TYPE: PRT
<213> ORGANISM: Artificial Sequence
<220> FEATURE:
<223> OTHER INFORMATION: Scaffold Y Sequence

<400> SEQUENCE: 258

Gly Gly Lys Leu Ser Lys Lys Lys Lys Gly Tyr Asn Val Asn Asp Glu
1 5 10 15

Lys Ala Lys Glu Lys Asp Lys Lys Ala Glu Gly Ala
20 25

<210> SEQ ID NO 259
<211> LENGTH: 27
<212> TYPE: PRT
<213> ORGANISM: Artificial Sequence
<220> FEATURE:
<223> OTHER INFORMATION: Scaffold Y Sequence

<400> SEQUENCE: 259

Gly Gly Lys Leu Ser Lys Lys Lys Lys Gly Tyr Asn Val Asn Asp Glu
1 5 10 15

Lys Ala Lys Glu Lys Asp Lys Lys Ala Glu Gly
20 25

<210> SEQ ID NO 260
<211> LENGTH: 26
<212> TYPE: PRT
<213> ORGANISM: Artificial Sequence
<220> FEATURE:
<223> OTHER INFORMATION: Scaffold Y Sequence

<400> SEQUENCE: 260

Gly Gly Lys Leu Ser Lys Lys Lys Lys Gly Tyr Asn Val Asn Asp Glu
1 5 10 15

Lys Ala Lys Glu Lys Asp Lys Lys Ala Glu
20 25

<210> SEQ ID NO 261
<211> LENGTH: 25
<212> TYPE: PRT
<213> ORGANISM: Artificial Sequence
<220> FEATURE:
<223> OTHER INFORMATION: Scaffold Y Sequence

<400> SEQUENCE: 261

Gly Gly Lys Leu Ser Lys Lys Lys Lys Gly Tyr Asn Val Asn Asp Glu
1 5 10 15

Lys Ala Lys Glu Lys Asp Lys Lys Ala
20 25

<210> SEQ ID NO 262
<211> LENGTH: 24
<212> TYPE: PRT
<213> ORGANISM: Artificial Sequence
<220> FEATURE:
<223> OTHER INFORMATION: Scaffold Y Sequence

<400> SEQUENCE: 262

Gly Gly Lys Leu Ser Lys Lys Lys Lys Gly Tyr Asn Val Asn Asp Glu
1 5 10 15

Lys Ala Lys Glu Lys Asp Lys Lys
20

<210> SEQ ID NO 263
<211> LENGTH: 23
<212> TYPE: PRT
<213> ORGANISM: Artificial Sequence
<220> FEATURE:
<223> OTHER INFORMATION: Scaffold Y Sequence

<400> SEQUENCE: 263

Gly Gly Lys Leu Ser Lys Lys Lys Lys Gly Tyr Asn Val Asn Asp Glu
1 5 10 15

Lys Ala Lys Glu Lys Asp Lys
20

<210> SEQ ID NO 264
<211> LENGTH: 22
<212> TYPE: PRT
<213> ORGANISM: Artificial Sequence
<220> FEATURE:
<223> OTHER INFORMATION: Scaffold Y Sequence

<400> SEQUENCE: 264

Gly Gly Lys Leu Ser Lys Lys Lys Lys Gly Tyr Asn Val Asn Asp Glu
1 5 10 15

Lys Ala Lys Glu Lys Asp
20

<210> SEQ ID NO 265
<211> LENGTH: 21
<212> TYPE: PRT
<213> ORGANISM: Artificial Sequence
<220> FEATURE:
<223> OTHER INFORMATION: Scaffold Y Sequence

<400> SEQUENCE: 265

Gly Gly Lys Leu Ser Lys Lys Lys Lys Gly Tyr Asn Val Asn Asp Glu
1 5 10 15

Lys Ala Lys Glu Lys
20

<210> SEQ ID NO 266
<211> LENGTH: 20
<212> TYPE: PRT
<213> ORGANISM: Artificial Sequence
<220> FEATURE:
<223> OTHER INFORMATION: Scaffold Y Sequence

<400> SEQUENCE: 266

Gly Gly Lys Leu Ser Lys Lys Lys Lys Gly Tyr Asn Val Asn Asp Glu
1 5 10 15

Lys Ala Lys Glu
20

<210> SEQ ID NO 267
<211> LENGTH: 19
<212> TYPE: PRT
<213> ORGANISM: Artificial Sequence
<220> FEATURE:
<223> OTHER INFORMATION: Scaffold Y Sequence

<400> SEQUENCE: 267

Gly Gly Lys Leu Ser Lys Lys Lys Lys Gly Tyr Asn Val Asn Asp Glu
1 5 10 15

Lys Ala Lys

<210> SEQ ID NO 268
<211> LENGTH: 18
<212> TYPE: PRT
<213> ORGANISM: Artificial Sequence
<220> FEATURE:
<223> OTHER INFORMATION: Scaffold Y Sequence

<400> SEQUENCE: 268

Gly Gly Lys Leu Ser Lys Lys Lys Lys Gly Tyr Asn Val Asn Asp Glu
1 5 10 15

Lys Ala

<210> SEQ ID NO 269
<211> LENGTH: 17
<212> TYPE: PRT
<213> ORGANISM: Artificial Sequence
<220> FEATURE:
<223> OTHER INFORMATION: Scaffold Y Sequence

<400> SEQUENCE: 269

Gly Gly Lys Leu Ser Lys Lys Lys Lys Gly Tyr Asn Val Asn Asp Glu
1 5 10 15

Lys

<210> SEQ ID NO 270
<211> LENGTH: 16
<212> TYPE: PRT
<213> ORGANISM: Artificial Sequence
<220> FEATURE:
<223> OTHER INFORMATION: Scaffold Y Sequence

<400> SEQUENCE: 270

Gly Gly Lys Leu Ser Lys Lys Lys Lys Gly Tyr Asn Val Asn Asp Glu
1 5 10 15

<210> SEQ ID NO 271
<211> LENGTH: 15
<212> TYPE: PRT
<213> ORGANISM: Artificial Sequence
<220> FEATURE:
<223> OTHER INFORMATION: Scaffold Y Sequence

<400> SEQUENCE: 271

Gly Gly Lys Leu Ser Lys Lys Lys Lys Gly Tyr Asn Val Asn Asp
1 5 10 15

<210> SEQ ID NO 272
<211> LENGTH: 13
<212> TYPE: PRT
<213> ORGANISM: Artificial Sequence
<220> FEATURE:
<223> OTHER INFORMATION: Scaffold Y Sequence

<400> SEQUENCE: 272

Gly Gly Lys Leu Ser Lys Lys Lys Lys Gly Tyr Asn Val
1 5 10

<210> SEQ ID NO 273
<211> LENGTH: 12
<212> TYPE: PRT
<213> ORGANISM: Artificial Sequence
<220> FEATURE:
<223> OTHER INFORMATION: Scaffold Y Sequence

<400> SEQUENCE: 273

Gly Gly Lys Leu Ser Lys Lys Lys Lys Gly Tyr Asn
1 5 10

<210> SEQ ID NO 274
<211> LENGTH: 11
<212> TYPE: PRT
<213> ORGANISM: Artificial Sequence
<220> FEATURE:
<223> OTHER INFORMATION: Scaffold Y Sequence

<400> SEQUENCE: 274

Gly Gly Lys Leu Ser Lys Lys Lys Lys Gly Tyr
1 5 10

<210> SEQ ID NO 275
<211> LENGTH: 10
<212> TYPE: PRT
<213> ORGANISM: Artificial Sequence
<220> FEATURE:
<223> OTHER INFORMATION: Scaffold Y Sequence

<400> SEQUENCE: 275

Gly Gly Lys Leu Ser Lys Lys Lys Lys Gly
1 5 10

<210> SEQ ID NO 276
<211> LENGTH: 9
<212> TYPE: PRT
<213> ORGANISM: Artificial Sequence
<220> FEATURE:
<223> OTHER INFORMATION: Scaffold Y Sequence

<400> SEQUENCE: 276

Gly Gly Lys Leu Ser Lys Lys Lys Lys
1 5

<210> SEQ ID NO 277
<211> LENGTH: 28
<212> TYPE: PRT
<213> ORGANISM: Artificial Sequence
<220> FEATURE:
<223> OTHER INFORMATION: Scaffold Y Sequence

<400> SEQUENCE: 277

Gly Ala Lys Lys Ser Lys Lys Arg Phe Ser Phe Lys Lys Ser Phe Lys
1 5 10 15

Leu Ser Gly Phe Ser Phe Lys Lys Asn Lys Lys Glu
20 25

<210> SEQ ID NO 278
<211> LENGTH: 27
<212> TYPE: PRT
<213> ORGANISM: Artificial Sequence
<220> FEATURE:
<223> OTHER INFORMATION: Scaffold Y Sequence

<400> SEQUENCE: 278

Gly Ala Lys Lys Ser Lys Lys Arg Phe Ser Phe Lys Lys Ser Phe Lys
1 5 10 15

Leu Ser Gly Phe Ser Phe Lys Lys Asn Lys Lys
20 25

<210> SEQ ID NO 279
<211> LENGTH: 26
<212> TYPE: PRT
<213> ORGANISM: Artificial Sequence
<220> FEATURE:
<223> OTHER INFORMATION: Scaffold Y Sequence

<400> SEQUENCE: 279

Gly Ala Lys Lys Ser Lys Lys Arg Phe Ser Phe Lys Lys Ser Phe Lys
1 5 10 15

Leu Ser Gly Phe Ser Phe Lys Lys Asn Lys
20 25

<210> SEQ ID NO 280
<211> LENGTH: 25
<212> TYPE: PRT
<213> ORGANISM: Artificial Sequence
<220> FEATURE:
<223> OTHER INFORMATION: Scaffold Y Sequence

<400> SEQUENCE: 280

Gly Ala Lys Lys Ser Lys Lys Arg Phe Ser Phe Lys Lys Ser Phe Lys
1 5 10 15

```
Leu Ser Gly Phe Ser Phe Lys Lys Asn
            20                  25


<210> SEQ ID NO 281
<211> LENGTH: 24
<212> TYPE: PRT
<213> ORGANISM: Artificial Sequence
<220> FEATURE:
<223> OTHER INFORMATION: Scaffold Y Sequence

<400> SEQUENCE: 281

Gly Ala Lys Lys Ser Lys Lys Arg Phe Ser Phe Lys Lys Ser Phe Lys
1               5                   10                  15

Leu Ser Gly Phe Ser Phe Lys Lys
            20


<210> SEQ ID NO 282
<211> LENGTH: 23
<212> TYPE: PRT
<213> ORGANISM: Artificial Sequence
<220> FEATURE:
<223> OTHER INFORMATION: Scaffold Y Sequence

<400> SEQUENCE: 282

Gly Ala Lys Lys Ser Lys Lys Arg Phe Ser Phe Lys Lys Ser Phe Lys
1               5                   10                  15

Leu Ser Gly Phe Ser Phe Lys
            20


<210> SEQ ID NO 283
<211> LENGTH: 22
<212> TYPE: PRT
<213> ORGANISM: Artificial Sequence
<220> FEATURE:
<223> OTHER INFORMATION: Scaffold Y Sequence

<400> SEQUENCE: 283

Gly Ala Lys Lys Ser Lys Lys Arg Phe Ser Phe Lys Lys Ser Phe Lys
1               5                   10                  15

Leu Ser Gly Phe Ser Phe
            20


<210> SEQ ID NO 284
<211> LENGTH: 21
<212> TYPE: PRT
<213> ORGANISM: Artificial Sequence
<220> FEATURE:
<223> OTHER INFORMATION: Scaffold Y Sequence

<400> SEQUENCE: 284

Gly Ala Lys Lys Ser Lys Lys Arg Phe Ser Phe Lys Lys Ser Phe Lys
1               5                   10                  15

Leu Ser Gly Phe Ser
            20


<210> SEQ ID NO 285
<211> LENGTH: 20
<212> TYPE: PRT
<213> ORGANISM: Artificial Sequence
<220> FEATURE:
<223> OTHER INFORMATION: Scaffold Y Sequence

<400> SEQUENCE: 285

Gly Ala Lys Lys Ser Lys Lys Arg Phe Ser Phe Lys Lys Ser Phe Lys
1               5                   10                  15
```

Leu Ser Gly Phe
20

<210> SEQ ID NO 286
<211> LENGTH: 19
<212> TYPE: PRT
<213> ORGANISM: Artificial Sequence
<220> FEATURE:
<223> OTHER INFORMATION: Scaffold Y Sequence

<400> SEQUENCE: 286

Gly Ala Lys Lys Ser Lys Lys Arg Phe Ser Phe Lys Lys Ser Phe Lys
1 5 10 15

Leu Ser Gly

<210> SEQ ID NO 287
<211> LENGTH: 18
<212> TYPE: PRT
<213> ORGANISM: Artificial Sequence
<220> FEATURE:
<223> OTHER INFORMATION: Scaffold Y Sequence

<400> SEQUENCE: 287

Gly Ala Lys Lys Ser Lys Lys Arg Phe Ser Phe Lys Lys Ser Phe Lys
1 5 10 15

Leu Ser

<210> SEQ ID NO 288
<211> LENGTH: 17
<212> TYPE: PRT
<213> ORGANISM: Artificial Sequence
<220> FEATURE:
<223> OTHER INFORMATION: Scaffold Y Sequence

<400> SEQUENCE: 288

Gly Ala Lys Lys Ser Lys Lys Arg Phe Ser Phe Lys Lys Ser Phe Lys
1 5 10 15

Leu

<210> SEQ ID NO 289
<211> LENGTH: 16
<212> TYPE: PRT
<213> ORGANISM: Artificial Sequence
<220> FEATURE:
<223> OTHER INFORMATION: Scaffold Y Sequence

<400> SEQUENCE: 289

Gly Ala Lys Lys Ser Lys Lys Arg Phe Ser Phe Lys Lys Ser Phe Lys
1 5 10 15

<210> SEQ ID NO 290
<211> LENGTH: 15
<212> TYPE: PRT
<213> ORGANISM: Artificial Sequence
<220> FEATURE:
<223> OTHER INFORMATION: Scaffold Y Sequence

<400> SEQUENCE: 290

Gly Ala Lys Lys Ser Lys Lys Arg Phe Ser Phe Lys Lys Ser Phe
1 5 10 15

<210> SEQ ID NO 291

<400> SEQUENCE: 291

000

<210> SEQ ID NO 292
<211> LENGTH: 13
<212> TYPE: PRT
<213> ORGANISM: Artificial Sequence
<220> FEATURE:
<223> OTHER INFORMATION: Scaffold Y Sequence

<400> SEQUENCE: 292

Gly Ala Lys Lys Ser Lys Lys Arg Phe Ser Phe Lys Lys
1               5                   10

<210> SEQ ID NO 293
<211> LENGTH: 12
<212> TYPE: PRT
<213> ORGANISM: Artificial Sequence
<220> FEATURE:
<223> OTHER INFORMATION: Scaffold Y Sequence

<400> SEQUENCE: 293

Gly Ala Lys Lys Ser Lys Lys Arg Phe Ser Phe Lys
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Scaffold Y Sequence

<400> SEQUENCE: 294

Gly Ala Lys Lys Ser Lys Lys Arg Phe Ser Phe
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Scaffold Y Sequence

<400> SEQUENCE: 295

Gly Ala Lys Lys Ser Lys Lys Arg Phe Ser
1               5                   10

<210> SEQ ID NO 296
<211> LENGTH: 9
<212> TYPE: PRT
<213> ORGANISM: Artificial Sequence
<220> FEATURE:
<223> OTHER INFORMATION: Scaffold Y Sequence

<400> SEQUENCE: 296

Gly Ala Lys Lys Ser Lys Lys Arg Phe
1               5

<210> SEQ ID NO 297
<211> LENGTH: 8
<212> TYPE: PRT
<213> ORGANISM: Artificial Sequence
<220> FEATURE:
<223> OTHER INFORMATION: Scaffold Y Sequence

<400> SEQUENCE: 297

Gly Ala Lys Lys Ser Lys Lys Arg 1 5

<210> SEQ ID NO 298
<211> LENGTH: 7
<212> TYPE: PRT
<213> ORGANISM: Artificial Sequence
<220> FEATURE:
<223> OTHER INFORMATION: Scaffold Y Sequence

<400> SEQUENCE: 298

Gly Ala Lys Lys Ser Lys Lys
1 5

<210> SEQ ID NO 299

<400> SEQUENCE: 299

000

<210> SEQ ID NO 300
<211> LENGTH: 29
<212> TYPE: PRT
<213> ORGANISM: Artificial Sequence
<220> FEATURE:
<223> OTHER INFORMATION: Scaffold Y Sequence

<400> SEQUENCE: 300

Gly Ala Lys Lys Ser Lys Lys Arg Phe Ser Phe Lys Lys Ser Phe Lys
1 5 10 15

Leu Ser Gly Phe Ser Phe Lys Lys Asn Lys Lys Glu Ala
20 25

<210> SEQ ID NO 301
<211> LENGTH: 29
<212> TYPE: PRT
<213> ORGANISM: Artificial Sequence
<220> FEATURE:
<223> OTHER INFORMATION: Scaffold Y Sequence

<400> SEQUENCE: 301

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys Glu Ala
20 25

<210> SEQ ID NO 302
<211> LENGTH: 28
<212> TYPE: PRT
<213> ORGANISM: Artificial Sequence
<220> FEATURE:
<223> OTHER INFORMATION: Scaffold Y Sequence

<400> SEQUENCE: 302

Gly Ala Gln Glu Ser Lys Lys Lys Lys Lys Lys Arg Phe Ser Phe Lys
1 5 10 15

Lys Ser Phe Lys Leu Ser Gly Phe Ser Phe Lys Lys
20 25

<210> SEQ ID NO 303
<211> LENGTH: 27
<212> TYPE: PRT
<213> ORGANISM: Artificial Sequence
<220> FEATURE:
<223> OTHER INFORMATION: Scaffold Y Sequence

<400> SEQUENCE: 303

```
Gly Ala Gln Glu Ser Lys Lys Lys Lys Lys Lys Arg Phe Ser Phe Lys
1               5                   10                  15

Lys Ser Phe Lys Leu Ser Gly Phe Ser Phe Lys
            20                  25


<210> SEQ ID NO 304
<211> LENGTH: 26
<212> TYPE: PRT
<213> ORGANISM: Artificial Sequence
<220> FEATURE:
<223> OTHER INFORMATION: Scaffold Y Sequence

<400> SEQUENCE: 304

Gly Ala Gln Glu Ser Lys Lys Lys Lys Lys Lys Arg Phe Ser Phe Lys
1               5                   10                  15

Lys Ser Phe Lys Leu Ser Gly Phe Ser Phe
            20                  25


<210> SEQ ID NO 305
<211> LENGTH: 25
<212> TYPE: PRT
<213> ORGANISM: Artificial Sequence
<220> FEATURE:
<223> OTHER INFORMATION: Scaffold Y Sequence

<400> SEQUENCE: 305

Gly Ala Gln Glu Ser Lys Lys Lys Lys Lys Lys Arg Phe Ser Phe Lys
1               5                   10                  15

Lys Ser Phe Lys Leu Ser Gly Phe Ser
            20                  25


<210> SEQ ID NO 306
<211> LENGTH: 24
<212> TYPE: PRT
<213> ORGANISM: Artificial Sequence
<220> FEATURE:
<223> OTHER INFORMATION: Scaffold Y Sequence

<400> SEQUENCE: 306

Gly Ala Gln Glu Ser Lys Lys Lys Lys Lys Lys Arg Phe Ser Phe Lys
1               5                   10                  15

Lys Ser Phe Lys Leu Ser Gly Phe
            20


<210> SEQ ID NO 307
<211> LENGTH: 23
<212> TYPE: PRT
<213> ORGANISM: Artificial Sequence
<220> FEATURE:
<223> OTHER INFORMATION: Scaffold Y Sequence

<400> SEQUENCE: 307

Gly Ala Gln Glu Ser Lys Lys Lys Lys Lys Lys Arg Phe Ser Phe Lys
1               5                   10                  15

Lys Ser Phe Lys Leu Ser Gly
            20


<210> SEQ ID NO 308
<211> LENGTH: 22
<212> TYPE: PRT
<213> ORGANISM: Artificial Sequence
<220> FEATURE:
<223> OTHER INFORMATION: Scaffold Y Sequence
```

<400> SEQUENCE: 308

Gly Ala Gln Glu Ser Lys Lys Lys Lys Lys Lys Arg Phe Ser Phe Lys
1               5                   10                  15

Lys Ser Phe Lys Leu Ser
            20

<210> SEQ ID NO 309
<211> LENGTH: 21
<212> TYPE: PRT
<213> ORGANISM: Artificial Sequence
<220> FEATURE:
<223> OTHER INFORMATION: Scaffold Y Sequence

<400> SEQUENCE: 309

Gly Ala Gln Glu Ser Lys Lys Lys Lys Lys Lys Arg Phe Ser Phe Lys
1               5                   10                  15

Lys Ser Phe Lys Leu
            20

<210> SEQ ID NO 310
<211> LENGTH: 20
<212> TYPE: PRT
<213> ORGANISM: Artificial Sequence
<220> FEATURE:
<223> OTHER INFORMATION: Scaffold Y Sequence

<400> SEQUENCE: 310

Gly Ala Gln Glu Ser Lys Lys Lys Lys Lys Lys Arg Phe Ser Phe Lys
1               5                   10                  15

Lys Ser Phe Lys
            20

<210> SEQ ID NO 311
<211> LENGTH: 19
<212> TYPE: PRT
<213> ORGANISM: Artificial Sequence
<220> FEATURE:
<223> OTHER INFORMATION: Scaffold Y Sequence

<400> SEQUENCE: 311

Gly Ala Gln Glu Ser Lys Lys Lys Lys Lys Lys Arg Phe Ser Phe Lys
1               5                   10                  15

Lys Ser Phe

<210> SEQ ID NO 312
<211> LENGTH: 18
<212> TYPE: PRT
<213> ORGANISM: Artificial Sequence
<220> FEATURE:
<223> OTHER INFORMATION: Scaffold Y Sequence

<400> SEQUENCE: 312

Gly Ala Gln Glu Ser Lys Lys Lys Lys Lys Lys Arg Phe Ser Phe Lys
1               5                   10                  15

Lys Ser

<210> SEQ ID NO 313
<211> LENGTH: 17
<212> TYPE: PRT
<213> ORGANISM: Artificial Sequence
<220> FEATURE:
<223> OTHER INFORMATION: Scaffold Y Sequence

<400> SEQUENCE: 313

Gly Ala Gln Glu Ser Lys Lys Lys Lys Lys Lys Arg Phe Ser Phe Lys
1 5 10 15

Lys

<210> SEQ ID NO 314
<211> LENGTH: 16
<212> TYPE: PRT
<213> ORGANISM: Artificial Sequence
<220> FEATURE:
<223> OTHER INFORMATION: Scaffold Y Sequence

<400> SEQUENCE: 314

Gly Ala Gln Glu Ser Lys Lys Lys Lys Lys Lys Arg Phe Ser Phe Lys
1 5 10 15

<210> SEQ ID NO 315
<211> LENGTH: 15
<212> TYPE: PRT
<213> ORGANISM: Artificial Sequence
<220> FEATURE:
<223> OTHER INFORMATION: Scaffold Y Sequence

<400> SEQUENCE: 315

Gly Ala Gln Glu Ser Lys Lys Lys Lys Lys Lys Arg Phe Ser Phe
1 5 10 15

<210> SEQ ID NO 316
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 316

Gly Ala Gln Glu Ser Lys Lys Lys Lys Lys Lys Arg Phe Ser
1 5 10

<210> SEQ ID NO 317
<211> LENGTH: 13
<212> TYPE: PRT
<213> ORGANISM: Artificial Sequence
<220> FEATURE:
<223> OTHER INFORMATION: Scaffold Y Sequence

<400> SEQUENCE: 317

Gly Ala Gln Glu Ser Lys Lys Lys Lys Lys Lys Arg Phe
1 5 10

<210> SEQ ID NO 318
<211> LENGTH: 12
<212> TYPE: PRT
<213> ORGANISM: Artificial Sequence
<220> FEATURE:
<223> OTHER INFORMATION: Scaffold Y Sequence

<400> SEQUENCE: 318

Gly Ala Gln Glu Ser Lys Lys Lys Lys Lys Lys Arg
1 5 10

<210> SEQ ID NO 319
<211> LENGTH: 11
<212> TYPE: PRT
<213> ORGANISM: Artificial Sequence
<220> FEATURE:
<223> OTHER INFORMATION: Scaffold Y Sequence

<400> SEQUENCE: 319

Gly Ala Gln Glu Ser Lys Lys Lys Lys Lys Lys
1 5 10

<210> SEQ ID NO 320
<211> LENGTH: 10
<212> TYPE: PRT
<213> ORGANISM: Artificial Sequence
<220> FEATURE:
<223> OTHER INFORMATION: Scaffold Y Sequence

<400> SEQUENCE: 320

Gly Ala Gln Glu Ser Lys Lys Lys Lys Lys
1 5 10

<210> SEQ ID NO 321
<211> LENGTH: 9
<212> TYPE: PRT
<213> ORGANISM: Artificial Sequence
<220> FEATURE:
<223> OTHER INFORMATION: Scaffold Y Sequence

<400> SEQUENCE: 321

Gly Ala Gln Glu Ser Lys Lys Lys Lys
1 5

<210> SEQ ID NO 322
<211> LENGTH: 8
<212> TYPE: PRT
<213> ORGANISM: Artificial Sequence
<220> FEATURE:
<223> OTHER INFORMATION: Scaffold Y Sequence

<400> SEQUENCE: 322

Gly Ala Gln Glu Ser Lys Lys Lys
1 5

<210> SEQ ID NO 323
<211> LENGTH: 7
<212> TYPE: PRT
<213> ORGANISM: Artificial Sequence
<220> FEATURE:
<223> OTHER INFORMATION: Scaffold Y Sequence

<400> SEQUENCE: 323

Gly Ala Gln Glu Ser Lys Lys
1 5

<210> SEQ ID NO 324
<211> LENGTH: 30
<212> TYPE: PRT
<213> ORGANISM: Artificial Sequence
<220> FEATURE:
<223> OTHER INFORMATION: Scaffold Y Sequence

<400> SEQUENCE: 324

Gly Ser Gln Ser Ser Lys Lys Lys Lys Lys Lys Phe Ser Phe Lys Lys
1 5 10 15

Pro Phe Lys Leu Ser Gly Leu Ser Phe Lys Arg Asn Arg Lys
20 25 30

<210> SEQ ID NO 325
<211> LENGTH: 29
<212> TYPE: PRT
<213> ORGANISM: Artificial Sequence
<220> FEATURE:

<223> OTHER INFORMATION: Scaffold Y Sequence

<400> SEQUENCE: 325

Gly Ser Gln Ser Ser Lys Lys Lys Lys Lys Lys Phe Ser Phe Lys Lys
1               5                   10                  15

Pro Phe Lys Leu Ser Gly Leu Ser Phe Lys Arg Asn Arg
            20                  25

<210> SEQ ID NO 326
<211> LENGTH: 28
<212> TYPE: PRT
<213> ORGANISM: Artificial Sequence
<220> FEATURE:
<223> OTHER INFORMATION: Scaffold Y Sequence

<400> SEQUENCE: 326

Gly Ser Gln Ser Ser Lys Lys Lys Lys Lys Lys Phe Ser Phe Lys Lys
1               5                   10                  15

Pro Phe Lys Leu Ser Gly Leu Ser Phe Lys Arg Asn
            20                  25

<210> SEQ ID NO 327
<211> LENGTH: 27
<212> TYPE: PRT
<213> ORGANISM: Artificial Sequence
<220> FEATURE:
<223> OTHER INFORMATION: Scaffold Y Sequence

<400> SEQUENCE: 327

Gly Ser Gln Ser Ser Lys Lys Lys Lys Lys Lys Phe Ser Phe Lys Lys
1               5                   10                  15

Pro Phe Lys Leu Ser Gly Leu Ser Phe Lys Arg
            20                  25

<210> SEQ ID NO 328
<211> LENGTH: 26
<212> TYPE: PRT
<213> ORGANISM: Artificial Sequence
<220> FEATURE:
<223> OTHER INFORMATION: Scaffold Y Sequence

<400> SEQUENCE: 328

Gly Ser Gln Ser Ser Lys Lys Lys Lys Lys Lys Phe Ser Phe Lys Lys
1               5                   10                  15

Pro Phe Lys Leu Ser Gly Leu Ser Phe Lys
            20                  25

<210> SEQ ID NO 329
<211> LENGTH: 25
<212> TYPE: PRT
<213> ORGANISM: Artificial Sequence
<220> FEATURE:
<223> OTHER INFORMATION: Scaffold Y Sequence

<400> SEQUENCE: 329

Gly Ser Gln Ser Ser Lys Lys Lys Lys Lys Lys Phe Ser Phe Lys Lys
1               5                   10                  15

Pro Phe Lys Leu Ser Gly Leu Ser Phe
            20                  25

<210> SEQ ID NO 330
<211> LENGTH: 24
<212> TYPE: PRT
<213> ORGANISM: Artificial Sequence
<220> FEATURE:
<223> OTHER INFORMATION: Scaffold Y Sequence

<400> SEQUENCE: 330

Gly Ser Gln Ser Ser Lys Lys Lys Lys Lys Lys Phe Ser Phe Lys Lys
1               5                   10                  15

Pro Phe Lys Leu Ser Gly Leu Ser
            20

<210> SEQ ID NO 331
<211> LENGTH: 23
<212> TYPE: PRT
<213> ORGANISM: Artificial Sequence
<220> FEATURE:
<223> OTHER INFORMATION: Scaffold Y Sequence

<400> SEQUENCE: 331

Gly Ser Gln Ser Ser Lys Lys Lys Lys Lys Lys Phe Ser Phe Lys Lys
1               5                   10                  15

Pro Phe Lys Leu Ser Gly Leu
            20

<210> SEQ ID NO 332
<211> LENGTH: 22
<212> TYPE: PRT
<213> ORGANISM: Artificial Sequence
<220> FEATURE:
<223> OTHER INFORMATION: Scaffold Y Sequence

<400> SEQUENCE: 332

Gly Ser Gln Ser Ser Lys Lys Lys Lys Lys Lys Phe Ser Phe Lys Lys
1               5                   10                  15

Pro Phe Lys Leu Ser Gly
            20

<210> SEQ ID NO 333
<211> LENGTH: 21
<212> TYPE: PRT
<213> ORGANISM: Artificial Sequence
<220> FEATURE:
<223> OTHER INFORMATION: Scaffold Y Sequence

<400> SEQUENCE: 333

Gly Ser Gln Ser Ser Lys Lys Lys Lys Lys Lys Phe Ser Phe Lys Lys
1               5                   10                  15

Pro Phe Lys Leu Ser
            20

<210> SEQ ID NO 334
<211> LENGTH: 20
<212> TYPE: PRT
<213> ORGANISM: Artificial Sequence
<220> FEATURE:
<223> OTHER INFORMATION: Scaffold Y Sequence

<400> SEQUENCE: 334

Gly Ser Gln Ser Ser Lys Lys Lys Lys Lys Lys Phe Ser Phe Lys Lys
1               5                   10                  15

Pro Phe Lys Leu
            20

<210> SEQ ID NO 335
<211> LENGTH: 19
<212> TYPE: PRT

<213> ORGANISM: Artificial Sequence
<220> FEATURE:
<223> OTHER INFORMATION: Scaffold Y Sequence

<400> SEQUENCE: 335

Gly Ser Gln Ser Ser Lys Lys Lys Lys Lys Lys Phe Ser Phe Lys Lys
1 5 10 15

Pro Phe Lys

<210> SEQ ID NO 336
<211> LENGTH: 18
<212> TYPE: PRT
<213> ORGANISM: Artificial Sequence
<220> FEATURE:
<223> OTHER INFORMATION: Scaffold Y Sequence

<400> SEQUENCE: 336

Gly Ser Gln Ser Ser Lys Lys Lys Lys Lys Lys Phe Ser Phe Lys Lys
1 5 10 15

Pro Phe

<210> SEQ ID NO 337
<211> LENGTH: 17
<212> TYPE: PRT
<213> ORGANISM: Artificial Sequence
<220> FEATURE:
<223> OTHER INFORMATION: Scaffold Y Sequence

<400> SEQUENCE: 337

Gly Ser Gln Ser Ser Lys Lys Lys Lys Lys Lys Phe Ser Phe Lys Lys
1 5 10 15

Pro

<210> SEQ ID NO 338
<211> LENGTH: 16
<212> TYPE: PRT
<213> ORGANISM: Artificial Sequence
<220> FEATURE:
<223> OTHER INFORMATION: Scaffold Y Sequence

<400> SEQUENCE: 338

Gly Ser Gln Ser Ser Lys Lys Lys Lys Lys Lys Phe Ser Phe Lys Lys
1 5 10 15

<210> SEQ ID NO 339
<211> LENGTH: 15
<212> TYPE: PRT
<213> ORGANISM: Artificial Sequence
<220> FEATURE:
<223> OTHER INFORMATION: Scaffold Y Sequence

<400> SEQUENCE: 339

Gly Ser Gln Ser Ser Lys Lys Lys Lys Lys Lys Phe Ser Phe Lys
1 5 10 15

<210> SEQ ID NO 340
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 340

Gly Ser Gln Ser Ser Lys Lys Lys Lys Lys Lys Phe Ser Phe
1 5 10

<210> SEQ ID NO 341
<211> LENGTH: 13
<212> TYPE: PRT
<213> ORGANISM: Artificial Sequence
<220> FEATURE:
<223> OTHER INFORMATION: Scaffold Y Sequence

<400> SEQUENCE: 341

Gly Ser Gln Ser Ser Lys Lys Lys Lys Lys Lys Phe Ser
1 5 10

<210> SEQ ID NO 342
<211> LENGTH: 12
<212> TYPE: PRT
<213> ORGANISM: Artificial Sequence
<220> FEATURE:
<223> OTHER INFORMATION: Scaffold Y Sequence

<400> SEQUENCE: 342

Gly Ser Gln Ser Ser Lys Lys Lys Lys Lys Lys Phe
1 5 10

<210> SEQ ID NO 343
<211> LENGTH: 11
<212> TYPE: PRT
<213> ORGANISM: Artificial Sequence
<220> FEATURE:
<223> OTHER INFORMATION: Scaffold Y Sequence

<400> SEQUENCE: 343

Gly Ser Gln Ser Ser Lys Lys Lys Lys Lys Lys
1 5 10

<210> SEQ ID NO 344
<211> LENGTH: 10
<212> TYPE: PRT
<213> ORGANISM: Artificial Sequence
<220> FEATURE:
<223> OTHER INFORMATION: Scaffold Y Sequence

<400> SEQUENCE: 344

Gly Ser Gln Ser Ser Lys Lys Lys Lys Lys
1 5 10

<210> SEQ ID NO 345
<211> LENGTH: 9
<212> TYPE: PRT
<213> ORGANISM: Artificial Sequence
<220> FEATURE:
<223> OTHER INFORMATION: Scaffold Y Sequence

<400> SEQUENCE: 345

Gly Ser Gln Ser Ser Lys Lys Lys Lys
1 5

<210> SEQ ID NO 346
<211> LENGTH: 8
<212> TYPE: PRT
<213> ORGANISM: Artificial Sequence
<220> FEATURE:
<223> OTHER INFORMATION: Scaffold Y Sequence

<400> SEQUENCE: 346

Gly Ser Gln Ser Ser Lys Lys Lys
1 5

<210> SEQ ID NO 347
<211> LENGTH: 7
<212> TYPE: PRT
<213> ORGANISM: Artificial Sequence
<220> FEATURE:
<223> OTHER INFORMATION: Scaffold Y Sequence

<400> SEQUENCE: 347

Gly Ser Gln Ser Ser Lys Lys
1 5

<210> SEQ ID NO 348
<211> LENGTH: 28
<212> TYPE: PRT
<213> ORGANISM: Artificial Sequence
<220> FEATURE:
<223> OTHER INFORMATION: Scaffold Y Sequence

<400> SEQUENCE: 348

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys Glu
20 25

<210> SEQ ID NO 349
<211> LENGTH: 27
<212> TYPE: PRT
<213> ORGANISM: Artificial Sequence
<220> FEATURE:
<223> OTHER INFORMATION: Scaffold Y Sequence

<400> SEQUENCE: 349

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys
20 25

<210> SEQ ID NO 350
<211> LENGTH: 26
<212> TYPE: PRT
<213> ORGANISM: Artificial Sequence
<220> FEATURE:
<223> OTHER INFORMATION: Scaffold Y Sequence

<400> SEQUENCE: 350

Gly Ala Lys Lys Ala Lys Lys Arg Phe Ser Phe Lys Lys Ser Phe Lys
1 5 10 15

Leu Ser Gly Phe Ser Phe Lys Lys Asn Lys
20 25

<210> SEQ ID NO 351
<211> LENGTH: 25
<212> TYPE: PRT
<213> ORGANISM: Artificial Sequence
<220> FEATURE:
<223> OTHER INFORMATION: Scaffold Y Sequence

<400> SEQUENCE: 351

Gly Ala Lys Lys Ala Lys Lys Arg Phe Ser Phe Lys Lys Ser Phe Lys
1 5 10 15

Leu Ser Gly Phe Ser Phe Lys Lys Asn
20 25

<210> SEQ ID NO 352

<211> LENGTH: 24
<212> TYPE: PRT
<213> ORGANISM: Artificial Sequence
<220> FEATURE:
<223> OTHER INFORMATION: Scaffold Y Sequence

<400> SEQUENCE: 352

Gly Ala Lys Lys Ala Lys Lys Arg Phe Ser Phe Lys Lys Ser Phe Lys
1               5                   10                  15

Leu Ser Gly Phe Ser Phe Lys Lys
            20

<210> SEQ ID NO 353
<211> LENGTH: 23
<212> TYPE: PRT
<213> ORGANISM: Artificial Sequence
<220> FEATURE:
<223> OTHER INFORMATION: Scaffold Y Sequence

<400> SEQUENCE: 353

Gly Ala Lys Lys Ala Lys Lys Arg Phe Ser Phe Lys Lys Ser Phe Lys
1               5                   10                  15

Leu Ser Gly Phe Ser Phe Lys
            20

<210> SEQ ID NO 354
<211> LENGTH: 22
<212> TYPE: PRT
<213> ORGANISM: Artificial Sequence
<220> FEATURE:
<223> OTHER INFORMATION: Scaffold Y Sequence

<400> SEQUENCE: 354

Gly Ala Lys Lys Ala Lys Lys Arg Phe Ser Phe Lys Lys Ser Phe Lys
1               5                   10                  15

Leu Ser Gly Phe Ser Phe
            20

<210> SEQ ID NO 355
<211> LENGTH: 21
<212> TYPE: PRT
<213> ORGANISM: Artificial Sequence
<220> FEATURE:
<223> OTHER INFORMATION: Scaffold Y Sequence

<400> SEQUENCE: 355

Gly Ala Lys Lys Ala Lys Lys Arg Phe Ser Phe Lys Lys Ser Phe Lys
1               5                   10                  15

Leu Ser Gly Phe Ser
            20

<210> SEQ ID NO 356
<211> LENGTH: 20
<212> TYPE: PRT
<213> ORGANISM: Artificial Sequence
<220> FEATURE:
<223> OTHER INFORMATION: Scaffold Y Sequence

<400> SEQUENCE: 356

Gly Ala Lys Lys Ala Lys Lys Arg Phe Ser Phe Lys Lys Ser Phe Lys
1               5                   10                  15

Leu Ser Gly Phe
            20

<210> SEQ ID NO 357
<211> LENGTH: 19
<212> TYPE: PRT
<213> ORGANISM: Artificial Sequence
<220> FEATURE:
<223> OTHER INFORMATION: Scaffold Y Sequence

<400> SEQUENCE: 357

Gly Ala Lys Lys Ala Lys Lys Arg Phe Ser Phe Lys Lys Ser Phe Lys
1               5                   10                  15

Leu Ser Gly

<210> SEQ ID NO 358
<211> LENGTH: 18
<212> TYPE: PRT
<213> ORGANISM: Artificial Sequence
<220> FEATURE:
<223> OTHER INFORMATION: Scaffold Y Sequence

<400> SEQUENCE: 358

Gly Ala Lys Lys Ala Lys Lys Arg Phe Ser Phe Lys Lys Ser Phe Lys
1               5                   10                  15

Leu Ser

<210> SEQ ID NO 359
<211> LENGTH: 17
<212> TYPE: PRT
<213> ORGANISM: Artificial Sequence
<220> FEATURE:
<223> OTHER INFORMATION: Scaffold Y Sequence

<400> SEQUENCE: 359

Gly Ala Lys Lys Ala Lys Lys Arg Phe Ser Phe Lys Lys Ser Phe Lys
1               5                   10                  15

Leu

<210> SEQ ID NO 360
<211> LENGTH: 16
<212> TYPE: PRT
<213> ORGANISM: Artificial Sequence
<220> FEATURE:
<223> OTHER INFORMATION: Scaffold Y Sequence

<400> SEQUENCE: 360

Gly Ala Lys Lys Ala Lys Lys Arg Phe Ser Phe Lys Lys Ser Phe Lys
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Scaffold Y Sequence

<400> SEQUENCE: 361

Gly Ala Lys Lys Ala Lys Lys Arg Phe Ser Phe Lys Lys Ser Phe
1               5                   10                  15

<210> SEQ ID NO 362
<211> LENGTH: 14
<212> TYPE: PRT
<213> ORGANISM: Artificial Sequence
<220> FEATURE:
<223> OTHER INFORMATION: Scaffold Y Sequence

<400> SEQUENCE: 362

```
Gly Ala Lys Lys Ala Lys Lys Arg Phe Ser Phe Lys Lys Ser
1               5                   10


<210> SEQ ID NO 363
<211> LENGTH: 13
<212> TYPE: PRT
<213> ORGANISM: Artificial Sequence
<220> FEATURE:
<223> OTHER INFORMATION: Scaffold Y Sequence

<400> SEQUENCE: 363

Gly Ala Lys Lys Ala Lys Lys Arg Phe Ser Phe Lys Lys
1               5                   10


<210> SEQ ID NO 364
<211> LENGTH: 12
<212> TYPE: PRT
<213> ORGANISM: Artificial Sequence
<220> FEATURE:
<223> OTHER INFORMATION: Scaffold Y Sequence

<400> SEQUENCE: 364

Gly Ala Lys Lys Ala Lys Lys Arg Phe Ser Phe Lys
1               5                   10


<210> SEQ ID NO 365
<211> LENGTH: 11
<212> TYPE: PRT
<213> ORGANISM: Artificial Sequence
<220> FEATURE:
<223> OTHER INFORMATION: Scaffold Y Sequence

<400> SEQUENCE: 365

Gly Ala Lys Lys Ala Lys Lys Arg Phe Ser Phe
1               5                   10


<210> SEQ ID NO 366
<211> LENGTH: 10
<212> TYPE: PRT
<213> ORGANISM: Artificial Sequence
<220> FEATURE:
<223> OTHER INFORMATION: Scaffold Y Sequence

<400> SEQUENCE: 366

Gly Ala Lys Lys Ala Lys Lys Arg Phe Ser
1               5                   10


<210> SEQ ID NO 367
<211> LENGTH: 9
<212> TYPE: PRT
<213> ORGANISM: Artificial Sequence
<220> FEATURE:
<223> OTHER INFORMATION: Scaffold Y Sequence

<400> SEQUENCE: 367

Gly Ala Lys Lys Ala Lys Lys Arg Phe
1               5


<210> SEQ ID NO 368
<211> LENGTH: 8
<212> TYPE: PRT
<213> ORGANISM: Artificial Sequence
<220> FEATURE:
<223> OTHER INFORMATION: Scaffold Y Sequence

<400> SEQUENCE: 368
```

Gly Ala Lys Lys Ala Lys Lys Arg
1               5

<210> SEQ ID NO 369
<211> LENGTH: 7
<212> TYPE: PRT
<213> ORGANISM: Artificial Sequence
<220> FEATURE:
<223> OTHER INFORMATION: Scaffold Y Sequence

<400> SEQUENCE: 369

Gly Ala Lys Lys Ala Lys Lys
1               5

<210> SEQ ID NO 370
<211> LENGTH: 94
<212> TYPE: PRT
<213> ORGANISM: Artificial Sequence
<220> FEATURE:
<223> OTHER INFORMATION: ESAT6 Protein Sequence

<400> SEQUENCE: 370

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Asp Glu Gly Lys
            20                  25                  30

Gln Ser Leu Thr Lys Leu Ala Ala Ala Trp Gly Gly Ser Gly Ser Glu
        35                  40                  45

Ala Tyr Gln Gly Val Gln Gln Lys Trp Asp Ala Thr Ala Thr Glu Leu
    50                  55                  60

Asn Asn Ala Leu Gln Asn Leu Ala Arg Thr Ile Ser Glu Ala Gly Gln
65                  70                  75                  80

Ala Met Ala Ser Thr Glu Gly Asn Val Thr Gly Met Phe Ala
                85                  90

<210> SEQ ID NO 371
<211> LENGTH: 96
<212> TYPE: PRT
<213> ORGANISM: Artificial Sequence
<220> FEATURE:
<223> OTHER INFORMATION: TB10.4 Protein Sequence

<400> SEQUENCE: 371

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

<210> SEQ ID NO 372
<211> LENGTH: 8
<212> TYPE: PRT
<213> ORGANISM: Artificial Sequence
<220> FEATURE:
<223> OTHER INFORMATION: Scaffold Y Sequence

```
<220> FEATURE:
<221> NAME/KEY: misc_feature
<222> LOCATION: (2)..(2)
<223> OTHER INFORMATION: Xaa can be any naturally occurring amino acid

<400> SEQUENCE: 372

Gly Xaa Lys Leu Ser Lys Lys Lys
1               5


<210> SEQ ID NO 373
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (5)..(5)
<223> OTHER INFORMATION: wherein Xaa is any integer between 1-100

<400> SEQUENCE: 373

Gly Gly Gly Gly Xaa
1               5


<210> SEQ ID NO 374
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: misc_Feature
<222> LOCATION: (2)..(2)
<223> OTHER INFORMATION: Wherein Xaa is any integer from 1 to 100
<220> FEATURE:
<221> NAME/KEY: misc_Feature
<222> LOCATION: (4)..(4)
<223> OTHER INFORMATION: Wherein Xaa is any integer from 1 to 100

<400> SEQUENCE: 374

Gly Xaa Ser Xaa
1


<210> SEQ ID NO 375
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Wherein Xaa is any integer from 1 to 4
<220> FEATURE:
<221> NAME/KEY: misc_feature
<222> LOCATION: (4)..(4)
<223> OTHER INFORMATION: Wherein Xaa  is 0 or 1
<220> FEATURE:
<221> NAME/KEY: misc_feature
<222> LOCATION: (5)..(5)
<223> OTHER INFORMATION: Wherein Xaa is any integer from 1 to 50

<400> SEQUENCE: 375

Gly Xaa Ser Xaa Xaa
1               5


<210> SEQ ID NO 376
<211> LENGTH: 2
<212> TYPE: PRT
<213> ORGANISM: Artificial Sequence
<220> FEATURE:
```

-continued

<223> OTHER INFORMATION: Linker
<220> FEATURE:
<221> NAME/KEY: misc_feature
<222> LOCATION: (2)..(2)
<223> OTHER INFORMATION: wherein Xaa can be any integer between 1-100

<400> SEQUENCE: 376

Gly Asn
1

<210> SEQ ID NO 377
<211> LENGTH: 3
<212> TYPE: PRT
<213> ORGANISM: Artificial Sequence
<220> FEATURE:
<223> OTHER INFORMATION: wherein Xaa is an integer between 1 and 100
<220> FEATURE:
<221> NAME/KEY: misc_feature
<222> LOCATION: (3)..(3)
<223> OTHER INFORMATION: Xaa can be any naturally occurring amino acid

<400> SEQUENCE: 377

Gly Ala Xaa
1

<210> SEQ ID NO 378
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (4)..(4)
<223> OTHER INFORMATION: Wherein Xaa is an integer between 1 and 100

<400> SEQUENCE: 378

Gly Gly Ser Xaa
1

<210> SEQ ID NO 379
<211> LENGTH: 28
<212> TYPE: PRT
<213> ORGANISM: Artificial Sequence
<220> FEATURE:
<223> OTHER INFORMATION: Lama4 Peptide

<400> SEQUENCE: 379

```
Gln Lys Ile Ser Phe Phe Asp Gly Phe Glu Val Gly Phe Asn Phe Arg
1               5                   10                  15

Thr Leu Gln Pro Asn Gly Leu Leu Phe Tyr Tyr Thr
            20                  25
```

<210> SEQ ID NO 380
<211> LENGTH: 23
<212> TYPE: PRT
<213> ORGANISM: Artificial Sequence
<220> FEATURE:
<223> OTHER INFORMATION: Itgb1 Peptide

<400> SEQUENCE: 380

```
Trp Phe Tyr Phe Thr Tyr Ser Val Asn Gly Tyr Asn Glu Ala Ile Val
1               5                   10                  15

His Val Val Glu Thr Pro Asp
            20
```